US010961247B2

(12) United States Patent
Kim et al.

(10) Patent No.: US 10,961,247 B2
(45) Date of Patent: Mar. 30, 2021

(54) PYRAZOLOPYRIMIDINE DERIVATIVES AS KINASE INHIBITOR

(71) Applicant: Daewoong Pharmaceutical Co., Ltd., Gyeonggi-do (KR)

(72) Inventors: In Woo Kim, Seoul (KR); Mi Ryeong Han, Gyeonggi-do (KR); Jakyung Yoo, Gyeonggi-do (KR); Yun Ju Oh, Chungcheongbuk-do (KR); Ji Duck Kim, Gyeonggi-do (KR); Nam Youn Kim, Gyeonggi-do (KR); Sun Ah Jun, Gyeonggi-do (KR); Jun Hee Lee, Seoul (KR); Joon Seok Park, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 203 days.

(21) Appl. No.: 16/304,798

(22) PCT Filed: Jun. 30, 2017

(86) PCT No.: PCT/KR2017/006980
§ 371 (c)(1),
(2) Date: Nov. 27, 2018

(87) PCT Pub. No.: WO2018/004306
PCT Pub. Date: Jan. 4, 2018

(65) Prior Publication Data
US 2020/0317673 A1 Oct. 8, 2020

(30) Foreign Application Priority Data
Jun. 30, 2016 (KR) .................. 10-2016-0083050

(51) Int. Cl.
C07D 487/04 (2006.01)
A61P 37/00 (2006.01)
A61P 35/00 (2006.01)
A61P 29/00 (2006.01)

(52) U.S. Cl.
CPC ............ *C07D 487/04* (2013.01); *A61P 29/00* (2018.01); *A61P 35/00* (2018.01); *A61P 37/00* (2018.01)

(58) Field of Classification Search
CPC .. C07D 403/14; C07D 473/16; C07D 471/04; C07D 487/04; A61K 31/52; A61K 31/4375; A61P 35/00; A61P 19/02
See application file for complete search history.

(56) References Cited

U.S. PATENT DOCUMENTS

| 9,469,644 | B2 | 10/2016 | De Vicente Fidalgo et al. |
| 9,840,517 | B2 | 12/2017 | Liu et al. |
| 10,081,635 | B2 | 9/2018 | Kim et al. |
| 2009/0298823 | A1 | 12/2009 | Song et al. |
| 2012/0094999 | A1 | 4/2012 | Gray et al. |
| 2013/0029944 | A1 | 1/2013 | Song et al. |
| 2016/0002243 | A1 | 1/2016 | De Vicente Fidalgo et al. |
| 2019/0040065 | A1 | 2/2019 | Gray et al. |

FOREIGN PATENT DOCUMENTS

| CA | 2849357 A1 | 3/2013 | |
| CN | 102066338 A | 5/2011 | |
| CN | 102482277 A | 5/2012 | |
| CN | 105073750 A | 11/2015 | |
| CN | 105732637 A | 7/2016 | |
| JP | 2012-526113 | 10/2012 | |
| RU | 2285527 C2 | 10/2006 | |
| WO | WO-2002/096909 A1 | 12/2002 | |
| WO | WO-2007/007919 | 1/2007 | |
| WO | WO-2007/070514 A1 | 6/2007 | |
| WO | WO-2008/039218 A2 | 4/2008 | |
| WO | WO-2009/012283 | 1/2009 | |
| WO | WO-2009/054941 | 4/2009 | |
| WO | WO-2009/131687 A2 | 10/2009 | |
| WO | WO-2010/009342 A2 | 1/2010 | |
| WO | WO 2010/129053 | * 11/2010 | ........... C07D 473/16 |
| WO | WO-2010/129053 A2 | 11/2010 | |
| WO | WO-2011/068899 | 6/2011 | |
| WO | WO-2011/162515 | 12/2011 | |
| WO | WO-2013/043964 A1 | 3/2013 | |
| WO | WO-2015/006754 A2 | 1/2015 | |
| WO | WO-2015/039612 A1 | 3/2015 | |
| WO | WO 2015/083028 | * 6/2015 | ........... C07D 471/04 |
| WO | WO-2015/083028 A1 | 6/2015 | |
| WO | WO-2016/032209 A2 | 3/2016 | |
| WO | WO-2016/130920 | 8/2016 | |

OTHER PUBLICATIONS

Office Action in CO Application No. NC2018//0013293 dated Sep. 12, 2019, 12 pages.
Office Action in JP Application No. 2018-568407 dated Oct. 29, 2019, 4 pages.
Office Action in NZ Application No. 748746 dated Aug. 19, 2019, 3 pages.
Office Action in RU Application No. 2019102376 dated Sep. 6, 2019, 14 pages.
Search Report and Written Opinion in International Application No. PCT/KR2017/006980 dated Oct. 13, 2017, 13 pages.
Zhou et al., "Discovery of Selective Irreversible Inhibitors for EGFR-T790M", Bioorg. Med. Chem. Lett., vol. 21, No. 2, 2011, pp. 638-643.
D'Aura et al., "Tyrosine Kinases as Targets for the Treatment of Rheumatoid Arthritis", Nature Reviews Rheumatology, vol. 5, Jun. 2009, pp. 317-324.
Whang et al., "Bruton's Tyrosine Kinase Inhibitors for the Treatment of Rheumatoid Arthritis", Drug Discovery Today, vol. 19(8), Aug. 2014, pp. 1200-1204 (8 pages).
Peter Norman, "Selective JAK Inhibitors in Development for Rheumatoid Arthritis", Expert Opinion Investig. Drugs, vol. 23(8), Aug. 2014, pp. 1067-1077 (11 pages).

(Continued)

*Primary Examiner* — Erich A Leeser
(74) *Attorney, Agent, or Firm* — Marshall, Gerstein & Borun LLP

(57) ABSTRACT

The present invention relates to a pyrazolopyrimidine derivative, or a pharmaceutically acceptable salt thereof. The compound according to the present invention can be usefully used for the prevention or treatment of diseases which are associated with kinase inhibitory actions.

13 Claims, No Drawings

(56) References Cited

OTHER PUBLICATIONS

Office Action in Chilean Application No. 201803511 dated Nov. 29, 2019, 17 pages.
Liu et al., "Preparation of Heteroaromatic Compounds for Treating Autoimmune or Proliferative Diseases", Database Caplus, Chemical Abstracts, Jul. 6, 2016, 2 pages.
Extended European Search Report in EP Application No. 17820582.9 dated Jan. 22, 2020, 6 pages.
Office Action in CN Application No. 201780039336.0 dated Sep. 17, 2020, 9 pages.
Gaikwad et al., "The Use of Bioisosterism in Drug Design and Molecular Modification", Am. J. Pham Tech Res. 2(4), 2012, 23 pages.

\* cited by examiner

PYRAZOLOPYRIMIDINE DERIVATIVES AS KINASE INHIBITOR

TECHNICAL FIELD

The present invention relates to a pyrazolopyrimidine derivative having kinase inhibitory activity, a process for preparing the same and use thereof.

BACKGROUND OF ART

Protein kinase is an enzyme that catalyzes phosphorylation of specific residues of other proteins, and plays an important role in signal-transduction pathways that transduce extracellular signals to the nucleus. Further, it is involved in various diseases in vivo. In the onset or development of inflammatory disease, autoimmune disease, proliferative disease or hyperproliferative disease, and/or immunity mediated disease, there is various evidence that T-cells (or T-lymphocytes) and B-cells (or B-lymphocytes) play an important role.

Janus kinase (hereinafter referred to as "JAK") is a cytoplasmic protein tyrosine kinase that plays pivotal roles in regulating cell function in the lympho-hematopoietic system. Cytokines are known to play an important role in regulating inflammation, immunity and normal cell function, and JAK activates STAT (Signal Transducer and Activators of Transcription) proteins through tyrosine phosphorylation to provide rapid signaling pathways to cytokines. JAK/STAT signaling is known to be associated with allergies, asthma, autoimmune diseases (e.g., transplant rejection, rheumatoid arthritis, amyotrophic lateral sclerosis, multiple sclerosis etc.), solid cancers, blood cancers (e.g., leukemia, lymphoma and so on).

The JAK family is classified into four members: JAK 1, JAK 2, JAK 3, and TYK 2. Members of the JAK family pair with each other to mediate signals from a variety of cytokines. It includes JAK2 and JAK1 associated with hematopoietic growth factor signaling, and a combination of TYK2 and JAK2 is important for interferon signaling and contributes to host tolerance. JAK2 can induce anemia, thrombocytopenia, leukopenia, especially when it is involved in the hematopoietic growth factor signaling and causes excessive inhibition.

The expression of JAK1, JAK2, and TYK2 was found to be widely distributed, whereas the expression of JAK3 was restricted to lymphocytes and is associated with signaling for the common gamma chains, members of IL-2, IL-4, IL-7, IL-9, IL-15 and IL-21 receptors, particularly the common gamma chain of the IL-2 family. As soon as the cytokine is bound, the receptor carries adjacent JAK3 nearby, which induces autophosphorylation of the β-chain C-terminus. As a result, it causes activation of the STAT protein, which is an important step in retransmitting the signal to the nucleus. JAK3 controls the signal pathways of various cytokines through this process. This makes JAK3 as an attractive target for immunosuppression.

B cells play an important role in the development of autoimmune and/or inflammatory diseases. Protein-based therapeutic agents that reduce B cells, for example Rituxan, are effective in autoantibody-induced inflammatory diseases such as rheumatoid arthritis. Thus, protein kinase inhibitors that play a role in B cell activation are useful therapeutic agents for the treatment of B cell-mediated diseases, for example, for the production of autoantibodies.

Signal transduction through B cell receptor (BCR) regulates various B cell responses, including proliferation and differentiation into mature antibody-producing cells. BCR is an important regulatory element of B cell activity, and abnormal signal transduction can cause the formation of pathogenic autoantibodies leading to a plurality of autoimmune and/or inflammatory diseases and the proliferation of deregulated B cell.

Bruton's tyrosine kinase (hereinafter, referred to as "BTK") is an important regulator of the development, activation, signaling and survival of B-cells. BTK is involved in signal transduction pathways initiated by binding various extracellular ligands to their cell surface receptors. Following ligation of the B cell antigen receptor (BCR), the activity of BTK by the coincident action of the protein tyrosine kinases Lyn and Syk is required for the induction of the phospholipase C-γ2-mediated calcium mobilization. Therefore, inhibition of BTK can be a useful therapeutic approach in blocking the onset process of B-cell mediated diseases.

As mentioned above, Janus kinase and TEC-based kinases play an important role in the activation of T-cells and/or B-cells involved in the development of inflammatory diseases, autoimmune diseases, proliferative diseases or hyperproliferative diseases, and immunity mediated diseases. Therefore, the development of substances that effectively inhibit these diseases can be useful as a related therapeutic agent. Specific examples of the diseases which can be treated and prevented include cancer, transplant rejection, multiple sclerosis, rheumatoid arthritis, psoriatic arthritis, psoriasis, asthma, allergic dermatitis, atopic dermatitis, eczema, type I diabetes, diabetic complication, ulcerative colitis, Crohn's disease, autoimmune thyroid disorder, systemic depilation, Sjogren's syndrome and the like.

JAK3 kinase inhibitor, tofacitinib (CP-690550) (Pfizer Inc.) is currently approved and marketed for the treatment of rheumatoid arthritis. In addition, a BTK kinase inhibitor, ibrutinib (PCI-32765) (Pharmacyclics) is in a clinical stage, but severe side effects such as skin rash and diarrhea have been reported in clinical cases. Thus, there is a need to develop a more stable and effective substance that inhibits JAK and/or BTK (see, Nat Rev Rheumatol. 2009 Jun. 5(6) 317-24; Expert Opin Investig Drugs. 2014 Aug. 23(8) 1067-77; Drug Discov Today 2014 Aug. 19(8) 1200-4; WO2002/096909; WO2010-009342).

Therefore, the present inventors have found a new compound having an excellent inhibitory activity as a kinase inhibitor, thereby completing the present invention. Specifically, the compounds of the present invention show affinity for JAK and/or BTK. The compounds belonging to the present invention themselves have mainly a kinase-inhibitory activity, but do not exclude a possibility of exhibiting a pharmacological action as an efficacious agent by a special body environment or by products of metabolic process, after absorption into the body.

DETAILED DESCRIPTION OF THE INVENTION

Technical Problem

It is an object of the present invention to provide a pyrazolopyrimidine derivative having kinase inhibitory activity, and a process for preparing the same.

It is another object of the present invention to provide a pharmaceutical composition comprising the pyrazolopyrimidine derivative as an active ingredient.

Technical Solution

In order to achieve the above objects, the present invention provides a compound represented by the following Chemical Formula 1, or a pharmaceutically acceptable salt thereof:

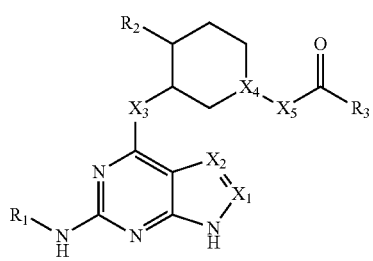

in Chemical Formula 1,

R$_1$ is benzothiazolyl, isothiazolyl, isoxazolyl, phenyl, or pyrazolyl;

wherein R$_1$ is unsubstituted, or substituted with a substituent selected from the group consisting of piperazinyl unsubstituted or substituted with C$_{1-4}$ alkyl; benzyl unsubstituted or substituted with C$_{1-4}$ alkoxy; one or two C$_{1-4}$ alkyl unsubstituted or substituted with morpholino, —N(C$_{1-4}$ alkyl)$_2$, C$_{1-4}$ alkoxy, cyano, or —CONH(C$_{1-4}$ alkyl); C$_{1-4}$ haloalkyl; C$_{3-6}$ cycloalkyl; morpholino; —CO-(molpolino); morpholino and halogen; —N(C$_{1-4}$ alkyl)$_2$; —NHCO(C$_{2-4}$ alkenyl); —NHCO(pyrrolidinyl); C$_{1-4}$ alkoxy unsubstituted or substituted with —N(C$_{1-4}$ alkyl)$_2$; C$_{6-10}$ aryloxy; pyrazolyl unsubstituted or substituted with one or two C$_{1-4}$ alkyl; pyrrolidinyl; tetrahydropyranyl; and halogen, R$_2$ is hydrogen, C$_{1-4}$ alkyl, or halogen;

R$_3$ is C$_{1-4}$ alkyl unsubstituted or substituted with cyano, or halogen; C$_{2-6}$ alkenyl unsubstituted or substituted with one or two substituents independently selected from the group consisting of cyano, C$_{3-6}$ cycloalkyl, and —N(C$_{1-4}$alkyl)$_2$; or C$_{2-4}$ alkynyl unsubstituted or substituted with C$_{3-6}$ cycloalkyl, X$_1$ is CR$_4$ or N, wherein R$_4$ is hydrogen, C$_{1-4}$ alkyl, or halogen, X$_2$ is CR$_5$, wherein R$_5$ is hydrogen, C$_{1-4}$ alkyl, C$_{1-4}$ alkoxy, C$_{1-4}$ haloalkyl, halogen, cyano, or C$_{1-4}$ alkylthio, X$_3$ is NR$_6$, O, or S, wherein R$_6$ is hydrogen or C$_{1-4}$ alkyl, X$_4$ is CH, or N, and X$_5$ is a bond, or NH.

Preferably, R$_1$ is phenyl, wherein the R$_1$ is piperazinyl substituted with C$_{1-4}$ alkyl; morpholino; —CO-(molpolino); —N(C$_{1-4}$ alkyl)$_2$; —NHCO(C$_{2-4}$ alkenyl); —NHCO(pyrrolidinyl); C$_{1-4}$ alkoxy substituted with —N(C$_{1-4}$ alkyl)$_2$; phenoxy; pyrazolyl unsubstituted or substituted with one or two C$_{1-4}$ alkyl; or pyrrolidinyl. More preferably, R$_3$ is C$_{2-4}$ alkenyl unsubstituted or substituted with cyano, or C$_{2-4}$ alkenyl unsubstituted or substituted with cyano or —N(C$_{1-4}$ alkyl)$_2$.

Preferably, R$_1$ is pyrazoly, wherein the R$_1$ is benzyl substituted with C$_{1-4}$ alkoxy; one or two C$_{1-4}$ alkyl unsubstituted or substituted with morpholino, —N(C$_{1-4}$ alkyl)$_2$, C$_{1-4}$ alkoxy, cyano, or —CONH(C$_{1-4}$ alkyl); C$_{1-4}$ haloalkyl; C$_{3-6}$ cycloalkyl; or tetrahydropyranyl. More preferably, R$_3$ is C$_{2-6}$ alkenyl unsubstituted or substituted with cyano or —N(C$_{1-4}$ alkyl)$_2$; or C$_{2-4}$ alkynyl.

Preferably, R$_1$ is unsubstituted benzothiazolyl, isothiazolyl substituted with C$_{1-4}$ alkyl, or unsubstituted isoxazolyl. More preferably, R$_3$ is C$_{2-4}$ alkenyl unsubstituted or substituted with cyano or —N(C$_{1-4}$ alkyl)$_2$; or C$_{2-4}$ alkynyl.

Preferably, R$_1$ is
unsubstituted benzothiazolyl;
isothiazolyl substituted by C$_{1-4}$ alkyl;
isoxazolyl unsubstituted or substituted by C$_{1-4}$ alkyl;
pyrazolyl substituted by benzyl substituted by C$_{1-4}$ alkoxy, one or two C$_{1-4}$ alkyl unsubstituted or substituted by morpholino, —N(C$_{1-4}$ alkyl)$_2$, C$_{1-4}$ alkoxy, cyano, or —CONH(C$_{1-4}$ alkyl), C$_{1-4}$ haloalkyl, C$_{3-6}$ cycloalkyl, or tetrahydropyranyl; or
phenyl substituted by piperazinyl substituted by C$_{1-4}$ alkyl, morpholino, —CO-(morpholino), morpholino and halogen, —N(C$_{1-4}$ alkyl)$_2$, —NHCO(C$_{2-4}$ alkenyl), —NHCO(pyrrolidinyl), C$_{1-4}$ alkoxy substituted by —N(C$_{1-4}$ alkyl)$_2$, phenoxy, pyrazolyl unsubstituted or substituted by one or two C$_{1-4}$ alkyl, or pyrrolidinyl.

Preferably, R$_2$ is hydrogen, methyl, or fluoro.

Preferably, R$_3$ is —CH$_2$Cl, —CH$_2$CN, —CH=CH$_2$, —CH=CHCH$_3$, —C(ON)=CHCH(CH$_3$)$_2$, —C(CN)=CH (cyclopentyl), —C(CN)=CH(cyclopropyl), —C(CN)=CHC(CH$_3$)$_3$, —C(CN)=CHCH(CH$_3$)$_2$, —C≡CCH$_3$, —C≡CCH$_2$CH$_3$, or —C≡C-(cyclopropyl).

Preferably, X$_1$ is CH, or N.

Preferably, X$_2$ is CR$_5$, and R$_5$ is hydrogen, methyl, fluoro, chloro, cyano, or methylthio.

Preferably, X$_3$ is NH, N(CH$_3$), S, or O.

Preferably, X$_4$ is N, and X$_5$ is a bond; or X$_4$ is CH, and X$_5$ is NH.

Preferably, the compound represented by Chemical Formula 1 is represented by the following Chemical Formula 1-1:

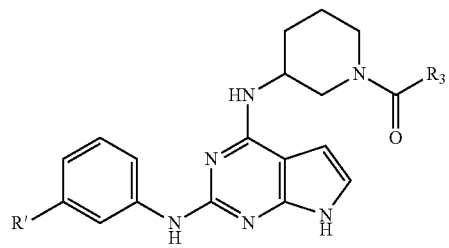

in Chemical Formula 1-1,

R' is —NHCO(C$_{2-4}$ alkenyl); —NHCO(pyrrolidinyl); or pyrazolyl unsubstituted or substituted with two C$_{1-4}$ alkyl, R$_3$ is C$_{1-4}$ alkyl unsubstituted or substituted with cyano; or C$_{2-4}$ alkenyl unsubstituted or substituted with cyano or —N(C$_{1-4}$ alkyl).

Preferably, the compound represented by Chemical Formula 1 is represented by the following Chemical Formula 1-2:

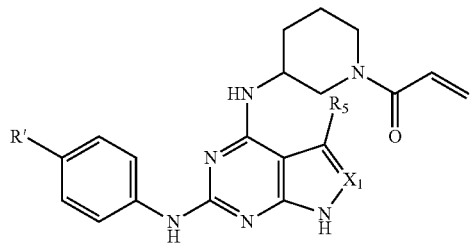

in Chemical Formula 1-2,

X$_1$ is CH, or N,

R' is piperazinyl unsubstituted or substituted with C$_{1-4}$ alkyl; morpholino; —CO-(molpolino); —N(C$_{1-4}$ alkyl)$_2$; C$_{1-4}$ alkoxy unsubstituted or substituted with —N(C$_{1-4}$ alkyl)$_2$; phenoxy; pyrazolyl unsubstituted or substituted with one or two $C_{1-4}$ alkyl; or pyrrolidinyl, and $R_5$ is hydrogen or halogen.

Preferably, the compound represented by Chemical Formula 1 is represented by the following chemical formula 1-3:

[Chemical Formula 1-3]

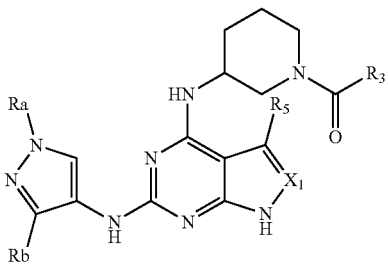

in Chemical Formula 1-3, $X_1$ is CH, or N,

Ra is benzyl unsubstituted or substituted with $C_{1-4}$ alkoxy; $C_{1-4}$ alkyl unsubstituted or substituted with morpholino, —N($C_{1-4}$ alkyl)$_2$, $C_{1-4}$ alkoxy, cyano, or —CONH($C_{1-4}$ alkyl); $C_{1-4}$ haloalkyl; $C_{3-6}$ cycloalkyl; or tetrahydropyranyl, Rb is hydrogen or $C_{1-4}$ alkyl, $R_3$ is $C_{2-4}$ alkenyl unsubstituted or substituted with cyano or —N($C_{1-4}$ alkyl)$_2$; or $C_{2-4}$ alkynyl, and $R_5$ is hydrogen or halogen.

Representative examples of the compounds represented by Chemical Formula 1 are as follows:

1) (R)-1-(3-(2-(4-(4-methylpiperazin-1-yl)phenylamino)-7H-pyrrolo[2,3-d]pyrimidin-4-ylamino)piperidin-1-yl)prop-2-en-1-one,
2) (R)—N-(3-(4-(1-acryloylpiperidin-3-ylamino)-7H-pyrrolo[2,3-d]pyrimidin-2-ylamino)phenyl)pyrrolidine-1-carboxamide,
3) (S)—N-(3-(4-(1-acryloylpiperidin-3-ylamino)-7H-pyrrolo[2,3-d]pyrimidin-2-ylamino)phenyl)pyrrolidine-1-carboxamide,
4) (R)-1-(3-(2-(4-morpholinophenylamino)-7H-pyrrolo[2,3-d]pyrimidin-4-ylamino)piperidin-1-yl)prop-2-en-1-one,
5) (R)-1-(3-(2-(4-(pyrrolidin-1-yl)phenylamino)-7H-pyrrolo[2,3-d]pyrimidin-4-ylamino)piperidin-1-yl)prop-2-en-1-one,
6) (R)-1-(3-(2-(4-(3,5-dimethyl-1H-pyrazol-1-yl)phenylamino)-7H-pyrrolo[2,3-d]pyrimidin-4-ylamino)pipendin-1-yl)prop-2-en-1-one,
7) (R)-1-(3-(2-(4-(2-(diethylamino)ethoxy)phenylamino)-7H-pyrrolo[2,3-d]pyrimidin-4-ylamino)pipendin-1-yl)prop-2-en-1-one,
8) (R)-1-(3-(2-(4-(morpholine-4-carbonyl)phenylamino)-7H-pyrrolo[2,3-d]pyrimidin-4-ylamino)piperidin-1-yl)prop-2-en-1-one,
9) (R)-1-(3-(2-(4-(dimethylamino)phenylamino)-7H-pyrrolo[2,3-d]pyrimidin-4-ylamino)pipendin-1-yl)prop-2-en-1-one,
10) (R)-1-(3-(2-(3-(3,5-dimethyl-1H-pyrazol-1-yl)phenylamino)-7H-pyrrolo[2,3-d]pyrimidin-4-ylamino)pipendin-1-yl)prop-2-en-1-one,
11) (S)-1-(3-(2-(4-(4-methylpiperazin-1-yl)phenylamino)-7H-pyrrolo[2,3-d]pyrimidin-4-ylamino)piperidin-1-yl)prop-2-en-1-one,
12) (R)-1-(3-(2-(benzo[d]thiazol-6-ylamino)-7H-pyrrolo[2,3-d]pyrimidin-4-ylamino)pipendin-1-yl)prop-2-en-1-one,
13) (R)-1-(3-(2-(4-phenoxyphenylamino)-7H-pyrrolo[2,3-d]pyrimidin-4-ylamino)pipendin-1-yl)prop-2-en-1-one,
14) (R)-1-(3-(2-(1-methyl-1H-pyrazol-4-ylamino)-7H-pyrrolo[2,3-d]pyrimidin-4-ylamino)pipendin-1-yl)prop-2-en-1-one,
15) (R)-1-(3-(2-(1-(2,2-difluoroethyl)-1H-pyrazol-4-ylamino)-7H-pyrrolo[2,3-d]pyrimidin-4-ylamino)pipendin-1-yl)prop-2-en-1-one,
16) (R)-1-(3-(2-(1-(difluoromethyl)-1H-pyrazol-4-ylamino)-7H-pyrrolo[2,3-d]pyrimidin-4-ylamino)pipendin-1-yl)prop-2-en-1-one,
17) (R)-1-(3-(2-(1-(2-methoxyethyl)-1H-pyrazol-4-ylamino)-7H-pyrrolo[2,3-d]pyrimidin-4-ylamino)pipendin-1-yl)prop-2-en-1-one,
18) (R)-1-(3-(2-(1-(2-morpholinoethyl)-1H-pyrazol-4-ylamino)-7H-pyrrolo[2,3-d]pyrimidin-4-ylamino)pipendin-1-yl)prop-2-en-1-one,
19) (R)-1-(3-(2-(1-(2-(diethylamino)ethyl)-1H-pyrazol-4-ylamino)-7H-pyrrolo[2,3-d]pyrimidin-4-ylamino)pipendin-1-yl)prop-2-en-1-one,
20) (R)-1-(3-(2-(1-(3-methoxybenzyl)-1H-pyrazol-4-ylamino)-7H-pyrrolo[2,3-d]pyrimidin-4-ylamino)piperidin-1-yl)prop-2-en-1-one,
21) (R)-1-(3-(2-(1-ethyl-1H-pyrazol-4-ylamino)-7H-pyrrolo[2,3-d]pyrimidin-4-ylamino)piperidin-1-yl)prop-2-en-1-one,
22) (R)-1-(3-(2-(1,3-dimethyl-1H-pyrazol-4-ylamino)-7H-pyrrolo[2,3-d]pyrimidin-4-ylamino)piperidin-1-yl)prop-2-en-1-one,
23) (R)-1-(3-(2-(isoxazol-4-ylamino)-7H-pyrrolo[2,3-d]pyrimidin-4-ylamino)piperidin-1-yl)prop-2-en-1-one,
24) (R)-2-(4-(4-(1-acryloylpiperidin-3-ylamino)-7H-pyrrolo[2,3-d]pyrimidin-2-ylamino)-1H-pyrazol-1-yl)-N-methylacetamide,
25) (R)-1-(3-(2-(1-(2,2-difluoroethyl)-1H-pyrazol-4-ylamino)-7H-pyrrolo[2,3-d]pyrimidin-4-ylamino)piperidin-1-yl)but-2-yn-1-one,
26) (R)—N-(3-(4-(1-(2-cyanoacetyl)piperidin-3-ylamino)-7H-pyrrolo[2,3-d]pyrimidin-2-ylamino)phenyl)acrylamide,
27) 1-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)prop-2-en-1-one,
28) 3-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)-3-oxopropanenitrile,
29) N-(3-(2-(4-(4-methylpiperazin-1-yl)phenylamino)-7H-pyrrolo[2,3-d]pyrimidin-4-ylamino)cyclohexyl)acrylamide,
30) (R)-1-(3-(6-(4-(4-methylpiperazin-1-yl)phenylamino)-1H-pyrazolo[3,4-d]pyrimidin-4-ylamino)piperidin-1-yl)prop-2-en-1-one,
31) (R)-1-(3-(6-(1-(2,2-difluoroethyl)-1H-pyrazol-4-ylamino)-1H-pyrazolo[3,4-d]pyrimidin-4-ylamino)piperidin-1-yl)prop-2-en-1-one,
32) (R)-1-(3-(6-(1-methyl-1H-pyrazol-4-ylamino)-1H-pyrazolo[3,4-d]pyrimidin-4-ylamino)piperidin-1-yl)prop-2-en-1-one,
33) (R)-1-(3-(6-(1-ethyl-1H-pyrazol-4-ylamino)-1H-pyrazolo[3,4-d]pyrimidin-4-ylamino)piperidin-1-yl)prop-2-en-1-one,
34) (R)-1-(3-(6-(1-(difluoromethyl)-1H-pyrazol-4-ylamino)-1H-pyrazolo[3,4-d]pyrimidin-4-ylamino)piperidin-1-yl)prop-2-en-1-one,
35) (R)-2-(4-(4-(1-acryloylpiperidin-3-ylamino)-1H-pyrazolo[3,4-d]pyrimidin-6-ylamino)-1H-pyrazol-1-yl)-N-methylacetamide, 36) (R)-1-(3-(5-chloro-2-(4-(4-methylpiperazin-1-yl)phenylamino)-7H-pyrrolo[2,3-d]pyrimidin-4-ylamino)piperidin-1-yl)prop-2-en-1-one,
37) (R)-1-(3-(5-chloro-2-(1-ethyl-1H-pyrazol-4-ylamino)-7H-pyrrolo[2,3-d]pyrimidin-4-ylamino)piperidin-1-yl)prop-2-en-1-one,
38) (R)-1-(3-(5-chloro-2-(1-(difluoromethyl)-1H-pyrazol-4-ylamino)-7H-pyrrolo[2,3-d]pyrimidin-4-ylamino)piperidin-1l1)prop-2-en-1-one,
39) (R)-1-(3-(5-chloro-2-(1-(2,2-difluoroethyl)-1H-pyrazol-4-ylamino)-7H-pyrrolo[2,3-d]pyrimidin-4-ylamino)piperidin-1-yl)prop-2-en-1-one,
40) (R)-1-(3-(5-chloro-2-(1-(2-morpholinoethyl)-1H-pyrazol-4-ylamino)-7H-pyrrolo[2,3-d]pyrimidin-4-ylamino)piperidin-1-yl)prop-2-en-1-one,
41) (R)-1-(3-(5-chloro-2-(1-(3-methoxybenzyl)-1H-pyrazol-4-ylamino)-7H-pyrrolo[2,3-d]pyrimidin-4-ylamino)piperidin-1-yl)prop-2-en-1-one,
42) (R)-1-(3-(3-chloro-6-(4-(4-methylpiperazin-1-yl)phenylamino)-1H-pyrazolo[3,4-d]pyrimidin-4-ylamino)piperidin-1-yl)prop-2-en-1-one,
43) (R)-1-(3-(3-chloro-6-(4-(3,5-dimethyl-1H-pyrazol-1-yl)phenylamino)-1H-pyrazolo[3,4-d]pyrimidin-4-ylamino)piperidin-1-yl)prop-2-en-1-one,
44) (R)-1-(3-(3-chloro-6-(1-(2,2-difluoroethyl)-1H-pyrazol-4-ylamino)-1H-pyrazolo[3,4-d]pyrimidin-4-ylamino)piperidin-1-yl)prop-2-en-1-one,
45) (R)-1-(3-(3-chloro-6-(1-methyl-1H-pyrazol-4-ylamino)-1H-pyrazolo[3,4-d]pyrimidin-4-ylamino)piperidin-1-yl)prop-2-en-1-one,
46) (R)-1-(3-(3-chloro-6-(1-ethyl-1H-pyrazol-4-ylamino)-1H-pyrazolo[3,4-d]pyrimidin-4-ylamino)piperidin-1-yl)prop-2-en-1-one,
47) (R)-2-(4-(4-(1-acryloylpiperidin-3-ylamino)-3-chloro-1H-pyrazolo[3,4-d]pyrimidin-6-ylamino)-1H-pyrazol-1-yl)-N-methylacetamide,
48) (R)-1-(3-(3-chloro-6-(1-(tetrahydro-2H-pyran-4-yl)-1H-pyrazol-4-ylamino)-1H-pyrazolo[3,4-d]pyrimidin-4-ylamino)piperidin-1-yl)prop-2-en-1-one,
49) (R)-1-(3-(3-chloro-6-(1-cyclopropyl-1H-pyrazol-4-ylamino)-1H-pyrazolo[3,4-d]pyrimidin-4-ylamino)piperidin-1-yl)prop-2-en-1-one,
50) (R)-1-(3-(3-chloro-6-(1-isopropyl-1H-pyrazol-4-ylamino)-1H-pyrazolo[3,4-d]pyrimidin-4-ylamino)piperidin-1-yl)prop-2-en-1-one,
51) (R)-1-(3-(3-chloro-6-(1-propyl-1H-pyrazol-4-ylamino)-1H-pyrazolo[3,4-d]pyrimidin-4-ylamino)piperidin-1-yl)prop-2-en-1-one,
52) (R)-2-(4-(4-(1-acryloylpiperidin-3-ylamino)-3-chloro-1H-pyrazolo[3,4-d]pyrimidin-6-ylamino)-1H-pyrazol-1-yl)acetonitrile,
53) (R)-1-(3-(6-(1-tert-butyl-1H-pyrazol-4-ylamino)-3-chloro-1H-pyrazolo[3,4-d]pyrimidin-4-ylamino)piperidin-1-yl)prop-2-en-1-one,
54) (R)-1-(3-(3-chloro-6-(1-(2-morpholinoethyl)-1H-pyrazol-4-ylamino)-1H-pyrazolo[3,4-d]pyrimidin-4-ylamino)piperidin-1-yl)prop-2-en-1-one,
55) (R)-1-(3-(3-chloro-6-(1-isobutyl-1H-pyrazol-4-ylamino)-1H-pyrazolo[3,4-d]pyrimidin-4-ylamino)piperidin-1-yl)prop-2-en-1-one,
56) (R)-1-(3-(3-chloro-6-(1-(2,2,2-trifluoroethyl)-1H-pyrazol-4-ylamino)-1H-pyrazolo[3,4-d]pyrimidin-4-ylamino)piperidin-1-yl)prop-2-en-1-one,
57) (R)-1-(3-(3-chloro-6-(1-(2-(diethylamino)ethyl)-1H-pyrazol-4-ylamino)-1H-pyrazolo[3,4-d]pyrimidin-4-ylamino)piperidin-1-yl)prop-2-en-1-one,
58) (R)-1-(3-(3-chloro-6-(1-(3-methoxybenzyl)-1H-pyrazol-4-ylamino)-1H-pyrazolo[3,4-d]pyrimidin-4-ylamino)piperidin-1-yl)prop-2-en-1-one,
59) (R)-1-(3-(3-chloro-6-(isoxazol-4-ylamino)-1H-pyrazolo[3,4-d]pyrimidin-4-ylamino)piperidin-1-yl)prop-2-en-1-one,
60) (R)-2-(4-((4-((1-acryloylpiperidin-3-yl)amino)-5-chloro-7H-pyrrolo[2,3-d]pyrimidin-2-yl)amino)-1H-pyrazol-1-yl)-N-methylacetamide,
61) (R)-1-(3-((5-chloro-2-((4-morpholinophenyl)amino)-7H-pyrrolo[2,3-d]pyrimidin-4-yl)amino)piperidin-1-yl)prop-2-en-1-one,
62) (R)-1-(3-((5-chloro-2-((1-cyclopropyl-1H-pyrazol-4-yl)amino)-7H-pyrrolo[2,3-d]pyrimidin-4-yl)amino)piperidin-1-yl)prop-2-en-1-one,
63) (R)-1-(3-((5-chloro-2-((1-isobutyl-1H-pyrazol-4-yl)amino)-7H-pyrrolo[2,3-d]pyrimidin-4-yl)amino)piperidin-1-yl)prop-2-en-1-one,
64) (R)-1-(3-((3-chloro-6-((1-(difluoromethyl)-1H-pyrazol-4-yl)amino)-1H-pyrazolo[3,4-d]pyrimidin-4-yl)amino)piperidin-1-yl)prop-2-en-1-one,
65) (R)-1-(3-((6-((1-isobutyl-1H-pyrazol-4-yl)amino)-1H-pyrazolo[3,4-d]pyrimidin-4-yl)amino)piperidin-1-yl)prop-2-en-1-one,
66) (R)-1-(3-((6-((1-(tert-butyl)-1H-pyrazol-4-yl)amino)-1H-pyrazolo[3,4-d]pyrimidin-4-yl)amino)piperidin-1-yl)prop-2-en-1-one,
67) (R)-1-(3-((6-((1-cyclopropyl-1H-pyrazol-4-yl)amino)-1H-pyrazolo[3,4-d]pyrimidin-4-yl)amino)piperidin-1-yl)prop-2-en-1-one,
68) (R)-1-(3-((5-chloro-2-((4-(morpholine-4-carbonyl)phenyl)amino)-7H-pyrrolo[2,3-d]pyrimidin-4-yl)amino)piperidin-1-yl)prop-2-en-1-one,
69) (R)-1-(3-((5-chloro-2-((1-methyl-1H-pyrazol-4-yl)amino)-7H-pyrrolo[2,3-d]pyrimidin-4-yl)amino)piperidin-1-yl)prop-2-en-1-one,
70) (R)-1-(3-((2-((1-(tert-butyl)-1H-pyrazol-4-yl)amino)-5-chloro-7H-pyrrolo[2,3-d]pyrimidin-4-yl)amino)piperidin-1-yl)prop-2-en-1-one,
71) (R)-1-(3-((6-((1-(tetrahydro-2H-pyran-4-yl)-1H-pyrazol-4-yl)amino)-1H-pyrazolo[3,4-d]pyrimidin-4-yl)amino)piperidin-1-yl)prop-2-en-1-one,
72) (R)-1-(3-((6-((1-(2-morpholinoethyl)-1H-pyrazol-4-yl)amino)-1H-pyrazolo[3,4-d]pyrimidin-4-yl)amino)piperidin-1-yl)prop-2-en-1-one,
73) (R)-1-(3-((6-((1-propyl-1H-pyrazol-4-yl)amino)-1H-pyrazolo[3,4-d]pyrimidin-4-yl)amino)piperidin-1-yl)prop-2-en-1-one,
74) (R)-1-(3-((6-((1-(2-methoxyethyl)-1H-pyrazol-4-yl)amino)-1H-pyrazolo[3,4-d]pyrimidin-4-yl)amino)piperidin-1-yl)prop-2-en-1-one,
75) (R)-1-(3-((2-((3-methylisothiazol-5-yl)amino)-7H-pyrrolo[2,3-d]pyrimidin-4-ylamino)piperidin-1-yl)prop-2-en-1-one,
76) 1-((3S,4R)-3-((2-((1-ethyl-1H-pyrazol-4-yl)amino)-7H-pyrrolo[2,3-d]pyrimidin-4-yl)amino)-4-fluoropiperidin-1-yl)prop-2-en-1-one,
77) 1-((3S,4R)-3-((6-((1-ethyl-1H-pyrazol-4-yl)amino)-1H-pyrazolo[3,4-d]pyrimidin-4-yl)amino)-4-fluoropiperidin-1-yl)prop-2-en-1-one,
78) (R)-1-(3-((2-((1-cyclopropyl-1H-pyrazol-4-yl)amino)-5-methyl-7H-pyrrolo[2,3-d]pyrimidin-4-yl)amino)piperidin-1-yl)prop-2-en-1-one,
79) (R)-1-(3-((2-((1-ethyl-1H-pyrazol-4-yl)amino)-5-methyl-7H-pyrrolo[2,3-d]pyrimidin-4-yl)amino)piperidin-1-yl)prop-2-en-1-one, 80) (R)-1-(3-((2-((4-(3,5-dimethyl-1H-pyrazol-1-yl)phenyl)amino)-5-methyl-7H-pyrrolo[2,3-d]pyrimidin-4-yl)amino)piperidin-1-yl)prop-2-en-1-one,
81) (R)-1-(3-((2-(benzo[d]thiazol-6-ylamino)-5-methyl-7H-pyrrolo[2,3-d]pyrimidin-4-yl)amino)piperidin-1-yl)prop-2-en-1-one,
82) (R)-1-(3-((2-((1-ethyl-1H-pyrazol-4-yl)amino)-5-fluoro-7H-pyrrolo[2,3-d]pyrimidin-4-yl)amino)piperidin-1-yl)prop-2-en-1-one,
83) (R)-1-(3-((5-fluoro-2-((3-methylisothiazol-5-yl)amino)-7H-pyrrolo[2,3-d]pyrimidin-4-yl)amino)piperidin-1-yl)prop-2-en-1-one,
84) 1-((3R,4R)-3-((2-((1-ethyl-1H-pyrazol-4-yl)amino)-5-fluoro-7H-pyrrolo[2,3-d]pyrimidin-4-yl)amino)-4-methylpiperidin-1-yl)prop-2-en-1-one,
85) (R)-1-(3-((2-((1-ethyl-1H-pyrazol-4-yl)amino)-5-fluoro-7H-pyrrolo[2,3-d]pyrimidin-4-yl)thio)piperidin-1-yl)prop-2-en-1-one,
86) 1-((3S,4R)-3-((2-((1-ethyl-1H-pyrazol-4-yl)amino)-5-fluoro-7H-pyrrolo[2,3-d]pyrimidin-4-yl)amino)-4-fluoropiperidin-1-yl)prop-2-en-1-one,
87) (R)-1-(3-((2-((1-ethyl-1H-pyrazol-4-yl)amino)-5-fluoro-7H-pyrrolo[2,3-d]pyrimidin-4-yl)(methyl)amino)piperidin-1-yl)prop-2-en-1-one,
88) (R)-4-((1-acryloylpiperidin-3-yl)amino)-2-((1-ethyl-1H-pyrazol-4-yl)amino)-7H-pyrrolo[2,3-d]pyrimidine-5-carbonitrile,
89) (R)-4-((1-acryloylpiperidin-3-yl)amino)-2-((1-cyclopropyl-1H-pyrazol-4-yl)amino)-7H-pyrrolo[2,3-d]pyrimidine-5-carbonitrile,
90) (R)-1-(3-((3-chloro-6-((1-(2,2-difluoroethyl)-1H-pyrazol-4-yl)amino)-1H-pyrazolo[3,4-d]pyrimidin-4-yl)amino)piperidin-1-yl)prop-2-en-1-one,
91) (R)-1-(3-((3-chloro-6-((1-ethyl-1H-pyrazol-4-yl)amino)-1H-pyrazolo[3,4-d]pyrimidin-4-yl)amino)piperidin-1-yl)prop-2-en-1-one,
92) 1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)prop-2-en-1-one,
93) 1-((3R,4R)-3-((3-chloro-6-((1-(2,2-difluoroethyl)-1H-pyrazol-4-yl)amino)-1H-pyrazolo[3,4-d]pyrimidin-4-yl)amino)-4-methylpiperidin-1-yl)prop-2-en-1-one,
94) 1-((3R,4R)-3-((3-chloro-6-((1-cyclopropyl-1H-pyrazol-4-yl)amino)-1H-pyrazolo[3,4-d]pyrimidin-4-yl)amino)-4-methylpiperidin-1-yl)prop-2-en-1-one,
95) (R)-1-(3-((5-chloro-2-((1-(2-(diethylamino)ethyl)-1H-pyrazol-4-yl)amino)-7H-pyrrolo[2,3-d]pyrimidin-4-yl)amino)piperidin-1-yl)prop-2-en-1-one,
96) (R)-1-(3-((5-chloro-2-(isoxazol-4-ylamino)-7H-pyrrolo[2,3-d]pyrimidin-4-yl)amino)piperidin-1-yl)prop-2-en-1-one,
97) (R)-1-(3-((5-chloro-2-((2-fluoro-4-morpholinophenyl)amino)-7H-pyrrolo[2,3-d]pyrimidin-4-yl)amino)piperidin-1-yl)prop-2-en-1-one,
98) (R)-1-(3-((5-chloro-2-((3-fluoro-4-morpholinophenyl)amino)-7H-pyrrolo[2,3-d]pyrimidin-4-yl)amino)piperidin-1-yl)prop-2-en-1-one,
99) (R)-1-(3-((5-chloro-2-((5-methylisoxazol-4-yl)amino)-7H-pyrrolo[2,3-d]pyrimidin-4-yl)amino)piperidin-1-yl)prop-2-en-1-one,
100) (R)-1-(3-((5-chloro-2-((1-ethyl-1H-pyrazol-4-yl)amino)-7H-pyrrolo[2,3-d]pyrimidin-4-yl)(methyl)amino)piperidin-1-yl)prop-2-en-1-one,
101) (R)-1-(3-((2-((1-ethyl-1H-pyrazol-4-yl)amino)-7H-pyrrolo[2,3-d]pyrimidin-4-yl)(methyl)amino)piperidin-1-yl)prop-2-en-1-one,
(R)-1-(3-((2-(isoxazol-4-ylamino)-7H-pyrrolo[2,3-d]pyrimidin-4-yl)(methyl)amino)piperidin-1-yl)prop-2-en-1-one,
103) (R)-1-(3-((2-((1-(2,2-difluoroethyl)-1H-pyrazol-4-yl)amino)-7H-pyrrolo[2,3-d]pyrimidin-4-yl)(methyl)amino)piperidin-1-yl)prop-2-en-1-one,
104) (R)-1-(3-((2-((1-ethyl-1H-pyrazol-4-yl)amino)-7H-pyrrolo[2,3-d]pyrimidin-4-yl)thio)piperidin-1-yl)prop-2-en-1-one,
105) (R)-1-(3-((6-((1-ethyl-1H-pyrazol-4-yl)amino)-1H-pyrazolo[3,4-d]pyrimidin-4-yl)thio)piperidin-1-yl)prop-2-en-1-one,
106) 1-((3R,4R)-3-((6-((1-ethyl-1H-pyrazol-4-yl)amino)-1H-pyrazolo[3,4-d]pyrimidin-4-yl)amino)-4-methylpiperidin-1-yl)prop-2-en-1-one,
107) 1-((3R,4R)-3-((2-((1-ethyl-1H-pyrazol-4-yl)amino)-7H-pyrrolo[2,3-d]pyrimidin-4-yl)amino)-4-methylpiperidin-1-yl)prop-2-en-1-one,
108) (R)-1-(3-((3-chloro-6-((1-(2,2-difluoroethyl)-1H-pyrazol-4-yl)amino)-1H-pyrazolo[3,4-d]pyrimidin-4-yl)thio)piperidin-1-yl)prop-2-en-1-one,
109) (R)-1-(3-((5-chloro-2-((1-ethyl-1H-pyrazol-4-yl)amino)-7H-pyrrolo[2,3-d]pyrimidin-4-yl)thio)piperidin-1-yl)prop-2-en-1-one,
110) (R)-1-(3-((3-chloro-6-((1-cyclopropyl-1H-pyrazol-4-yl)amino)-1H-pyrazolo[3,4-d]pyrimidin-4-yl)thio)piperidin-1-yl)prop-2-en-1-one,
111) (R)-1-(3-((3-chloro-6-((1-ethyl-1H-pyrazol-4-yl)amino)-1H-pyrazolo[3,4-d]pyrimidin-4-yl)thio)piperidin-1-yl)prop-2-en-1-one,
112) (R)-1-(3-((6-((1-(tert-butyl)-1H-pyrazol-4-yl)amino)-3-chloro-1H-pyrazolo[3,4-d]pyrimidin-4-yl)thio)piperidin-1-yl)prop-2-en-1-one,
113) (R)-1-(3-((3-chloro-6-((1-isobutyl-1H-pyrazol-4-yl)amino)-1H-pyrazolo[3,4-d]pyrimidin-4-yl)thio)piperidin-1-yl)prop-2-en-1-one,
114) (R)-1-(3-((3-chloro-6-((1-(2,2,2-trifluoroethyl)-1H-pyrazol-4-yl)amino)-1H-pyrazolo[3,4-d]pyrimidin-4-yl)thio)piperidin-1-yl)prop-2-en-1-one,
115) (R)-1-(3-((3-chloro-6-((1-propyl-1H-pyrazol-4-yl)amino)-1H-pyrazolo[3,4-d]pyrimidin-4-yl)thio)piperidin-1-yl)prop-2-en-1-one,
116) (R)-1-(3-((3-chloro-6-(isoxazol-4-ylamino)-1H-pyrazolo[3,4-d]pyrimidin-4-yl)thio)piperidin-1-yl)prop-2-en-1-one,
(117) (R)-1-(3-(3-chloro-6-(5-methylisoxazol-4-ylamino)-1H-pyrazolo[3,4-d]pyrimidin-4-ylamino)piperidin-1-yl)prop-2-en-1-one,
118) (R)-1-(3-((3-chloro-6-((1-ethyl-1H-pyrazol-4-yl)amino)-1H-pyrazolo[3,4-d]pyrimidin-4-yl)(methyl)amino)piperidin-1-yl)prop-2-en-1-one,
119) (R)-1-(3-((3-chloro-6-(isoxazol-4-ylamino)-1H-pyrazolo[3,4-d]pyrimidin-4-yl)(methyl)amino)piperidin-1-yl)prop-2-en-1-one,
120) 1-((3R,4R)-3-((3-chloro-6-((1-(2,2,2-trifluoroethyl)-1H-pyrazol-4-yl)amino)-1H-pyrazolo[3,4-d]pyrimidin-4-yl)amino)-4-methylpiperidin-1-yl)prop-2-en-1-one,
121) 1-((3R,4R)-3-((3-chloro-6-((1-propyl-1H-pyrazol-4-yl)amino)-1H-pyrazolo[3,4-d]pyrimidin-4-yl)amino)-4-methylpiperidin-1-yl)prop-2-en-1-one,
122) 1-((3R,4R)-3-((3-chloro-6-((1-(2-(diethylamino)ethyl)-1H-pyrazol-4-yl)amino)-1H-pyrazolo[3,4-d]pyrimidin-4-yl)amino)-4-methylpiperidin-1-yl)prop-2-en-1-one,
123) 1-((3R,4R)-3-((3-chloro-6-((1-(2-morpholinoethyl)-1H-pyrazol-4-yl)amino)-1H-pyrazolo[3,4-d]pyrimidin-4-yl)amino)-4-methylpiperidin-1-yl)prop-2-en-1-one, 124) 1-((3R,4R)-3-((3-chloro-6-((1-isobutyl-1H-pyrazol-4-yl)amino)-1H-pyrazolo[3,4-d]pyrimidin-4-yl)amino)-4-methylpiperidin-1-yl)prop-2-en-1-one, 125) 1-((3R,4R)-3-((3-chloro-6-((1-(3-methoxybenzyl)-1H-pyrazol-4-yl)amino)-1H-pyrazolo[3,4-d]pyrimidin-4-yl)amino)-4-methylpiperidin-1-yl)prop-2-en-1-one, 126) 2-(4-(((3R,4R)-1-acryloyl-4-methylpiperidin-3-yl)amino)-3-chloro-1H-pyrazolo[3,4-d]pyrimidin-6-yl)amino)-1H-pyrazol-1-yl)acetonitrile, 127) 1-((3R,4R)-3-((3-chloro-6-((1-(difluoromethyl)-1H-pyrazol-4-yl)amino)-1H-pyrazolo[3,4-d]pyrimidin-4-yl)amino)-4-methylpiperidin-1-yl)prop-2-en-1-one, 128) 1-((3R,4R)-3-((3-chloro-6-((1-methyl-1H-pyrazol-4-yl)amino)-1H-pyrazolo[3,4-d]pyrimidin-4-yl)amino)-4-methylpiperidin-1-yl)prop-2-en-1-one, 129) (R)-1-(3-((6-((1-cyclopropyl-1H-pyrazol-4-yl)amino)-3-(methylthio)-1H-pyrazolo[3,4-d]pyrimidin-4-yl)amino)piperidin-1-yl)prop-2-en-1-one, 130) (R)-1-(3-((6-(isoxazol-4-ylamino)-3-(methylthio)-1H-pyrazolo[3,4-d]pyrimidin-4-yl)amino)piperidin-1-yl)prop-2-en-1-one, 131) (R)-1-(3-((6-((1-ethyl-1H-pyrazol-4-yl)amino)-3-(methylthio)-1H-pyrazolo[3,4-d]pyrimidin-4-yl)(methyl)amino)piperidin-1-yl)prop-2-en-1-one, 132) 1-((3R,4R)-3-((6-((1-ethyl-1H-pyrazol-4-yl)amino)-3-(methylthio)-1H-pyrazolo[3,4-d]pyrimidin-4-yl)amino)-4-methylpiperidin-1-yl)prop-2-en-1-one, 133) 1-((3R,4R)-3-((6-((1-(2,2-difluoroethyl)-1H-pyrazol-4-yl)amino)-3-(methylthio)-1H-pyrazolo[3,4-d]pyrimidin-4-yl)amino)-4-methylpiperidin-1-yl)prop-2-en-1-one, 134) 2-(4-(((3R,4R)-1-acryloyl-4-methylpiperidin-3-yl)amino)-3-(methylthio)-1H-pyrazolo[3,4-d]pyrimidin-6-yl)amino)-1H-pyrazol-1-yl)acetonitrile, 135) 1-((3R,4R)-3-((6-((1-cyclopropyl-1H-pyrazol-4-yl)amino)-3-(methylthio)-1H-pyrazolo[3,4-d]pyrimidin-4-yl)amino)-4-methylpiperidin-1-yl)prop-2-en-1-one, 136) (R)-1-(3-((5-chloro-2-((3-methylisothiazol-5-yl)amino)-7H-pyrrolo[2,3-d]pyrimidin-4-yl)amino)piperidin-1-yl)prop-2-en-1-one, 137) (R)-1-(3-((5-chloro-2-(pyridin-3-ylamino)-7H-pyrrolo[2,3-d]pyrimidin-4-yl)amino)piperidin-1-yl)prop-2-en-1-one, 138) 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropanenitrile, 139) (R)-3-(3-((3-chloro-6-((1-cyclopropyl-1H-pyrazol-4-yl)amino)-1H-pyrazolo[3,4-d]pyrimidin-4-yl)amino)piperidin-1-yl)-3-oxopropanitrile, 140) (R,E)-1-(3-((5-chloro-2-((4-(4-methylpiperazin-1-yl)phenyl)amino)-7H-pyrrolo[2,3-d]pyrimidin-4-yl)amino)piperidin-1-yl)but-2-en-1-one, 141) 1-((R)-3-((5-chloro-2-((4-(4-methylpiperazin-1-yl)phenyl)amino)-7H-pyrrolo[2,3-d]pyrimidin-4-yl)amino)piperidin-1-yl)-3-cyclopropylprop-2-yn-1-ol, 142) 1-((R)-3-((5-chloro-2-((4-(4-methylpiperazin-1-yl)phenyl)amino)-7H-pyrrolo[2,3-d]pyrimidin-4-yl)amino)piperidin-1-yl)pent-2-yn-1-ol, 143) 1-((R)-3-((5-chloro-2-((4-(4-methylpiperazin-1-yl)phenyl)amino)-7H-pyrrolo[2,3-d]pyrimidin-4-yl)amino)piperidin-1-yl)but-2-yn-1-ol, 144) (R)-1-(3-((6-((1-(2,2,2-trifluoroethyl)-1H-pyrazol-4-yl)amino)-1H-pyrazolo[3,4-d]pyrimidin-4-yl)amino)piperidin-1-yl)prop-2-en-1-one, 145) (R)-1-(3-((6-((1-(2-(diethylamino)ethyl)-1H-pyrazol-4-yl)amino)-1H-pyrazolo[3,4-d]pyrimidin-4-yl)amino)piperidin-1-yl)prop-2-en-1-one, 146) (R)-1-(3-((6-(isoxazol-4-ylamino)-1H-pyrazolo[3,4-d]pyrimidin-4-yl)amino)piperidin-1-yl)prop-2-en-1-one, 147) (R)-1-(3-((3-chloro-6-((1-ethyl-1H-pyrazol-4-yl)amino)-1H-pyrazolo[3,4-d]pyrimidin-4-yl)oxy)piperidin-1-yl)prop-2-en-1-one, 148) (R)-4-((1-acryloylpiperidin-3-yl)oxy)-2-((1-cyclopropyl-1H-pyrazol-4-yl)amino)-7H-pyrrolo[2,3-d]pyrimidine-5-carbonitrile, 149) (R)-4-((1-acryloylpiperidin-3-yl)oxy)-2-((1-(2,2-difluoroethyl)-1H-pyrazol-4-yl)amino)-7H-pyrrolo[2,3-d]pyrimidine-5-carbonitrile, 150) (R)-4-((1-acryloylpiperidin-3-yl)oxy)-2-((1-ethyl-1H-pyrazol-4-yl)amino)-7H-pyrrolo[2,3-d]pyrimidine-5-carbonitrile, 151) (R)-1-(3-((2-((1-ethyl-1H-pyrazol-4-yl)amino)-7H-pyrrolo[2,3-d]pyrimidin-4-yl)oxy)piperidin-1-yl)prop-2-en-1-one, 152) (R)-1-(3-((2-((4-morpholinophenyl)amino)-7H-pyrrolo[2,3-d]pyrimidin-4-yl)oxy)piperidin-1-yl)prop-2-en-1-one, 153) (R)-1-(3-((3-chloro-6-((1-cyclopropyl-1H-pyrazol-4-yl)amino)-1H-pyrazolo[3,4-d]pyrimidin-4-yl)oxy)piperidin-1-yl)prop-2-en-1-one, 154) (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile, 155) (R,E)-2-(3-((3-chloro-6-((1-ethyl-1H-pyrazol-4-yl)amino)-1H-pyrazolo[3,4-d]pyrimidin-4-yl)oxy)piperidine-1-carbonyl)-3-cyclopropylacrylonitrile, 156) (R,E)-4-((1-(2-cyano-4-methylpent-2-enoyl)piperidin-3-yl)oxy)-2-((1-ethyl-1H-pyrazol-4-yl)amino)-7H-pyrrolo[2,3-d]pyrimidine-5-carbonitrile, 157) (R,E)-4-((1-(2-cyano-3-cyclopropylacryloyl)piperidin-3-yl)oxy)-2-((1-ethyl-1H-pyrazol-4-yl)amino)-7H-pyrrolo[2,3-d]pyrimidine-5-carbonitrile, 158) (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-4-methylpent-2-enenitrile, 159) 1-((3R,4R)-3-((3-chloro-6-((1-ethyl-1H-pyrazol-4-yl)amino)-1H-pyrazolo[3,4-d]pyrimidin-4-yl)(methyl)amino)-4-methylpiperidin-1-yl)prop-2-en-1-one, 160) (E)-2-((3S,4R)-3-((3-chloro-6-((1-ethyl-1H-pyrazol-4-yl)amino)-1H-pyrazolo[3,4-d]pyrimidin-4-yl)amino)-4-fluoropipendine-1-carbonyl)-4-methylpent-2-enenitrile, 161) (E)-2-((3S,4R)-3-((3-chloro-6-((1-ethyl-1H-pyrazol-4-yl)amino)-1H-pyrazolo[3,4-d]pyrimidin-4-yl)amino)-4-fluoropipendine-1-carbonyl)-3-cyclopropylacrylonitrile, 162) (R,E)-2-(3-((3-chloro-6-((1-cyclopropyl-1H-pyrazol-4-yl)amino)-1H-pyrazolo[3,4-d]pyrimidin-4-yl)amino)pipendine-1-carbonyl)-4-methylpent-2-enenitrile, 163) (R,E)-2-(3-((3-chloro-6-((1-cyclopropyl-1H-pyrazol-4-yl)amino)-1H-pyrazolo[3,4-d]pyrimidin-4-yl)amino)pipendine-1-carbonyl)-4,4-dimethylpent-2-enenitrile, 164) (R,E)-2-(3-((3-chloro-6-((1-cyclopropyl-1H-pyrazol-4-yl)amino)-1H-pyrazolo[3,4-d]pyrimidin-4-yl)amino)pipendine-1-carbonyl)-3-cyclopropylacrylonitrile, 165) (R,E)-2-(3-((3-chloro-6-((1-cyclopropyl-1H-pyrazol-4-yl)amino)-1H-pyrazolo[3,4-d]pyrimidin-4-yl)amino)pipendine-1-carbonyl)-3-cyclopentylacrylonitrile, 166) (R,E)-2-(3-((3-chloro-6-((1-ethyl-1H-pyrazol-4-yl)amino)-1H-pyrazolo[3,4-d]pyrimidin-4-yl)amino)pipendine-1-carbonyl)-3-cyclopropylacrylonitrile, 167) (R,E)-2-(3-((3-chloro-6-((1-ethyl-1H-pyrazol-4-yl)amino)-1H-pyrazolo[3,4-d]pyrimidin-4-yl)(methyl)amino)pipendine-1-carbonyl)-3-cyclopropylacrylonitrile, 168) (R,E)-2-(3-((3-chloro-6-((1-ethyl-1H-pyrazol-4-yl)amino)-1H-pyrazolo[3,4-d]pyrimidin-4-yl)(methyl)amino)pipendine-1-carbonyl)-4-methylpent-2-enenitrile, 169) (E)-2-((3R,4R)-3-((3-chloro-6-((1-ethyl-1H-pyrazol-4-yl)amino)-1H-pyrazolo[3,4-d]pyrimidin-4-yl)amino)-4-methylpipendine-1-carbonyl)-3-cyclopropylacrylonitrile, 170) (E)-2-((3R,4R)-3-((3-chloro-6-((1-ethyl-1H-pyrazol-4-yl)amino)-1H-pyrazolo[3,4-d]pyrimidin-4-yl)amino)-4-methylpipendine-1-carbonyl)-4-methylpent-2-enenitrile, 171) (R,E)-3-cyclopropyl-2-(3-((2-((1-ethyl-1H-pyrazol-4-yl)amino)-7H-pyrrolo[2,3-d]pyrimidin-4-yl)amino)pipendine-1-carbonyl)acrylonitrile, 172) (R,E)-2-(3-((2-((1-ethyl-1H-pyrazol-4-yl)amino)-7H-pyrrolo[2,3-d]pyrimidin-4-yl)amino)piperidine-1-carbonyl)-4-methylpent-2-enenitrile, 173) (R,E)-3-cyclopropyl-2-(3-((2-((1-ethyl-1H-pyrazol-4-yl)amino)-7H-pyrrolo[2,3-d]pyrimidin-4-yl)thio)piperidine-1-carbonyl)acrylonitrile, 174) (R,E)-2-(3-((2-((1-ethyl-1H-pyrazol-4-yl)amino)-7H-pyrrolo[2,3-d]pyrimidin-4-yl)thio)piperidine-1-carbonyl)-4-methylpent-2-enenitrile, 175) (R,E)-3-cyclopropyl-2-(3-((6-((1-ethyl-1H-pyrazol-4-yl)amino)-1H-pyrazolo[3,4-d]pyrimidin-4-yl)amino)pipendine-1-carbonyl)acrylonitrile, 176) (R,E)-3-cyclopropyl-2-(3-((6-((1-ethyl-1H-pyrazol-4-yl)amino)-1H-pyrazolo[3,4-d]pyrimidin-4-yl)thio)pipendine-1-carbonyl)acrylonitrile, 177) (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-3-cyclopropylacrylonitrile, 178) (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-4-methylpent-2-enenitrile, 179) (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-3-cyclopropylacrylonitrile, 180) (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-4-methylpent-2-enenitrile, 181) (R,E)-2-(3-((3-chloro-6-((1-ethyl-1H-pyrazol-4-yl)amino)-1H-pyrazolo[3,4-d]pyrimidin-4-yl)thio)pipendine-1-carbonyl)-3-cyclopropylacrylonitrile, 182) (R,E)-3-cyclopropyl-2-(3-((2-((1-ethyl-1H-pyrazol-4-yl)amino)-5-fluoro-7H-pyrrolo[2,3-d]pyrimidin-4-yl)amino)pipendine-1-carbonyl)acrylonitrile, 183) 2-chloro-1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)ethan-1-one, 184) (R)-1-(3-((6-((1-(2,2-difluoroethyl)-1H-pyrazol-4-yl)amino)-3-methyl-1H-pyrazolo[3,4-d]pyrimidin-4-yl)amino)piperidin-1-yl)prop-2-en-1-one, 185) (R)-1-(3-((6-((1-ethyl-1H-pyrazol-4-yl)amino)-3-methyl-1H-pyrazolo[3,4-d]pyrimidin-4-yl)amino)piperidin-1-yl)prop-2-en-1-one, 186) (R)-1-(3-((6-((1-isobutyl-1H-pyrazol-4-yl)amino)-3-methyl-1H-pyrazolo[3,4-d]pyrimidin-4-yl)amino)piperidin-1-yl)prop-2-en-1-one, 187) (R)-1-(3-((6-((1-(tert-butyl)-1H-pyrazol-4-yl)amino)-3-methyl-1H-pyrazolo[3,4-d]pyrimidin-4-yl)amino)piperidin-1-yl)prop-2-en-1-one, 188) (R)-1-(3-((6-((1-cyclopropyl-1H-pyrazol-4-yl)amino)-3-methyl-1H-pyrazolo[3,4-d]pyrimidin-4-yl)amino)piperidin-1-yl)prop-2-en-1-one, 189) (R)-1-(3-((6-((1-ethyl-1H-pyrazol-4-yl)amino)-3-(methylthio)-1H-pyrazolo[3,4-d]pyrimidin-4-yl)amino)piperidin-1-yl)prop-2-en-1-one, 190) (R)-1-(3-((6-((1-(2,2-difluoroethyl)-1H-pyrazol-4-yl)amino)-3-(methylthio)-1H-pyrazolo[3,4-d]pyrimidin-4-yl)amino)piperidin-1-yl)prop-2-en-1-one, 191) (R)-1-(3-((6-((1-methyl-1H-pyrazol-4-yl)amino)-3-(methylthio)-1H-pyrazolo[3,4-d]pyrimidin-4-yl)amino)piperidin-1-yl)prop-2-en-1-one, 192) (R)-1-(3-((6-((1-(tert-butyl)-1H-pyrazol-4-yl)amino)-3-(methylthio)-1H-pyrazolo[3,4-d]pyrimidin-4-yl)amino)piperidin-1-yl)prop-2-en-1-one, and 193) 1-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)prop-2-en-1-one.

In addition, the compounds of the present invention may exist in the form of salts, especially pharmaceutically acceptable salts. As salts, salts commonly used in the art, such as acid addition salts formed by pharmaceutically acceptable free acids can be used without limitation. The term "pharmaceutically acceptable salt" as used herein refers to any organic or inorganic addition salt of the compound represented by Chemical Formula 1, whose concentration is relatively non-toxic and harmless to a patient and activates effectively and whose side effects do not degrade the beneficial efficacy of the above compounds.

Pharmaceutically acceptable salts can be obtained by conventional methods using inorganic or organic acids. For example, the pharmaceutically acceptable salt can be prepared by dissolving the compound represented by Chemical Formula 1 in a water-miscible organic solvent. e.g., acetone, methanol, ethanol or acetonitrile, followed by adding an organic acid or an inorganic acid, and filtering and drying the precipitated crystals. Alternatively, it may be prepared by removing a solvent or an excessive amount of acid from the acid-added reaction mixture under reduced pressure, followed by drying the residue, or by adding a different organic solvent and then filtering the precipitated salt. At this time, the preferred salts may include salts derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid, and the like.

A pharmaceutically unacceptable salt or solvate of the compound of Chemical Formula 1 may be used as an intermediate when preparing the compound of Chemical Formula 1, or the pharmaceutically acceptable salt or the solvate thereof.

The compound of Chemical Formula 1 according to the present invention includes not only pharmaceutically acceptable salts thereof, but all solvates and hydrates that can be prepared therefrom, and includes all possible stereoisomers as well. The solvate, the hydrate and the stereoisomer of the compound of Chemical Formula 1 may be prepared and used from the compound of Chemical Formula 1 using common methods.

In addition, the compound of Chemical Formula 1 according to the present invention may be prepared either in a crystalline form or in a non-crystalline form, and when the compound of Chemical Formula 1 is prepared in a crystalline form, it may be optionally hydrated or solvated. In the present invention, the compound of Chemical Formula 1 may not only include a stoichiometric hydrate, but include a compound containing various amounts of water. The solvate of the compound of Chemical Formula 1 according to the present invention includes both stoichiometric solvates and non-stoichiometric solvates.

Furthermore, as an example, the present invention can produce the compound represented by Chemical Formula 1 through Reaction Scheme 1 below.

by Chemical Formula 1-4 with $R_3$-acyl chloride. The reaction is preferably carried out at −20° C. to 0° C. under conditions of triethylamine or sodium hydrogencarbonate. Further, the solvent is preferably dichloromethane or a mixed solution of tetrahydrofuran and water. Alternatively,

[Reaction Scheme 1]

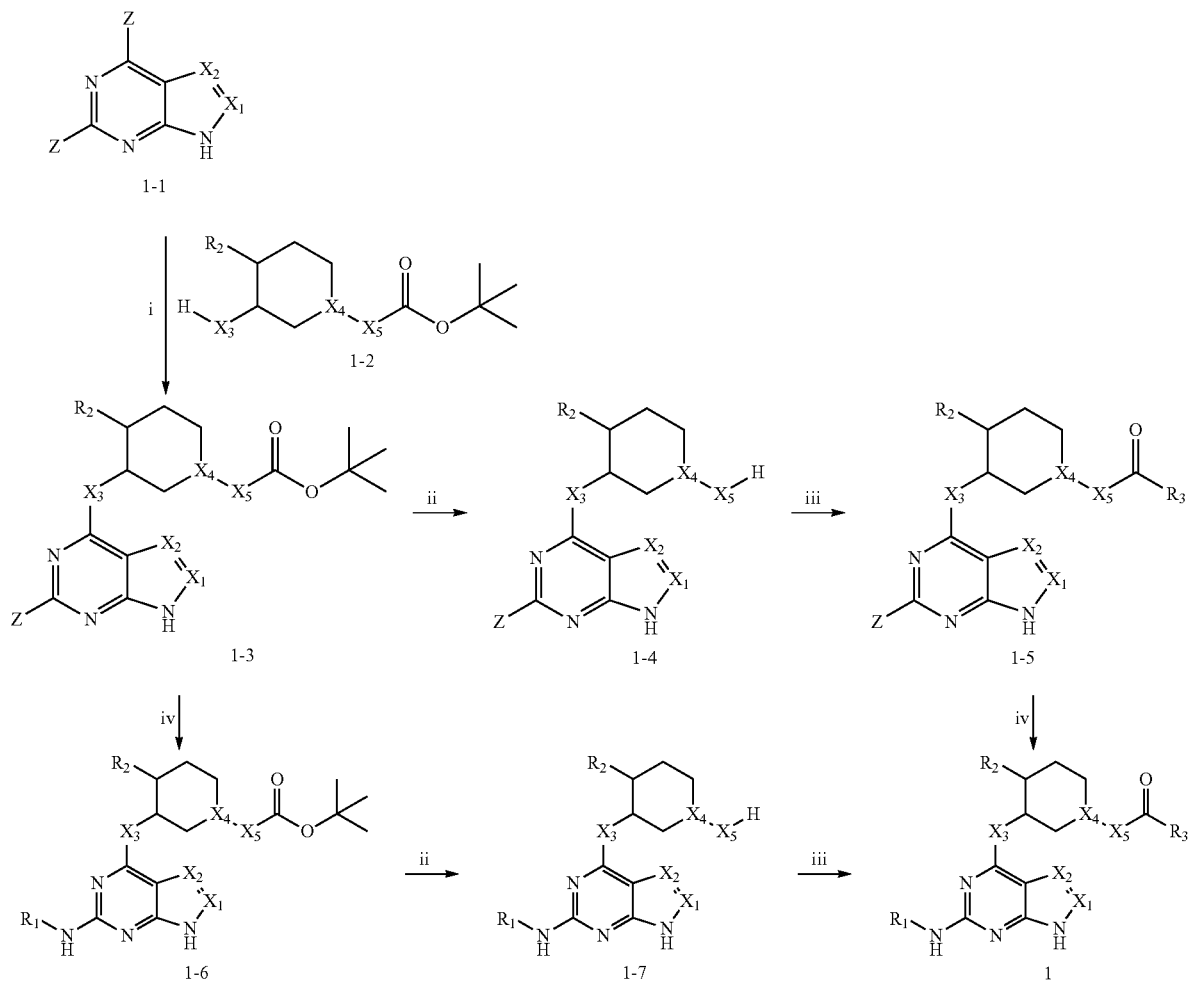

(in Reaction Scheme 1, $X_1$ to $X_3$, and $R_1$ to $R_3$ are as previously defined, and when $X_4$ is N, $X_5$ is a bond, and when $X_4$ is CH, $X_5$ is NH, and Z is halogen. Preferably, Z is chloro)

Step i is a step of preparing a compound represented by Chemical Formula 1-3 by reacting a compound represented by Chemical Formula 1-1 with a compound represented by Chemical Formula 1-2. The reaction is preferably carried out in the presence of N,N-diisopropylethylamine at room temperature to high temperature, and the solvent is preferably ethanol.

Step ii is a step of preparing a compound represented by Chemical Formula 1-4 by eliminating a protecting group from a compound represented by Chemical Formula 1-3. The reaction is preferably carried out under a hydrochloric acid condition (preferably, 6 N hydrochloric acid condition), and the solvent is preferably methanol.

Step iii is a step of preparing a compound represented by Chemical Formula 1-5 by reacting a compound represented step iii may be carried out by reacting an $R_3$-carboxylic acid instead of an $R_3$-acyl chloride. In this case, the reaction is preferably carried out under the conditions of N,N-diisopropylethylamine, 1-[bis(dimethylamino)methylene]-1H-1,2,3-triazolo[4,5-b]pyridinium 3-oxide hexafluorophosphate at room temperature, and the solvent is preferably tetrahydrofuran or N,N-dimethylformamide.

Step iv is a step of preparing a compound represented by Chemical Formula 1 by reacting a compound represented by Chemical Formula 1-5 with $R_1$—$NH_2$. The reaction is preferably carried out at a high temperature under conditions of trifluoroacetic acid, and the solvent is preferably 2-butanol.

In addition, as shown in the above Reaction Scheme 1, starting from the compound represented by Chemical Formula 1-3, the compound represented by Chemical Formula 1-6, the compound represented by Chemical Formula 1-7 and the compound represented by Chemical Formula 1 can be prepared in this order, and each of Steps iv, ii and iii is the same as described above, except for the reactants.

Furthermore, as an example, the present invention can produce the compound represented by Chemical Formula 1 through Reaction Scheme 2 below.

[Reaction Scheme 2]

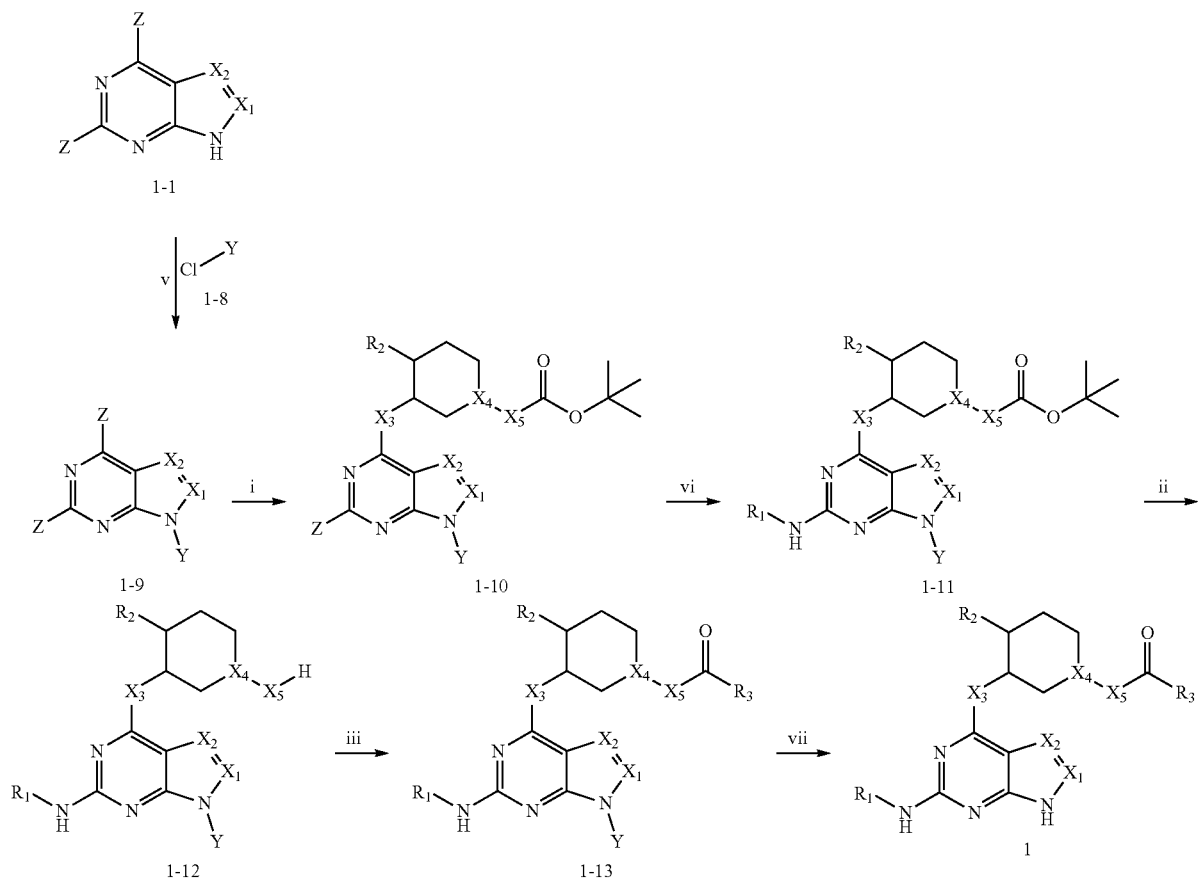

(in Reaction Scheme 2, $X_1$ to $X_3$, and $R_1$ to $R_3$ are as previously defined, and when $X_4$ is N, $X_5$ is a bond, and when $X_4$ is CH, $X_5$ is NH. Y is 4-methylbenzyl sulfonyl or 2-(trimethylsilyl)ethoxymethyl, Z is halogen, and preferably Z is chloro)

Step v is a step of preparing a compound represented by Chemical Formula 1-9 by reacting a compound represented by Chemical Formula 1-1 with a compound represented by Chemical Formula 1-8. The reaction is preferably carried out at a temperature of 0° C. or less under a basic condition, and the solvent is preferably acetone or N,N-dimethylformamide.

Step i is a step for preparing a compound represented by Chemical Formula 1-10 from the compound represented by Chemical Formula 1-9, which is the same as Step i of Reaction Scheme 1 except for the reactants.

Step vi is a step of preparing a compound represented by Chemical Formula 1-11 by reacting a compound represented by Chemical Formula 1-10 with $R_1$—$NH_2$. The reaction is preferably carried out at a temperature of 100° C. to 120° C. under conditions of a ligand, a palladium catalyst and a base, and the solvent is preferably 1,4-dioxane.

Step ii is a step for preparing a compound represented by Chemical Formula 1-12 from the compound represented by Chemical Formula 1-11, which is the same as Step ii of Reaction Scheme 1 except for the reactants.

Step iii is a step for preparing a compound represented by Chemical Formula 1-13 from the compound represented by Chemical Formula 1-12, which is the same as Step iii of Reaction Scheme 1 except for the reactants.

Step vii is a step for preparing a compound represented by Chemical Formula 1 eliminating Y from a compound represented by Chemical Formula 1-13. When Y is 4-methylbenzylsulfonyl, the reaction is preferably carried out at a temperature of 40° C. to 60° C. under a basic condition, and the solvent is preferably methanol. Further, when Y is 2-(trimethylsilyl)ethoxymethyl, the reaction is preferably carried out at room temperature under trifluoroacetic acid conditions. The solvent is preferably dichloromethane.

In addition, the present invention provides a process for preparing a compound represented by the following chemical formula 1-15 as shown in the following Reaction Scheme 3 when $X_2$ is $CR_5$ and $R_5$ is halogen. The compound represented by Chemical Formula 1-15 can be used as the compound represented by Chemical Formula 1-1 in Reaction Schemes 1 and 2.

[Reaction Scheme 3]

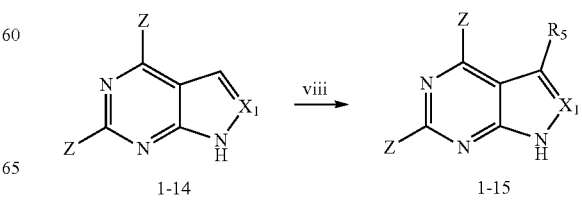

(in Reaction Scheme 3, $X_1$ and $R_5$ are as previously defined, and Z is halogen. Preferably, Z is chloro)

Step viii is a step for preparing a compound represented by Chemical Formula 1-15 from the compound represented by Chemical Formula 1-14. The reaction is preferably carried out at room temperature to 60° C. in the presence of N-halosuccinimide, and the solvent is preferably N,N-dimethylformamide.

Further, the present invention provides a pharmaceutical composition for preventing or treating diseases which are associated with kinase inhibitory actions, comprising the compound represented by Chemical Formula 1, or a pharmaceutically acceptable salt, hydrate, solvate or isomer thereof as an active ingredient.

In this case, the diseases which are associated with kinase inhibitory actions includes inflammatory diseases, autoimmune diseases, proliferative diseases or hyperproliferative diseases, and immunity mediated diseases.

As used herein, the term "prevention" refers to any act to delay or inhibit occurrence, spread or recurrence of the above-mentioned diseases by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

Pharmaceutical dosage forms of the compounds of the present invention may include using the compounds in the form of pharmaceutically acceptable salts or solvates thereof, and using the compounds alone or as a combination and/or a suitable mixture together with other pharmaceutically active compounds.

The compounds of the present invention can be formulated into injection solutions by dissolving, suspending or emulsifying the compounds in a water-soluble solvent such as normal saline, 5% dextrose or a non-aqueous solvent such as synthetic fatty acid glyceride, higher fatty acid ester or propylene glycol. Formulations of the present invention may include conventional additives such as solubilizers, isotonic agents, suspending agents, emulsifying agents, stabilizers and preservatives.

A preferred dose of the compound of the present invention may be varied according to the condition and weight of a patient, the severity of a disease, the type of a drug, and the route and duration of administration, but it may be suitably selected by those skilled in the art. In order to achieve the desirable effects, however, the compound of the present invention may be administrated daily at a dose of 0.0001 to 100 mg/kg (body weight), and preferably 0.001 to 100 mg/kg (body weight). The administration may be performed once a day or in divided doses each day through an oral or parenteral route. Depending on the method of administration, the composition may contain the compound of the present invention in an amount of 0.001 to 99% by weight, preferably 0.01 to 60% by weight.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention or a pharmaceutically acceptable salt, hydrate, solvate or isomer thereof can be usefully used for the prevention or treatment of diseases which are associated with kinase inhibitory actions.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

Preparation Example 1: Preparation of 1(R)-1-(3-(2-(4-(4-methylpiperazin-1-yl)phenylamino)-7H-pyrrolo[2,3-d]pyrimidin-4-ylamino)piperidin-1-yl)prop-2-en-1-one

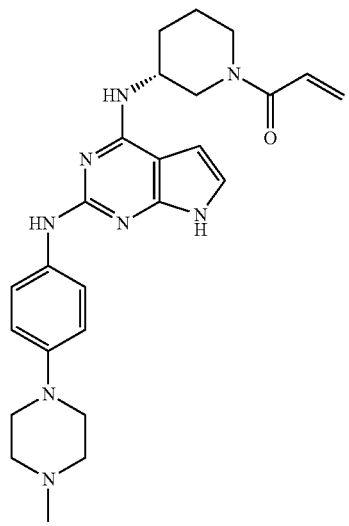 [SMILES: C=CC(=O)N1CCC[C@@H](Nc2nc(Nc3ccc(N4CCN(C)CC4)cc3)nc3[nH]ccc23)C1]

Step 1: Preparation of tert-butyl(R)-3-((2-chloro-7H-pyrrolo[2,3-d]pyrimidin-4-yl)amino)piperidine-1-carboxylate After 2,4-dichloro-7H-pyrrolo[2,3-d]pyrimidine (500.0 mg, 2.7 mmol) was dissolved in ethanol (10 mL), N,N-diisopropylethylamine (695.0 μL, 4.0 mmol) and tert-butyl-(R)-3-aminopiperidine-1-carboxylate (639.3 mg, 4.0 mmol) was added thereto. After stirring the reaction mixture at 110° C. for 12 hours, the organic layer was isolated, treated with magnesium sulfate, filtered and then concentrated under reduced pressure. The residue was isolated by column chromatography to obtain a title compound (900.0 mg, yield: 98.0%).

¹H NMR (500 MHz, CDCl₃) δ 7.06 (s, 1H), 6.38 (s, 1H), 4.24-4.20 (m, 1H), 3.84-3.82 (m, 1H), 3.80-3.30 (m, 3H), 2.01-1.90 (m, 1H), 1.80-1.75 (m, 1H), 1.65-1.55 (m, 2H), 1.43 (s, 9H)

Step 2: Preparation of (R)-2-chloro-N-(piperidin-3-yl)-7H-pyrrolo[2,3-d]pyrimidin-4-amine hydrochloride To tert-butyl(R)-3-((2-chloro-7H-pyrrolo[2,3-d]pyrimidin-4-yl)amino)piperidin-1-carboxylate (474.0 mg, 1.4 mmol), 6 N hydrochloric acid solution (5.0 mL, excessive amount) dissolved in methanol was added. After stirring at room temperature for 30 minutes, the reaction mixture was concentrated and the subsequent reaction was carried out without isolation.

¹H NMR (500 MHz, CD₃OD) δ 7.11 (d, 1H), 6.63 (d, 1H), 4.52-4.49 (m, 1H), 3.66-3.63 (m, 1H), 3.37-3.34 (m, 1H), 3.02-2.90 (m, 2H), 2.19-2.16 (m, 1H), 2.12-2.09 (m, 1H), 1.90-1.77 (m, 2H)

Step 3: Preparation of (R)-1-(3-((2-chloro-7H-pyrrolo[2,3-d]pyrimidin-4-yl)amino)piperidin-1-yl)prop-2-en-1-one After (R)-2-chloro-N-(piperidin-3-yl)-7H-pyrrolo[2,3-d]pyrimidin-4-amine hydrochloride (500.0 mg, 1.7 mmol) was dissolved in dichloromethane (10.0 mL), triethylamine (725.3 µL, 5.2 mmol) was added at 0° C. and then the mixture was stirred for 30 minutes. Acryloyl chloride (155.0 µL, 1.9 mmol) was added to the reaction mixture, following by stirring at 0° C. for 1 hour. The organic layer was isolated, treated with magnesium sulfate, filtered, and then concentrated under reduced pressure. The residue was isolated by column chromatography to obtain a title compound (250.0 mg, yield: 66.0%).

¹H NMR (500 MHz, CD₃OD) δ 7.02 (s, 1H), 6.92-6.86 (m, 1H), 6.57 (s, 1H), 5.73-5.68 (m, 1H), 4.60-4.28 (m, 2H), 4.06-4.02 (m, 1H), 3.25-2.96 (m, 2H), 2.14-2.12 (m, 1H), 1.92-1.88 (m, 1H), 1.81-1.78 (m, 1H), 1.67-1.63 (m, 1H)

Step 4: Preparation of (R)-1-(3-(2-(4-(4-methylpiperazin-1-yl)phenylamino)-7H-pyrrolo[2,3-d]pyrimidin-4-ylamino)piperidin-1-yl)prop-2-en-1-one (R)-1-(3-((2-chloro-7H-pyrrolo[2,3-d]pyrimidin-4-yl)amino)piperidin-1-yl)prop-2-one (27.0 mg, 0.09 mmol) and 4-(4-methylpiperazin-1-yl)aniline (11.5 mg, 0.06 mmol) were dissolved in 2-butanol (2.0 mL). Trifluoroacetic acid (6.9 µL, 0.07 mmol) was added thereto and the reaction mixture was reacted at 110° C. for 12 hours, and then the solvent was concentrated. The reaction mixture was neutralized by adding 7 N ammonia solution dissolved in methanol, and the residue was isolated by column chromatography to obtain a title compound (2.3 mg, yield: 6.4%)

¹H NMR (500 MHz, CD₃OD) δ 7.55-7.52 (m, 2H), 6.92-90 (m, 2H), 6.84-6.50 (m, 2H, 6.41 (s, 1H), 6.28-6.03 (m, 1H), 5.80-5.46 (m, 1H), 4.20-4.06 (m, 3H), 3.16-3.13 (m, 5H), 2.67-2.63 (m, 5H), 2.38 (s, 3H), 2.15-2.02 (m, 1H), 1.91-1.89 (m, 1H), 1.72-1.59 (m, 2H)

Example 2: Preparation of (R)—N-(3-(4-(1-acryloylpiperidin-3-ylamino)-7H-pyrrolo[2,3-d]pyrimidin-2-ylamino)phenyl)pyrrolidine-1-carboxamide

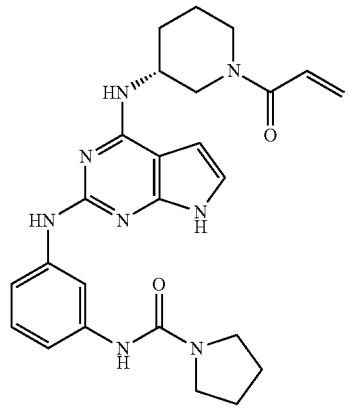 [SMILES: C=CC(=O)N1CCC[C@@H](Nc2nc(Nc3cccc(NC(=O)N4CCCC4)c3)nc3[nH]ccc23)C1]

Step 1: Preparation of 2,4-dichloro-7-tosyl-7H-pyrrolo[2,3-d]pyrimidine

After 2,4-dichloro-7H-pyrrolo[2,3-d]pyrimidine (3.0 g, 16.0 mmol) was dissolved in acetone (20.0 mL), 4-methylbenzenesulfonyl chloride (4.6 g, 23.9 mmol) was added thereto. After cooling to 0° C., 2 M sodium hydroxide solution (12.0 mL) was slowly added dropwise and then stirred at room temperature for 2 hours. The organic layer was isolated, treated with magnesium sulfate, filtered, and then concentrated under reduced pressure. The residue was isolated by column chromatography to obtain a title compound (2.9 g, yield: 80.0%).

¹H NMR (500 MHz, CD₃OD) δ 8.12 (d, 2H), 7.76 (d, 1H), 7.37 (d, 2H), 6.68 (d, 1H), 2.43 (s, 3H)

Step 2: Preparation of tert-butyl-(R)-3-((2-chloro-7-tosyl-7H-pyrrolo[2,3-d]pyrimidin-4-yl)amino)piperidine-1-carboxylate After 2,4-dichloro-7-tosyl-7H-pyrrolo[2,3-d]pyrimidine (500.0 mg, 1.5 mmol) was dissolved in ethanol (10 mL), N,N-diisopropylethylamine 382.0 µL, 2.2 mmol) and tert-butyl(R)-3-aminopiperidine-1-carboxylate (322.0 mg, 1.6 mmol) were added thereto. The reaction mixture was stirred at 110° C. for 12 hours, and then the organic layer was isolated, treated with magnesium sulfate, filtered, and then concentrated under reduced pressure. The residue was isolated by column chromatography to obtain a title compound (681.0 mg, yield: 92.0%).

¹H NMR (500 MHz, CDCl₃) δ 8.10 (d, 1H), 7.39 (d, 1H), 7.31-7.23 (m, 4H), 4.17-4.13 (m, 1H), 3.70-3.60 (m, 1H), 3.45-3.35 (m, 3H), 2.40 (s, 3H), 1.95-1.85 (m, 1H), 1.70-1.65 (m, 1H), 1.60-1.55 (m, 2H), 1.40-1.37 (m, 9H)

Step 3: Preparation of N-(3-nitrophenyl)pyrrolidine-1-carboxamide

After 1-isocyanato-3-nitrobenzene (1.0 g, 6.1 mmol) was dissolved in tetrahydrofuran (10.0 mL), pyrrolidine (0.6 mL, 7.3 mmol) was added thereto. The reaction mixture was allowed to react for 1 hour and then the solvent was concentrated under reduced pressure. The residue was isolated by column chromatography to obtain a title compound (1.3 g, yield: 89.0%).

$^1$H NMR (500 MHz, CD$_3$OD) δ 8.47 (s, 1H), 7.85-7.81 (m, 2H), 7.49 (t, 1H), 3.49-3.47 (m, 4H), 1.98 (s, 4H)

Step 4: Preparation of
N-(3-aminophenyl)pyrrolidine-1-carboxamide

After N-(3-nitrophenyl)pyrrolidine-1-carboxamide (1.3 g, 5.5 mmol) was dissolved in methanol (30.0 mL), excess Raney nickel was added thereto and replaced with hydrogen gas. The reaction mixture was stirred for 1 hour, filtered through celite, and the filtrate was concentrated to obtain a title compound (1.1 g, yield: 100.0%).

$^1$H NMR (500 MHz, CD$_3$OD) δ 6.88-6.85 (m, 1H), 6.74 (s, 1H), 6.61 (d, 1H), 6.31 (d, 1H), 3.18 (s, 4H), 1.83 (s, 4H)

Step 5: Preparation of tert-butyl-(R)-3-((2-((3-(pyr-rolidin-1-carboxamido)phenyl)amino)-7-tosyl-7H-pyrrolo[2,3-d]pyrimidin-4-yl)amino)piperidine-1-carboxylate After tert-butyl-(R)-3-((2-chloro-7-tosyl-7H-pyrrolo[2,3-d]pyrimidin-4-yl)amino)piperidin-1-carboxylate (200.0 mg, 0.4 mmol) was dissolved in anhydrous 1,4-dioxane (2.0 mL), N-(3-aminophenyl)pyrrolidine-1-carboxamide (73.8 mg, 0.4 mmol), palladium acetate (4.0 mg, 0.02 mmol), 4,5-bis-9,9-dimethylxanthene (20.8 mg, 0.04 mmol) and cesium carbonate (234.1 mg, 0.7 mmol) were added thereto. The reaction mixture was reacted at 120° C. for 30 minutes using microwave. The organic layer was isolated, treated with magnesium sulfate, filtered and then concentrated under reduced pressure. The residue was isolated by column chromatography to obtain a title compound (190.0 mg, yield: 78.2%).

$^1$H NMR (500 MHz, CDCl$_3$) δ 8.57 (s, 1H), 7.98 (d, 1H), 7.59-7.55 (m, 1H), 7.22-7.18 (m, 2H), 6.91-6.89 (m, 2H), 6.51 (s, 1H), 6.30 (s, 1H), 3.72-3.69 (m, 1H), 3.47-3.39 (m, 7H), 2.33 (m, 3H), 1.95-1.90 (m, 6H), 1.69-1.64 (m, 2H), 1.59-1.56 (m, 1H), 1.44-1.36 (m, 9H)

Step 6: Preparation of (R)—N-(3-((4-(piperidin-3-ylamino)-7-tosyl-7H-pyrrolo[2,3-d]pyrimidin-2-yl)amino)phenyl) pyrrolidine-1-carboxamide hydrochloride To tert-butyl-(R)-3-((2-((3-(pyrrolidin-1-carboxamido)phenyl)amino)-7-tosyl-7H-pyrrolo[2,3-d]pyrimidin-4-yl)amino)piperidin-1-carboxylate (190.0 mg, 0.3 mmol), 6 N hydrochloric acid solution (5.0 mL, excessive amount) was added. After stirring at room temperature for 30 minutes, the reaction mixture was concentrated and the subsequent reaction was carried out without isolation.

$^1$H NMR (500 MHz, CD$_3$OD) δ 8.38 (s, 1H), 8.02 (d, 2H), 7.47-7.44 (m, 2H), 7.38-7.36 (m, 1H), 7.32-7.28 (m, 1H), 6.98-6.86 (m, 3H), 3.69-3.66 (m, 1H), 3.48-3.39 (m, 5H), 2.98-2.94 (m, 1H), 2.82-2.80 (m, 1H), 2.43 (s, 3H), 2.16-2.14 (m, 1H), 2.06-1.98 (m, 7H), 1.79-1.75 (m, 1H)

Step 7: Preparation of (R)—N-(3-((4-(1-acryloylpiperidin-3-yl)amino)-7-tosyl-7H-pyrrolo[2,3-d]pyrimidin-2-yl)amino)phenyl)pyrrolidine-1-carboxamide After (R)—N-(3-((4-(piperidin-3-ylamino)-7-tosyl-7H-pyrrolo[2,3-d]pyrimidin-2-yl)amino)phenyl)pyrrolidin-1-carboxamide hydrochloride (160.8 mg, 0.3 mmol) was dissolved in dichloromethane (10.0 mL), triethylamine (110.0 μL, 0.8 mmol) was added thereto at 0° C. and stirred for 30 minutes. Acryloyl chloride (60.6 μL, 0.4 mmol) was added to the reaction mixture, followed by stirring at 0° C. for 1 hour. The organic layer was isolated, treated with magnesium sulfate, filtered, and then concentrated under reduced pressure. The residue was isolated by column chromatography to obtain a title compound (250.0 mg, yield: 66.9%).

$^1$H NMR (500 MHz, CD$_3$OD) δ 8.13 (s, 1H), 7.96 (d, 1H), 7.31-6.99 (m, 5H), 6.85-6.45 (m, 2H), 6.30-5.94 (m, 1H), 6.80-5.32 (m, 1H), 4.30-4.07 (m, 2H), 3.45 (s, 4H), 3.20-3.16 (m, 2H), 3.10-2.70 (m, 1H), 2.33 (s, 3H), 2.15-2.10 (m, 1H), 1.94 (s, 4H), 1.89-1.87 (m, 1H), 1.75-1.57 (m, 2H)

Step 8: Preparation of (R)—N-(3-((4-(1-acryloylpiperidin-3-yl)amino)-7H-pyrrolo[2,3-d]pyrimidin-2-ylamino)phenyl)pyrrolidine-1-carboxamide (R)—N-(3-((4-(1-acryloylpiperidin-3-yl)amino)-7-tosyl-7H-pyrrolo[2,3-d]pyrimidin-2-yl)amino)phenyl)pyrrolidine-1-carboxamide (25.0 mg, 0.04 mmol) was dissolved in methanol (1.0 mL). Potassium hydroxide (4.5 mg, 0.08 mmol) was added to the reaction mixture and stirred at 50° C. for 12 hours. The organic layer was isolated, treated with magnesium sulfate, filtered, and then concentrated under reduced pressure. The residue was isolated by column chromatography to obtain a title compound (2.0 mg, yield: 11.1%).

$^1$H NMR (500 MHz, CD$_3$OD) δ 8.09 (s, 1H), 7.18-7.12 (m, 3H), 7.10-6.43 (m, 2H, 6.43 (s, 1H), 6.31-6.00 (m, 1H), 5.81-5.41 (m, 1H), 4.21-4.16 (m, 1H), 3.52-3.41 (m, 4H), 3.43-3.17 (m, 2H), 3.19-3.00 (m, 1H), 2.89-2.76 (m, 1H), 2.11-2.07 (m, 1H), 1.93-1.92 (m, 4H), 1.82-1.80 (m, 1H), 1.79-1.59 (m, 2H)

Example 3: Preparation of (S)—N-(3-(4-(1-acryloylpiperidin-3-ylamino)-7H-pyrrolo[2,3-d]pyrimidin-2-ylamino)phenyl)pyrrolidine-1-carboxamide

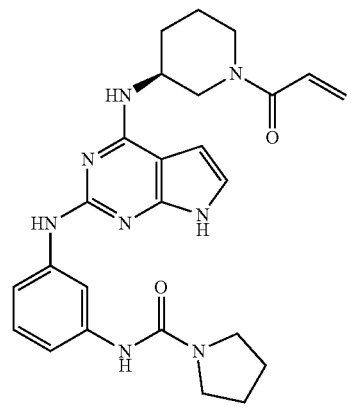 [SMILES: C=CC(=O)N1CCC[C@H](Nc2nc(Nc3cccc(NC(=O)N4CCCC4)c3)nc3[nH]ccc23)C1]

A title compound (10 mg, yield: 25.3%) was prepared in the same manner as in Example 2, except that tert-butyl-(R)-3-aminopiperidine-1-carboxylate was used instead of tell-butyl(S)-3-aminopipendine-1-carboxylate in Example 2.

$^1$H NMR (500 MHz, CD$_3$OD) δ 8.09 (s, 1H), 7.18-7.12 (m, 3H), 7.10-6.43 (m, 2H, 6.43 (s, 1H), 6.31-6.00 (m, 1H), 5.81-5.41 (m, 1H), 4.21-4.16 (m, 1H), 3.52-3.41 (m, 4H), 3.43-3.17 (m, 2H), 3.19-3.00 (m, 1H), 2.89-2.76 (m, 1H), 2.11-2.07 (m, 1H), 1.93-1.92 (m, 4H), 1.82-1.80 (m, 1H), 1.79-1.59 (m, 2H)

Example 4: Preparation of (R)-1-(3-(2-(4-morpholinophenylamino)-7H-pyrrolo[2,3-d]pyrimidin-4-ylamino)piperidin-1-yl)prop-2-en-1-one

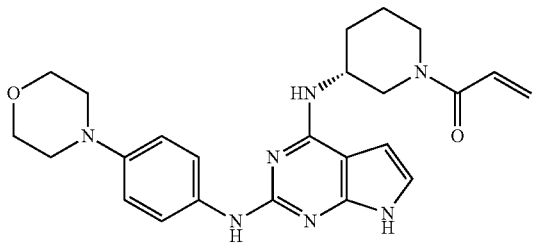 [SMILES: C=CC(=O)N1CCC[C@@H](Nc2nc(Nc3ccc(N4CCOCC4)cc3)nc3[nH]ccc23)C1]

A title compound (9.6 mg, yield: 20.0%) was prepared in the same manner as in Example 1, except that 4-morpholinoaniline was used instead of 4-(4-methylpiperazin-1-yl)aniline in Example 1.

$^1$H NMR (500 MHz, CD$_3$OD) δ 7.55-7.50 (m, 2H), 6.90-6.88 (m, 2H), 6.74-6.63 (m, 2H), 6.54 (s, 1H), 6.41-6.02 (m, 1H), 5.80-5.45 (m, 1H0, 4.21-4.05 (m, 2H), 3.83-3.81 (m, 4H), 3.05-3.03 (m, 4H), 2.79-2.73 (m, 3H), 2.15-2.10 (m, 1H), 1.94-1.90 (m, 1H), 1.75-1.59 (m, 2H)

Example 5: Preparation of (R)-1-(3-(2-(4-(pyrrolidin-1-yl)phenylamino)-7H-pyrrolo[2,3-d]pyrimidin-4-ylamino)piperidin-1-yl)prop-2-en-1-one

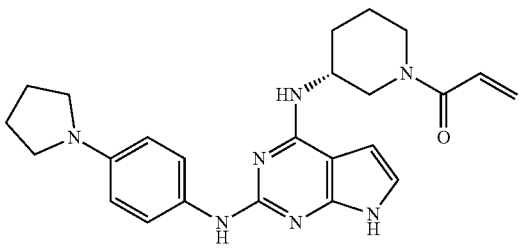 [SMILES: C=CC(=O)N1CCC[C@@H](Nc2nc(Nc3ccc(N4CCCC4)cc3)nc3[nH]ccc23)C1]

A title compound (5.6 mg, yield: 11.9%) was prepared in the same manner as in Example 1, except that 4-(pyrrolidin-1-yl)aniline was used instead of 4-(4-methylpiperazin-1-yl)aniline in Example 1.

$^1$H NMR (500 MHz, CD$_3$OD) δ 7.45-7.36 (m, 2H), 6.85-6.50 (m, 4H), 6.47 (s, 1H), 6.39-6.05 (m, 1H), 5.85-5.54 (m, 1H), 4.21-4.08 (m, 2H), 3.26-3.05 (m, 6H), 2.20-2.13 (m, 1H), 2.00-1.98 (m, 4H), 1.92-1.90 (m, 1H), 1.76-1.58 (m, 3H)

Example 6: Preparation of (R)-1-(3-(2-(4-(3,5-dimethyl-1H-pyrazol-1-yl)phenylamino)-7H-pyrrolo[2,3-d]pyrimidin-4-ylamino)piperidin-1-yl)prop-2-en-1-one

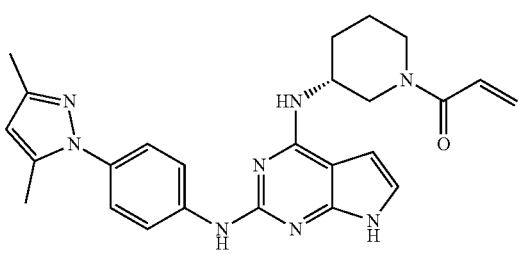 [SMILES: C=CC(=O)N1CCC[C@@H](Nc2nc(Nc3ccc(-n4nc(C)cc4C)cc3)nc3[nH]ccc23)C1]

A title compound (17.3 mg, yield: 34.0%) was prepared in the same manner as in Example 1, except that 4-(3,5-dimethyl-1H-pyrazol-1-yl)aniline was used instead of 4-(4-methylpiperazin-1-yl)aniline in Example 1.

$^1$H NMR (500 MHz, CD$_3$OD) δ 7.86-7.84 (m, 2H), 7.24-7.23 (m, 2H), 7.04-6.68 (m, 2H), 6.44 (s, 1H), 6.24-6.01 (m, 2H), 5.76-5.50 (m, 1H), 4.35-4.11 (m, 2H), 3.50-2.74 (m, 3H), 2.20 (s, 6H), 2.00-1.92 (m, 1H), 1.87-1.60 (m, 3H)

Example 7: Preparation of (R)-1-(3-(2-(4-(2-(diethylamino)ethoxy)phenylamino)-7H-pyrrolo[2,3-d]pyrimidin-4-ylamino)piperidin-1-yl)prop-2-en-1-one

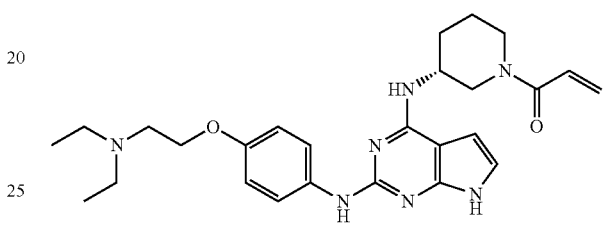

A title compound (10.0 mg, yield: 19.0%) was prepared in the same manner as in Example 1, except that 4-(2-(diethylamino)ethoxy)aniline was used instead of 4-(4-methylpiperazin-1-yl)aniline in Example 1.

$^1$H NMR (500 MHz, CD$_3$OD) δ 7.54-7.50 (m, 2H), 6.85-6.82 (m, 2H), 6.74-6.50 (m, 2H), 6.40 (s, 1H), 6.30-6.06 (m, 1H), 5.80-5.46 (m, 1H), 4.21-4.06 (m, 4H), 3.20-3.10 (m, 1H), 2.92-2.90 (m, 3H), 2.72-2.66 (m, 5H), 2.20-2.15 (m, 1H), 1.91-1.88 (m, 1H), 1.85-1.59 (m, 2H), 1.12-1.05 (m, 6H)

Example 8: Preparation of (R)-1-(3-(2-(4-(morpholine-4-carbonyl)phenylamino)-7H-pyrrolo[2,3-d]pyrimidin-4-ylamino)piperidin-1-yl)prop-2-en-1-one

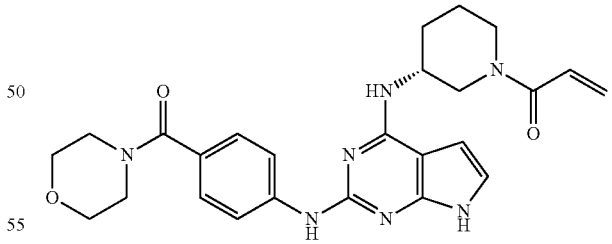

A title compound (6.9 mg, yield: 13.3%) was prepared in the same manner as in Example 1, except that (4-aminophenyl)(morpholino)methanone was used instead of 4-(4-methylpiperazin-1-yl)aniline in Example 1.

$^1$H NMR (500 MHz, CD$_3$OD) δ 7.84-7.79 (m, 2H), 7.34-7.33 (m, 2H), 6.82-6.80 (m, 1H), 6.64-6.55 (m, 1H), 6.44 (s, 1H), 6.27-6.03 (m, 1H), 5.80-5.46 (m, 1H), 4.40-4.16 (m, 2H), 3.68-3.57 (m, 9H), 3.16-3.11 (m, 1H), 2.90-2.73 (m, 1H), 2.20-2.17 (m, 1H), 2.15-1.93 (m, 1H), 1.85-1.61 (m, 2H)

Example 9: Preparation of (R)-1-(3-(2-(4-(dimethylamino)phenylamino)-7H-pyrrolo[2,3-d]pyrimidin-4-ylamino)piperidin-1-yl)prop-2-en-1-one

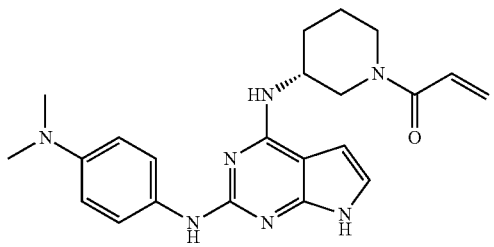 [SMILES: C=CC(=O)N1CCC[C@@H](Nc2nc(Nc3ccc(N(C)C)cc3)nc3[nH]ccc23)C1]

A title compound (8.1 mg, yield: 18.4%) was prepared in the same manner as in Example 1, except that N,N-dimethylbenzene-1,4-diamine was used instead of 4-(4-methylpiperazin-1-yl)aniline in Example 1.

$^1$H NMR (500 MHz, CD$_3$OD) δ 7.48-7.43 (m, 2H), 6.83-6.47 (m, 4H), 6.40 (s, 1H), 6.27-6.02 (m, 1H), 5.78-5.46 (m, 1H), 4.21-4.10 (m, 2H), 3.26-3.07 (m, 2H), 2.84 (s, 6H), 2.80-2.74 (m, 1H), 2.14-2.13 (m, 1H), 1.94-1.90 (m, 1H), 1.62-1.55 (m, 2H)

Example 10: Preparation of (R)-1-(3-(2-(3-(3,5-dimethyl-1H-pyrazol-1-yl)phenylamino)-7H-pyrrolo[2,3-d]pyrimidin-4-ylamino)piperidin-1-yl)prop-2-en-1-one

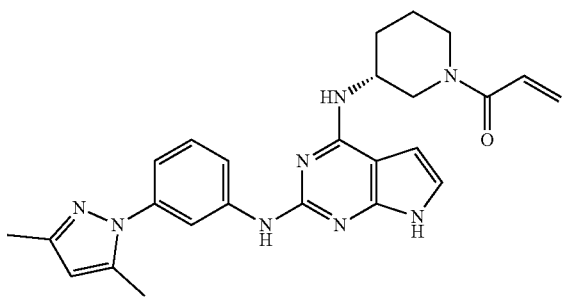 [SMILES: C=CC(=O)N1CCC[C@@H](Nc2nc(Nc3cccc(-n4nc(C)cc4C)c3)nc3[nH]ccc23)C1]

A title compound (9.8 mg, yield: 19.6%) was prepared in the same manner as in Example 1, except that 3-(3,5-dimethyl-1H-pyrazol-1-yl) aniline was used instead of 4-(4-methylpiperazin-1-yl)aniline in Example 1.

$^1$H NMR (500 MHz, CD$_3$OD) δ 8.19-8.17 (m, 1H), 7.60-7.50 (m, 1H), 7.35-7.31 (m, 1H), 6.90-6.88 (m, 1H), 6.64-6.55 (m, 2H), 6.44-6.42 (m, 1H), 6.23-6.03 (m, 2H), 5.85-5.55 (m, 1H), 4.36-4.00 (m, 2H), 3.67-3.40 (m, 1H), 3.16-3.13 (m, 1H), 2.77-2.74 (m, 1H), 2.28 (s, 3H), 2.24 (s, 3H), 2.18-2.05 (m, 1H), 1.86-1.48 (m, 3H)

Example 11: Preparation of (S)-1-(3-(2-(4-(4-methylpiperazin-1-yl)phenylamino)-7H-pyrrolo[2,3-d]pyrimidin-4-ylamino)piperidin-1-yl)prop-2-en-1-one

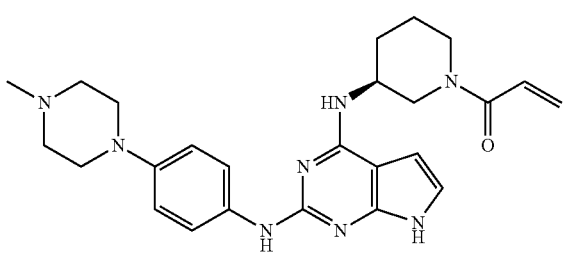 [SMILES: C=CC(=O)N1CCC[C@H](Nc2nc(Nc3ccc(N4CCN(C)CC4)cc3)nc3[nH]ccc23)C1]

A title compound (9.8 mg, yield: 19.6%) was prepared in the same manner as in Example 1, except that tert-butyl-(R)-3-aminopiperidine-1-carboxylate was used instead of tell-butyl (S)-3-aminopiperidine-1-carboxylate in Example 1.

$^1$H NMR (500 MHz, CD$_3$OD) δ 7.58-7.51 (m, 2H), 6.92-6.86 (m, 2H), 6.50-6.41 (m, 2H), 6.28-6.03 (m, 1H), 5.80-5.46 (m, 1H), 4.20-4.06 (m, 2H), 3.72-3.66 (m, 2H), 3.12 (m, 4H), 2.65 (m, 4H), 2.36 (s, 3H), 2.15-2.02 (m, 1H), 1.91-1.89 (m, 2H), 1.72-1.59 (m, 2H)

Example 12: Preparation of (R)-1-(3-(2-(benzo[d]thiazol-6-ylamino)-7H-pyrrolo[2,3-d]pyrimidin-4-ylamino)piperidin-1-yl)prop-2-en-1-one

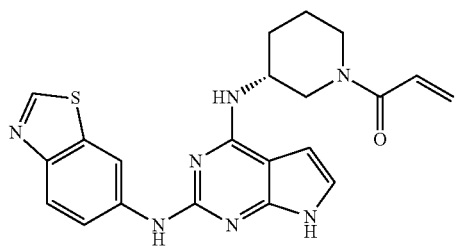 [SMILES: C=CC(=O)N1CCC[C@@H](Nc2nc(Nc3ccc4ncsc4c3)nc3[nH]ccc23)C1]

A title compound (7.5 mg, yield: 29.8%) was prepared in the same manner as in Example 1, except that benzo[d]thiazol-6-amine was used instead of 4-(4-methylpiperazin-1-yl)aniline in Example 1.

$^1$H NMR (500 MHz, CD$_3$OD) δ 8.97 (s, 1H), 8.80 (d, 1H), 7.87 (d, 1H), 7.62-7.56 (m, 1H), 6.81-6.43 (m, 3H), 6.27-5.93 (m, 1H), 5.80-5.33 (m, 1H), 4.28-4.23 (m, 2H), 3.26-2.74 (m, 3H), 2.20-2.14 (m, 2H), 1.94-1.93 (m, 1H), 1.68-1.63 (m, 2H)

Example 13: Preparation of (R)-1-(3-(2-(4-phenoxyphenylamino)-7H-pyrrolo[2,3-d]pyrimidin-4-ylamino)piperidin-1-yl)prop-2-en-1-one

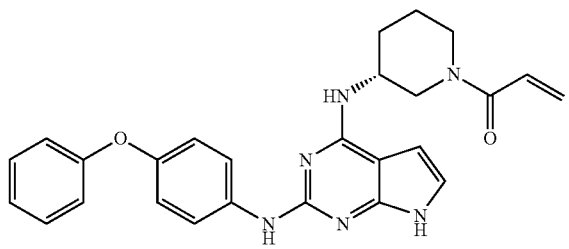 [SMILES: C=CC(=O)N1CCC[C@@H](Nc2nc(Nc3ccc(Oc4ccccc4)cc3)nc3[nH]ccc23)C1]

A title compound (6.0 mg, yield: 12.2%) was prepared in the same manner as in Example 1, except that 4-phenoxyaniline was used instead of 4-(4-methylpiperazin-1-yl)aniline in Example 1.

$^1$H NMR (500 MHz, CD$_3$OD) δ 7.37-7.35 (m, 2H), 7.29-7.28 (m, 2H), 7.12-7.10 (m, 2H, 7.03-6.98 (m, 3H), 6.71-6.49 (m, 2H), 6.37-6.10 (m, 1H), 5.70-5.58 (m, 1H), 4.22-4.19 (m, 1H), 3.28-3.25 (m, 1H), 2.89-2.78 (m, 1H), 2.59-2.54 (m, 2H), 2.07-2.05 (m, 1H), 1.85-1.81 (m, 1H), 1.79-1.53 (m, 2H)

Example 14: Preparation of (R)-1-(3-(2-(1-methyl-1H-pyrazol-4-ylamino)-7H-pyrrolo[2,3-d]pyrimidin-4-ylamino)piperidin-1-yl)prop-2-en-1-one

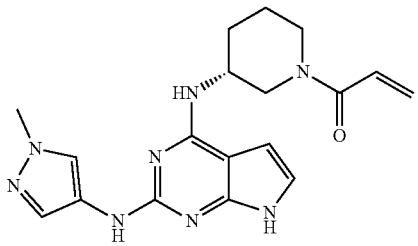 [SMILES: C=CC(=O)N1CCC[C@@H](Nc2nc(Nc3cnn(C)c3)nc3[nH]ccc23)C1]

A title compound (10.0 mg, yield: 28.6%) was prepared in the same manner as in Example 1, except that 1-methyl-1H-pyrazol-4-amine was used instead of 4-(4-methylpiperazin-1-yl)aniline in Example 1.
$^1$H NMR (500 MHz, CD$_3$OD) δ 7.89 (d, 1H), 7.59 (d, 1H), 6.84-6.52 (m, 2H), 6.40 (s, 1H), 6.25-6.07 (m, 1H), 5.78-5.50 (m, 1H), 4.22-4.16 (m, 2H), 3.81 (s, 3H), 3.27-2.80 (m, 2H), 2.17-2.14 (m, 1H), 1.93-1.91 (m, 1H), 1.76-1.61 (m, 2H)

Example 15: Preparation of (R)-1-(3-(2-(1-(2,2-difluoroethyl)-1H-pyrazol-4-ylamino)-7H-pyrrolo[2,3-d]pyrimidin-4-ylamino)piperidin-1-yl)prop-2-en-1-one

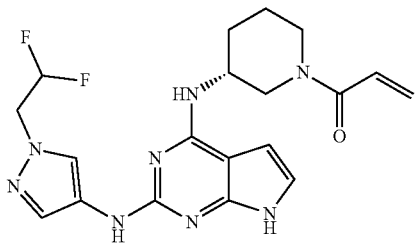 [SMILES: C=CC(=O)N1CCC[C@@H](Nc2nc(Nc3cnn(CC(F)F)c3)nc3[nH]ccc23)C1]

A title compound (14.0 mg, yield: 30.9%) was prepared in the same manner as in Example 1, except that 1-(2,2-difluoroethyl)-1H-pyrazol-4-amine was used instead of 4-(4-methylpiperazin-1-yl)aniline in Example 1.
$^1$H NMR (500 MHz, CD$_3$OD) δ 8.12-7.99 (m, 1H), 7.61-7.52 (m, 1H), 6.83-6.52 (m, 2H), 6.40 (s, 1H), 6.26-6.05 (m, 2H) 5.79-5.50 (m, 1H), 4.48-4.43 (m, 2H), 4.24-4.21 (m, 1H), 4.11-4.08 (m, 2H), 3.16-3.11 (m, 1H), 2.16-2.13 (m, 1H), 1.95-1.89 (m, 1H), 1.73-1.61 (m, 2H)

Example 16: Preparation of (R)-1-(3-(2-(1-(difluoromethyl)-1H-pyrazol-4-ylamino)-7H-pyrrolo[2,3-d]pyrimidin-4-ylamino)piperidin-1-yl)prop-2-en-1-one

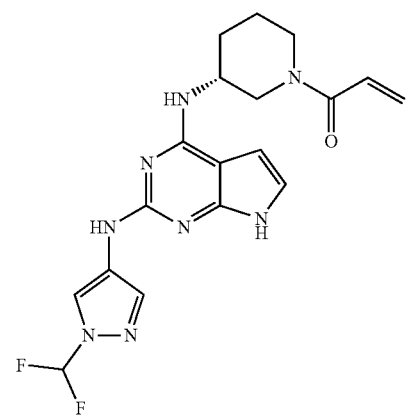 [SMILES: C=CC(=O)N1CCC[C@@H](Nc2nc(Nc3cnn(C(F)F)c3)nc3[nH]ccc23)C1]

A title compound (7.0 mg, yield: 24.2%) was prepared in the same manner as in Example 1, except that 1-(difluoromethyl)-1H-pyrazol-4-amine was used instead of 4-(4-methylpiperazin-1-yl)aniline in Example 1.
$^1$H NMR (500 MHz, CD$_3$OD) δ 8.39 (d, 1H), 7.76 (d, 1H), 7.36-7.34 (m, 2H, 7.22-7.0.2 (m, 1H), 6.77-6.57 (m, 2H), 6.41 (s, 1H), 6.25-6.06 (m, 1H), 5.78-5.52 (m, 1H), 4.12-4.08 (m, 2H), 3.16-3.14 (m, 1H), 2.72-2.65 (m, 1H), 2.19-2.17 (m, 1H), 1.96-1.92 (m, 1H), 1.82-1.73 (m, 1H), 1.64-1.61 (m, 2H)

Example 17: Preparation of (R)-1-(3-(2-(1-(2-methoxyethyl)-1H-pyrazol-4-ylamino)-7H-pyrrolo[2,3-d]pyrimidin-4-ylamino)piperidin-1-yl)prop-2-en-1-one

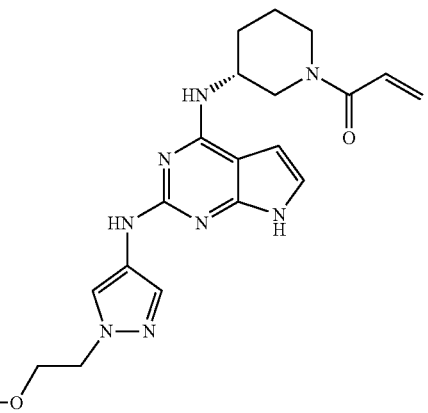

A title compound (6.5 mg, yield: 27.1%) was prepared in the same manner as in Example 1, except that 1-(2-methoxyethyl)-1H-pyrazol-4-amine was used instead of 4-(4-methylpiperazin-1-yl)aniline in Example 1.
$^1$H NMR (500 MHz, CD$_3$OD) δ 8.00 (d, 1H), 7.55 (d, 1H), 6.74-6.52 (m, 2H, 6.41 (s, 1H), 6.26-6.06 (m, 1H), 5.78-5.51 (m, 1H), 4.23-4.19 (m, 3H), 4.15-4.10 (m, 1H), 3.71-3.67 (m, 4H), 3.35 (s, 3H), 3.16-3.14 (m, 1H), 2.18-2.17 (m, 1H), 1.96-1.93 (m, 1H), 1.65-1.63 (m, 2H)

Example 18: Preparation of (R)-1-(3-(2-(1-(2-morpholinoethyl)-1H-pyrazol-4-ylamino)-7H-pyrrolo[2,3-d]pyrimidin-4-ylamino)piperidin-1-yl)prop-2-en-1-one

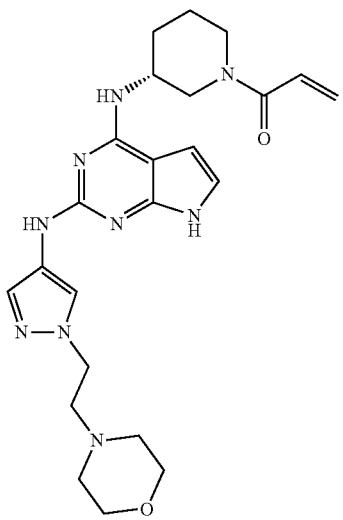 [SMILES: C=CC(=O)N1CCC[C@@H](Nc2nc(Nc3cnn(CCN4CCOCC4)c3)nc3[nH]ccc23)C1]

A title compound (17.5 mg, yield: 34.3%) was prepared in the same manner as in Example 1, except that 1-(2-morpholinoethyl)-1H-pyrazol-4-amine was used instead of 4-(4-methylpiperazin-1-yl)aniline in Example 1.

¹H NMR (500 MHz, CD₃OD) δ 7.98 (d, 1H), 7.55 (d, 1H), 6.73-6.56 (m, 2H), 6.41 (s, 1H), 6.40-6.07 (m, 1H), 5.78-5.51 (m, 1H), 4.23-4.18 (m, 4H), 3.65-3.64 (m, 4H), 3.30-3.16 (m, 1H), 2.78-2.71 (m, 3H), 2.46 (s, 4H), 2.18-2.13 (m, 1H), 1.94-1.92 (m, 1H), 1.62-1.60 (m, 2H)

Example 19: Preparation of (R)-1-(3-(2-(1-(2-(diethylamino)ethyl)-1H-pyrazol-4-ylamino)-7H-pyrrolo[2,3-d]pyrimidin-4-ylamino)piperidin-1-yl)prop-2-en-1-one

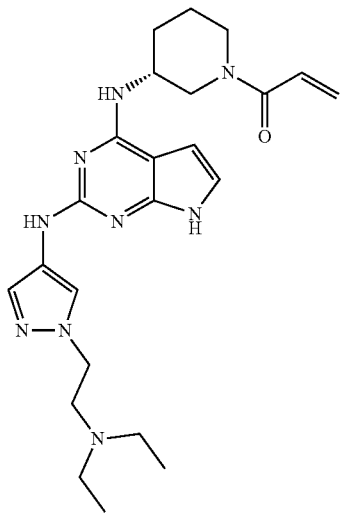 [SMILES: C=CC(=O)N1CCC[C@@H](Nc2nc(Nc3cnn(CCN(CC)CC)c3)nc3[nH]ccc23)C1]

A title compound (4.5 mg, yield: 10.0%) was prepared in the same manner as in Example 1, except that 1-(2-(diethylamino)ethyl-1H-pyrazol-4-amine was used instead of 4-(4-methylpiperazin-1-yl)aniline in Example 1.
¹H NMR (500 MHz, CD₃OD) δ 7.99 (d, 1H), 7.56 (d, 1H), 6.74-6.57 (m, 2H), 6.42 (s, 1H), 6.41-6.08 (m, 1H), 5.78-5.52 (m, 1H), 4.25-4.19 (m, 4H), 3.31-3.12 (m, 1H), 3.02-2.92 (m, 2H), 2.66-2.60 (m, 6H), 2.20-2.17 (m, 1H), 2.00-1.92 (m, 1H), 1.80-1.72 (m, 2H), 1.71-1.59 (m, 2H), 1.34-1.29 (m, 4H)

Example 20: Preparation of (R)-1-(3-(2-(1-(3-methoxybenzyl)-1H-pyrazol-4-ylamino)-7H-pyrrolo[2,3-d]pyrimidin-4-ylamino)piperidin-1-yl)prop-2-en-1-one

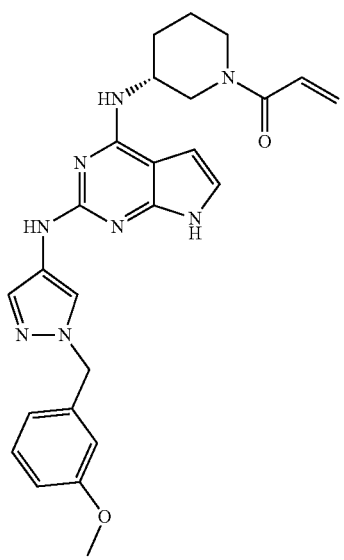 [SMILES: C=CC(=O)N1CCC[C@@H](Nc2nc(Nc3cnn(Cc4cccc(OC)c4)c3)nc3[nH]ccc23)C1]

A title compound (9.0 mg, yield: 17.6%) was prepared in the same manner as in Example 1, except that 1-(3-methoxybenzyl)-1H-pyrazol-4-amine was used instead of 4-(4-methylpiperazin-1-yl)aniline in Example 1.
¹H NMR (500 MHz, CD₃OD) δ 8.09 (d, 1H), 7.57 (d, 1H), 7.23-7.22 (m, 1H), 6.85-6.78 (m, 3H), 6.76-6.70 (m, 2H), 6.40 (s, 1H), 6.21-6.18 (m, 1H), 5.73-5.71 (m, 1H), 5.24-5.19 (m, 2H), 4.13-4.11 (m, 1H), 3.74 (s, 3H), 3.83-3.75 (m, 1H), 3.38-3.01 (m, 1H), 2.07-2.01 (m, 1H), 1.92-1.87 (m, 1H), 1.86-1.71 (m, 1H), 1.69-1.49 (m, 2H)

Example 21: Preparation of (R)-1-(3-(2-(1-ethyl-1H-pyrazol-4-ylamino)-7H-pyrrolo[2,3-d]pyrimidin-4-ylamino)piperidin-1-yl)prop-2-en-1-one

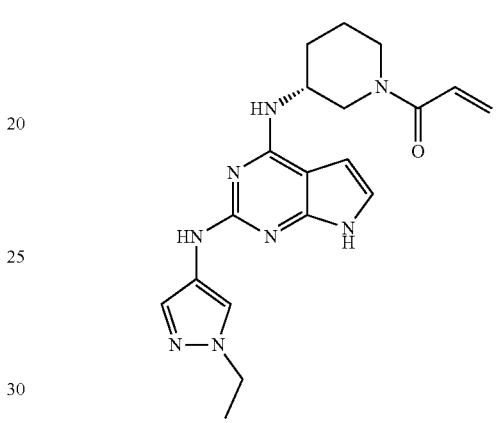

A title compound (15.0 mg, yield: 36.6%) was prepared in the same manner as in Example 1, except that 1-ethyl-1H-pyrazol-4-amine was used instead of 4-(4-methylpiperazin-1-yl)aniline in Example 1.
¹H NMR (500 MHz, CD₃OD) δ 7.96 (d, 1H), 7.52 (d, 1H), 6.73-6.52 (m, 2H), 6.39 (s, 1H), 6.26-6.06 (m, 1H), 5.78-5.51 (m, 1H), 4.23-4.21 (m, 3H), 4.20-4.07 (m, 3H), 3.28-3.08 (m, 1H), 2.16-2.14 (m, 1H), 1.92-1.90 (m, 1H), 1.61-1.59 (m, 1H), 1.39-1.23 (m, 2H)

Example 22: Preparation of (R)-1-(3-(2-(1,3-dimethyl-1H-pyrazol-4-ylamino)-7H-pyrrolo[2,3-d]pyrimidin-4-ylamino)piperidin-1-yl)prop-2-en-1-one

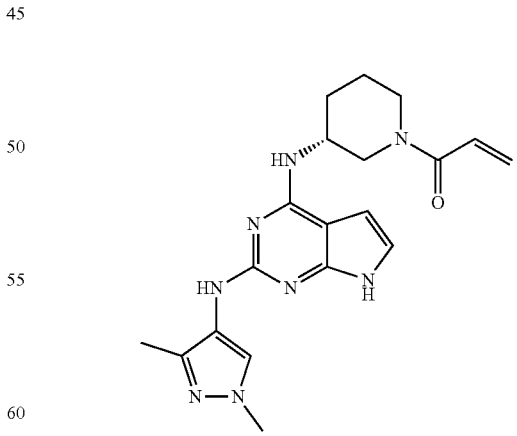

A title compound (3.5 mg, yield: 8.5%) was prepared in the same manner as in Example 1, except that 1,3-dimethyl-1H-pyrazol-4-amine was used instead of 4-(4-methylpiperazin-1-yl)aniline in Example 1.
¹H NMR (500 MHz, CD₃OD) δ 7.83 (d, 1H), 6.73-6.56 (m, 2H), 6.55 (s, 1H), 6.40-6.39 (m, 1H), 5.35-5.33 (m, 1H), 4.18-4.10 (m, 3H), 3.76 (s, 3H), 3.22-3.16 (m, 1H), 2.22 (s, 3H), 2.19-2.17 (m, 1H), 2.16-2.14 (m, 1H), 1.95-1.90 (m, 1H), 1.78-1.70 (m, 1H), 1.65-1.60 (m, 2H)

Example 23: Preparation of (R)-1-(3-(2-(isoxazol-4-ylamino)-7H-pyrrolo[2,3-d]pyrimidin-4-ylamino)piperidin-1-yl)prop-2-en-1-one

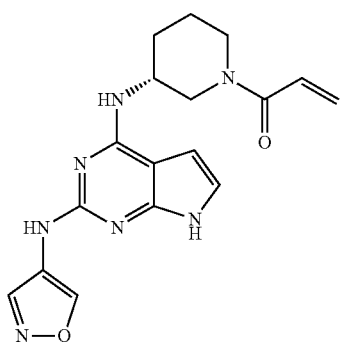 [SMILES: C=CC(=O)N1CCC[C@@H](Nc2nc(Nc3cnoc3)nc3[nH]ccc23)C1]

A title compound (4.5 mg, yield: 11.8%) was prepared in the same manner as in Example 1, except that isoxazole-4-amine was used instead of 4-(4-methylpiperazin-1-yl)aniline in Example 1.

$^1$H NMR (500 MHz, CD$_3$OD) δ 9.04 (d, 1H), 8.49 (d, 1H), 6.78-6.57 (m, 2H), 6.43-6.12 (m, 1H), 5.56-5.34 (m, 1H), 4.18-4.12 (m, 3H), 3.25-3.16 (m, 1H), 2.20-2.16 (m, 1H), 1.93-1.91 (m, 1H), 1.79-1.74 (m, 1H), 1.71-1.60 (m, 2H)

Example 24: Preparation of (R)-2-(4-(4-(1-acryloylpiperidin-3-ylamino)-7H-pyrrolo[2,3-d]pyrimidin-2-ylamino)-1H-pyrazol-1-yl)-N-methylacetamide

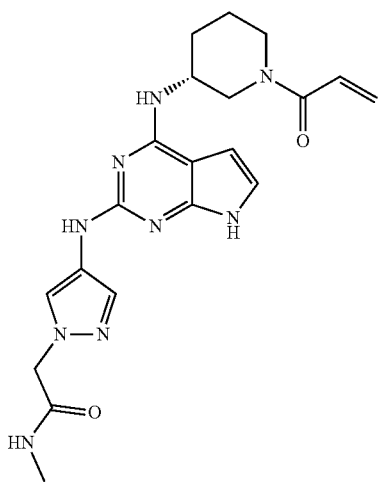 [SMILES: C=CC(=O)N1CCC[C@@H](Nc2nc(Nc3cnn(CC(=O)NC)c3)nc3[nH]ccc23)C1]

A title compound (11.9 mg, yield: 40.2%) was prepared in the same manner as in Example 1, except that 2-(4-amino-1H-pyrazol-1-yl)-N-methylacetamide was used instead of 4-(4-methylpiperazin-1-yl)aniline in Example 1.

$^1$H NMR (500 MHz, CD$_3$OD) δ 7.96-7.90 (m, 1H), 7.57-7.50 (m, 1H), 6.86-6.50 (m, 1H), 6.27-6.09 (m, 1H), 5.80-5.56 (m, 1H), 4.42-4.29 (m, 2H), 4.14-4.09 (m, 2H), 3.97-3.41 (m, 3H), 2.15-2.09 (m, 1H), 1.93-1.86 (m, 2H), 1.64-1.60 (m, 1H0, 1.45-1.40 (m, 3H)

Example 25: Preparation of (R)-1-(3-(2-(1-(2,2-difluoroethyl)-1H-pyrazol-4-ylamino)-7H-pyrrolo[2,3-d]pyrimidin-4-ylamino)piperidin-1-yl)but-2-yn-1-one

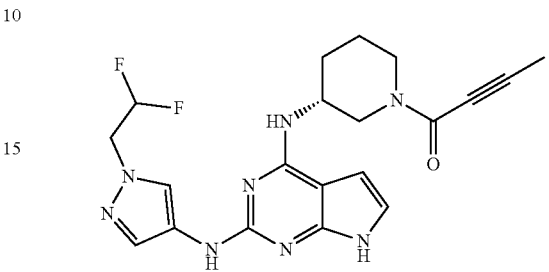

Step 1: Preparation of tert-butyl-(R)-3-((2-chloro-7H-pyrrolo[2,3-d]pyrimidin-4-yl)amino)piperidine-1-carboxylate After 2,4-dichloro-7H-pyrrolo[2,3-d]pyrimidine (500.0 mg, 2.7 mmol) was dissolved in ethanol (10 mL), N,N-diisopropylethylamine (695.0 μL, 4.0 Mmol) and tert-butyl (R)-3-aminopiperidine-1-carboxylate (639.3 mg, 4.0 eq) were added thereto. The reaction mixture was stirred at 110° C. for 12 hours, and the organic layer was isolated, treated with magnesium sulfate, filtered, and concentrated under reduced pressure. The residue was isolated by column chromatography to obtain a title compound (900.0 mg, yield: 98%).

$^1$H NMR (500 MHz, CD$_3$OD) δ 7.06 (s, 1H), 6.38 (s, 1H), 4.24-4.20 (m, 1H), 3.84-3.82 (m, 1H), 3.80-3.30 (m, 3H), 2.01-1.90 (m, 1H), 1.80-1.75 (m, 1H), 1.65-1.55 (m, 2H), 1.43 (s, 9H)

Step 2: Preparation of (R)-2-chloro-N-(piperidin-3-yl)-7H-pyrrolo[2,3-d]pyrimidine-4-amine To tert-butyl-(R)-3-((2-chloro-7H-pyrrolo[2,3-d]pyrimidine-4-yl)amino)piperidine-1-carboxylate (474.0 mg, 1.4 mmol), 6 N hydrochloric acid solution (5.0 mL, excessive amount) dissolved in methanol was added. After stirring at room temperature for 30 minutes, the reaction mixture was neutralized with saturated sodium bicarbonate solution. The organic layer was isolated, treated with magnesium sulfate, filtered, and then concentrated under reduced pressure to obtain a title compound without isolation.

$^1$H NMR (500 MHz, CD$_3$OD) δ 7.11 (d, 1H), 6.63 (d, 1H), 4.52-4.49 (m, 1H), 3.66-3.63 (m, 1H), 3.37-3.34 (m, 1H), 3.02-2.90 (m, 2H), 2.19-2.16 (m, 1H), 2.12-2.09 (m, 1H), 1.90-1.77 (m, 2H)

Step 3: Preparation of (R)-1-(34(2-chloro-7H-pyrrolo[2,3-d]pyrimidine-4-yl)amino)piperidin-1-yl)but-2-yn-1-one After 2-butenoic acid (84.1 mg, 0.2 mmol) was dissolved in tetrahydrofuran (3.0 mL), N,N-diisopropylethylamine (69.2 mg, 0.4 mmol) and 1-[bis(dimethylamino)methylene]-1H-1,2,3-triazole[4,5-b]pyridinium 3-oxide hexafluorophosphate (90.6 mg, 0.2 mmol) was added thereto and stirred for 30 minutes. (R)-2-chloro-N-(piperidin-3-yl)-7H- pyrrolo[2,3-d]pyrimidine-3-amine (50.0 mg, 0.2 mmol) was added to this reaction mixture, followed by stirring at room temperature for 12 hours. The organic layer was isolated, treated with magnesium sulfate, filtered, and then concentrated under reduced pressure. The residue was isolated by column chromatography to obtain a title compound (49.0 mg, yield: 77.8%).

$^1$H NMR (500 MHz, CD$_3$OD) δ 7.03-7.01 (m, 1H), 6.61-6.55 (m, 1H), 4.45-3.83 (m, 3H), 3.65-3.58 (m, 1H), 2.94-2.80 (m, 1H), 2.15-2.09 (m, 1H), 1.92-1.90 (m, 2H), 1.85-1.79 (m, 3H), 1.67-1.58 (m, 1H)

Step 4: Preparation of R)-1-(3-(2-(1-(2,2-difluoro-ethyl)-1H-pyrazol-4-ylamino)-7H-pyrrolo[2,3-d]pyrimidin-4-ylamino)piperidin-1-yl)but-2-yn-1-one (R)-1-(3-((2-chloro-7H-pyrrolo[2,3-d]pyrimidine-4-yl)amino)piperidin-1-yl)but-2-yn-1-one (25.0 mg, 0.08 mmol) and 2,2-difluoroethyl-1H-pyrazol-4-amine (7.2 mg, 0.05 mmol) were dissolved in 2-butanol (2.0 mL). Trifluoroacetic acid (4.8 μL, 0.06 mmol) was added to the reaction mixture and reacted at 110° C. for 5 hours, and then the solvent was concentrated. This reaction mixture was neutralized by adding 7 N ammonia solution dissolved in methanol. The residue was isolated by column chromatography to obtain a title compound (5.1 mg, yield: 24.3%).

$^1$H NMR (500 MHz, CD$_3$OD) δ 8.08 (s, 1H), 7.65-7.50 (m, 1H), 6.76-6.73 (m, 1H), 6.44-6.38 (m, 1H), 6.30-6.06 (m, 1H), 5.60-4.29 (m, 6H), 3.29-3.15 (m, 1H), 2.15-2.11 (m, 1H). 2.04-2.00 (m, 1H), 1.94-1.91 (m, 1H), 1.85-1.65 (m, 4H)

Example 26: Preparation of (R)—N-(3-(4-(1-(2-cyanoacetyl)piperidin-3-ylamino)-7H-pyrrolo[2,3-d]pyrimidin-2-ylamino)phenyl)acrylamide

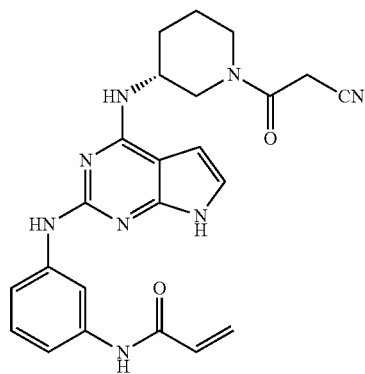 [SMILES: C=CC(=O)Nc1cccc(Nc2nc(N[C@@H]3CCCN(C(=O)CC#N)C3)c3cc[nH]c3n2)c1]

Step 1: Preparation of tert-butyl-(R)-3-((2-chloro-7H-pyrrolo[2,3-d]pyrimidin-4-yl)amino)piperidine-1-carboxylate After 2,4-dichloro-7H-pyrrolo[2,3-d]pyrimidine (500.0 mg, 2.7 mmol) was dissolved in ethanol (10 mL), N,N-diisopropylethylamine (695.0 μL, 4.0 mmol) and tert-butyl-(R)-3-aminopiperidine-1-carboxylate (639.3 mg, 4.0 eq) were added thereto. The reaction mixture was stirred at 110° C. for 12 hours, and the organic layer was isolated, treated with magnesium sulfate, filtered, and then concentrated under reduced pressure. The residue was isolated by column chromatography to obtain a title compound (900.0 mg, yield: 98.0%).

$^1$H NMR (500 MHz, CD$_3$OD) δ 7.06 (s, 1H), 6.38 (s, 1H), 4.24-4.20 (m, 1H), 3.84-3.82 (m, 1H), 3.80-3.30 (m, 3H), 2.01-1.90 (m, 1H), 1.80-1.75 (m, 1H), 1.65-1.55 (m, 2H), 1.43 (s, 9H)

Step 2: Preparation of (R)-2-chloro-N-(piperidin-3-yl)-7H-pyrrolo[2,3-d]pyrimidin-4-amine To tert-butyl-(R)-3-((2-chloro-7H-pyrrolo[2,3-d]pyrimidin-4-yl)amino)piperidine-1-carboxylate (474.0 mg, 1.4 mmol), 6 N hydrochloric acid solution (5.0 mL, excessive amount) dissolved in methanol was added. After stirring at room temperature for 30 minutes, the reaction mixture was neutralized with saturated sodium bicarbonate solution. The organic layer was isolated, treated with magnesium sulfate, filtered, and then concentrated under reduced pressure to obtain a title compound without isolation.

$^1$H NMR (500 MHz, CD$_3$OD) δ 7.11 (d, 1H), 6.63 (d, 1H), 4.52-4.49 (m, 1H), 3.66-3.63 (m, 1H), 3.37-3.34 (m, 1H), 3.02-2.90 (m, 2H), 2.19-2.16 (m, 1H), 2.12-2.09 (m, 1H), 1.90-1.77 (m, 2H)

Step 3: Preparation of (R)-1-(3-chloro-7H-pyrrolo[2,3-d]pyrimidin-4-yl)amino)piperidin-1-yl)prop-2-en-1-one After cyanoacetic acid (40.6 mg, 0.4 mmol) was dissolved in tetrahydrofuran (3.0 mL), N,N-diisopropylethylamine (140 uL, 0.8 mmol) and 1-[bis(dimethylamino)methylene]-1H-1,2,3-triazole[4,5-b]-pyridinium 3-oxide hexafluorophosphate (181.3 mg, 0.4 mmol) were added thereto and stirred for 30 minutes. (R)-2-chloro-N-(piperidin-3-yl)-7H-pyrrolo[2,3-d]pyrimidin-4-amine (100.0 mg, 0.3 mmol) was added to this reaction mixture and stirred at room temperature for 12 hours. The organic layer was isolated, treated with magnesium sulfate, filtered, and then concentrated under reduced pressure. The residue was isolated by column chromatography to obtain a title compound (49.0 mg, yield: 77.8%).

$^1$H NMR (500 MHz, CD$_3$OD) δ 6.99 (d, 1H), 6.45 (d, 1H), 4.20-4.00 (m, 2H), 3.84-3.62 (m, 1H), 3.48-3.41 (m, 1H), 2.97 (s, 2H), 2.10 (s, 1H), 1.85-1.82 (m, 1H), 1.72-1.70 (m, 1H)

Step 4: Preparation of N-(3-nitrophenyl)acrylamide

3-Nitroaniline (300.0 mg, 2.2 mmol) was dissolved in tetrahydrofuran (3.0 mL) to which triethylamine (450.04, 3.3 mmol) was added, and the mixture was stirred for 10 minutes. After cooling to 0° C., acryloyl chloride (260.0 μL, 3.3 mmol) was added, followed by stirring for 2 hours. The organic layer was isolated, treated with magnesium sulfate, filtered, and then concentrated under reduced pressure. The residue was isolated by column chromatography to obtain a title compound (365.0 mg, yield: 87.0%).

$^1$H NMR (500 MHz, CD$_3$OD) δ 8.70 (s, 1H), 7.98-7.93 (m, 2H), 7.59-7.55 (m, 1H), 6.45-6.42 (m, 2H), 5.83 (s, 1H)

Step 5: Preparation of N-(3-aminophenyl)acrylamide

N-(3-nitrophenyl)acrylamide (365.0 mg, 1.9 mmol) was dissolved in ethanol (3.0 mL). Tin chloride (857.0 mg, 3.8 mmol) was added thereto and the mixture was stirred at 100° C. for 2 hours and then neutralized with 1 N sodium hydroxide solution. The reaction mixture was extracted with dichloromethane and concentrated under reduced pressure to obtain a title compound (300.3 mg, yield: 98.0%).

¹H NMR (500 MHz, CD₃OD) δ 7.47 (s, 1H), 7.26-7.23 (m, 1H), 7.01 (t, 1H), 6.74 (d, 1H), 6.45-6.42 (m, 1H), 6.30-6.21 (m, 1H), 5.74-5.72 (m, 1H)

Step 6: Preparation of (R)—N-(3-(4-(1-(2-cyano-acetyl)piperidin-3-ylamino)-7H-pyrrolo[2,3-d]pyrimidin-2-ylamino)phenyl)acrylamide (R)-1-(3-((2-chloro-7H-pyrrolo[2,3-d]pyrimidin-4-yl)amino)piperidin-1-yl)prop-2-en-1-one (25.0 mg, 0.08 mmol) and N-(3-aminophenyl)acrylamide (7.2 mg, 0.05 mmol) were dissolved in 2-butanol (2.0 mL). Trifluoroacetic acid (4.8 μL, 0.06 mmol) was added to the reaction mixture and reacted at 110° C. for 5 hours, and then the solvent was concentrated. This reaction mixture was neutralized by adding 7 N ammonia solution dissolved in methanol. The residue was isolated by column chromatography to obtain a title compound (5.1 mg, yield: 24.3%).

¹H NMR (500 MHz, CD₃OD) δ 7.22-7.21 (m, 1H), 7.19-7.18 (m, 1H), 7.15-7.14 (m, 1H), 6.97-7.95 (m, 1H), 6.79 (s, 1H), 6.47-6.42 (m, 2H), 6.37-6.31 (m, 1H), 5.76-5.73 (m, 1H), 5.49 (s, 1H), 4.59-4.52 (m, 1H), 4.40-4.34 (m, 1H), 3.95-3.87 (m, 1H), 3.44 (s, 2H), 2.81-2.74 (m, 1H), 2.17-2.15 (m, 1H), 2.01-1.96 (m, 1H), 1.85-1.83 (m, 1H), 1.73-1.60 (m, 2H)

Example 27: Preparation of 14(3R,4R)-4-methyl-3-(methyl(2-(4-(4-methylpiperazin-1-yl)phenylamino)-7H-pyrrolo[2,3-d]pyrimidin-4-yl)amino)piperidin-1-yl)prop-2-en-1-one

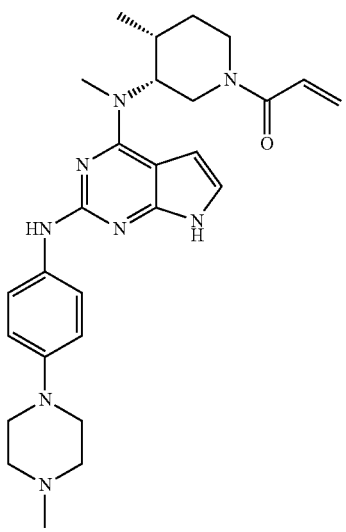 [SMILES: C=CC(=O)N1CC[C@@H](C)[C@@H](N(C)c2nc(Nc3ccc(N4CCN(C)CC4)cc3)nc3[nH]ccc23)C1]

Step 1: Preparation of 2,4-dichloro-7-tosyl-7H-pyrrolo[2,3-d]pyrimidine 2,4-Dichloro-7H-pyrrolo[2,3-d]pyrimidine (3.0 g, 15.9 mmol) and 4-toluenesulfonyl chloride (3.7 g, 23.9 mmol) were dissolved in acetone (20.0 mL). After cooling to 0° C., 2 M sodium hydroxide solution (12.0 ml) was slowly added dropwise thereto, stirred for 2 hours, and then filtered through acetone to obtain a title compound (2.9 g, yield: 80.0%).

¹H NMR (500 MHz, CD₃OD) δ 8.12 (d, 2H), 7.76 (d, 1H), 7.37 (d, 2H), 6.68 (d, 1H), 2.43 (s, 3H)

Step 2: Preparation of tert-butyl(3R,4R)-3-((2-chloro-7-tosyl-7H-pyrrolo[2,3-d]pyrimidin-4-yl)(methyl)amino)-4-methylpiperidine-1-carboxylate 2,4-dichloro-7-tosyl-7H-pyrrolo[2,3-d]pyrimidine (1.5 g, 5.1 mmol) and (3R,4R)-1-benzyl-N,4-dimethylpiperidin-3-amine (965.0 mg, 5.1 mmol) were dissolved in ethanol (20.0 mL). N,N-Diisopropylethylamine (4.2 g, 30.6 mmol) was added dropwise thereto and reacted at 110° C. for 12 hours, then concentrated under reduced pressure, and the residue was isolated with column chromatography to obtain a title compound (1.3 g, yield: 85.0%).

¹H NMR (500 MHz, CD₃OD) δ 8.18 (d, 2H), 7.45 (d, 1H), 7.37-7.22 (m, 7H), 6.62 (s, 1H), 3.76-3.51 (m, 2H), 3.49-3.31 (m, 3H), 2.89-2.45 (m, 1H), 2.38 (s, 3H), 2.35-2.13 (m, 1H), 1.70-1.56 (m, 3H), 0.88 (s, 3H)

Step 3: Preparation of tert-butyl(3R,4R)-4-methyl-3-(methyl(2-(4-(4-methylpiperazin-1-yl)phenyl)amino)-7-tosyl-7H-pyrrolo[2,3-d]pyrimidin-4-yl)amino)piperidine-1-carboxylate After tert-butyl(3R,4R)-3-((2-chloro-7-tosyl-7H-pyrrolo[2,3-d]pyrimidin-4-yl)(methyl)amino)-4-methylpiperidine-1-carboxylate (100 mg, 0.3 mmol), palladium acetate (3.04 mg, 0.02 mmol), 4,5-bis(diphenylphosphino)-9,9-dimethylxanthene (7.87 mg, 0.01 mmol), 4-(4-methylpiperazin-1-yl)aniline (53.26 mg, 0.2 mmol) and cesium carbonate (184 mg, 0.6 mmol) were dissolved in dioxane (1.0 mL), and the mixture was reacted at 120° C. using a microwave apparatus for 30 minutes. The organic layer was isolated, treated with magnesium sulfate, filtered, and then concentrated under reduced pressure. The residue was isolated by column chromatography to obtain a title compound (75.0 mg, yield: 65.0%).

¹H NMR (500 MHz, CD₃OD) δ 7.93 (d, 2H), 7.64 (d, 1H), 7.31-7.22 (m, 4H), 7.20-7.16 (m, 4H), 6.98 (d, 2H), 6.12 (d, 1H), 3.50 (s, 2H), 3.32-3.31 (m, 1H), 3.15 (s, 4H), 2.72 (t, 1H), 2.68 (s, 3H), 2.69 (s, 4H), 2.65 (d, 1H), 2.51 (s, 1H), 2.43 (s, 1H), 2.35 (s, 3H), 2.27 (s, 3H), 2.20 (s, 1H), 1.85 (s, 1H), 1.56 (s, 1H), 0.89 (d, 3H)

Step 4: Preparation of tert-butyl(3R,4R)-4-methyl-3-(methyl(2-((4-(4-methylpiperazin-1-yl)phenyl)amino)-7H-pyrrolo[2,3-d]pyrimidin-4-yl)amino)piperidine-1-carboxylate After tert-butyl(3R,4R)-4-methyl-3-(methyl(2-(4-(4-methylpiperazin-1-yl)phenyl)amino)-7-tosyl-7H-pyrrolo[2,3-d]pyrimidin-4-yl)amino)piperidine-1-carboxylate (100 mg, 0.2 mmol) was dissolved in methanol (3.0 mL), potassium hydroxide (16 mg, 0.4 mmol) was added thereto. After reacting at 70° C. for 12 hours, the methanol was removed, and water and diethyl ether were added. The organic layer was isolated, treated with magnesium sulfate, filtered, and then concentrated under reduced pressure. The residue was isolated by column chromatography to obtain a title compound (80.0 mg, yield: 88.0%).

¹H NMR (500 MHz, CD₃OD) δ 7.58 (d, 2H), 7.32-7.29 (m, 4H), 7.24-7.22 (m, 1H), 6.94 (d, 2H), 6.77 (d, 1H), 6.56 (d, 1H), 3.50 (s, 2H), 3.33-3.30 (m, 1H), 3.15 (s, 4H), 2.72 (t, 1H), 2.70 (s, 4H), 2.67 (d, 1H), 2.52 (s, 1H), 2.45 (s, 1H), 2.37 (s, 3H), 2.29 (s, 3H), 2.23 (s, 1H), 1.87 (s, 1H), 1.57 (s, 1H), 0.88 (d, 3H)

Step 5: Preparation of N4-methyl-N2-(4-(4-methylpiperazin-1-yl)phenyl)-N4-((3R,4R)-4-methylpiperidin-3-yl)-7H-pyrrolo[2,3-d]pyrimidine-2,4-diamine After tert-butyl(3R,4R)-4-methyl-3-(methyl(2-((4-(4-methylpiperazin-1-yl)phenyl)amino)-7H-pyrrolo[2,3-d]pyrimidin-4-yl)amino)piperidine-1-carboxylate (70.0 mg, 0.1 mmol) was dissolved in methanol, an excess of 10 wt. % palladium carbon was added and replaced with hydrogen gas. After stirring for 5 hours, the reaction mixture was filtered through celite. The filtrate was concentrated to obtain a title compound (65.0 mg, yield: 98.0%).

$^1$H NMR (500 MHz, CD$_3$OD) δ 7.71 (d, 2H), 6.94 (d, 2H), 6.93 (d, 1H), 6.47 (d, 1H), 3.37-3.33 (m, 2H), 3.16 (s, 4H), 2.74 (t, 1H), 2.72 (s, 4H), 2.66 (d, 1H), 2.54 (s, 1H), 2.42 (s, 1H), 2.36 (s, 3H), 2.30 (s, 3H), 2.24 (s, 1H), 1.88 (s, 1H), 0.99 (d, 3H)

Step 6: Preparation of 1-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)prop-2-en-1-one N4-methyl-N2-(4-(4-methylpiperazin-1-yl)phenyl)-N4-((3R,4R)-4-methylpiperidin-3-yl)-7H-pyrrolo[2,3-d]pyrimidin-2,4-diamine (40 mg, 0.1 mmol) was dissolved in dichloromethane (1.0 mL) to which triethylamine (40.0 μL, 0.3 mmol) was added, and the mixture was stirred for 10 minutes. After cooling to 0° C., acryloyl chloride (8.0 μL, 0.1 mmol) was added, followed by stirring for 2 hours. The organic layer was isolated, treated with magnesium sulfate, filtered, and then concentrated under reduced pressure. The residue was isolated by column chromatography to obtain a title compound (11.0 mg, yield: 23.0%).

$^1$H NMR (500 MHz, CD$_3$OD) δ 7.16 (d, 2H), 7.09 (s, 1H), 6.98 (d, 2H), 6.83-6.39 (m, 2H), 6.345-6.19 (m, 1H), 5.77-5.65 (m, 1H), 4.76 (s, 1H), 3.81-3.77 (m, 2H), 3.68-3.63 (m, 2H), 3.36 (s, 3H), 3.22 (s, 4H), 2.64 (s, 4H), 2.37 (s, 3H), 2.24 (s, 1H), 1.64 (s, 1H), 1.59 (s, 1H), 0.99-0.97 (m, 3H)

Example 28: Preparation of 3-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)-3-oxopropanenitrile

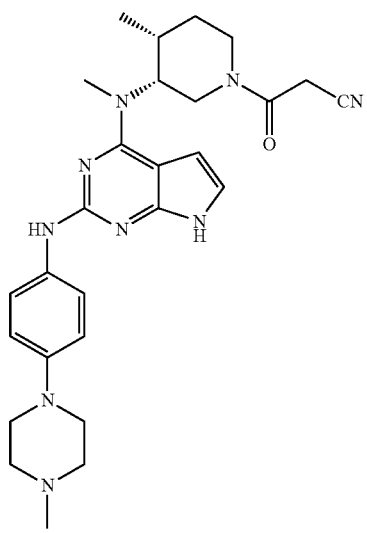 [SMILES: C[C@@H]1CCN(C(=O)CC#N)C[C@@H]1N(C)c1nc(Nc2ccc(N3CCN(C)CC3)cc2)nc2[nH]ccc12]

Step 1: Preparation of 2,4-dichloro-7-tosyl-7H-pyrrolo[2,3-d]pyrimidine 2,4-Dichloro-7H-pyrrolo[2,3-d]pyrimidine (3.0 g, 15.9 mmol) and 4-toluenesulfonyl chloride (3.7 g, 23.9 mmol) were dissolved in acetone (20.0 mL). After cooling to 0° C., 2 M sodium hydroxide solution (12.0 mL) was slowly added dropwise, followed by stirring for 2 hours, and then washed and filtered with acetone to obtain a title compound (2.9 g, yield: 80.0%).

$^1$H NMR (500 MHz, CD$_3$OD) δ 8.12 (d, 2H), 7.76 (d, 1H), 7.37 (d, 2H), 6.68 (d, 1H), 2.43 (s, 3H)

Step 2: Preparation of tert-butyl(3R,4R)-3-((2-chloro-7-tosyl-7H-pyrrolo[2,3-d]pyrimidin-4-yl)(methyl)amino)-4-methylpiperidine-1-carboxylate 2,4-dichloro-7-tosyl-7H-pyrrolo[2,3-d]pyrimidine (1.5 g, 5.1 mmol) and (3R,4R)-1-benzyl-N,4-dimethylpiperidine-3-amine (965.0 mg, 5.1 mmol) were dissolved in ethanol (20.0 mL). N,N-Diisopropylethylamine (4.2 g, 30.6 mmol) was added dropwise and the mixture was reacted at 110° C. for 12 hours and then concentrated under reduced pressure. The residue was isolated by column chromatography to obtain a title compound (1.3 g, yield: 85.0%).

$^1$H NMR (500 MHz, CD$_3$OD) δ 8.18 (d, 2H), 7.45 (d, 1H), 7.37-7.22 (m, 7H), 6.62 (s, 1H), 3.76-3.51 (m, 2H), 3.49-3.31 (m, 3H), 2.89-2.45 (m, 1H), 2.38 (s, 3H), 2.35-2.13 (m, 1H), 1.70-1.56 (m, 3H), 0.88 (s, 3H)

Step 3: Preparation of tert-butyl(3R,4R)-4-methyl-3-(methyl(2-((4-(4-methylpiperazin-1-yl)phenyl)amino)-7-tosyl-7H-pyrrolo[2,3-d]pyrimidin-4-yl)amino)piperidine-1-carboxylate After tert-butyl(3R,4R)-3-((2-chloro-7-tosyl-7H-pyrrolo[2,3-d]pyrimidin-4-yl)(methyl)amino)-4-methylpiperidine-1-carboxylate (100 mg, 0.3 mmol), palladium acetate (3.04 mg, 0.02 mmol), 4,5-bis(diphenylphosphino)-9,9-dimethylxanthene (7.87 mg, 0.01 mmol), 4-(4-methylpiperazin-1-yl)aniline (53.26 mg, 0.2 mmol) and cesium carbonate (184 mg, 0.6 mmol) were dissolved in dioxane (1.0 mL), the mixture was reacted at 120° C. using a microwave apparatus for 30 minutes. The organic layer was isolated, treated with magnesium sulfate, filtered, and then concentrated under reduced pressure. The residue was isolated by column chromatography to obtain a title compound (75.0 mg, yield: 65%).

$^1$H NMR (500 MHz, CD$_3$OD) δ 7.93 (d, 2H), 7.64 (d, 1H), 7.31-7.22 (m, 4H), 7.20-7.16 (m, 4H), 6.98 (d, 2H), 6.12 (d, 1H), 3.50 (s, 2H), 3.32-3.31 (m, 1H), 3.15 (s, 4H), 2.72 (t, 1H), 2.68 (s, 3H), 2.69 (s, 4H), 2.65 (d, 1H), 2.51 (s, 1H), 2.43 (s, 1H), 2.35 (s, 3H), 2.27 (s, 3H), 2.20 (s, 1H), 1.85 (s, 1H), 1.56 (s, 1H), 0.89 (d, 3H)

Step 4: Preparation of tert-butyl(3R,4R)-4-methyl-3-(methyl(2-((4-(4-methylpiperazin-1-yl)phenyl)amino)-7H-pyrrolo[2,3-d]pyrimidin-4-yl)amino)piperidine-1-carboxylate After tert-butyl(3R,4R)-4-methyl-3-(methyl(2-((4-(4-methylpiperazin-1-yl)phenyl)amino)-7-tosyl-7H-pyrrolo[2,3-d]pyrimidin-4-yl)amino)piperidine-1-carboxylate (100.0 mg, 0.2 mmol) was dissolved in methanol (3.0 mL), potassium hydroxide (16.0 mg, 0.4 mmol) was added thereto. After reacting at 70° C. for 12 hours, methanol was removed, and water and diethyl ether were added. The organic layer was isolated, treated with magnesium sulfate, filtered, and then concentrated under reduced pressure. The residue was isolated by column chromatography to obtain 80.0 mg (yield: 88.0%) of the title compound (80.0 mg, yield: 88.0%).

$^1$H NMR (500 MHz, CD$_3$OD) δ 7.58 (d, 2H), 7.32-7.29 (m, 4H), 7.24-7.22 (m, 1H), 6.94 (d, 2H), 6.77 (d, 1H), 6.56

(d, 1H), 3.50 (s, 2H), 3.33-3.30 (m, 1H), 3.15 (s, 4H), 2.72 (t, 1H), 2.70 (s, 4H), 2.67 (d, 1H), 2.52 (s, 1H), 2.45 (s, 1H), 2.37 (s, 3H), 2.29 (s, 3H), 2.23 (s, 1H), 1.87 (s, 1H), 1.57 (s, 1H), 0.88 (d, 3H)

Step 5: Preparation of N4-methyl-N2-(4-(4-methylpiperazin-1-yl)phenyl)-N4-((3R,4R)-4-methylpiperidin-[2,3-d]pyrimidine-2,4-diamine After tert-butyl(3R,4R)-4-methyl-3-(methyl(2-((4-(4-methylpiperazin-1-yl)phenyl)amino)-7H-pyrrolo[2,3-d]pyrimidin-4-yl)amino)piperidine-1-carboxylate (70.0 mg, 0.1 mmol) was dissolved in methanol, an excess of 10 wt. % palladium carbon was added and replaced with hydrogen gas. The reaction mixture was stirred for 5 hours, filtered through celite, and the filtrate was concentrated to obtain a title compound (65.0 mg, yield: 98.0%).
$^{1}$H NMR (500 MHz, CD$_{3}$OD) δ 7.71 (d, 2H), 6.94 (d, 2H), 6.93 (d, 1H), 6.47 (d, 1H), 3.37-3.33 (m, 2H), 3.16 (s, 4H), 2.74 (t, 1H), 2.72 (s, 4H), 2.66 (d, 1H), 2.54 (s, 1H), 2.42 (s, 1H), 2.36 (s, 3H), 2.30 (s, 3H), 2.24 (s, 1H), 1.88 (s, 1H), 0.99 (d, 3H)

Step 6: Preparation of 3-((3R,4R)-4-methyl-3-(methyl 2-(4-(4-methylpiperazin-1-yl)phenyl)amino)-7H-pyrrolo[2,3-d]pyrimidin-4-yl)amino)piperidin7-1-yl)-3-oxopropanenitrile After N4-methyl-N2-(4-(4-methylpiperazin-1-yl)phenyl)-N4-((3R,4R)-4-methylpiperidin-[2,3-d]pyrimidine-2,4-diamine (50.0 mg, 0.1 mmol) and 2-cyanoacetic acid (20.1 mg, 0.1 mmol) were dissolved in tetrahydrofuran, 1-[bis(dimethylamino)methylene]-1H-1,2,3-triazolo[4,5-b]pyridinium 3-oxyhexafluorophosphate (89.9 mg, 0.1 mmol) and N,N-diisopropylethylamine (30.64, 0.2 mmol) were added thereto. The mixture was stirred for 20 hours and then water and diethyl ether were added. The organic layer was isolated, treated with magnesium sulfate, filtered, and then concentrated under reduced pressure. The residue was isolated by column chromatography to obtain a title compound (9.0 mg, yield: 20.0%).
$^{1}$H NMR (500 MHz, CD$_{3}$OD) δ 7.49 (d, 2H), 6.93 (d, 2H), 6.91 (d, 1H), 6.49 (d, 1H), 4.09-4.01 (dd, 1H), 3.89-3.82 (m, 1H), 3.72-3.60 (m, 1H), 3.58-3.52 (m, 1H), 3.34 (s, 3H), 3.16 (s, 4H), 2.64 (s, 4H), 2.46 (s, 1H), 2.35 (s, 3H), 2.19 (s, 2H), 1.89-1.75 (m, 1H), 1.69-1.55 (m, 2H), 1.13-1.09 (m, 3H)

Example 29: Preparation of N-(3-(2-(4-(4-methylpiperazin-1-yl)phenylamino)-7H-pyrrolo[2,3-d]pyrimidin-4-ylamino)cyclohexyl)acrylamide

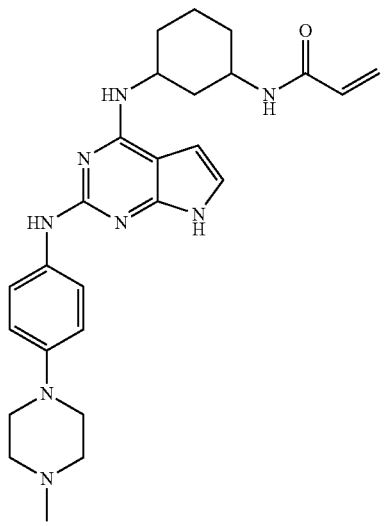 [SMILES: C=CC(=O)NC1CCCC(Nc2nc(Nc3ccc(N4CCN(C)CC4)cc3)nc3[nH]ccc23)C1]

A title compound (4.0 mg, yield: 17.4%) was prepared in the same manner as in Example 1, except that tert-butyl(3-aminocyclohexyl)carbonate was used instead of tert-butyl (R)-3-aminopiperidine-1-carboxylate in Example 1.
$^{1}$H NMR (500 MHz, CD$_{3}$OD) δ 7.55 (d, 2H), 6.94 (d, 2H), 6.92 (d, 1H), 6.84-6.69 (m, 1H), 6.47-6.30 (m, 1H), 6.28-6.23 (m, 1H), 5.65-5.63 (m, 1H), 4.45 (s, 1H), 3.16 (s, 4H), 3.09-2.98 (m1 3H), 2.64-2.61 (m, 4H), 2.33 (s, 3H), 2.08-2.01 (m, 1H), 1.92-1.91 (m, 1H), 1.75-1.62 (m, 2H)

Example 30: Preparation of (R)-1-(3-(6-(4-(4-methylpiperazin-1-yl)phenylamino)-1H-pyrazolo[3,4-d]pyrimidin-4-ylamino)piperidin-1-yl)prop-2-en-1-one

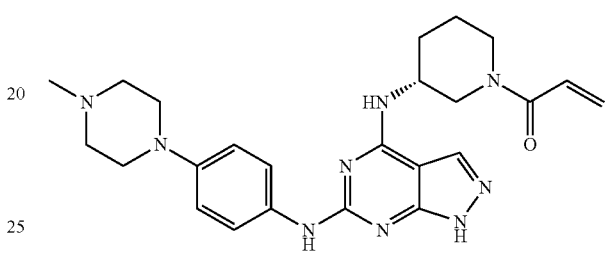

Step 1: Preparation of tert-butyl(R)-3-((6-chloro-1H-pyrazolo[3,4-d]pyrimidin-4-yl)amino)piperidine-1-carboxylate After 4,6-dichloro-1H-pyrazolo[3,4-d]pyrimidine (1.0 g, 5.3 mmol) was dissolved in ethanol (10 mL), N,N-diisopropylethylamine (695 µL, 7.9 mmol) and tert-butyl(R)-3-aminopiperidine-1-carboxylate (1.3 g, 6.35 mmol) were added thereto. The reaction mixture was stirred at 110° C. for 12 hours, and the organic layer was isolated, treated with magnesium sulfate, filtered, and then concentrated under reduced pressure. The residue was isolated by column chromatography to obtain a title compound (1.2 g, yield: 62.9%).
$^{1}$H NMR (500 MHz, CD$_{3}$OD) δ 8.11 (s, 1H), 4.26-4.07 (m, 1H), 3.98-3.90 (m, 1H), 3.70-3.65 (m, 1H), 3.16-3.10 (m, 2H), 2.10-2.05 (m, 1H), 1.87-1.75 (m, 1H), 1.71-1.58 (m, 2H), 1.45-1.34 (m, 9H)

Step 2: Preparation of (R)-6-chloro-N-(piperidin-3-yl)-1H-pyrazolo[3,4-d]pyrimidin-4-amine hydrochloride To tert-butyl(R)-3-((6-chloro-1H-pyrazolo[3,4-d]pyrimidin-4-yl)amino)piperidine-1-carboxylate (500.0 mg, 1.4 mmol), 6 N hydrochloric acid solution (5.0 mL, excessive amount) dissolved in methanol was added. After stirring at room temperature for 30 minutes, the reaction mixture was concentrated and the subsequent reaction was carried out without isolation.
$^{1}$H NMR (500 MHz, CD$_{3}$OD) δ 8.17 (s, 1H), 4.55-4.51 (m, 1H), 3.68-3.65 (m, 2H), 3.16-2.92 (m, 2H), 2.21-2.10 (m, 2H), 1.98-1.83 (m, 2H)

Step 3: Preparation of (R)-1-(3-((6-chloro-1H-pyrazolo[3,4-d]pyrimidin-4-yl)amino)piperidin-1-yl)prop-2-en-1-one After (R)-6-chloro-N-(piperidin-3-yl)-1H-pyrazolo[3,4-d]pyrimidin-4-amine hydrochloride (421.0 mg, 1.5 mmol)

was dissolved in dichloromethane (10.0 mL), triethylamine (608.8 μL, 4.4 mmol) was added at 0° C., and the mixture was stirred for 30 minutes. Acryloyl chloride (124.2 μL, 1.5 mmol) was added to the reaction mixture and was stirred at 0° C. for 1 hour. The organic layer was isolated, treated with magnesium sulfate, filtered, and then concentrated under reduced pressure. The residue was isolated by column chromatography to obtain a title compound (130.0 mg, yield: 29.3%).

$^1$H NMR (500 MHz, CD$_3$OD) δ 8.10 (s, 1H), 6.88-6.77 (m, 1H), 6.19-6.16 (m, 1H), 5.76-5.64 (m, 1H), 4.47-4.24 (m, 2H), 4.10 (d, 1H), 3.98 (d, 1H), 3.21-3.06 (m, 1H), 2.17 (s, 1H), 1.94-1.91 (m, 1H), 1.83-1.79 (m, 1H), 1.67-1.64 (m, 1H)

Step 4: Preparation of (R)-1-(3-(6-(4-(4-methylpiperazin-1-yl)phenylamino)-1H-pyrazolo[3,4-d]pyrimidin-4-ylamino)piperidin-1-yl)prop-2-en-1-one (R)-1-(3-((6-chloro-1H-pyrazolo[3,4-d]pyrimidin-4-yl)amino)piperidin-1-yl)prop-2-en-1-one (30.0 mg, 0.10 mmol) and 4-(4-methylpiperazin-1-yl)aniline (12.5 mg, 0.07 mmol) were dissolved in 2-butanol (2.0 mL). Trifluoroacetic acid (6.0 μL, 0.08 mmol) was added to the reaction mixture, followed by reacting at 110° C. for 12 hours, and then the solvent was concentrated. This reaction mixture was neutralized by adding 7 N ammonia solution dissolved in methanol. The residue was isolated by column chromatography to obtain a title compound (6.6 mg, yield: 24.4%).

$^1$H NMR (500 MHz, CD$_3$OD) δ 7.90-7.88 (m, 1H), 7.59-7.53 (m, 2H), 6.96-6.91 (m, 2H), 6.90-6.49 (m, 1H), 6.31-6.05 (m, 1H), 5.84-5.48 (m, 1H), 4.43-4.20 (m, 1H), 4.07-4.05 (m, 1H), 3.18-3.13 (m, 4H), 2.75-2.73 (m, 2H), 2.62-2.54 (m, 5H), 2.32 (s, 3H), 2.17-2.10 (m, 1H), 1.99-1.88 (m, 1H), 1.80-1.67 (m, 2H)

Example 31: Preparation of (R)-1-(3-(6-(1-(2,2-difluoroethyl)-1H-pyrazol-4-ylamino)-1H-pyrazolo[3,4-d]pyrimidin-4-ylamino)piperidin-1-yl)prop-2-en-1-one

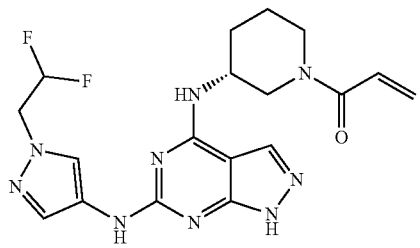

A title compound (9.3 mg, yield: 28.2%) was prepared in the same manner as in Example 30, except that 1-(2,2-difluoroethyl)-1H-pyrazol-4-amine was used instead of 4-(4-methylpiperazin-1-yl)aniline in Example 30.

$^1$H NMR (500 MHz, CD$_3$OD) δ 8.12-8.5 (m, 1H), 7.91 (s, 1H), 7.65-7.55 (m, 1H), 6.89-6.50 (m, 1H), 6.27-6.07 (m, 2H), 5.80-5.55 (m, 1H), 4.58-4.45 (m, 2H), 4.28-4.20 (m, 1H), 4.11-4.03 (m, 1H), 3.20-3.16 (m, 2H), 2.75-2.69 (m, 1H), 2.20-2.15 (m, 1H), 1.94-1.80 (m, 1H), 1.78-1.62 (m, 2H)

Example 32: Preparation of (R)-1-(3-(6-(1-methyl-1H-pyrazol-4-ylamino)-1H-pyrazolo[3,4-d]pyrimidin-4-ylamino)piperidin-1-yl)prop-2-en-1-one

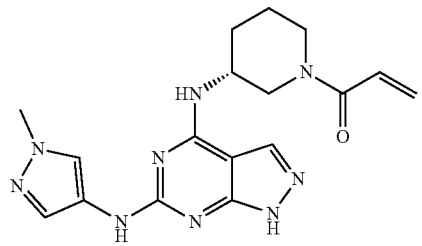

A title compound (5.2 mg, yield: 12.8%) was prepared in the same manner as in Example 30, except that 1-methyl-1H-pyrazol-4-amine was used instead of 4-(4-methylpiperazin-1-yl)aniline in Example 30.

$^1$H NMR (500 MHz, CD$_3$OD) δ 7.95 (d, 2H), 7.55 (s, 1H), 6.86-6.56 (m, 1H), 6.26-6.07 (m, 1H), 5.79-5.53 (m, 1H), 4.26-4.20 (m, 1H), 4.09 (d, 2H), 3.82 (s, 3H), 3.22-3.16 (m, 1H), 2.23-2.17 (m, 1H), 1.96-1.92 (m, 1H), 1.80-1.71 (m, 1H), 1.67-1.60 (m, 2H)

Example 33: Preparation of (R)-1-(3-(6-(1-ethyl-1H-pyrazol-4-ylamino)-1H-pyrazolo[3,4-d]pyrimidin-4-ylamino)piperidin-1-yl)prop-2-en-1-one

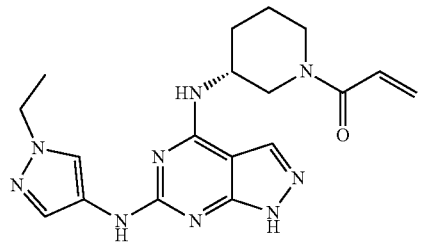 [SMILES: C=CC(=O)N1CCC[C@@H](Nc2nc(Nc3cnn(CC)c3)nc3[nH]ncc23)C1]

A title compound (7.5 mg, yield: 17.9%) was prepared in the same manner as in Example 30, except that 1-ethyl-1H-pyrazol-4-amine was used instead of 4-(4-methylpiperazin-1-yl)aniline in Example 30.

$^1$H NMR (500 MHz, CD$_3$OD) δ 7.99 (d, 1H), 7.91 (s, 1H), 7.57 (d, 1H), 6.86-6.57 (m, 1H), 6.26-6.07 (m, 1H), 5.79-5.54 (m, 1H), 4.27-4.21 (m, 1H), 4.14-4.07 (m, 2H), 3.45-3.36 (m, 1H), 3.22-3.16 (m, 2h), 2.20-2.17 (m, 1H), 1.97-1.94 (m, 1H), 1.80-1.72 (m, 1H), 1.68-1.61 (m, 2H), 1.46-1.41 (d, 3H)

Example 34: Preparation of (R)-1-(3-(6-(1-(difluoromethyl)-1H-pyrazol-4-ylamino)-1H-pyrazolo[3,4-d]pyrimidin-4-ylamino)piperidin-1-yl)prop-2-en-1-one

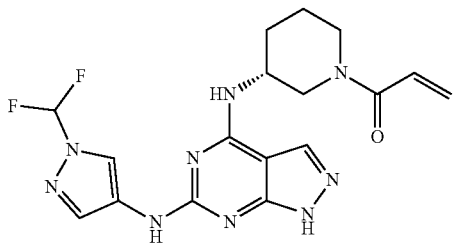 [SMILES: C=CC(=O)N1CCC[C@@H](Nc2nc(Nc3cnn(C(F)F)c3)nc3[nH]ncc23)C1]

A title compound (6.5 mg, yield: 14.7%) was prepared in the same manner as in Example 30, except that 1-(difluoromethyl)-1H-pyrazol-4-amine was used instead of 4-(4-methylpiperazin-1-yl)aniline in Example 30.

$^1$H NMR (500 MHz, CD$_3$OD) δ 8.42 (s, 1H), 7.93 (d, 1H), 7.79 (d, 1H), 7.50-7.26 (m, 1H), 6.85-6.61 (m, 1H), 6.26-6.07 (m, 1H), 5.79-5.55 (m, 1H), 4.29-4.21 (m, 1H), 4.09-4.04 (m, 2H), 3.50-3.44 (m, 1H), 2.21-2.17 (m, 1H), 1.94-1.80 (m, 1H), 1.71-1.66 (m, 3H)

Example 35: Preparation of (R)-2-(4-(4-(1-acryloylpiperidin-3-ylamino)-1H-pyrazolo[3,4-d]pyrimidin-6-ylamino)-1H-pyrazol-1-yl)-N-methylacetamide

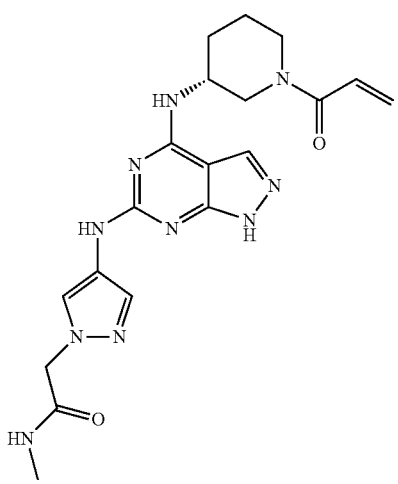 [SMILES: C=CC(=O)N1CCC[C@@H](Nc2nc(Nc3cnn(CC(=O)NC)c3)nc3[nH]ncc23)C1]

A title compound (12.4 mg, yield: 26.6%) was prepared in the same manner as in Example 30, except that 2-(4-amino-1H-pyrazol-1-yl)-N-methylacetamide was used instead of 4-(4-methylpiperazin-1-yl)aniline in Example 30.

$^1$H NMR (500 MHz, CD$_3$OD) δ 8.10 (d, 1H), 7.91 (s, 1H), 7.65-7.59 (m, 1H), 6.84-6.60 (m, 1H), 6.26-6.07 (m, 1H), 5.78-5.55 (m, 1H), 4.79-4.77 (m, 2H), 4.28-4.21 (m, 1H), 4.07-4.05 (m, 1H), 3.49-3.13 (m, 2H), 2.76 (d, 3H), 2.17-2.13 (m, 1H), 1.94-1.82 (m, 1H), 1.80-1.61 (m, 3H)

Example 36: Preparation of (R)-1-(3-(5-chloro-2-(4-(4-methylpiperazin-1-yl)phenylamino)-7H-pyrrolo[2,3-d]pyrimidin-4-ylamino)piperidin-1-yl)prop-2-en-1-one

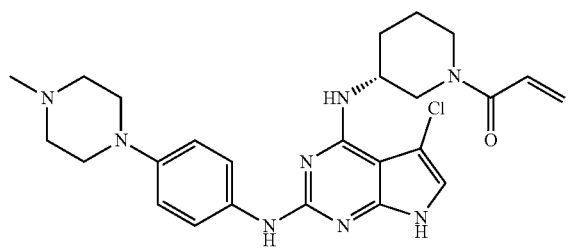 [SMILES: C=CC(=O)N1CCC[C@@H](Nc2nc(Nc3ccc(N4CCN(C)CC4)cc3)nc3[nH]cc(Cl)c23)C1]

Step 1: Preparation of 2,4,5-trichloro-7H-pyrrolo[2,3-d]pyrimidine

After 2,4-dichloro-7H-pyrrolo[2,3-d]pyrimidine (3.0 g, 16.0 mmol) and N-chlorosuccinimide (2.6 g, 19.2 mmol) were dissolved in N,N-dimethylformamide (20.0 mL), the mixture was stirred at 0° C. for 8 hours. The organic layer was isolated, treated with magnesium sulfate, filtered, and then concentrated under reduced pressure. The residue was isolated by column chromatography to obtain a title compound (2.6 g, yield: 72.5%).

$^1$H NMR (500 MHz, DMSO-d$_6$) δ 13.07 (s, 1H), 7.94 (s, 1H)

Step 2: Preparation of (R)-tert-butyl 3-((2,5-dichloro-7H-pyrrolo[2,3-d]pyrimidin-4-yl)amino)piperidine-1-carboxylate After 2,4,5-trichloro-7H-pyrrolo[2,3-d]pyrimidine (2.6 g, 11.6 mmol) was dissolved in ethanol (25.0 mL), N,N-diisopropylethylamine (3.0 mL, 17.4 mmol) and tert-butyl (R)-3-aminopiperidine-1-carboxylate (2.8 g, 13.9 mmol) were added thereto. After stirring the reaction mixture at 110° C. for 12 hours, the organic layer was isolated, treated with magnesium sulfate, filtered and then concentrated under reduced pressure. The residue was isolated by column chromatography to obtain a title compound (3.5 g, yield: 77.4%).

$^1$H NMR (500 MHz, DMSO-d$_6$) δ 6.96 (s, 1H), 6.09 (bs, 1H), 4.14 (bs, 1H), 3.60-3.30 (m, 4H), 1.98-1.15 (m, 13H)

Step 3: Preparation of (R)-2,5-dichloro-N-(piperidin-3-yl)-7H-pyrrolo[2,3-d]pyrimidin-4-amine hydrochloride To (R)-tert-butyl 3-((2,5-dichloro-7H-pyrrolo[2,3-d]pyrimidin-4-yl)amino)piperidine-1-carboxylate (3.5 g, 9.0 mmol), 6 N hydrochloric acid solution (15.0 mL, excessive amount) dissolved in methanol was added. After stirring at room temperature for 30 minutes, the reaction mixture was concentrated and the subsequent reaction was carried out without isolation.

$^1$H NMR (500 MHz, DMSO-d$_6$) δ 12.2 (bs, 1H), 9.53-9.51 (m, 1H), 9.10-9.08 (m, 1H), 7.34 (s, 1H), 6.63-6.61 (m, 1H), 4.48-4.47 (m, 1H), 3.29-3.27 (m, 1H), 3.17-3.14 (m, 1H), 3.08-3.02 (m, 1H), 2.71-2.69 (m, 1H), 1.95-1.94 (m, 1H), 1.85-1.84 (m, 1H), 1.79-1.72 (m, 2H)

Step 4: Preparation of (R)-1-(3-((2,5-dichloro-7H-pyrrolo[2,3-d]pyrimidin-4-yl)amino)piperidin-1-yl)prop-2-en-1-one After (R)-2,5-dichloro-N-(piperidin-3-yl)-7H-pyrrolo[2,3-d]pyrimidin-4-amine hydrochloride (3.4 g, 10.5 mmol) was dissolved in a 3:1 mixed solution of tetrahydrofuran:distilled water, sodium bicarbonate (2.6 g, 31.4 mmol) was added at 0° C. and the mixture was stirred for 30 minutes. Acryloyl chloride (1.3 mL, 10.5 mmol) was added to the reaction mixture and was stirred at 0° C. for 1 hour. The organic layer was isolated, treated with magnesium sulfate, filtered, and then concentrated under reduced pressure. The residue was isolated by column chromatography to obtain a title compound (2.7 g, yield: 87.1%).

$^1$H NMR (500 MHz, DMSO-d$_6$) δ 12.1 (bs, 1H), 7.34-7.32 (m, 1H), 6.81-6.79 (m, 1H), 6.42-6.40 (m, 1H), 5.68-5.59 (m, 1H), 4.16-3.33 (m, 4H), 3.10-3.02 (m, 1H), 1.94-1.83 (m, 2H), 1.66-1.50 (m, 2H)

Step 5: Preparation of (R)-1-(3-(5-chloro-2-(4-(4-methylpiperazin-1-yl)phenylamino)-7H-pyrrolo[2,3-d]pyrimidin-4-ylamino)piperidin-1-yl)prop-2-en-1-one (R)-1-(3-((2,5-dichloro-7H-pyrrolo[2,3-d]pyrimidin-4-yl)amino)piperidin-1-yl)prop-2-en-1-one (200.0 mg, 0.6 mmol) and 4-(4-methylpiperazin-1-yl)aniline (75.0 mg, 0.4 mmol) were dissolved in 2-butanol (15.0 mL). Trifluoroacetic acid (36.0 μL, 0.5 mmol) was added to the reaction mixture, followed by reacting at 110° C. for 12 hours, and then the solvent was concentrated. The reaction mixture was neutralized by adding 7 N ammonia solution dissolved in methanol, and the residue was isolated by column chromatography to obtain a title compound (4 mg, yield: 9.6%).

$^1$H NMR (500 MHz, CD$_3$OD) δ 7.56-7.51 (m, 2H), 6.95-6.91 (m, 2H), 6.86-6.49 (m, 2H), 6.26-6.04 (m, 1H), 5.79-5.43 (m, 1H), 4.39-4.25 (m, 1H), 3.93-3.80 (m, 1H), 3.70-3.63 (m, 2H), 3.50-3.31 (m, 1H), 3.13-3.12 (m, 4H), 2.67-2.66 (m, 4H), 2.37 (s, 3H), 2.08-2.02 (m, 1H), 1.91-1.84 (m, 2H), 1.66-1.59 (m, 1H)

Example 37: Preparation of (R)-1-(3-(5-chloro-2-(1-ethyl-1H-pyrazol-4-ylamino)-7H-pyrrolo[2,3-d]pyrimidin-4-ylamino)piperidin-1-yl)prop-2-en-1-one

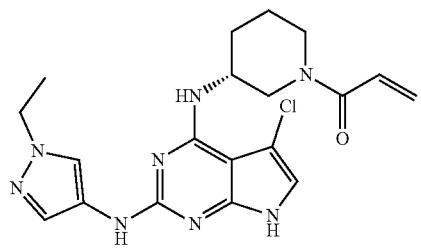

A title compound (33.1 mg, yield: 23.5%) was prepared in the same manner as in Example 36, except that 1-ethyl-1H-pyrazol-4-amine was used instead of 4-(4-methylpiperazin-1-yl)aniline in Example 36.

$^1$H NMR (500 MHz, CD$_3$OD) δ 7.94-7.91 (m, 1H), 7.54-7.50 (m, 1H), 6.85-6.52 (m, 2H), 6.25-6.06 (m, 1H), 5.78-5.48 (m, 1H), 4.39-4.28 (m, 1H), 4.10 (q, J=7.0 Hz, 2H), 3.91-3.82 (m, 1H), 3.71-3.60 (m, 2H), 3.44-3.31 (m, 1H), 2.09-2.01 (m, 1H), 1.88-1.84 (m, 2H), 1.66-1.59 (m, 1H), 1.43 (t, J=7.0 Hz, 3H)

Example 38: Preparation of (R)-1-(3-(5-chloro-2-(1-(difluoromethyl)-1H-pyrazol-4-ylamino)-7H-pyrrolo[2,3-d]pyrimidin-4-ylamino)piperidin-1-yl)prop-2-en-1-one

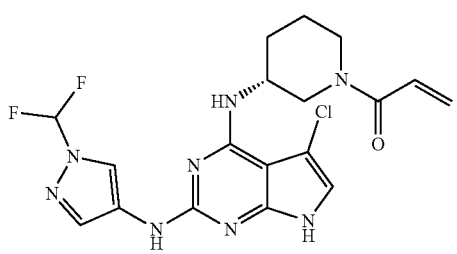 [SMILES: C=CC(=O)N1CCC[C@@H](Nc2nc(Nc3cnn(C(F)F)c3)nc3[nH]cc(Cl)c23)C1]

A title compound (6.6 mg, yield: 26.7%) was prepared in the same manner as in Example 36, except that 1-(difluoromethyl)-1H-pyrazol-4-amine was used instead of 4-(4-methylpiperazin-1-yl)aniline in Example 36.

$^1$H NMR (500 MHz, CD$_3$OD) δ 8.38-8.36 (m, 1H), 7.76-7.73 (m, 1H), 7.50-7.21 (m, 1H), 6.85-6.50 (m, 2H), 6.24-6.06 (m, 1H), 5.78-5.51 (m, 1H), 4.36-4.27 (m, 1H), 3.86-3.62 (m, 3H), 3.50-3.45 (m, 1H), 2.10-2.08 (m, 1H), 1.89-1.87 (m, 2H), 1.70-1.60 (m, 1H)

Example 39: Preparation of (R)-1-(3-(5-chloro-2-(1-(2,2-difluoroethyl)-1H-pyrazol-4-ylamino)-7H-pyrrolo[2,3-d]pyrimidin-4-ylamino)piperidin-1-yl)prop-2-en-1-one

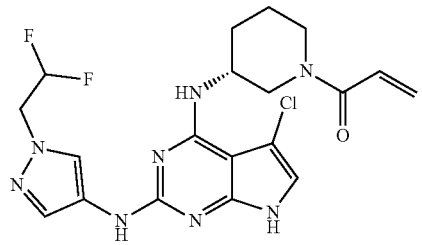 [SMILES: C=CC(=O)N1CCC[C@@H](Nc2nc(Nc3cnn(CC(F)F)c3)nc3[nH]cc(Cl)c23)C1]

A title compound (54.7 mg, yield: 32.6%) was prepared in the same manner as in Example 36, except that 1-(2,2-difluoroethyl)-1H-pyrazol-4-amine was used instead of 4-(4-methylpiperazin-1-yl)aniline in Example 36.

$^1$H NMR (500 MHz, CD$_3$OD) δ 8.08-8.00 (m, 1H), 7.62-7.55 (m, 1H), 6.85-6.52 (m, 2H), 6.25-5.99 (m, 2H), 5.78-5.49 (m, 1H), 4.47-4.44 (m, 2H), 4.34-4.27 (m, 1H), 3.88-3.86 (m, 1H), 3.65-3.62 (m, 2H), 3.44-3.40 (m, 1H), 2.10-2.07 (m, 1H), 1.85-1.84 (m, 2H), 1.70-1.59 (m, 1H)

Example 40: Preparation of (R)-1-(3-(5-chloro-2-(1-(2-morpholinoethyl)-1H-pyrazol-4-ylamino)-7H-pyrrolo[2,3-d]pyrimidin-4-ylamino)piperidin-1-yl)prop-2-en-1-one

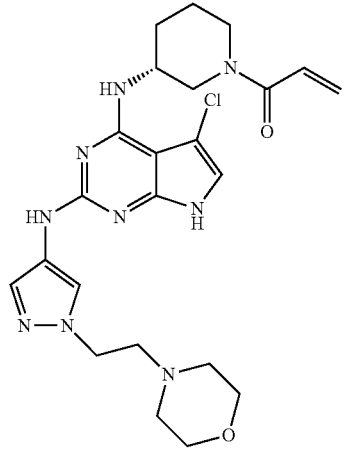 [SMILES: C=CC(=O)N1CCC[C@@H](Nc2nc(Nc3cnn(CCN4CCOCC4)c3)nc3[nH]cc(Cl)c23)C1]

A title compound (5.2 mg, yield: 18.4%) was prepared in the same manner as in Example 36, except that 1-(2-morpholinoethyl)-1H-pyrazol-4-amine was used instead of 4-(4-methylpiperazin-1-yl)aniline in Example 36.

$^1$H NMR (500 MHz, CD$_3$OD) δ 7.97-7.94 (m, 1H), 7.57-7.55 (m, 1H), 6.85-6.55 (m, 1H), 6.25-6.05 (m, 1H), 5.78-5.48 (m, 1H), 4.34-4.21 (m, 4H), 3.95-3.80 (m, 1H), 3.75-3.60 (m, 6H), 2.79 (t, J=6.5 Hz, 3H), 2.60-2.40 (m, 4H), 2.09-2.06 (m, 1H), 1.67-1.59 (m, 1H), 2.03-2.00 (m, 2H)

Example 41: Preparation of (R)-1-(3-(5-chloro-2-(1-(3-methoxybenzyl)-1H-pyrazol-4-ylamino)-7H-pyrrolo[2,3-d]pyrimidin-4-ylamino)piperidin-1-yl)prop-2-en-1-one

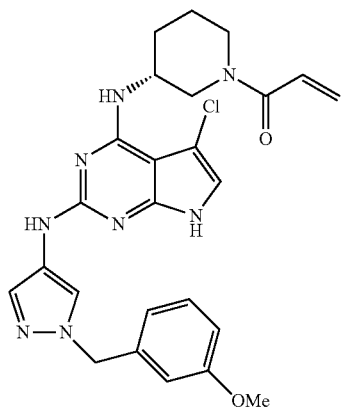 [SMILES: C=CC(=O)N1CCC[C@@H](Nc2nc(Nc3cnn(Cc4cccc(OC)c4)c3)nc3[nH]cc(Cl)c23)C1]

A title compound (4.4 mg, yield: 15.4%) was prepared in the same manner as in Example 36, except that 1-(3-methoxybenzyl)-1H-pyrazol-4-amine was used instead of 4-(4-methylpiperazin-1-yl)aniline in Example 36.

$^1$H NMR (500 MHz, CD$_3$OD) δ 8.03-7.92 (m, 1H), 7.57-7.53 (m, 1H), 7.23-7.21 (m, 1H), 6.86-6.45 (m, 6H), 6.24-6.00 (m, 1H), 5.80-5.45 (m, 1H), 5.27-5.25 (m, 2H), 4.30-4.18 (m, 1H), 3.75 (s, 3H), 3.70-3.40 (m, 3H), 1.84-1.79 (m, 2H), 1.63-1.59 (m, 1H)

Example 42: Preparation of (R)-1-(3-(3-chloro-6-(4-(4-methylpiperazin-1-yl)phenylamino)-1H-pyrazolo[3,4-d]pyrimidin-4-ylamino)piperidin-1-yl)prop-2-en-1-one

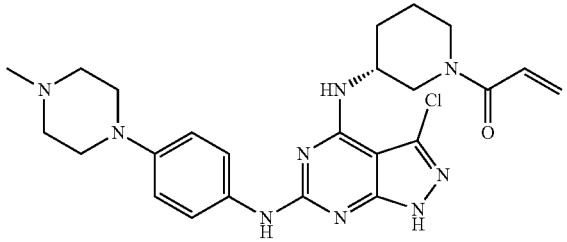 [SMILES: C=CC(=O)N1CCC[C@@H](Nc2nc(Nc3ccc(N4CCN(C)CC4)cc3)nc3[nH]nc(Cl)c23)C1]

Step 1: Preparation of 3,4,6-trichloro-1H-pyrazolo[3,4-d]pyrimidine 4,6-Dichloro-1H-pyrazolo[3,4-d]pyrimidine (5.0 g, 26.5 mmol) and N-chlorosuccinimide (5.3 g, 39.7 mmol) were dissolved in N,N-dimethylformamide (50.0 mL). After stirring at room temperature for 24 hours, the organic layer was isolated, treated with magnesium sulfate, filtered, and then concentrated under reduced pressure. The residue was isolated by column chromatography to obtain a title compound (3.3 g, yield: 56.0%).

Step 2: Preparation of tert-butyl(R)-3-((3,6-dichloro-1H-pyrazolo[3,4-d]pyrimidin-4-yl)amino)piperidine-1-carboxylate After 3,4,6-trichloro-1H-pyrazolo[3,4-d]pyrimidine (3.3 g, 14.8 mmol) was dissolved in ethanol (50 mL), N,N-diisopropylethylamine (3.9 mL, 22.2 mmol) and tert-butyl (R)-3-aminopiperidine-1-carboxylate (3.1 g, 15.6 mmol) were added thereto. The reaction mixture was stirred at 110° C. for 3 hours, and then the organic layer was isolated, treated with magnesium sulfate, filtered, and then concentrated under reduced pressure. The residue was isolated by column chromatography to obtain a title compound (4.3 g, yield: 75.8%).

$^1$H NMR (500 MHz, CD$_3$OD) δ 4.30-4.25 (m, 1H), 3.76-3.74 (m, 1H), 3.52-3.51 (m, 2H), 3.45-3.40 (m, 1H), 2.00-1.98-(m, 1H), 1.92-1.85 (m, 1H), 1.80-1.75 (m, 1H), 1.65-1.60 (m, 1H), 1.45-1.34 (m, 9H)

Step 3: Preparation of (R)-3,6-dichloro-N-(piperidin-3-yl)-1H-pyrazolo[3,4-d]pyrimidin-4-amine To tert-butyl(R)-3-((3,6-dichloro-1H-pyrazolo[3,4-d]pyrimidin-4-yl)amino)piperidine-1-carboxylate (4.3 g, 11.2 mmol), 6 N hydrochloric acid solution (30.0 mL, excessive amount) dissolved in methanol was added. After stirring at room temperature for 30 minutes, the reaction mixture was concentrated and the subsequent reaction was carried out without isolation.

$^1$H NMR (500 MHz, CD$_3$OD) δ 4.40-4.36 (m, 1H), 3.44-3.40 (m, 1H), 2.99-2.96 (m, 1H), 2.74-2.66 (m, 2H), 2.10-2.04 (m, 1H), 1.89-1.81 (m, 1H), 1.76-1.68 (m, 1H)

Step 4: Preparation of (R)-1-(3-((3,6-dichloro-1H-pyrazolo[3,4-d]pyrimidin-4-yl)amino)piperidin-1-yl)prop-2-en-1-one After (R)-3,6-dichloro-N-(piperidin-3-yl)-1H-pyrazolo[3,4-d]pyrimidin-4-amine (4.0 g, 12.4 mmol) was dissolved in a 3:1 mixed solution of tetrahydrofuran and distilled water, sodium bicarbonate (3.1 g, 3.7 mmol) was added at −20° C. and then stirred for 30 minutes. Acryloyl chloride (4.1 mL, 13.0 mmol) was slowly added dropwise to the reaction mixture and then stirred at −20° C. for 30 minutes. The organic layer was isolated, treated with magnesium sulfate, filtered, and then concentrated under reduced pressure. The residue was isolated by column chromatography to obtain a title compound (4.0 g, yield: 95.2%).

$^1$H NMR (500 MHz, CD$_3$OD) δ 6.86-6.78 (m, 1H), 6.22-6.17 (m, 1H), 5.78-5.68 (m, 1H), 4.55-4.03 (m, 3H), 3.71-3.66 (m, 1H), 3.58-3.50 (m, 1H), 2.12-2.00 (m, 1H), 1.93-1.84 (m, 2H), 1.73-1.68 (m, 1H)

Step 5: Preparation of (R)-1-(3-(3-chloro-6-(4-(4-methylpiperazin-1-yl)phenylamino)-1H-pyrazolo[3,4-d]pyrimidin-4-ylamino)piperidin-1-yl)prop-2-en-1-one (R)-1-(3-((3,6-dichloro-1H-pyrazolo[3,4-d]pyrimidin-4-yl)amino)piperidin-1-yl)prop-2-en-1-one (30.0 mg, 0.09 mmol) and 4-(4-methylpiperazin-1-yl)aniline (11.2 mg, 0.06 mmol) were dissolved in 2-butanol (2.0 mL). Trifluoroacetic acid (5.6 μL, 0.07 mmol) was added to the reactant, followed by reacting at 110° C. for 12 hours, and then the solvent was concentrated. This reaction mixture was neutralized by adding 7 N ammonia solution dissolved in methanol. The residue was isolated by column chromatography to obtain a title compound (15.0 mg, yield: 51.7%).

$^1$H NMR (500 MHz, CD$_3$OD) δ 7.57-7.52 (m, 2H), 6.92-6.90 (m, 2H), 6.83-6.50 (m, 1H), 6.28-6.07 (m, 1H), 5.80-8.51 (m, 1H), 4.40-3.88 (m, 3H), 3.66-3.39 (m, 2H), 3.13 (s, 4H), 2.63 (s, 4H), 2.35 (s, 3H), 2.08-2.00 (m, 1H), 1.91-1.84 (m, 2H), 1.63-1.60 (m, 1H)

Example 43: Preparation of (R)-1-(3-(3-chloro-6-(4-(3,5-dimethyl-1H-pyrazol-1-yl)phenylamino)-1H-pyrazolo[3,4-d]pyrimidin-4-ylamino)piperidin-1-yl)prop-2-en-1-one

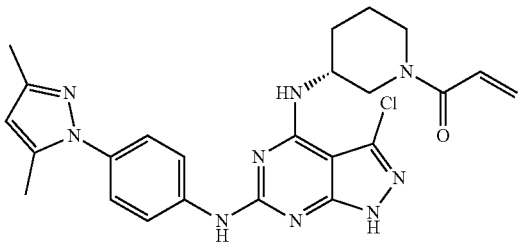 [SMILES: C=CC(=O)N1CCC[C@@H](Nc2nc(Nc3ccc(-n4nc(C)cc4C)cc3)nc3[nH]nc(Cl)c23)C1]

A title compound (6.1 mg, yield: 21.0%) was prepared in the same manner as in Example 42, except that 4-(3,5-dimethyl-1H-pyrazol-1-yl)aniline was used instead of 4-(4-methylpiperazin-1-yl)aniline in Example 42.

$^1$H NMR (500 MHz, CD$_3$OD) δ 7.91-7.87 (m, 2H), 7.30-7.28 (m, 2H), 6.89-6.62 (m, 1H), 6.27-6.10 (m, 1H), 6.03 (s, 1H), 5.79-5.58 (m, 1H), 4.43-4.34 (m, 1H), 4.01-3.87 (m, 2H), 3.70-3.42 (m, 2H), 2.20 (s, 6H), 2.15-2.11 (m, 1H), 1.95-1.85 (m, 2H), 1.70-1.64 (m, 1H)

Example 44: Preparation of (R)-1-(3-(3-chloro-6-(1-(2,2-difluoroethyl)-1H-pyrazol-4-ylamino)-1H-pyrazolo[3,4-d]pyrimidin-4-ylamino)piperidin-1-yl)prop-2-en-1-one

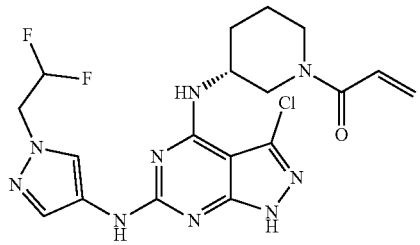 [SMILES: C=CC(=O)N1CCC[C@@H](Nc2nc(Nc3cnn(CC(F)F)c3)nc3[nH]nc(Cl)c23)C1]

A title compound (10.1 mg, yield: 37.4%) was prepared in the same manner as in Example 42, except that 1-(2,2-difluoroethyl)-1H-pyrazol-4-amine was used instead of 4-(4-methylpiperazin-1-yl)aniline in Example 42.

$^1$H NMR (500 MHz, CD$_3$OD) δ 8.08-8.04 (m, 1H), 7.65-7.61 (m, 1H), 6.86-6.60 (m, 1H), 6.27-6.01 (m, 2H), 5.80-5.48 (m, 1H), 4.58-4.30 (m, 4H), 3.95-3.82 (m, 1H), 3.65-3.38 (m, 2H), 2.09-2.05 (m, 1H), 1.92-1.85 (m, 2H), 1.73-1.65 (m, 1H)

Example 45: Preparation of (R)-1-(3-(3-chloro-6-(1-methyl-1H-pyrazol-4-ylamino)-1H-pyrazolo[3,4-d]pyrimidin-4-ylamino)piperidin-1-yl)prop-2-en-1-one

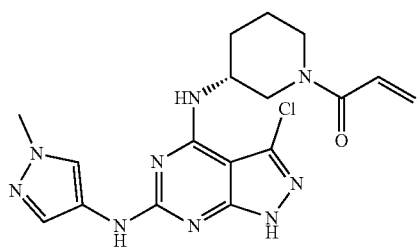 [SMILES: C=CC(=O)N1CCC[C@@H](Nc2nc(Nc3cnn(C)c3)nc3[nH]nc(Cl)c23)C1]

A title compound (10.1 mg, yield: 35.7%) was prepared in the same manner as in Example 42, except that 1-methyl-1H-pyrazol-4-amine was used instead of 4-(4-methylpiperazin-1-yl)aniline in Example 42.

$^1$H NMR (500 MHz, CD$_3$OD) δ 7.92 (s, 1H), 7.55 (s, 1H), 6.86-6.56 (m, 1H), 6.26-6.10 (m, 1H), 5.79-5.57 (m, 1H), 4.43-4.29 (m, 2H), 3.98-3.56 (m, 5H), 3.46-3.41 (m, 1H), 2.15-2.10 (m, 1H), 1.91-1.86 (m, 2H), 1.70-1.65 (m, 1H)

Example 46: Preparation of (R)-1-(3-(3-chloro-6-(1-ethyl-1H-pyrazol-4-ylamino)-1H-pyrazolo[3,4-d]pyrimidin-4-ylamino)piperidin-1-yl)prop-2-en-1-one

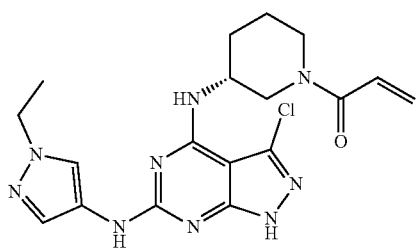

A title compound (11.2 mg, yield: 38.6%) was prepared in the same manner as in Example 42, except that 1-ethyl-1H-pyrazol-4-amine was used instead of 4-(4-methylpiperazin-1-yl)aniline in Example 42.

$^1$H NMR (500 MHz, CD$_3$OD) δ 7.96 (s, 1H), 7.57 (s, 1H), 6.86-6.56 (m, 1H), 6.27-7.09 (m, 1H), 5.80-5.56 (m, 1H), 4.42-4.29 (m, 2H), 4.14-4.09 (m, 2H), 3.97-3.86 (m, 1H), 3.66-3.41 (m, 2H), 2.10-2.05 (m, 1H), 1.93-1.86 (m, 2H), 1.70-1.60 (m, 1H), 1.43 (s, 3H)

Example 47: Preparation of (R)-2-(4-(4-(1-acryloylpiperidin-3-ylamino)-3-chloro-1H-pyrazolo[3,4-d]pyrimidin-6-ylamino)-1H-pyrazol-1-yl)-N-methylacetamide

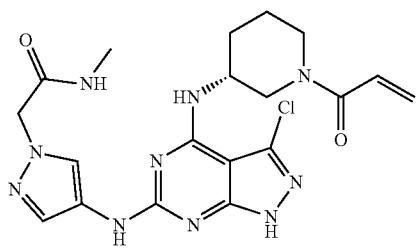 [SMILES: C=CC(=O)N1CCC[C@@H](Nc2nc(Nc3cnn(CC(=O)NC)c3)nc3[nH]nc(Cl)c23)C1]

A title compound (11.9 mg, yield: 37.2%) was prepared in the same manner as in Example 42, except that 2-(4-amino-1H-pyrazol-1-yl)-N-methyl acetamide was used instead of 4-(4-methylpiperazin-1-yl)aniline in Example 42.

$^1$H NMR (500 MHz, CD$_3$OD) δ 8.06-8.02 (m, 1H), 7.64-7.60 (m, 1H), 6.85-6.60 (m, 1H), 6.26-6.09 (m, 1H), 5.79-5.50 (m, 1H), 4.78 (s, 2H), 4.42-4.32 (m, 2H), 3.96-3.88 (m, 1H), 3.81-3.41 (m, 2H), 2.74 (s, 3H), 2.25-2.10 (m, 1H), 1.92-1.84 (m, 2H), 1.70-1.65 (m, 1H)

Example 48: Preparation of (R)-1-(3-(3-chloro-6-(1-(tetrahydro-2H-pyran-4-yl)-1H-pyrazol-4-ylamino)-1H-pyrazolo[3,4-d]pyrimidin-4-ylamino)piperidin-1-yl)prop-2-en-1-one

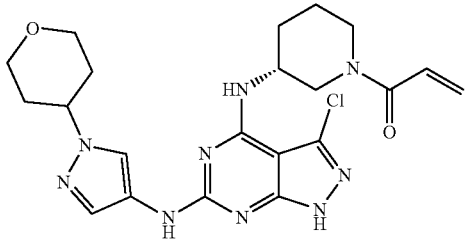 [SMILES: C=CC(=O)N1CCC[C@@H](Nc2nc(Nc3cnn(C4CCOCC4)c3)nc3[nH]nc(Cl)c23)C1]

A title compound (79.3 mg, yield: 80.9%) was prepared in the same manner as in Example 42, except that 1-(tetrahydro-2H-pyran-4-yl)-1H-pyrazol-4-amine was used instead of 4-(4-methylpiperazin-1-yl)aniline in Example 42.
$^1$H NMR (500 MHz, CD$_3$OD) δ 8.03 (s, 1H), 7.59 (s, 1H), 6.86-6.62 (m, 1H), 6.27-6.09 (m, 1H), 5.87-5.58 (m, 1H), 4.38-4.32 (m, 3H), 4.11-3.86 (m, 4H), 3.59-3.44 (m, 3H), 2.15-2.00 (m, 5H), 1.92-1.87 (m, 2H), 1.66-1.64 (m, 1H)

Example 49: Preparation of (R)-1-(3-(3-chloro-6-(1-cyclopropyl-1H-pyrazol-4-ylamino)-1H-pyrazolo[3,4-d]pyrimidin-4-ylamino)piperidin-1-yl)prop-2-en-1-one

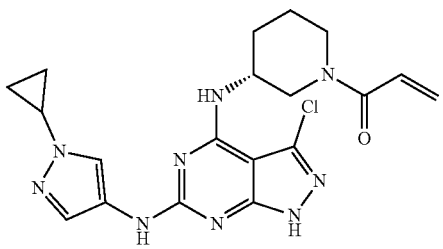 [SMILES: C=CC(=O)N1CCC[C@@H](Nc2nc(Nc3cnn(C4CC4)c3)nc3[nH]nc(Cl)c23)C1]

A title compound (20.2 mg, yield: 39.4%) was prepared in the same manner as in Example 42, except that 1-cyclo-1H-propyl-4-amine was used instead of 4-(4-methylpiperazin-1-yl)aniline in Example 42.
$^1$H NMR (500 MHz, CD$_3$OD) δ 8.00 (s, 1H), 7.54 (s, 1H), 6.86-6.61 (m, 1H), 6.26-6.10 (m, 1H), 5.79-5.58 (m, 1H), 4.37-4.30 (m, 1H), 3.97-3.85 (m, 1H), 3.57 (s, 1H), 3.45 (s, 1H), 2.11 (s, 1H), 1.87-1.67 (m, 2H), 1.66 (s, 1H), 1.32-1.28 (m, 2H), 1.05 (d, 4H)

Example 50: Preparation of (R)-1-(3-(3-chloro-6-(1-isopropyl-1H-pyrazol-4-ylamino)-1H-pyrazolo[3,4-d]pyrimidin-4-ylamino)piperidin-1-yl)prop-2-en-1-one

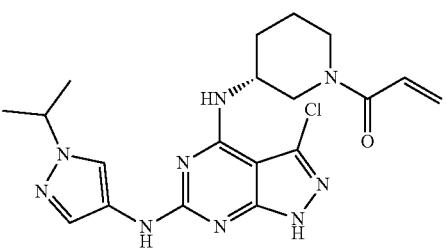 [SMILES: C=CC(=O)N1CCC[C@@H](Nc2nc(Nc3cnn(C(C)C)c3)nc3[nH]nc(Cl)c23)C1]

A title compound (5 mg, yield: 17.0%) was prepared in the same manner as in Example 42, except that 1-isopropyl-1H-pyrazol-4-amine was used instead of 4-(4-methylpiperazin-1-yl)aniline in Example 42.
$^1$H NMR (500 MHz, CD$_3$OD) δ 7.97 (s, 1H), 7.58 (s, 1H), 6.86-6.67 (m, 1H), 6.26-6.09 (m, 1H), 5.80-5.57 (m, 1H), 4.47-4.31 (m, 2H), 3.97-3.85 (m, 2H), 3.59-3.45 (m, 1H), 2.10-2.00 (m, 1H), 1.91-1.87 (m, 2H), 1.73-1.66 (m, 1H), 1.48 (s, 6H)

Example 51: Preparation of (R)-1-(3-(3-chloro-6-(1-propyl-1H-pyrazol-4-ylamino)-1H-pyrazolo[3,4-d]pyrimidin-4-ylamino)piperidin-1-yl)prop-2-en-1-one

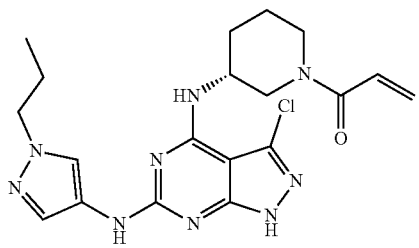 [SMILES: C=CC(=O)N1CCC[C@@H](Nc2nc(Nc3cnn(CCC)c3)nc3[nH]nc(Cl)c23)C1]

A title compound (47.7 mg, yield: 48.7%) was prepared in the same manner as in Example 42, except that 1-propyl-1H-pyrazol-4-amine was used instead of 4-(4-methylpiperazin-1-yl)aniline in Example 42.
$^1$H NMR (500 MHz, CD$_3$OD) δ 7.96 (s, 1H), 7.57 (s, 1H), 6.87-6.63 (m, 1H), 6.27-6.10 (m, 1H), 5.80-5.57 (m, 1H), 4.43-4.30 (m, 2H), 4.11-3.87 (m, 3H), 3.66-3.44 (m, 2H), 2.15-2.00 (s, 1H), 1.90-1.84 (m, 5H), 1.70-1.65 (m, 1H), 0.90-0.87 (m, 3H)

Example 52: Preparation of (R)-2-(4-(4-(1-acryloylpiperidin-3-ylamino)-3-chloro-1H-pyrazolo[3,4-d]pyrimidin-6-ylamino)-1H-pyrazol-1-yl)acetonitrile

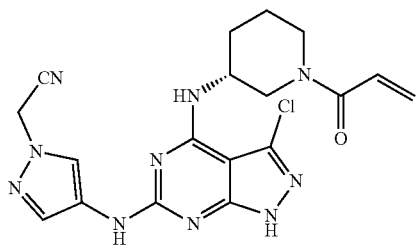 [SMILES: C=CC(=O)N1CCC[C@@H](Nc2nc(Nc3cnn(CC#N)c3)nc3[nH]nc(Cl)c23)C1]

A title compound (52.8 mg, yield: 53.9%) was prepared in the same manner as in Example 42, except that 2-(4-amino-1H-pyrazol-1-yl)acetonitrile was used instead of 4-(4-methylpiperazin-1-yl)aniline in Example 42.
$^1$H NMR (500 MHz, CD$_3$OD) δ 8.16-8.10 (m, 1H), 7.68-7.63 (m, 1H), 6.85-6.65 (m, 1H), 6.28-6.10 (m, 1H), 5.81-5.58 (m, 1H), 5.30-5.26 (m, 2H), 4.58-4.39 (m, 2H), 3.96-3.82 (m, 1H), 3.68-3.44 (m, 2H), 2.15-2.05 (m, 1H), 1.89-1.85 (m, 2H), 1.75-1.69 (m, 1H)

Example 53: Preparation of (R)-1-(3-(6-(1-tert-butyl-1H-pyrazol-4-ylamino)-3-chloro-1H-pyrazolo[3,4-d]pyrimidin-4-ylamino)piperidin-1-yl)prop-2-en-1-one

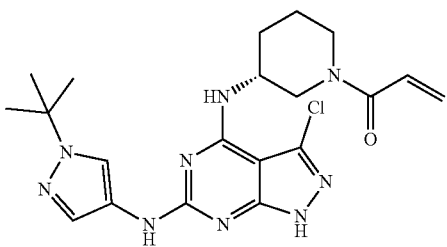 [SMILES: C=CC(=O)N1CCC[C@@H](Nc2nc(Nc3cnn(C(C)(C)C)c3)nc3[nH]nc(Cl)c23)C1]

A title compound (27.3 mg, yield: 51.2%) was prepared in the same manner as in Example 42, except that 1-(tert-butyl)-1H-pyrazol-4-amine was used instead of 4-(4-methylpiperazin-1-yl)aniline in Example 42.

$^1$H NMR (500 MHz, CD$_3$OD) δ 8.05 (s, 1H), 7.61 (s, 1H), 6.85-6.61 (m, 1H), 6.26-6.09 (m, 1H), 5.79-5.58 (m, 1H), 4.37-4.31 (m, 1H), 3.97-3.84 (m, 1H), 3.62-3.47 (m, 1H), 2.09-2.07 (m, 1H), 1.97-1.84 (m, 2H), 1.56 (s, 9H), 1.34-1.28 (m, 3H)

Example 54: Preparation of (R)-1-(3-(3-chloro-6-(1-(2-morpholinoethyl)-1H-pyrazol-4-ylamino)-1H-pyrazolo[3,4-d]pyrimidin-4-ylamino)piperidin-1-yl)prop-2-en-1-one

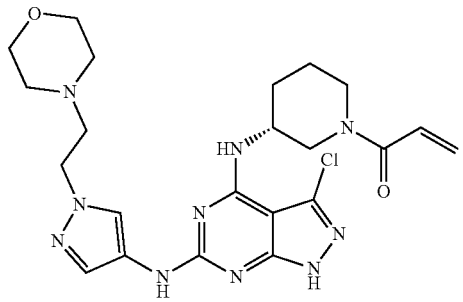 [SMILES: C=CC(=O)N1CCC[C@@H](Nc2nc(Nc3cnn(CCN4CCOCC4)c3)nc3[nH]nc(Cl)c23)C1]

A title compound (42.0 mg, yield: 69.0%) was prepared in the same manner as in Example 42, except that 1-(2-morpholinoethyl)-1H-pyrazol-4-amine was used instead of 4-(4-methylpiperazin-1-yl)aniline in Example 42.

$^1$H NMR (500 MHz, CD$_3$OD) δ 7.98 (s, 1H), 7.61 (s, 1H), 6.85-6.62 (m, 1H), 6.27-6.10 (m, 1H), 5.80-5.56 (m, 1H), 4.40-4.35 (m, 2H), 4.28-4.22 (m, 2H), 3.92-3.85 (m, 1H), 3.66 (s, 4H), 3.51-3.42 (m, 2H), 2.79 (t, 2H), 2.48 (s, 4H), 2.13-2.07 (m, 1H), 1.91-1.86 (m, 2H), 1.65-1.23 (m, 2H)

Example 55: Preparation of (R)-1-(3-(3-chloro-6-(1-isobutyl-1H-pyrazol-4-ylamino)-1H-pyrazolo[3,4-d]pyrimidin-4-ylamino)piperidin-1-yl)prop-2-en-1-one

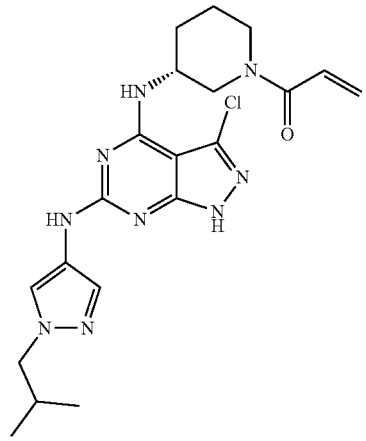 [SMILES: C=CC(=O)N1CCC[C@@H](Nc2nc(Nc3cnn(CC(C)C)c3)nc3[nH]nc(Cl)c23)C1]

A title compound (12.6 mg, yield: 23.6%) was prepared in the same manner as in Example 42, except that 1-isobutyl-1H-pyrazol-4-amine was used instead of 4-(4-methylpiperazin-1-yl)aniline in Example 42.

$^1$H NMR (500 MHz, CD$_3$OD) δ 7.95 (s, 1H), 7.58 (s, 1H), 6.87-6.62 (m, 1H), 6.28-6.11 (m, 1H), 5.81-5.57 (m, 1H), 4.44-4.29 (m, 2H), 3.67-3.94 (m, 1H), 3.88 (d, 2H), 3.65-3.41 (m, 2H), 2.15-2.11 (m, 2H), 1.93-1.87 (m, 2H), 1.65-1.63 (m, 1H), 0.91-0.90 (d, 6H)

Example 56: Preparation of (R)-1-(3-(3-chloro-6-(1-(2,2,2-trifluoroethyl)-1H-pyrazol-4-ylamino)-1H-pyrazolo[3,4-d]pyrimidin-4-ylamino)piperidin-1-yl)prop-2-en-1-one

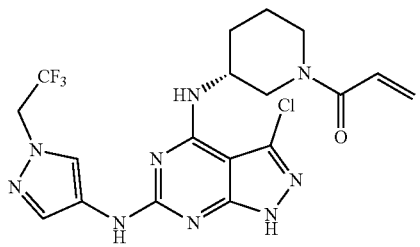 [SMILES: C=CC(=O)N1CCC[C@@H](Nc2nc(Nc3cnn(CC(F)(F)F)c3)nc3[nH]nc(Cl)c23)C1]

A title compound (55.8 mg, yield: 56.9%) was prepared in the same manner as in Example 42, except that 1-(2,2,2-trifluoroethyl)-1H-pyrazol-4-amine was used instead of 4-(4-methylpiperazin-1-yl)aniline in Example 42.

$^1$H NMR (500 MHz, CD$_3$OD) δ 8.16-8.10 (m, 1H), 7.68-7.63 (m, 1H), 6.87-6.65 (m, 1H), 6.28-6.10 (m, 1H), 5.81-5.59 (m, 1H), 4.93-4.91 (m, 2H), 4.78-4.29 (m, 2H), 3.95-3.54 (m, 2H), 3.44-3.38 (m, 1H), 2.09-2.05 (m, 1H), 1.89-1.75 (m, 2H), 1.70-1.65 (m, 1H)

Example 57: Preparation of (R)-1-(3-(3-chloro-6-(1-(2-(diethylamino)ethyl)-1H-pyrazol-4-ylamino)-1H-pyrazolo[3,4-d]pyrimidin-4-ylamino)piperidin-1-yl)prop-2-en-1-one

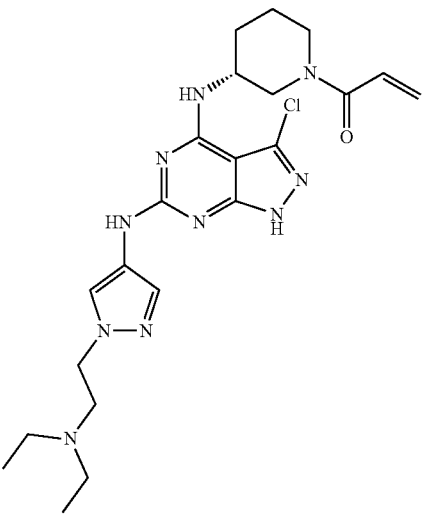 [SMILES: C=CC(=O)N1CCC[C@@H](Nc2nc(Nc3cnn(CCN(CC)CC)c3)nc3[nH]nc(Cl)c23)C1]

A title compound (27.8 mg, yield: 47.6%) was prepared in the same manner as in Example 42, except that 1-(2-(diethylamino)ethyl)-1H-pyrazol-4-amine was used instead of 4-(4-methylpiperazin-1-yl)aniline in Example 42.

¹H NMR (500 MHz, CD₃OD) δ 8.03 (s, 1H), 7.64 (s, 1H), 6.86-6.12 (m, 1H), 6.26-6.10 (m, 1H), 5.80-5.56 (m, 1H), 4.43-4.30 (m, 3H), 3.97-3.86 (m, 2H), 3.42 (d, 4H), 3.21-3.17 (m, 2H), 2.86-2.83 (m, 2H), 2.10 (s, 1H), 2.03-2.01 (m, 2H), 1.67 (s, 1H), 1.61-1.15 (m, 6H)

Example 58: Preparation of (R)-1-(3-(3-chloro-6-(1-(3-methoxybenzyl)-1H-pyrazol-4-ylamino)-1H-pyrazolo[3,4-d]pyrimidin-4-ylamino)piperidin-1-yl)prop-2-en-1-one

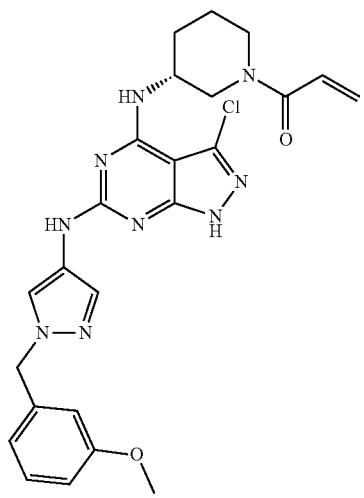 [SMILES: C=CC(=O)N1CCC[C@@H](Nc2nc(Nc3cnn(Cc4cccc(OC)c4)c3)nc3[nH]nc(Cl)c23)C1]

A title compound (23.4 mg, yield: 38.4%) was prepared in the same manner as in Example 42, except that 1-(3-methoxybenzyl)-1H-pyrazol-4-amine was used instead of 4-(4-methylpiperazin-1-yl)aniline in Example 42.

¹H NMR (500 MHz, CD₃OD) δ 8.04 (s, 1H), 7.61 (s, 1H), 7.25 (t, 1H), 6.85-6.59 (m, 4H), 6.24-6.08 (m, 1H), 5.77-5.56 (m, 1H), 4.33-4.23 (m, 3H), 3.75 (s, 3H), 3.67-3.44 (m, 2H), 2.03 (s, 1H), 1.88-1.80 (m, 2H), 1.63-1.60 (m, 1H)

Example 59: Preparation of (R)-1-(3-(3-chloro-6-(isoxazol-4-ylamino)-1H-pyrazolo[3,4-d]pyrimidin-4-ylamino)piperidin-1-yl)prop-2-en-1-one

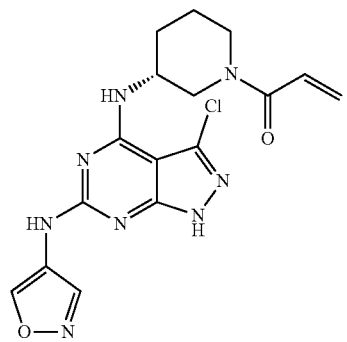 [SMILES: C=CC(=O)N1CCC[C@@H](Nc2nc(Nc3cnoc3)nc3[nH]nc(Cl)c23)C1]

A title compound (23.1 mg, yield: 49.6%) was prepared in the same manner as in Example 42, except that isoxazol-4-amine was used instead of 4-(4-methylpiperazin-1-yl)aniline in Example 42.

¹H NMR (500 MHz, CD₃OD) δ 9.04 (s, 1H), 8.49 (s, 1H), 6.85-6.62 (m, 1H), 6.27-6.11 (m, 1H), 5.80-5.58 (m, 1H), 4.37-4.29 (m, 2H), 3.97-3.95 (m, 1H), 3.68-3.48 (m, 2H), 2.10 (s, 1H), 1.95-1.84 (m, 2H), 1.66-1.65 (m, 1H)

Example 60: Preparation of (R)-2-(4-((4(1-acryloylpiperidin-3-yl)amino)-5-chloro-7H-pyrrolo[2,3-d]pyrimidin-2-yl)amino)-1H-pyrazol-1-yl)-N-methylacetamide

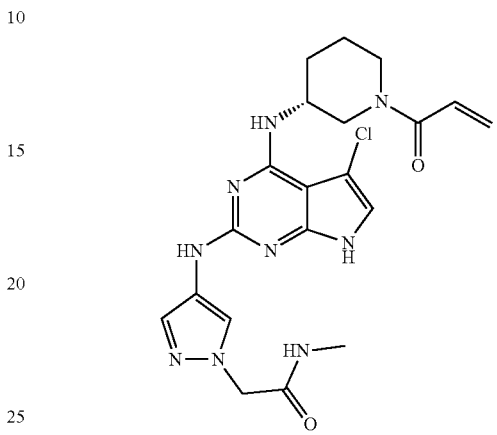

A title compound (5.9 mg, yield: 22.8%) was prepared in the same manner as in Example 36, except that 2-(4-amino-1H-pyrazol-1-yl)-N-methylacetamide was used instead of 4-(4-methylpiperazin-1-yl)aniline in Example 36.

¹H NMR (500 MHz, CD₃OD) δ 7.98-8.05 (m, 1H), 7.57-7.62 (m, 1H), 6.52-6.86 (m, 2H), 6.07-6.24 (m, 1H), 5.50-5.77 (m, 1H), 4.76-4.78 (m, 2H), 4.25-4.50 (m, 2H), 3.83-3.90 (m, 1H), 3.78-3.80 (m, 1H), 3.59-3.68 (m, 1H), 3.39-3.48 (m, 1H), 2.75 (s, 3H), 1.95-2.01 (m, 1H), 1.85-1.87 (m, 1H), 1.58-1.68 (m, 1H)

Example 61: Preparation of (R)-1-(3-((5-chloro-2-((4-morpholinophenyl)amino)-7H-pyrrolo[2,3-d]pyrimidin-4-yl)amino)piperidin-1-yl)prop-2-en-1-one

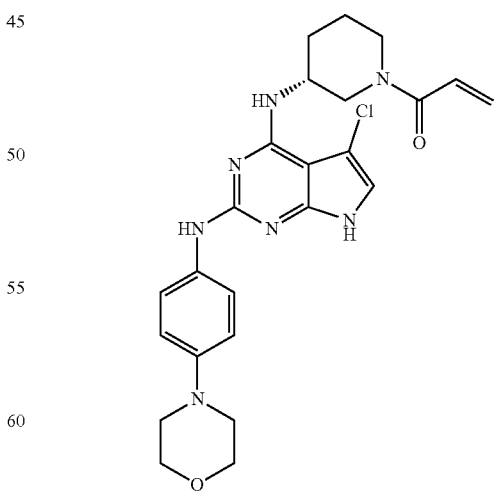

A title compound (7.4 mg, yield: 27.2%) was prepared in the same manner as in Example 36, except that 4-morpholinoaniline was used instead of 4-(4-methylpiperazin-1-yl)aniline in Example 36.

¹H NMR (500 MHz, CD₃OD) δ 7.51-7.55 (m, 2H), 6.89-6.90 (m, 2H), 6.46-6.85 (m, 2H), 6.03-6.25 (m, 1H), 5.45-5.80 (m, 1H), 3.96-4.18 (m, 1H), 3.88-3.94 (m, 1H), 3.80-3.82 (m, 4H), 3.70-3.78 (m, 1H), 3.53-3.66 (m, 1H), 3.41-3.50 (m, 1H), 3.35-3.40 (m, 1H), 3.00-3.05 (m, 4H), 1.97-2.02 (m, 1H), 1.83-1.85 (m, 1H), 1.59-1.65 (m, 1H)

Example 62: Preparation of (R)-1-(3-((5-chloro-24 (1-cyclopropyl-1H-pyrazol-4-yl)amino)-7H-pyrrolo [2,3-d]pyrimidin-4-yl)amino)piperidin-1-yl)prop-2-en-1-one

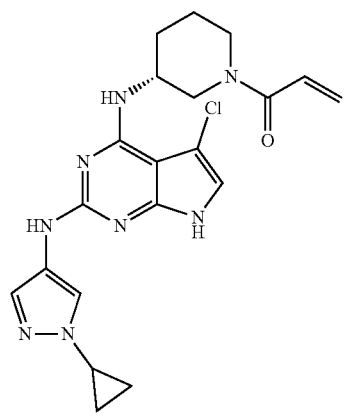 [SMILES: C=CC(=O)N1CCC[C@@H](Nc2nc(Nc3cnn(C4CC4)c3)nc3[nH]cc(Cl)c23)C1]

A title compound (7.2 mg, yield: 29.8%) was prepared in the same manner as in Example 36, except that 1-cyclo-1H-propyl-4-amine was used instead of 4-(4-methylpiperazin-1-yl)aniline in Example 36.

¹H NMR (500 MHz, CD₃OD) δ 7.97-7.93 (m, 1H), 7.49-7.45 (m, 1H), 6.84-6.52 (m, 2H), 6.24-6.06 (m, 1H), 5.77-5.50 (m, 1H), 4.31-4.27 (m, 1H), 3.93-3.37 (m, 5H), 2.08-2.05 (m, 1H), 1.80-1.90 (m, 1H), 1.55-1.70 (m, 1H), 1.03-0.98 (m, 4H)

Example 63: Preparation of (R)-1-(34(5-chloro-24 (1-isobutyl-1H-pyrazol-4-yl)amino)-7H-pyrrolo[2,3-d]pyrimidin-4-yl)amino)piperidin-1-yl)prop-2-en-1-one

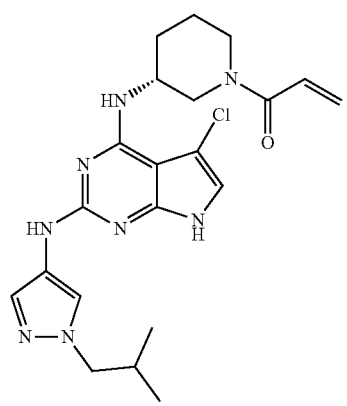 [SMILES: C=CC(=O)N1CCC[C@@H](Nc2nc(Nc3cnn(CC(C)C)c3)nc3[nH]cc(Cl)c23)C1]

A title compound (4.9 mg, yield: 19.6%) was prepared in the same manner as in Example 36, except that 1-isobutyl-1H-pyrazol-4-amine was used instead of 4-(4-methylpiperazin-1-yl)aniline in Example 36.

¹H NMR (500 MHz, CD₃OD) δ 7.93-7.88 (m, 1H), 7.55-7.51 (m, 1H), 6.89-6.53 (m, 2H), 6.26-6.07 (m, 1H), 5.79-5.51 (m, 1H), 4.38-3.42 (m, 7H), 2.18-2.08 (m, 3H), 1.90-1.84 (m, 1H), 1.70-1.55 (m, 1H)

Example 64: Preparation of (R)-1-(3-((3-chloro-6-((1-(difluoromethyl)-1H-pyrazol-4-yl)amino)-1H-pyrazolo[3,4-d]pyrimidin-4-yl)amino)piperidin-1-yl) prop-2-en-1-one

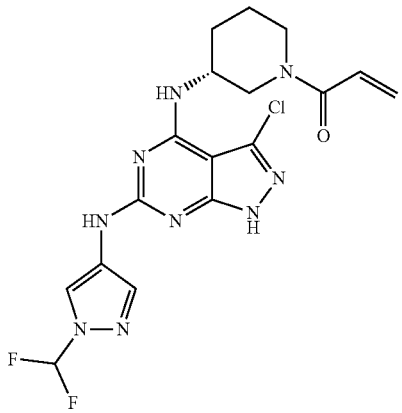 [SMILES: C=CC(=O)N1CCC[C@@H](Nc2nc(Nc3cnn(C(F)F)c3)nc3[nH]nc(Cl)c23)C1]

A title compound (24.0 mg, yield: 36.9%) was prepared in the same manner as in Example 42, except that 1-(difluoromethyl)-1H-pyrazol-4-amine was used instead of 4-(4-methylpiperazin-1-yl)aniline in Example 42.

¹H NMR (500 MHz, CD₃OD) δ 8.40 (s, 1H), 7.79 (d, 1H), 7.50-7.24 (m, 1H), 6.85-6.60 (m, 1H), 6.26-6.06 (m, 1H), 5.80-5.54 (m, 1H), 4.29-4.20 (m, 1H), 4.08-4.04 (m, 2H), 3.52-3.42 (m, 1H), 2.21-2.15 (m, 1H), 1.96-1.80 (m, 2H), 1.70-1.63 (m, 1H)

Example 65: Preparation of (R)-1-(3-((6-((1-isobutyl-1H-pyrazol-4-yl)amino)-1H-pyrazolo[3,4-d]pyrimidin-4-yl)amino)piperidin-1-yl)prop-2-en-1-one

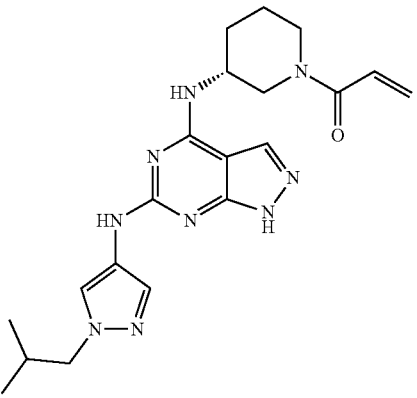 [SMILES: C=CC(=O)N1CCC[C@@H](Nc2nc(Nc3cnn(CC(C)C)c3)nc3[nH]ncc23)C1]

A title compound (26.0 mg, yield: 49.1%) was prepared in the same manner as in Example 30, except that 1-isobutyl-1H-pyrazol-4-amine was used instead of 4-(4-methylpiperazin-1-yl)aniline in Example 30.

¹H NMR (500 MHz, CD₃OD) δ 7.99 (m, 2H), 7.58 (d, 1H), 6.72-6.60 (m, 1H), 6.25-6.13 (m, 1H), 5.73-5.61 (m,

1H), 4.45-4.27 (m, 2H), 3.69-3.94 (m, 1H), 3.87 (d, 2H), 3.68-3.41 (m, 2H), 2.17-2.13 (m, 2H), 1.93-1.89 (m, 2H), 1.67-1.64 (m, 1H), 0.92-0.90 (d, 6H)

Example 66: Preparation of (R)-1-(34(6-((1-(tert-butyl)-1H-pyrazol-4-yl)amino)-1H-pyrazolo[3,4-d]pyrimidin-4-yl)amino)piperidin-1-yl)prop-2-en-1-one

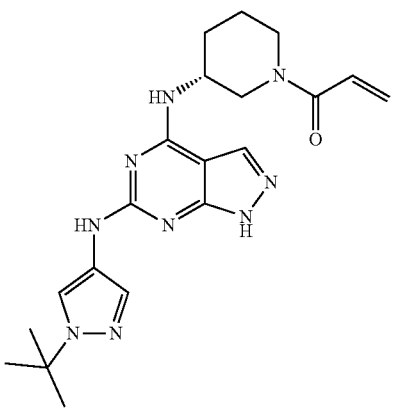 [SMILES: C=CC(=O)N1CCC[C@@H](Nc2nc(Nc3cnn(C(C)(C)C)c3)nc3[nH]ncc23)C1]

A title compound (27.0 mg, yield: 50.9%) was prepared in the same manner as in Example 30, except that 1-(tert-butyl)-1H-pyrazol-4-amine was used instead of 4-(4-methylpiperazin-1-yl)aniline in Example 30.

$^1$H NMR (500 MHz, CD$_3$OD) δ 8.07 (d, 1H), 8.06 (d, 1H), 7.90 (d, 1H), 6.84-6.57 (m, 1H), 6.25-6.08 (m, 1H), 5.80-5.59 (m, 1H), 4.42-4.34 (m, 1H), 3.98-3.83 (m, 1H), 3.62-3.50 (m, 1H), 2.12-2.09 (m, 1H), 1.99-1.85 (m, 2H), 1.57 (s, 9H), 1.35-1.29 (m, 3H)

Example 67: Preparation of (R)-1-(3-((6-((1-cyclopropyl-1H-pyrazol-4-yl)amino)-1H-pyrazolo[3,4-d]pyrimidin-4-yl)amino)piperidin-1-yl)prop-2-en-1-one

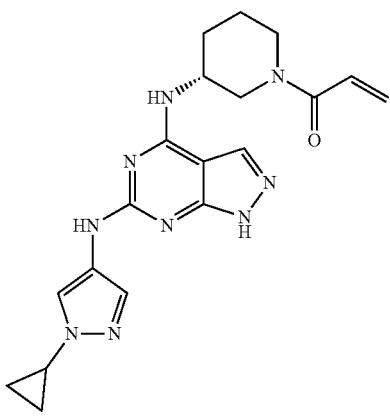 [SMILES: C=CC(=O)N1CCC[C@@H](Nc2nc(Nc3cnn(C4CC4)c3)nc3[nH]ncc23)C1]

A title compound (26.0 mg, yield: 50.9%) was prepared in the same manner as in Example 30, except that 1-cyclo-1H-propyl-4-amine was used instead of 4-(4-methylpiperazin-1-yl)aniline in Example 30.

$^1$H NMR (500 MHz, CD$_3$OD) δ 8.02 (d, 1H), 8.00 (s, 1H), 7.91 (d, 1H), 6.81-6.51 (m, 1H), 6.27-6.12 (m, 1H), 5.78-5.53 (m, 1H), 4.26-4.10 (m, 1H), 3.98-3.84 (m, 1H), 3.56 (s,

1H), 3.48 (s, 1H), 2.18 (s, 1H), 1.89-1.65 (m, 2H), 1.67 (s, 1H), 1.32-1.21 (m, 2H), 1.04 (d, 4H)

Example 68: Preparation of (R)-1-(3-((5-chloro-2-((4-(morpholine-4-carbonyl)phenyl)amino)-7H-pyrrolo[2,3-d]pyrimidin-4-yl)amino)piperidin-1-yl)prop-2-en-1-one

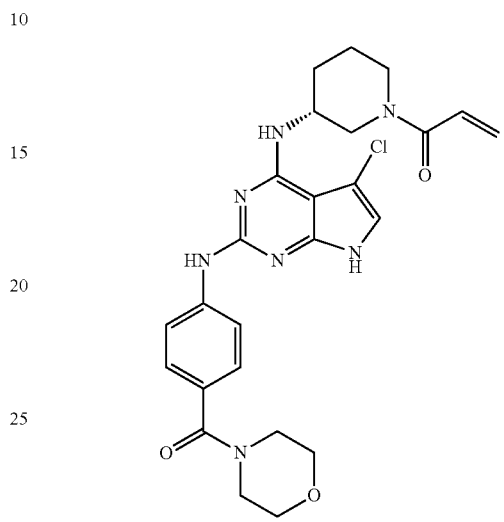

A title compound (2.5 mg, yield: 8.7%) was prepared in the same manner as in Example 36, except that (4-aminophenyl)(morpholino)methanone was used instead of 4-(4-methylpiperazin-1-yl)aniline in Example 36.

$^1$H NMR (500 MHz, CD$_3$OD) δ 7.85-7.81 (m, 2H), 7.36-7.34 (m, 2H), 6.86-6.54 (m, 2H), 6.26-6.04 (m, 1H), 5.79-5.47 (m, 1H), 4.38-4.31 (m, 1H), 3.93-3.46 (12H), 2.10-1.95 (m, 2H), 1.88-1.86 (m, 1H), 1.67-1.59 (m, 1H)

Example 69: Preparation of (R)-1-(3-((5-chloro-2-((1-methyl-1H-pyrazol-4-yl)amino)-7H-pyrrolo[2,3-d]pyrimidin-4-yl)amino)piperidin-1-yl)prop-2-en-1-one

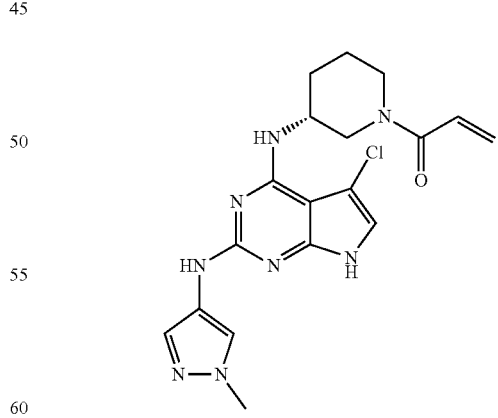

A title compound (2.1 mg, yield: 9.3%) was prepared in the same manner as in Example 36, except that 1-methyl-1H-pyrazol-4-amine was used instead of 4-(4-methylpiperazin-1-yl)aniline in Example 36.

$^1$H NMR (500 MHz, CD$_3$OD) δ 7.92-7.87 (m, 1H), 7.52-7.45 (m, 1H), 6.83-6.51 (m, 2H), 6.25-6.06 (m, 1H), 5.78-5.49 (m, 1H), 4.60-4.50 (m, 1H), 4.39-4.27 (m, 1H), 3.93-3.45 (m, 6H), 2.10-2.02 (m, 2H), 1.88-1.86 (m, 1H), 1.68-1.59 (m, 1H)

Example 70: Preparation of (R)-1-(3-((2-((1-(tert-butyl)-1H-pyrazol-4-yl)amino)-5-chloro-7H-pyrrolo[2,3-d]pyrimidin-4-yl)amino)piperidin-1-yl)prop-2-en-1-one

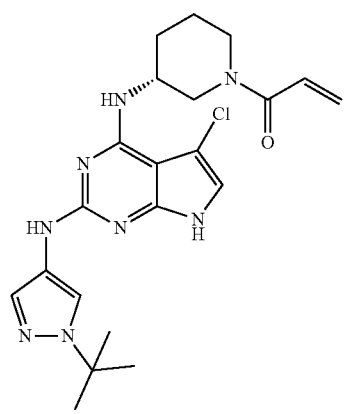 [SMILES: C=CC(=O)N1CCC[C@@H](Nc2nc(Nc3cnn(C(C)(C)C)c3)nc3[nH]cc(Cl)c23)C1]

A title compound (5.1 mg, yield: 20.4%) was prepared in the same manner as in Example 36, except that 1-(tert-butyl)-1H-pyrazol-4-amine was used instead of 4-(4-methylpiperazin-1-yl)aniline in Example 36.

$^1$H NMR (500 MHz, CD$_3$OD) δ 8.04-8.02 (m, 1H), 7.58-7.56 (m, 2H), 6.82-6.55 (m, 2H), 6.23-6.05 (m, 1H), 5.78-5.50 (m, 1H), 4.35-3.62 (m, 4H), 3.54-3.44 (m, 1H), 2.08-2.00 (m, 2H), 1.95-1.78 (m, 1H), 1.88-1.85 (m, 1H), 1.56 (s, 9H)

Example 71: Preparation of (R)-1-(3-((6-((1-(tetrahydro-2H-pyran-4-yl)-1H-pyrazol-4-yl)amino)-1H-pyrazolo[3,4-d]pyrimidin-4-yl)amino)piperidin-1-yl)prop-2-en-1-one

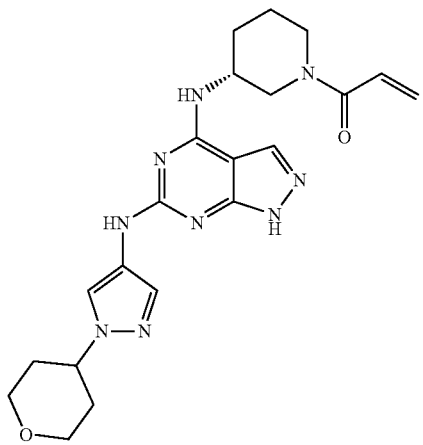 [SMILES: C=CC(=O)N1CCC[C@@H](Nc2nc(Nc3cnn(C4CCOCC4)c3)nc3[nH]ncc23)C1]

A title compound (22.0 mg, yield: 39.2%) was prepared in the same manner as in Example 30, except that 1-(tetrahydro-2H-pyran-4-yl)-1H-pyrazol-4-amine was used in Example 30.

$^1$H NMR (500 MHz, CD$_3$OD) δ 8.05 (d, 1H), 7.91 (s, 1H), 7.60 (d, 1H), 6.86-6.57 (m, 1H), 6.26-6.06 (m, 1H), 5.79-

5.54 (m, 1H), 4.31-4.21 (m, 1H), 4.10-4.04 (m, 4H), 3.59-3.53 (m, 2H), 3.18 (t, 1H), 2.20-2.17 (m, 1H), 2.03 (s, 4H), 1.95-1.93 (m, 1H), 1.79-1.70 (m, 1H), 1.56-32 (m, 2H)

Example 72: Preparation of (R)-1-(3-((6-((1-(2-morpholinoethyl)-1H-pyrazol-4-yl)amino)-1H-pyrazolo[3,4-d]pyrimidin-4-yl)amino)piperidin-1-yl)prop-2-en-1-one

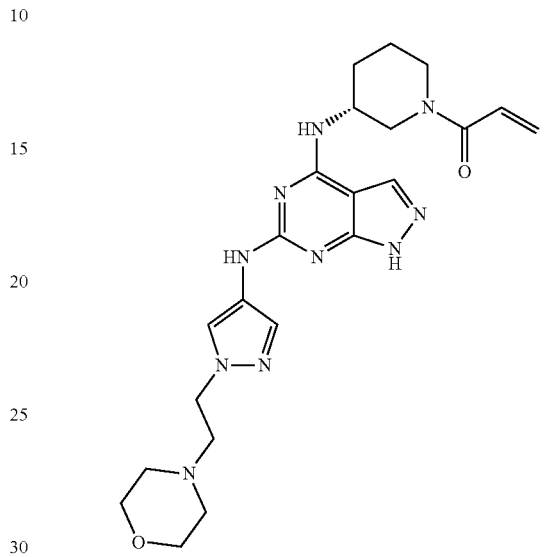

A title compound (21.0 mg, yield: 35.0%) was prepared in the same manner as in Example 30, except that 1-(2-morpholinoethyl)-1H-pyrazol-4-amine was used in Example 30.

$^1$H NMR (500 MHz, CD$_3$OD) δ 8.01 (d, 1H), 7.91 (s, 1H), 7.60 (d, 1H), 6.85-6.58 (m, 1H), 6.27-6.07 (m, 1H), 5.79-5.54 (m, 1H), 4.22-4.21 (m, 2H), 4.11-4.05 (m, 2H), 3.66 (s, 4H), 3.43-3.43 (m, 1H), 2.79 (t, 1H), 2.48 (s, 4H), 2.20-2.17 (m, 1H), 1.79-1.67 (m, 1H), 1.66-1.64 (m, 1H), 1.63-1.61 (m, 2H)

Example 73: Preparation of (R)-1-(3-((6-((1-propyl-1H-pyrazol-4-yl)amino)-1H-pyrazolo[3,4-d]pyrimidin-4-yl)amino)piperidin-1-yl)prop-2-en-1-one

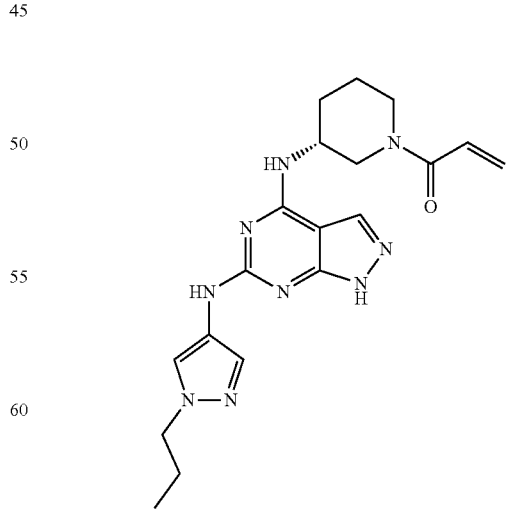

A title compound (21.0 mg, yield: 43.1%) was prepared in the same manner as in Example 30, except that 1-propyl-1H-pyrazol-4-amine was used in Example 30.

$^1$H NMR (500 MHz, CD$_3$OD) δ 7.99 (d, 1H), 7.90 (s, 1H), 7.57 (d, 1H), 6.86-6.59 (m, 1H), 6.27-6.08 (m, 1H), 5.79-5.55 (m, 1H), 4.27-4.21 (m, 1H), 4.05-4.03 (m, 2H), 3.44-3.16 (m, 2H), 2.19-2.17 (m, 1H), 1.95-1.93 (m, 1H), 1.84-1.80 (m, 2H), 1.79-1.67 (m, 1H), 1.65-1.60 (m, 2H), 0.91-0.90 (m, 3H)

Example 74: Preparation of (R)-1-(3-((6-((1-(2-methoxyethyl)-1H-pyrazol-4-yl)amino)-1H-pyrazolo[3,4-d]pyrimidin-4-yl)amino)piperidin-1-yl)prop-2-en-1-one

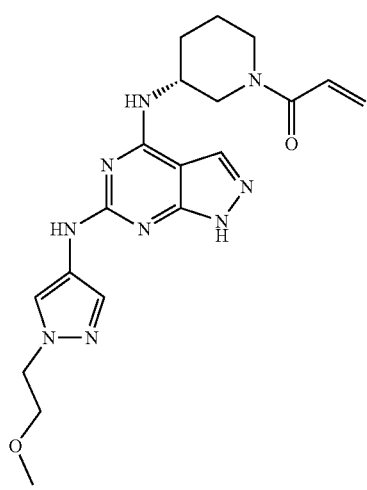 [SMILES: C=CC(=O)N1CCC[C@@H](Nc2nc(Nc3cnn(CCOC)c3)nc3[nH]ncc23)C1]

A title compound (20.7 mg, yield: 37.7%) was prepared in the same manner as in Example 30, except that 1-(2-methoxyethyl)-1H-pyrazol-4-amine was used in Example 30.

$^1$H NMR (500 MHz, CD$_3$OD) δ 8.02 (d, 1H), 7.91 (s, 1H), 7.59 (d, 1H), 6.85-6.57 (m, 1H), 6.26-6.07 (m, 1H), 5.79-5.53 (m, 1H), 4.26-4.22 (m, 3H), 4.07-4.05 (m, 3H), 3.72-3.70 (m, 2H), 3.48-3.44 (m, 1H), 3.40-3.22 (m, 2H), 2.19-2.17 (m, 1H), 2.01-1.95 (m, 1H), 1.80-1.71 (m, 1H), 1.67-1.56 (m, 2H)

Example 75: Preparation of (R)-1-(3-((2-((3-methylisothiazol-5-yl)amino)-7H-pyrrolo[2,3-d]pyrimidin-4-yl)amino)piperidin-1-yl)prop-2-en-1-one

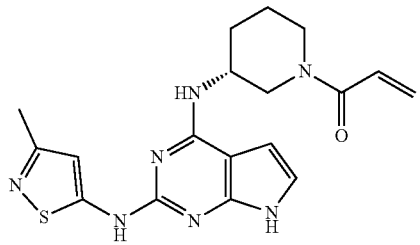 [SMILES: C=CC(=O)N1CCC[C@@H](Nc2nc(Nc3cc(C)ns3)nc3[nH]ccc23)C1]

Step 1: Preparation of 2,4-dichloro-7-tosyl-7H-pyrrolo[2,3-d]pyrimidine

After 2,4-dichloro-7H-pyrrolo[2,3-d]pyrimidine (3.0 g, 16.0 mmol) was dissolved in acetone (20.0 mL), 4-methylbenzenesulfonyl chloride (4.6 g, 23.9 mmol) was added thereto. After cooling to 0° C., 2 M sodium hydroxide solution (12.0 mL) was slowly added dropwise and then stirred at room temperature for 2 hours. The organic layer was isolated, treated with magnesium sulfate, filtered, and then concentrated under reduced pressure. The residue was isolated by column chromatography to obtain a title compound (2.9 g, yield: 80.0%).

$^1$H NMR (500 MHz, CD$_3$OD) δ 8.12 (d, 2H), 7.76 (d, 1H), 7.37 (d, 2H), 6.68 (d, 1H), 2.43 (s, 3H)

Step 2: Preparation of tert-butyl(R)-3-((2-chloro-7-tosyl-7H-pyrrolo[2,3-d]pyrimidin-4-yl)amino)piperidine-1-carboxylate After 2,4-dichloro-7-tosyl-7H-pyrrolo[2,3-d]pyrimidine (500.0 mg, 1.5 mmol) was dissolved in ethanol (10 mL), N,N-diisopropylethylamine (382.0 μL, 2.2 mmol) and tert-butyl(R)-3-aminopiperidine-1-carboxylate (322.0 mg, 1.6 mmol) were added thereto. The reaction mixture was stirred at 110° C. for 12 hours, and then the organic layer was isolated, treated with magnesium sulfate, filtered, and then concentrated under reduced pressure. The residue was isolated by column chromatography to obtain a title compound (681.0 mg, yield: 92.0%).

$^1$H NMR (500 MHz, CD$_3$OD) δ 8.10 (d, 1H), 7.39 (d, 1H), 7.31-7.23 (m, 4H), 4.17-4.13 (m, 1H), 3.70-3.60 (m, 1H), 3.45-3.35 (m, 3H), 2.40 (s, 3H), 1.95-1.85 (m, 1H), 1.70-1.65 (m, 1H), 1.60-1.55 (m, 2H), 1.40-1.37 (m, 9H)

Step 3: Preparation of tert-butyl(R)-3-((24(3-methylisothiazol-5-yl)amino)-7-tosyl-7H-pyrrolo[2,3-d]pyrimidin-4-yl)amino)piperidine-1-carboxylate After tert-butyl(R)-3-((2-chloro-7-tosyl-7H-pyrrolo[2,3-d]pyrimidin-4-yl)amino)piperidine-1-carboxylate (300.0 mg, 0.6 mmol) was dissolved in anhydrous tert-butanol (2.0 mL), 3-methylisothiazol-5-amine (67.7 mg, 0.6 mmol), tris(dibenzylideneacetone)dipalladium (27 mg, 0.03 mmol), 2'-dicyclohexylphosphino-2',4',6'-triisopropylbiphenyl (28.3 mg, 0.06 mmol), and potassium carbonate (163.9 mg, 1.2 mmol) were added thereto. Then, the mixture was reacted at 110° C. for 12 hours. The organic layer was isolated, treated with magnesium sulfate, filtered and then concentrated under reduced pressure. The residue was isolated by column chromatography to obtain a title compound (223.0 mg, yield: 64.5%).

$^1$H NMR (500 MHz, CD$_3$OD) δ 8.04 (d, 2H), 7.35-7.28 (m, 3H), 6.72 (s, 1H), 6.59 (s, 1H), 4.40-4.28 (m, 1H), 4.05-3.80 (m, 2H), 3.20-2.80 (m, 2H), 2.36 (s, 3H), 2.33 (s, 3H), 2.15-2.12 (m, 1H), 2.00-1.80 (m, 1H), 1.75-1.67 (m, 2H), 1.10-1.00 (m, 9H)

Step 4: Preparation of tert-butyl(R)-3-((2-((3-methyl isothiazol-5-yl)amino)-7H-pyrrolo[2,3-d]pyrimidin-4-yl)amino)piperidine-1-carboxylate Tert-butyl(R)-3-((2-((3-methylisothiazol-5-yl)amino)-7-tosyl-7H-pyrrolo[2,3-d]pyrimidin-4-yl)amino)piperidine-1-carboxylate (122.0 mg, 0.2 mmol) was dissolved in methanol (1.0 mL). Potassium hydroxide (23.5 mg, 0.4 mmol) was added to the reaction mixture and then stirred at 50° C. for 12 hours. The organic layer was isolated, treated with magnesium sulfate, filtered, and then concentrated under reduced pressure. The residue was isolated by column chromatography to obtain a title compound (60.0 mg, yield: 66.5%).

$^1$H NMR (500 MHz, CD$_3$OD) δ 6.84 (s, 1H), 6.53 (s, 1H), 6.48 (s, 1H), 4.50-4.25 (m, 1H), 4.10-3.90 (m, 1H), 3.80-

3.70 (m, 1H), 3.20-2.70 (m, 2H), 2.31 (s, 3H), 2.25-2.15 (m, 1H), 1.90-1.80 (m, 1H), 1.75-1.70 (m, 2H), 1.64-1.23 (m, 9H)

Step 5: Preparation of (R)—N2-(3-methylisothiazol-5-yl)-N4-(piperidin-3-yl)-7H-pyrrolo[2,3-d]pyrimidin-2,4-diamine hydrochloride To tert-butyl(R)-3-((2-((3-methylisothiazol-5-yl)amino)-7H-pyrrolo[2,3-d]pyrimidin-4-yl)amino)piperidine-1-carboxylate (60.0 mg, 0.14 mmol) was added 6 N hydrochloric acid solution (2.0 mL, excess) dissolved in methanol. After stirring at room temperature for 30 minutes, the reaction mixture was concentrated and the subsequent reaction was carried out without isolation.

$^1$H NMR (500 MHz, CD$_3$OD) δ 6.84 (s, 1H), 6.53 (s, 1H), 6.48 (s, 1H), 4.50-4.25 (m, 1H), 4.10-3.90 (m, 1H), 3.80-3.70 (m, 1H), 3.20-2.70 (m, 2H), 2.31 (s, 3H), 2.25-2.15 (m, 1H), 1.90-1.80 (m, 1H), 1.75-1.70 (m, 2H)

Step 6: Preparation of (R)-1-(3-((2-((3-methylisothiazol-5-yl)amino)-7H-pyrrolo[2,3-d]pyrimidin-4-yl)amino)piperidin-1-yl)prop-2-en-1-one After (R)—N2-(3-methylisothiazol-5-yl)-N4-(piperidin-3-yl)-7H-pyrrolo[2,3-d]pyrimidin-2,4-diamine hydrochloride (34.5 mg, 0.07 mmol) was dissolved in a 3:1 mixed solution of tetrahydrofuran:distilled water (2.5 mL), sodium bicarbonate (16.8 mg, 0.07 mmol) was added thereto at −20° C. and then stirred for 30 minutes. Acryloyl chloride (6.3 µL, 0.07 mmol) was slowly added dropwise to the reaction mixture, and then stirred at −20° C. for 1 hour. The organic layer was isolated, treated with magnesium sulfate, filtered, and then concentrated under reduced pressure. The residue was isolated by column chromatography to obtain a title compound (3.0 mg, yield: 8.6%).

$^1$H NMR (500 MHz, CD$_3$OD) δ 6.85 (s, 1H), 6.84-6.48 (m, 3H), 6.27-6.05 (m, 1H) 5.78-5.55 (m, 1H), 4.59-4.49 (m, 1H), 4.17-4.07 (m, 1H), 3.25-3.15 (m, 2H), 2.31 (s, 3H), 2.27-2.15 (m, 1H), 2.03-1.89 (m, 2H), 1.79-1.59 (m, 1H)

Example 76: Preparation of 1-((3S,4R)-3-((2-((1-ethyl-1H-pyrazol-4-yl)amino)-7H-pyrrolo[2,3-d]pyrimidin-4-yl)amino)-4-fluoropiperidin-1-yl)prop-2-en-1-one

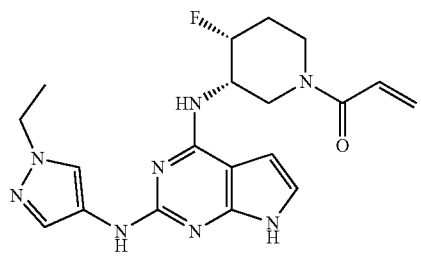 [SMILES: C=CC(=O)N1CC[C@@H](F)[C@@H](Nc2nc(Nc3cnn(CC)c3)nc3[nH]ccc23)C1]

A title compound (15.5 mg, yield: 36.6%) was prepared in the same manner as in Example 1, except using 1-ethyl-1H-pyrazol-4-amine instead of 4-(4-methylpiperazin-1-yl)aniline, and tert-butyl(3S,4R)-3-amino-4-fluoropiperidine-1-carboxylate instead of tert-butyl (R)-3-aminopiperidine-1-carboxylate in Example 1.

$^1$H NMR (500 MHz, CD$_3$OD) δ 7.89 (d, 1H), 7.50 (d, 1H), 6.85-6.75 (m, 2H), 6.46 (s, 1H), 6.28-6.14 (m, 1H), 5.81-5.62 (m, 1H), 5.12-5.02 (m, 1H), 4.80-4.30 (m, 2H), 4.09-4.03 (m, 3H), 3.51-3.43 (m, 1H), 3.14-3.05 (m, 1H), 2.21-2.18 (m, 1H), 1.96-1.85 (m, 1H), 1.43-1.39 (m, 3H)

Example 77: Preparation of 1-((3S,4R)-3-((6-((1-ethyl-1H-pyrazol-4-yl)amino)-1H-pyrazolo[3,4-d]pyrimidin-4-yl)amino)-4-fluoropiperidin-1-yl)prop-2-en-1-one

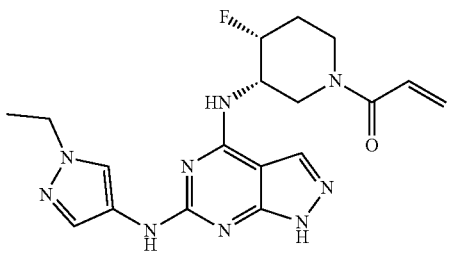 [SMILES: C=CC(=O)N1CC[C@@H](F)[C@@H](Nc2nc(Nc3cnn(CC)c3)nc3[nH]ncc23)C1]

A title compound (7.1 mg, yield: 20.0%) was prepared in the same manner as in Example 30, except using 1-ethyl-1H-pyrazol-4-amine instead of 4-(4-methylpiperazin-1-yl)aniline, and tert-butyl(3S,4R)-3-amino-4-fluoropiperidine-1-carboxylate instead of tert-butyl (R)-3-aminopiperidine-1-carboxylate in Example 30.

$^1$H NMR (500 MHz, CD$_3$OD) δ 7.97 (m, 2H), 7.54 (d, 1H), 6.86-6.60 (m, 1H), 6.29-6.15 (m, 1H), 5.81-5.79 (m, 1H), 5.09 (d, 1H), 4.72-4.25 (m, 2H), 4.13-4.03 (m, 3H), 3.57-3.45 (m, 1H), 3.21-3.08 (m, 1H), 2.22-2.18 (m, 1H), 1.94-1.86 (m, 1H), 1.50-1.40 (m, 3H)

Example 78: Preparation of (R)-1-(3-((2-((1-cyclopropyl-1H-pyrazol-4-yl)amino)-5-methyl-7H-pyrrolo[2,3-d]pyrimidin-4-yl)amino)piperidin-1-yl)prop-2-en-1-one

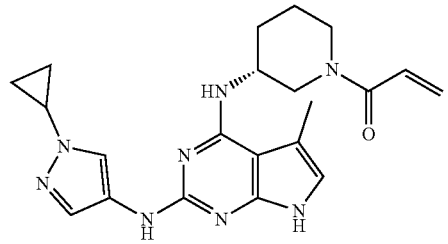

Step 1: Preparation of tert-butyl(R)-3-((2-chloro-5-methyl-7H-pyrrolo[2,3-d]pyrimidin-4-yl)amino)piperidine-1-carboxylate After 2,4-dichloro-5-methyl-7H-pyrrolo[2,3-d]pyrimidine (300.0 mg, 1.5 mmol) was dissolved in ethanol (10 mL), N,N-diisopropylethylamine (695.0 µL, 2.2 mmol) and tert-butyl (R)-3-aminopiperidine-1-carboxylate (356.9 mg, 1.8 mmol) were added thereto. The reaction mixture was stirred at 110° C. for 12 hours, and then the organic layer was isolated, treated with magnesium sulfate, filtered, and then concentrated under reduced pressure. The residue was isolated by column chromatography to obtain a title compound (461.6 mg, yield: 85.3%).

¹H NMR (500 MHz, CD₃OD) δ 6.84 (s, 1H), 4.57-4.50 (m, 1H), 3.63-3.61 (m, 1H), 3.44-3.34 (m, 1H), 3.03-2.93 (m, 2H), 2.42 (s, 3H), 2.17-2.15 (m, 1H), 2.09-2.06 (m, 1H), 1.98-1.86 (m, 2H), 1.50-1.30 (m, 9H)

Step 2: Preparation of (R)-2-chloro-5-methyl-N-(piperidin-3-yl)-7H-pyrrolo[2,3-d]pyrimidin-4-amine hydrochloride To tert-butyl-(R)-3-((2-chloro-5-methyl-7H-pyrrolo[2,3-d]pyrimidin-4-yl)amino)piperidine-1-carboxylate (461.6 mg, 1.3 mmol) was added 6 N hydrochloric acid solution (2.0 mL, excess) dissolved in methanol. After stirring at room temperature for 30 minutes, the reaction mixture was concentrated and the subsequent reaction was carried out without isolation.

¹H NMR (500 MHz, CD₃OD) δ 6.84 (s, 1H), 4.57-4.50 (m, 1H), 3.63-3.61 (m, 1H), 3.44-3.34 (m, 1H), 3.03-2.93 (m, 2H), 2.42 (s, 3H), 2.17-2.15 (m, 1H), 2.09-2.06 (m, 1H), 1.98-1.86 (m, 2H)

Step 3: Preparation of (R)-1-(3-((2-chloro-5-methyl-7H-pyrrolo[2,3-d]pyrimidin-4-yl)amino)piperidin-1-yl)prop-2-en-1-one After (R)-2-chloro-5-methyl-N-(piperidin-3-yl)-7H-pyrrolo[2,3-d]pyrimidin-4-amine hydrochloride (387.8 mg, 1.3 mmol) was dissolved in a 3:1 mixed solution of tetrahydrofuran:distilled water (4 mL), sodium bicarbonate (323.4 mg, 3.9 mmol) was added thereto at −20° C. and then stirred for 30 minutes. Acryloyl chloride (121.4 μL, 1.4 mmol) was slowly added dropwise to the reaction mixture, and then stirred at −20° C. for 1 hour. The organic layer was isolated, treated with magnesium sulfate, filtered, and then concentrated under reduced pressure. The residue was isolated by column chromatography to obtain a title compound (210.4 mg, yield: 61.0%).

¹H NMR (500 MHz, CD₃OD) δ 6.88-6.76 (m, 2H), 6.24-6.14 (m, 1H), 5.78-5.65 (m, 1H), 4.34-4.27 (m, 1H), 4.20-3.62 (m, 3H), 3.26-3.16 (m, 1H), 2.37 (d, 3H), 2.11-2.00 (m, 1H), 1.89-1.84 (m, 2H), 1.70-1.65 (m, 1H)

Step 4: Preparation of (R)-1-(3-((2-(1-cyclopropyl-1H-pyrazol-4-yl)amino)-5-methyl-7H-pyrrolo[2,3-d]pyrimidin-4-yl)amino)piperidin-1-yl)prop-2-yl-1-one (R)-1-(3-((2-chloro-5-methyl-7H-pyrrolo[2,3-d]pyrimidin-4-yl)amino)piperidin-1-yl)prop-2-en-1-one (30.0 mg, 0.09 mmol) and 1-cyclopropyl-1H-pyrazol-4-amine (9.6 mg, 0.08 mmol) were dissolved in 2-butanol (2.0 mL). Trifluoroacetic acid (5.8 μL, 0.08 mmol) was added to the reaction mixture, followed by reacting at 120° C. for 3 hours, and then the solvent was concentrated. The reaction mixture was neutralized by adding 7 N ammonia solution dissolved in methanol, and the residue was isolated by column chromatography to obtain a title compound (3.6 mg, yield: 11.3%).

¹H NMR (500 MHz, CD₃OD) δ 7.95 (d, 1H), 7.49 (s, 1H), 6.90-6.48 (m, 2H), 6.26-6.05 (m, 1H), 5.49-5.50 (m, 1H), 4.33-4.31 (m, 1H), 4.03-3.80 (m, 2H), 3.54-3.38 (m, 3H), 2.32 (s, 3H), 2.13-2.06 (m, 1H), 1.95-1.85 (m, 2H), 1.75-1.67 (m, 1H), 1.04-0.92 (m, 4H)

Example 79: Preparation of (R)-1-(3-((2-((1-ethyl-1H-pyrazol-4-yl)amino)-5-methyl-7H-pyrrolo[2,3-d]pyrimidin-4-yl)amino)piperidin-1-yl)prop-2-en-1-one

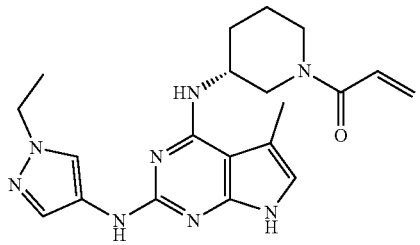 [SMILES: C=CC(=O)N1CCC[C@@H](Nc2nc(Nc3cnn(CC)c3)nc3[nH]cc(C)c23)C1]

A title compound (2.8 mg, yield: 8.43%) was prepared in the same manner as in Example 78, except that 1-ethyl-1H-pyrazol-4-amine was used instead of 1-cyclopropyl-1H-pyrazol-4-amine in Example 78.

¹H NMR (500 MHz, CD₃OD) δ 7.91 (d, 1H), 7.51 (d, 1H), 6.90-6.48 (m, 2H), 6.27-6.05 (d, 1H), 5.80-5.50 (d, 1H), 4.36-4.32 (d, 2H), 4.15-4.09 (m, 2H), 4.00-3.56 (m, 3H), 2.32 (s, 3H), 2.15-2.11 (m, 1H), 1.94-1.85 (m, 2H), 1.70-1.65 (m, 1H), 1.44-1.40 (m, 3H)

Example 80: Preparation of (R)-1-(3-((2-((4-(3,5-dimethyl-1H-pyrazol-1-yl)phenyl)amino)-5-methyl-7H-pyrrolo[2,3-d]pyrimidin-4-yl)amino)piperidin-1-yl)prop-2-en-1-one

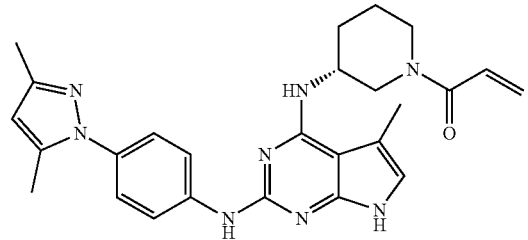 [SMILES: C=CC(=O)N1CCC[C@@H](Nc2nc(Nc3ccc(-n4nc(C)cc4C)cc3)nc3[nH]cc(C)c23)C1]

A title compound (7.1 mg, yield: 25.1%) was prepared in the same manner as in Example 78, except that 4-(3,5-dimethyl-1H-pyrazol-1-yl)aniline was used instead of 1-cyclopropyl-1H-pyrazol-4-amine in Example 78.

¹H NMR (500 MHz, CD₃OD) δ 7.86-7.82 (m, 2H), 7.25-7.23 (m, 2H), 6.85-6.54 (m, 2H), 6.26-6.01 (m, 2H), 5.78-5.48 (m, 1H), 4.36-4.34 (m, 2H), 3.84-3.82 (m, 1H), 3.48-3.39 (m, 2H), 2.35 (s, 3H), 2.22 (s, 6H), 2.18-2.15 (m, 1H), 1.92-1.83 (m, 2H), 1.70-1.65 (m, 1H)

Example 81: Preparation of (R)-1-(3-((2-(benzo[d]thiazol-6-ylamino)-5-methyl-7H-pyrrolo[2,3-d]pyrimidin-4-yl)amino)piperidin-1-yl)prop-2-en-1-one

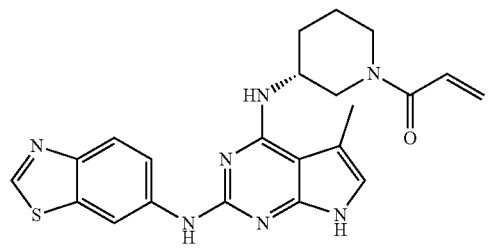 [SMILES: C=CC(=O)N1CCC[C@@H](Nc2nc(Nc3ccc4ncsc4c3)nc3[nH]cc(C)c23)C1]

A title compound (2.6 mg, yield: 10.0%) was prepared in the same manner as in Example 78, except that benzo[d]thiazol-6-amine was used instead of 1-cyclopropyl-1H-pyrazol-4-amine in Example 78.

$^1$H NMR (500 MHz, CD$_3$OD) δ 8.98 (s, 1H), 8.79-8.73 (m, 1H), 7.88-7.86 (m, 1H), 7.68-7.57 (m, 1H), 6.85-6.56 (m, 3H), 6.30-5.97 (m, 1H), 5.79-5.34 (m, 1H), 4.37-4.27 (m, 1H), 4.02-3.85 (m, 1H), 3.60-3.48 (m, 2H), 2.89-2.77 (m, 1H), 2.35 (s, 3H), 2.15-2.00 (m, 1H), 1.92-1.86 (m, 1H), 1.77-1.67 (m, 2H)

Example 82: Preparation of (R)-1-(3-((2-((1-ethyl-1H-pyrazol-4-yl)amino)-5-fluoro-7H-pyrrolo[2,3-d]pyrimidin-4-yl)amino)piperidin-1-yl)prop-2-en-1-one

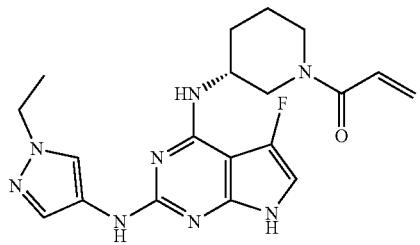 [SMILES: C=CC(=O)N1CCC[C@@H](Nc2nc(Nc3cnn(CC)c3)nc3[nH]cc(F)c23)C1]

Step 1: Preparation of 2,4-dichloro-5-fluoro-7H-pyrrolo[2,3-d]pyrimidine

After 2,4-dichloro-7H-pyrrolo[2,3-d]pyrimidine (200 mg, 1.06 mmol) was dissolved in acetonitrile (5.0 mL), 1-chloromethyl-4-fluoro-1,4-diazoniabicyclo[2.2.2]octane bis(tetrafluoroborate) (561.6 mg, 1.6 mmol) and acetic acid (1 mL) were added thereto. The mixture was heated at 80° C. and stirred for 24 hours, and then the organic layer was isolated, treated with magnesium sulfate, filtered and then concentrated under reduced pressure. The residue was isolated by column chromatography to obtain a title compound (170.0 mg, yield: 80.1%).

$^1$H NMR (500 MHz, CD$_3$OD) δ 7.36 (s, 1H)

Step 2: Preparation of 2,4-dichloro-5-fluoro-7-((2-(trimethylsilyl)ethoxy)methyl)-7H-pyrrolo[2,3-d]pyrimidine After 2,4-dichloro-5-fluoro-7H-pyrrolo[2,3-d]pyrimidine (100.0 mg, 0.5 mmol) was dissolved in N,N-dimethylformamide (2.0 mL), sodium hydride (29.1 mg, 0.7 mmol) was added thereto and then stirred for 30 minutes. To the reaction mixture was added 2-(chloromethoxy)ethyl)trimethylsilane (127.0 μL, 0.7 mmol) and stirred at room temperature for 2 hours. The organic layer was isolated, treated with magnesium sulfate, filtered and then concentrated under reduced pressure. The residue was isolated by column chromatography to obtain a title compound (138.7 mg, yield: 85.1%).

$^1$H NMR (500 MHz, CD$_3$OD) δ 7.56 (s, 1H), 5.59 (s, 2H), 3.57 (t. 2H), 0.90 (t, 2H), 0.00 (s, 9H)

Step 3: Preparation of tert-butyl(R)-3-((2-chloro-5-fluoro-7-((2-(trimethylsilyl)ethoxy)methyl)-7H-pyrrolo[2,3-d]pyrimidin-4-yl)amino)piperidine-1-carboxylate After 2,4-dichloro-5-fluoro-7-((2-(trimethylsilyl)ethoxy)methyl)-7H-pyrrolo[2,3-d]pyrimidine (138.7 mg, 0.4 mmol) was dissolved in ethanol (100 ml), N,N-diisopropylethylamine (107.8 μL, 0.6 mmol) and tert-butyl(R)-3-aminopiperidine-1-carboxylate (123.9 mg, 0.6 mmol) were added thereto. The reaction mixture was stirred at 110° C. for 12 hours, and then the organic layer was isolated, treated with magnesium sulfate, filtered and concentrated under reduced pressure. The residue was isolated by column chromatography to obtain a title compound (109.2 mg, yield: 53.2%).

$^1$H NMR (500 MHz, CD$_3$OD) δ 7.01 (s, 1H), 5.44 (s, 2H), 4.25-4.20 (m, 1H), 3.93-3.90 (m, 1H), 3.66-3.60 (m, 1H), 3.53 (t, 2H), 3.20-3.13 (m, 2H), 2.05-2.00 (m, 1H), 1.80-1.77 (m, 2H), 1.60-1.57 (m, 1H), 1.50-1.38 (m, 9H), 0.88 (t. 2H), 0.00 (s, 9H)

Step 4: Preparation of tert-butyl(R)-3-((2-((1-ethyl-1H-pyrazol-4-yl)amino)-5-fluoro-7-((2-(trimethylsilyl)ethoxy)methyl)-7H-pyrrolo[2,3-d]pyrimidin-4-yl)amino)piperidine-1-carboxylate After tert-butyl(R)-3-((2-chloro-5-fluoro-7-((2-(trimethylsilyl)ethoxy)methyl)-7H-pyrrolo[2,3-d]pyrimidin-4-yl)amino)piperidine-1-carboxylate (109.2 mg, 0.2 mmol) was dissolved in anhydrous tert-butanol (2.0 mL), 1-ethyl-1H-pyrazol-4-amine (20.2 mg, 0.2 mmol), tris(dibenzylideneacetone)dipalladium (8.3 mg, 0.01 mmol), 2-dicyclohexylphosphino-2',4',6'-triisopropylbiphenyl (8.7 mg, 0.02 mmol) and potassium carbonate (50.3 mg, 0.4 mmol) were added thereto. The mixture was reacted at 110° C. for 12 hours, and then the organic layer was isolated, treated with magnesium sulfate, filtered and then concentrated under reduced pressure. The residue was isolated by column chromatography to obtain a title compound (67.0 mg, yield: 65.0%).

$^1$H NMR (500 MHz, CD$_3$OD) δ 7.96 (s, 1H), 7.58 (s, 1H) 6.63 (s, 1H), 5.42 (s, 2H), 4.59-4.55 (m, 1H), 4.22-4.11 (m, 3H), 3.82-3.80 (m, 1H), 3.70-3.41 (m, 3H), 3.20-2.92 (m, 1H), 2.04-2.00 (m, 1H), 1.77-1.70 (m, 2H), 1.57-1.25 (m, 13H), 0.90 (t, 2H), 0.00 (s, 9H)

Step 5: Preparation of (R)—N2-(1-ethyl-1H-pyrazol-4-yl)-5-fluoro-N4-(piperidin-3-yl)-7H-pyrrolo[2,3-d]pyrimidine-2,4-diamine hydrochloride To tert-butyl(R)-3-((2-((1-ethyl-1H-pyrazol-4-yl)amino)-5-fluoro-7-((2-(trimethylsilyl)ethoxy)methyl)-7H-pyrrolo[2,3-d]pyrimidin-4-yl)amino)piperidine-1-carboxylate (67.0 mg, 0.15 mmol) was added 6 N hydrochloric acid solution (3.0 mL, excess) dissolved in methanol. After stirring at 60° C. to 70° C. for 2 hours, the reaction mixture was concentrated and the subsequent reaction was carried out without isolation.

$^1$H NMR (500 MHz, CD$_3$OD) δ 8.05-7.40 (m, 3H), 6.90-6.40 (m, 1H), 6.30-6.03 (m, 1H), 5.85-5.55 (m, 1H), 4.70-2.90 (m, 7H), 2.15-2.00 (m, 1H), 1.95-1.70 (m, 2H), 1.69-1.55 (m, 1H), 1.50-1.35 (m, 3H)

Step 6: Preparation of (R)-1-(3-((2-((1-ethyl-1H-pyrazol-4-yl)amino)-5-fluoro-7H-pyrrolo[2,3-d]pyrimidin-4-yl)amino)piperidin-1-yl)prop-2-en-1-one After (R)—N2-(1-ethyl-1H-pyrazol-4-yl)-5-fluoro-N4-(piperidin-3-yl)-7H-pyrrolo[2,3-d]pyrimidine-2,4-diamine hydrochloride (67.5 mg, 0.2 mmol) was dissolved in a 3:1 mixed solution of tetrahydrofuran:distilled water (4.0 ml), sodium bicarbonate (44.7 mg, 0.5 mmol) was added thereto at −20° C. and the mixture was stirred for 30 minutes. Acryloyl chloride (15.1 μL, 0.2 mmol) was slowly added dropwise to the reaction mixture and was stirred at −20° C. for 1 hour. The organic layer was isolated, treated with magnesium sulfate, filtered, and then concentrated under reduced pressure. The residue was isolated by column chromatography to obtain a title compound (4.3 mg, yield: 6.1%).

$^1$H NMR (500 MHz, CD$_3$OD) δ 8.00-7.97 (m, 1H), 7.57-7.45 (m, 1H), 6.90-6.40 (m, 1H), 6.27-6.05 (m, 1H), 5.79-5.48 (m-2H), 4.23-4.01 (m, 4H), 3.93-3.83 (m, 2H), 2.99-2.97 (m, 1H), 2.15-2.00 (m, 1H), 1.91-1.75 (m, 2H), 1.70-1.61 (m, 1H), 1.44-1.37 (m, 3H)

Example 83: Preparation of (R)-1-(3-((5-2-((3-methylisothiazol-5-yl)amino)-7H-pyrrolo[2,3-d]pyrimidin-4-yl)amino)piperidin-1-yl)prop-2-en-1-one

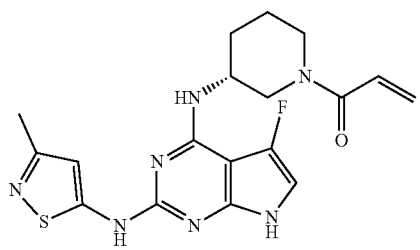 [SMILES: C=CC(=O)N1CCC[C@@H](Nc2nc(Nc3cc(C)ns3)nc3[nH]cc(F)c23)C1]

A title compound (2.0 mg, yield: 1.4%) was prepared in the same manner as in Example 82, except that 3-methylisothiazol-5-amine was used instead of 1-ethyl-1H-pyrazol-4-amine in Example 82.

$^1$H NMR (500 MHz, CD$_3$OD) δ 7.75-7.6 (m, 1H), 6.85-6.63 (m, 2H), 6.30-6.05 (m, 1H), 5.80-5.50 (m, 1H), 4.57-4.45 (m, 1H), 4.27-4.15 (m, 1H), 3.90-3.86 (m, 2H, 3.70-3.54 (m, 1H), 2.32 (s, 3H), 2.25-2.20 (m, 1H), 2.16-2.00 (m, 1H), 1.89-1.72 (m, 2H), 1.65-1.50 (m, 3H)

Example 84: Preparation of 1-((3R,4R)-3-((2-((1-ethyl-1H-pyrazol-4-yl)amino)-5-fluoro-7H-pyrrolo[2,3-d]pyrimidin-4-yl)amino)-4-methylpiperidin-1-yl)prop-2-en-1-one

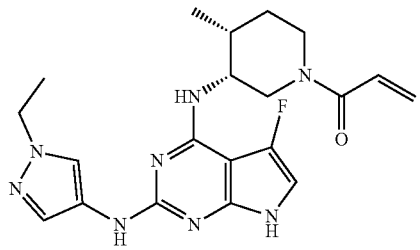 [SMILES: C=CC(=O)N1CC[C@@H](C)[C@@H](Nc2nc(Nc3cnn(CC)c3)nc3[nH]cc(F)c23)C1]

Step 1: Preparation of 2,4-dichloro-5-fluoro-7H-pyrrolo[2,3-d]pyrimidine

After 2,4-dichloro-7H-pyrrolo[2,3-d]pyrimidine (200 mg, 1.06 mmol) was dissolved in acetonitrile (5.0 mL), 1-chloromethyl-4-fluoro-1,4-diazoniabicyclo[2.2.2]octane bis (tetrafluoroborate) (561.6 mg, 1.6 mmol) and acetic acid (1 mL) were added thereto. The mixture was heated at 80° C. and stirred for 24 hours, and then the organic layer was isolated, treated with magnesium sulfate, filtered and then concentrated under reduced pressure. The residue was isolated by column chromatography to obtain a title compound (170.0 mg, yield: 80.1%).

$^1$H NMR (500 MHz, CD$_3$OD) δ 7.36 (s, 1H)

Step 2: Preparation of 2,4-dichloro-5-fluoro-7-tosyl-7H-pyrrolo[2,3-d]pyrimidine After 2,4-dichloro-7H-pyrrolo[2,3-d]pyrimidine (369.4 mg, 1.8 mmol) was dissolved in dichloromethane (30.0 mL), 4-dimethylaminopyridine (43.8 mg, 0.4 mmol) and triethylamine (499.8 mg, 3.6 mmol) were added thereto and then stirred for 30 minutes. 4-Methylbenzenesulfonyl chloride (393.1 mg, 2.1 mmol) was added to the reaction mixture, and the mixture was stirred at room temperature for 12 hours. The organic layer was isolated, treated with magnesium sulfate, filtered and then concentrated under reduced pressure. The residue was isolated by column chromatography to obtain a title compound (363.0 mg, yield 56.2%).

$^1$H NMR (500 MHz, CD$_3$OD) δ 8.07 (d, 1H), 7.92 (s, 1H), 7.45 (d, 1H), 2.42 (s, 3H)

Step 3: Preparation of tert-butyl(3R,4R)-3-((2-chloro-5-fluoro-7-tosyl-7H-pyrrolo[2,3-d]pyrimidin-4-yl)amino)-4-methylpiperidine-1-carboxylate After 2,4-dichloro-5-fluoro-7-tosyl-7H-pyrrolo[2,3-d]pyrimidine (100.0 mg, 0.3 mmol) was dissolved in ethanol (3 mL), N,N-diisopropylethylamine (72.5 μL, 2.2 mmol) and tert-butyl (3R,4R)-3-amino-4-methylpiperidine-1-carboxylate (89.3 mg, 0.3 mmol) were added thereto. The reaction mixture was stirred at 110° C. for 12 hours, and then the organic layer was isolated, treated with magnesium sulfate, filtered and then concentrated under reduced pressure. The residue was isolated by column chromatography to obtain a title compound (121.0 mg, yield: 81.7%).

$^1$H NMR (500 MHz, CD$_3$OD) δ 8.01 (d, 1H), 7.44-7.40 (m, 3H), 4.59-4.50 (m, 1H), 4.48-4.03 (m, 3H), 2.98-2.82 (m, 2H), 2.41 (s, 3H), 2.10-2.00 (m, 1H), 1.70-1.61 (m, 1H), 1.58-1.36 (m, 4H), 1.00-0.80 (m, 9H)

Step 4: Preparation of tert-butyl(3R,4R)-3-((2-((1-ethyl-1H-pyrazol-4-yl)amino)-5-fluoro-7-tosyl-7H-pyrrolo[2,3-d]pyrimidin-4-yl)amino)-4-methylpiperidine-1-carboxylate After tert-butyl(3R,4R)-3-((2-chloro-5-fluoro-7-tosyl-7H-pyrrolo[2,3-d]pyrimidin-4-yl)amino)-4-methylpiperidine-1-carboxylate (100.0 mg, 0.2 mmol) was dissolved in anhydrous tert-butanol (2.0 mL), 1-ethyl-1H-pyrazol-4-amine (21.3 mg, 0.2 mmol), tris(dibenzylideneacetone)dipalladium (8.5 mg, 0.01 mmol), 2-dicyclohexylphosphino-2',4', 6'-triisopropylbiphenyl (8.9 mg, 0.2 mmol) and potassium carbonate (51.5 mg, 0.4 mmol) were added thereto, followed by reacting at 100° C. for 12 hours. The organic layer was isolated, treated with magnesium sulfate, filtered and then concentrated under reduced pressure. The residue was isolated by column chromatography to obtain a title compound (58.3 mg, yield: 51.1%).

¹H NMR (500 MHz, CD₃OD) δ 8.55 (s, 1H), 7.94 (d, 1H), 7.62 (s, 1H), 7.30 (d, 1H), 7.02 (s, 1H), 4.60-4.55 (m, 1H), 4.21-4.07 (m, 4H), 2.95-2.78 (m, 2H), 2.34 (s, 3H), 2.06-2.00 (m, 1H), 1.57-1.32 (m, 8H), 0.98-0.86 (m, 9H)

Step 5: Preparation of tert-butyl(3R,4R)-3-((2-((1-ethyl-1H-pyrazol-4-yl)amino)-5-fluoro-7H-pyrrolo[2,3-d]pyrimidin-4-yl)amino)-4-methylpiperidine-1-carboxylate Tert-butyl(3R,4R)-3-[(2-((1-ethyl-1H-pyrazol-4-yl)amino]-5-fluoro-7-tosyl-7H-pyrrolo[2,3-d]pyrimidin-4-yl)amino)-4-methylpiperidine-1-carboxylate (58.3 mg, 0.1 mmol) was dissolved in methanol (2.0 mL). Potassium hydroxide (10.7 mg, 0.2 mmol) was added to the reaction mixture and then stirred at 50° C. for 5 hours. The organic layer was isolated, treated with magnesium sulfate, filtered and then concentrated under reduced pressure. The residue was isolated by column chromatography to obtain a title compound (28.6 mg, yield: 65.5%).

¹H NMR (500 MHz, CD₃OD) δ 7.90 (s, 1H), 7.55 (s, 1H), 6.50 (s, 1H), 4.59-4.50 (m, 1H), 4.27-4.07 (m, 3H), 3.16-2.85 (m, 2H), 2.07-2.00 (s, 1H), 1.63-1.61 (m, 1H), 1.46-1.28 (m, 7H), 1.15-1.00 (m, 9H)

Step 6: Preparation of N2-(1-ethyl-1H-pyrazol-4-yl)-5-fluoro-N4-((3R,4R)-4-methylpiperidin-3-yl)-7H-pyrrolo[2,3-d]pyrimidine-2,4-diamine hydrochloride To tert-butyl(3R,4R)-3-((2-((1-ethyl-1H-pyrazol-4-yl)amino)-5-fluoro-7H-pyrrolo[2,3-d]pyrimidin-4-yl)amino)-4-methylpiperidine-1-carboxylate (28.6 mg, 0.06 mmol) was added 6 N hydrochloric acid solution (2.0 mL, excess) dissolved in methanol. After stirring at room temperature for 30 minutes, the reaction mixture was concentrated and the subsequent reaction was carried out without isolation.

¹H NMR (500 MHz, CD₃OD) δ 7.96-7.88 (m, 1H), 7.69-7.63 (m, 2H), 4.22-4.20 (m, 2H), 4.10-4.05 (m, 1H), 3.66-3.63 (m, 1H), 3.16-3.11 (m, 1H), 2.32-2.20 (m, 1H), 1.98-1.94 (m, 1H), 1.78-1.73 (m, 1H) 1.48-1.46 (m, 3H), 1.30-1.25 (m, 1H), 1.15-1.05 (m, 4H)

Step 7: Preparation of 1-((3R,4R)-3-((2-((1-ethyl-1H-pyrazol-4-yl)amino)-5-fluoro-7H-pyrrolo[2,3-d]pyrimidin-4-yl)amino)-4-methylpiperidin-1-yl)prop-2-en-1-one After N2-(1-ethyl-1H-pyrazol-4-yl)-5-fluoro-N4-((3R,4R)-4-methylpiperidin-3-yl)-7H-pyrrolo[2,3-d]pyrimidine-2,4-diamine hydrochloride (22.5 mg, 0.06 mmol) was dissolved in a 3:1 mixed solution of tetrahydrofuran:distilled water (4.0 ml), sodium bicarbonate (14.4 mg, 0.2 mmol) was added thereto at −20° C. and the mixture was stirred for 30 minutes. Acryloyl chloride (5.1 μL, 0.07 mmol) was slowly added dropwise to the reaction mixture and then stirred at −20° C. for 1 hour. The organic layer was isolated, treated with magnesium sulfate, filtered, and then concentrated under reduced pressure. The residue was isolated by column chromatography to obtain a title compound (3.5 mg, yield: 14.9%).

¹H NMR (500 MHz, CD₃OD) δ 8.01-7.80 (m, 1H), 7.72-7.58 (m, 2H), 6.86-6.35 (m, 1H), 6.20-6.00 (m, 1H), 5.85-5.45 (m, 1H), 4.58-4.30 (m, 2H), 4.22-4.14 (m, 2H), 3.84-3.83 (m, 2H), 2.95-2.78 (m, 1H), 2.18-2.12 (m, 1H), 1.70-1.65 (m, 1H), 1.46-1.41 (m, 3H), 1.31-1.28 (m, 1H), 0.95-0.88 (m, 3H)

Example 85: Preparation of (R)-1-(3-((2-((1-ethyl-1H-pyrazol-4-yl)amino)-5-fluoro-7H-pyrrolo[2,3-d]pyrimidin-4-yl)thio)piperidin-1-yl)prop-2-en-1-one

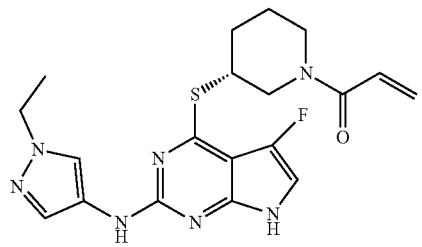 [SMILES: C=CC(=O)N1CCC[C@@H](Sc2nc(Nc3cnn(CC)c3)nc3[nH]cc(F)c23)C1]

A title compound (4.1 mg, yield: 19.9%) was prepared in the same manner as in Example 84, except that tert-butyl (R)-3-mercaptopiperidine-1-carboxylate was used instead of tert-butyl(3R,4R)-3-amino-4-methylpiperidine-1-carboxylate in Example 84.

¹H NMR (500 MHz, CD₃OD) δ 8.09-8.05 (m, 1H), 7.85-7.50 (m, 2H), 6.85-6.60 (m, 1H), 6.28-6.11 (m, 1H), 5.80-5.58 (m, 1H), 4.60-4.00 (m, 4H), 3.80-3.50 (m, 2H), 3.48-3.38 (m, 1H), 2.10-2.00 (m, 1H), 1.90-1.75 (m, 2H), 1.72-1.58 (m, 1H), 1.50-1.40 (m, 3H)

Example 86: Preparation of 1-((3S,4R)-3-((2-((1-ethyl-1H-pyrazol-4-yl)amino)-5-fluoro-7H-pyrrolo[2,3-d]pyrimidin-4-yl)amino)-4-fluoropiperidin-1-yl)prop-2-en-1-one

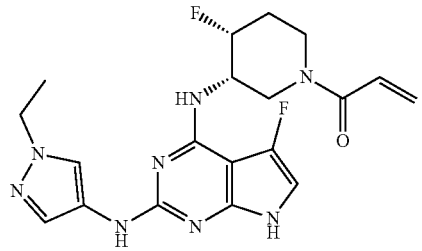 [SMILES: C=CC(=O)N1CC[C@@H](F)[C@@H](Nc2nc(Nc3cnn(CC)c3)nc3[nH]cc(F)c23)C1]

A title compound (7.9 mg, yield: 22.2%) was prepared in the same manner as in Example 84, except that tert-butyl (3R,4R)-3-amino-4-fluoropiperidine-1-carboxylate was used instead of tert-butyl(3R,4R)-3-amino-4-methylpiperidine-1-carboxylate in Example 84.

¹H NMR (500 MHz, CD₃OD) δ 8.00-7.98 (m, 1H), 7.57-7.41 (m, 2H), 6.95-6.85 (m, 1H), 6.27-6.15 (m, 1H), 5.89-5.81 (m, 1H), 5.07-4.97 (m, 1H), 4.58-4.40 (m, 1H), 4.22-4.06 (m, 2H), 3.87-3.84 (m, 1H), 3.44-3.34 (m, 1H), 3.00-2.98 (m, 1H), 2.20-2.15 (m, 1H), 1.93-1.85 (m, 1H), 1.46-1.33 (m, 3H)

Example 87: Preparation of (R)-1-(3-((2-((1-ethyl-1H-pyrazol-4-yl)amino)-5-fluoro-7H-pyrrolo[2,3-d]pyrimidin-4-yl)(methyl)amino)piperidin-1-yl)prop-2-en-1-one

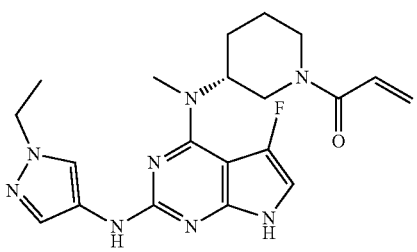 [SMILES: C=CC(=O)N1CCC[C@@H](N(C)c2nc(Nc3cnn(CC)c3)nc3[nH]cc(F)c23)C1]

A title compound (7.9 mg, yield: 22.2%) was prepared in the same manner as in Example 84, except that tert-butyl (R)-3-(methylamino)piperidine-1-carboxylate was used instead of tert-butyl(3R,4R)-3-amino-4-methylpiperidine-1-carboxylate in Example 84.

$^1$H NMR (500 MHz, CD$_3$OD) δ 7.95-7.61 (m, 3H), 6.85-6.80 (m, 1H), 6.25-6.05 (m, 1H), 5.75-5.60 (m, 1H), 4.68-4.58 (m, 1H), 4.22-4.12 (m, 3H), 3.85-3.75 (m, 1H), 3.16-3.07 (m, 3H), 2.70-2.55 (m, 1H), 2.00-1.97 (m, 1H), 1.69-1.65 (m, 2H), 1.44-1.33 (m, 3H)

Example 88: Preparation of (R)-4-((1-acryloylpiperidin-3-yl)amino)-2-((1-ethyl-1H-pyrazol-4-yl)amino)-7H-pyrrolo[2,3-d]pyrimidine-5-carbonitrile

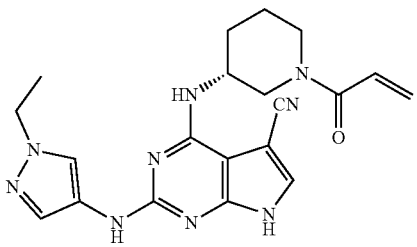

Step 1: Preparation of tert-butyl(R)-3-((2-chloro-5-cyano-7H-pyrrolo[2,3-d]pyrimidin-4-yl)amino)piperidine-1-carboxylate After 2,4-dichloro-7H-pyrrolo[2,3-d]pyrimidine-5-carbonitrile (300.0 mg, 1.4 mmol) was dissolved in ethanol (3.0 mL), N,N-diisopropylethylamine (369.8 μL, 2.1 mmol) and tell-butyl(R)-3-aminopiperidine-1-carboxylate (425.2 mg, 2.1 mmol) was added thereto. The reaction mixture was stirred at 110° C. for 12 hours, and then the organic layer was isolated, treated with magnesium sulfate, filtered, and then concentrated under reduced pressure. The residue was isolated by column chromatography to obtain a title compound (308 mg, yield: 57.7%).

$^1$H NMR (500 MHz, CD$_3$OD) δ 7.83 (m, 1H), 4.35-4.20 (m, 1H), 3.73-3.59 (m, 2H), 3.56-3.52 (m, 1H), 2.13-2.02 (m, 1H), 1.89-1.78 (m, 2H), 1.70-1.60 (m, 1H), 1.35-1.15 (m, 9H)

Step 2: Preparation of (R)-2-chloro-4-(piperidin-3-ylamino)-7H-pyrrolo[2,3-d]pyrimidine-5-carbonitrile hydrochloride To tert-butyl(R)-3-((2-chloro-5-cyano-7H-pyrrolo[2,3-d]pyrimidin-4-yl)amino)piperidine-1-carboxylate (308.0 mg, 0.8 mmol) was added 6 N hydrochloric acid solution (5.0 mL, excess) dissolved in methanol. After stirring at room temperature for 30 minutes, the reaction mixture was concentrated and the subsequent reaction was carried out without isolation.

$^1$H NMR (500 MHz, CD$_3$OD) δ 7.83 (m, 1H), 4.35-4.20 (m, 1H), 3.73-3.59 (m, 2H), 3.56-3.52 (m, 1H), 2.13-2.02 (m, 1H), 1.89-1.78 (m, 2H), 1.70-1.60 (m, 1H)

Step 3: Preparation of (R)-4-((1-acryloylpiperidin-3-yl)amino)-2-chloro-7H-pyrrolo[2,3-d]pyrimidine-5-carbonitrile After (R)-2-chloro-4-(piperidin-3-ylamino)-7H-pyrrolo[2,3-d]pyrimidine-5-carbonitrile hydrochloride (252.8 mg, 0.8 mmol) was dissolved in a 3:1 mixed solution of tetrahydrofuran: distilled water (4.0 ml), sodium bicarbonate (203.4 mg, 2.4 mmol) was added thereto at −20° C. and the mixture was stirred for 30 minutes. Acryloyl chloride (68.9 μL, 0.9 mmol) was slowly added dropwise to the reaction mixture and stirred at −20° C. for 1 hour. The organic layer was isolated, treated with magnesium sulfate, filtered, and then concentrated under reduced pressure. The residue was isolated by column chromatography to obtain a title compound (130.0 mg, yield: 48.6%).

$^1$H NMR (500 MHz, CD$_3$OD) δ 7.83 (d, 1H), 6.84-6.75 (m, 1H), 6.20-6.13 (m, 1H), 5.74-5.64 (m, 1H), 4.41-4.03 (m, 2H), 3.94-3.65 (m, 2H), 3.44-3.34 (m, 1H), 2.15-2.10 (m, 1H), 1.89-1.83 (m, 2H), 1.80-1.75 (m, 1H)

Step 4: Preparation of (R)-4-((1-acryloylpiperidin-3-yl)amino)-2-((1-ethyl-1H-pyrazol-4-yl)amino)-7H-pyrrolo[2,3-d]pyrimidine-5-carbonitrile (R)-4-((1-acryloylpiperidin-3-yl)amino)-2-chloro-7H-pyrrolo[2,3-d]pyrimidine-5-carbonitrile (30.0 mg, 0.09 mmol) and 1-ethyl-1H-pyrazol-4-amine (7.8 mg, 0.07 mmol) were dissolved in 2-butanol (2.0 mL). Trifluoroacetic acid (6.4 μL, 0.08 mmol) was added to the reaction mixture, followed by reacting at 120° C. for 3 hours, and then the solvent was concentrated. The reaction mixture was neutralized by adding 7 N ammonia solution dissolved in methanol, and the residue was isolated by column chromatography to obtain a title compound (5.5 mg, yield: 19.6%).

$^1$H NMR (500 MHz, CD$_3$OD) δ 7.95 (d, 1H), 7.56-7.50 (m, 2H), 6.90-6.52 (m, 1H) 6.25-6.04 (m, 1H), 5.78-5.50 (m, 1H), 4.35-4.25 (m, 1H), 4.14-4.11 (m, 2H), 3.93-3.85 (m, 1H), 3.80-3.65 (m, 1H), 3.59-3.28 (m, 2H), 2.23-2.13 (m, 1H), 1.90-1.79 (m, 2H), 1.68-1.66 (m, 1H), 1.44-1.36 (m, 3H)

Example 89: Preparation of (R)-4-((1-acryloylpiperidin-3-yl)amino)-2-((1-cyclopropyl-1H-pyrazol-4-yl)amino)-7H-pyrrolo[2,3-d]pyrimidine-5-carbonitrile

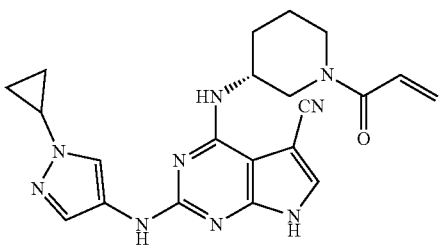 [SMILES: C=CC(=O)N1CCC[C@@H](Nc2nc(Nc3cnn(C4CC4)c3)nc3[nH]cc(C#N)c23)C1]

A title compound (2.8 mg, yield: 8.43%) was prepared in the same manner as in Example 88, except that 1-cyclopropyl-1H-pyrazol-4-amine was used instead of 1-ethyl-1H-pyrazol-4-amine in Example 88.

$^1$H NMR (500 MHz, CD$_3$OD) δ 8.00 (s, 1H), 7.53-7.51 (m, 2H), 6.85-6.51 (m, 1H), 6.24-6.04 (m, 1H), 5.77-5.50 (m, 1H), 4.41-3.95 (m, 2H), 3.85-3.45 (m, 2H), 2.15-2.10 (m, 1H), 1.87-1.80 (m, 3H), 1.70-1.67 (m, 1H), 1.05-1.04 (m, 4H)

Example 90: Preparation of (R)-1-(3-((3-chloro-6-((1-(2,2-difluoroethyl)-1H-pyrazol-4-yl)amino)-1H-pyrazolo[3,4-d]pyrimidin-4-yl)amino)piperidin-1-yl)prop-2-en-1-one hydrochloride

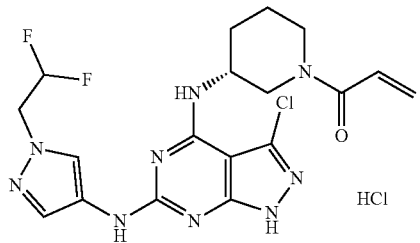 [SMILES: C=CC(=O)N1CCC[C@@H](Nc2nc(Nc3cnn(CC(F)F)c3)nc3[nH]nc(Cl)c23)C1 ; Cl]

After (R)-1-(3-(3-chloro-6-(1-(2,2-difluoroethyl)-1H-pyrazol-4-ylamino)-1H-pyrazolo[3,4-d]pyrimidin-4-yl)amino)piperidin-1-yl)prop-2-en-1-one (Example 44) (30.0 mg, 0.07 mmol) was dissolved in ethyl acetate, 2.0 N hydrochloric acid solution (3.0 mL, excess) dissolved in diethyl ether was added thereto. After stirring at room temperature for 1 hour, the reaction mixture was concentrated to obtain a title compound (28.0 mg, yield: 82.3%).

$^1$H NMR (500 MHz, CD$_3$OD) δ 8.10-8.04 (m, 1H), 7.68-7.63 (m, 1H), 6.87-6.50 (m, 1.H), 6.28-6.15 (m, 2H), 6.04-5.80 (m, 1H), 4.58-4.53 (m, 3H), 4.36-4.30 (m, 1H), 4.05-3.90 (m, 2H), 3.44-3.40 (m, 1H) 2.15-2.13 (m, 1H), 1.98-1.86 (m, 2H), 1.66-1.64 (m, 1H)

Example 91: Preparation of (R)-1-(3-((3-chloro-6-((1-ethyl-1H-pyrazol-4-yl)amino)-1H-pyrazolo[3,4-d]pyrimidin-4-yl)amino)piperidin-1-yl)prop-2-en-1-one hydrochloride

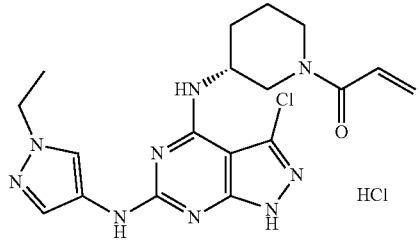 [SMILES: C=CC(=O)N1CCC[C@@H](Nc2nc(Nc3cnn(CC)c3)nc3[nH]nc(Cl)c23)C1 ; Cl]

A title compound (2.8 mg, yield: 8.43%) was prepared in the same manner as in Example 90, except that (R)-1-(3-((3-chloro-6-((1-ethyl-1H-pyrazol-4-yl)amino)-1H-pyrazolo[3,4-d]pyrimidin-4-yl)amino)piperidin-1-yl)prop-2-en-1-one (Example 46) was used instead of R)-1-(3-(3-chloro-6-(1-(2,2-difluoroethyl)-1H-pyrazol-4-ylamino)-1H-pyrazolo[3,4-d]pyrimidin-4-ylamino)piperidin-1-yl)prop-2-en-1-one in Example 90.

$^1$H NMR (500 MHz, CD$_3$OD) δ 8.07 (s, 1H), 7.96 (s, 1H), 6.86-6.81 (m, 1H), 6.27-6.15 (m, 1H) 5.81-5.58 (m, 1H) 4.37-4.30 (m, 2H), 4.11-4.06 (m, 2H), 3.92-3.82 (m, 1H), 3.43-3.39 (m, 2H), 2.15-2.10 (m, 1H), 1.90-1.80 (m, 2H), 1.70-1.63 (m, 1H), 1.46-1.40 (m, 3H)

Example 92: Preparation of 1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)prop-2-en-1-one

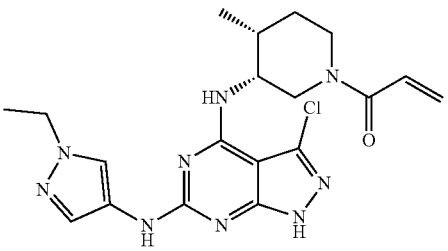 [SMILES: C=CC(=O)N1CC[C@@H](C)[C@@H](Nc2nc(Nc3cnn(CC)c3)nc3[nH]nc(Cl)c23)C1]

A title compound (5.7 mg, yield: 26.6%) was prepared in the same manner as in Example 42, except using 1-ethyl-1H-pyrazol-4-amine instead of 4-(4-methylpiperazin-1-yl)aniline, and tert-butyl(3R,4R)-3-amino-4-methylpiperidine-1-carboxylate instead of tert-butyl (R)-3-aminopiperidine-1-carboxylate in Example 42.

$^1$H NMR (500 MHz, CD$_3$OD) δ 7.96 (s, 1H), 7.59 (s, 1H), 6.90-6.46 (m, 1H), 6.20-6.01 (m, 1H), 5.77-5.42 (m, 1H), 4.68-4.58 (m, 2H), 4.46-4.39 (m, 2H), 4.16-4.13 (m, 2H), 3.16-3.12 (m, 1H), 2.89-2.85 (m, 1H), 2.25-2.15 (m, 1H), 1.76-1.74 (m, 1H), 1.46-1.44 (m, 3H), 1.05 (d, 3H)

Example 93: Preparation of 1-((3R,4R)-3-((3-chloro-6-((1-(2,2-difluoroethyl)-1H-pyrazol-4-yl)amino)-1H-pyrazolo[3,4-d]pyrimidin-4-yl)amino)-4-methylpiperidin-1-yl)prop-2-en-1-one

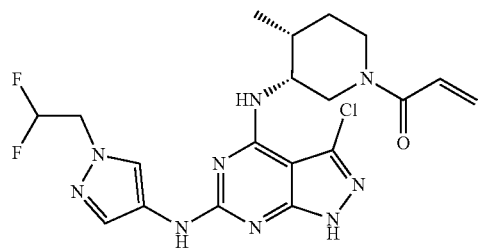 [SMILES: C=CC(=O)N1CC[C@@H](C)[C@@H](Nc2nc(Nc3cnn(CC(F)F)c3)nc3[nH]nc(Cl)c23)C1]

A title compound (31.5 mg, yield: 66.4%) was prepared in the same manner as in Example 42, except using tert-butyl (3R,4R)-3-amino-4-methylpiperidine-1-carboxylate instead of tert-butyl(R)-3-aminopiperidine-1-carboxylate, and 1-(2,2-difluoroethyl)-1H-pyrazol-4-amine instead of 4-(4-methylpiperazin-1-yl)aniline in Example 42.

¹H NMR (500 MHz, CD₃OD) δ 8.05 (s, 1H), 7.65 (s, 1H), 6.90-6.45 (m, 1H), 6.30-6.01 (m, 2H), 5.77-5.42 (m, 1H), 4.67-4.39d (m, 5H), 3.16-2.84 (m, 1H), 2.25-2.15 (m, 1H), 1.76-1.73 (m, 1H), 1.49-1.41 (m, 1H), 1.30-1.25 (m, 1H), 1.04 (d, 3H)

Example 94: Preparation of 1-((3R,4R)-3-((3-chloro-6-((1-cyclopropyl-1H-pyrazol-4-yl)amino)-1H-pyrazolo[3,4-d]pyrimidin-4-yl)amino)-4-methylpiperidin-1-yl)prop-2-en-1-one

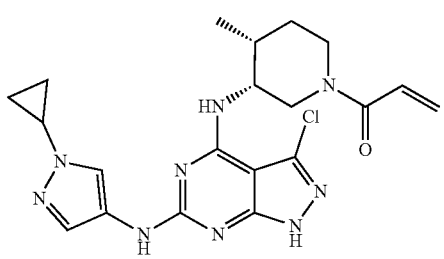 [SMILES: C=CC(=O)N1CC[C@@H](C)[C@@H](Nc2nc(Nc3cnn(C4CC4)c3)nc3[nH]nc(Cl)c23)C1]

A title compound (30.0 mg, yield: 66.1%) was prepared in the same manner as in Example 42, except using tert-butyl (3R,4R)-3-amino-4-methylpiperidine-1-carboxylate instead of tert-butyl(R)-3-aminopiperidine-1-carboxylate, and cyclopropyl-1H-pyrazol-4-amine instead of 4-(4-methylpiperazin-1-yl)aniline in Example 42.

¹H NMR (500 MHz, CD₃OD) δ 7.99 (s, 1H), 7.57 (s, 1H), 6.89-6.43 (m, 1H), 6.20-6.01 (m, 1H), 5.77-5.42 (m, 1H), 4.69-4.10 (m, 3H), 3.60-3.58 (m, 1H), 3.39-3.37 (m, 1H), 3.15-2.85 (m, 1H), 2.23-2.19 (m, 1H), 1.76-1.74 (m, 1H), 1.46-1.41 (m, 1H), 1.08-1.00 (m, 7H)

Example 95: Preparation of (R)-1-(3-((5-chloro-2-((1-(2-(diethylamino)ethyl)-1H-pyrazol-4-yl)amino)-7H-pyrrolo[2,3-d]pyrimidin-4-yl)amino)piperidin-1-yl)prop-2-en-1-one

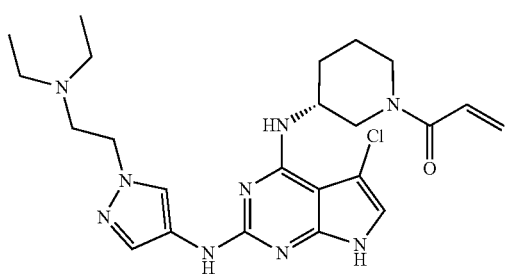 [SMILES: C=CC(=O)N1CCC[C@@H](Nc2nc(Nc3cnn(CCN(CC)CC)c3)nc3[nH]cc(Cl)c23)C1]

A title compound (4.5 mg, yield: 18.6%) was prepared in the same manner as in Example 36, except that 1-(2-(diethylamino)ethyl)-1H-pyrazol-4-amine was used instead of 4-(4-methylpiperazin-1-yl)aniline in Example 36.

¹H NMR (500 MHz, CD₃OD) δ 7.98-7.92 (m, 1H), 7.58-7.56 (m, 1H), 6.82-6.55 (m, 2H), 6.25-6.06 (m, 1H), 5.78-5.50 (m, 1H), 4.34-3.40 (m, 7H), 3.00-2.97 (m, 2H), 2.68-2.61 (m, 4H), 2.08-2.02 (m, 2H), 1.90-1.87 (m, 1H), 1.67-1.59 (m, 1H), 1.08-1.02 (m, 6H)

Example 96: Preparation of (R)-1-(3-((5-chloro-2-(isoxazol-4-ylamino)-7H-pyrrolo[2,3-d]pyrimidin-4-yl)amino)piperidin-1-yl)prop-2-en-1-one

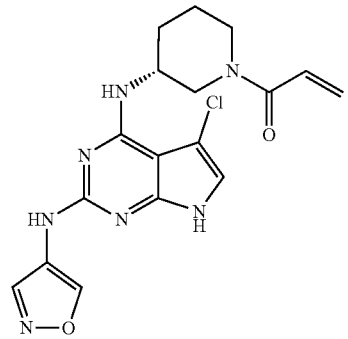 [SMILES: C=CC(=O)N1CCC[C@@H](Nc2nc(Nc3cnoc3)nc3[nH]cc(Cl)c23)C1]

A title compound (8.3 mg, yield: 42.8%) was prepared in the same manner as in Example 36, except that isoxazol-4-amine was used instead of 4-(4-methylpiperazin-1-yl)aniline in Example 36.

¹H NMR (500 MHz, CD₃OD) δ 9.03 (s, 1H), 8.48 (s, 1H), 6.90-6.53 (m, 2H), 6.25-6.08 (m, 1H), 5.78-5.50 (m, 1H), 4.40-4.20 (m, 2H), 3.90-3.70 (m, 2H), 3.60-3.40 (m, 1H), 2.13-2.00 (m, 2H), 1.92-1.73 (m, 1H), 1.72-1.55 (m, 1H)

Example 97: Preparation of (R)-1-(3-((5-chloro-2-(isoxazol-4-ylamino)-7H-pyrrolo[2,3-d]pyrimidin-4-yl)amino)piperidin-1-yl)prop-2-en-1-one

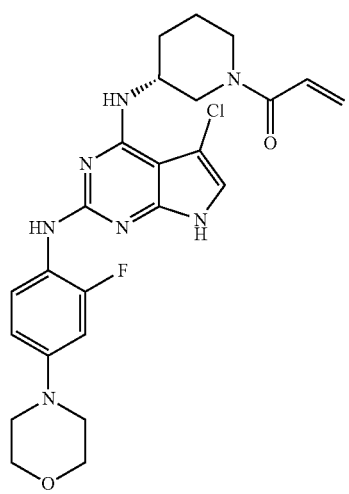

A title compound (11.4 mg, yield: 45.8%) was prepared in the same manner as in Example 36, except that 2-fluoro-4-morpholinoaniline was used instead of 4-(4-methylpiperazin-1-yl)aniline in Example 36.

¹H NMR (500 MHz, CD₃OD) δ 8.00-7.90 (m, 1H), 7.08-6.51 (m, 4H), 6.25-6.05 (m, 1H), 5.80-5.45 (m, 1H), 4.35-4.10 (m, 2H), 3.85-3.70 (m, 4H), 3.65-3.35 (m, 3H), 3.25-3.00 (m, 4H), 2.15-1.95 (m, 1H), 1.90-1.70 (m, 1H), 1.63-1.54 (m, 2H)

Example 98: Preparation of (R)-1-(3-((5-chloro-24 (3-fluoro-4-morpholinophenyl)amino)-7H-pyrrolo[2,3-d]pyrimidin-4-yl)amino)piperidin-1-yl)prop-2-en-1-one

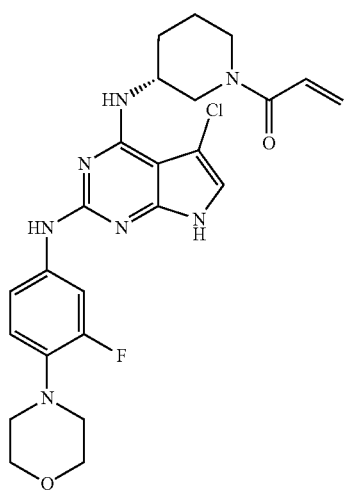 [SMILES: C=CC(=O)N1CCC[C@@H](Nc2nc(Nc3ccc(N4CCOCC4)c(F)c3)nc3[nH]cc(Cl)c23)C1]

A title compound (6.9 mg, yield: 27.8%) was prepared in the same manner as in Example 36, except that 3-fluoro-4-morpholinoaniline was used instead of 4-(4-methylpiperazin-1-yl)aniline in Example 36.

$^1$H NMR (500 MHz, CD$_3$OD) δ 7.84-7.72 (m, 1H), 7.27-7.18 (m, 1H), 6.98-6.90 (m, 1H), 6.87-6.50 (m, 2H), 6.28-6.00 (m, 1H), 5.80-5.43 (m, 1H), 4.48-3.90 (m, 2H), 3.85-3.77 (m, 4H), 3.76-3.58 (m, 2H), 3.52-3.33 (m, 1H), 3.02-2.95 (m, 4H), 2.15-2.00 (m, 1H), 1.90-1.75 (m, 2H), 1.70-1.55 (m, 1H)

Example 99: Preparation of (R)-1-(3-((5-chloro-24 (5-methylisoxazol-4-yl)amino)-7H-pyrrolo[2,3-d]pyrimidin-4-yl)amino)piperidin-1-yl)prop-2-en-1-one

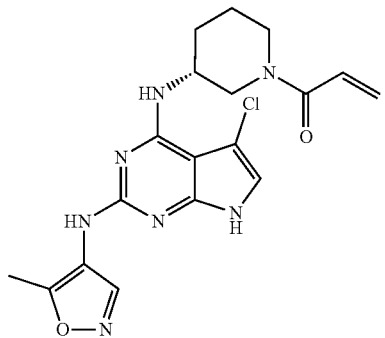 [SMILES: C=CC(=O)N1CCC[C@@H](Nc2nc(Nc3cnoc3C)nc3[nH]cc(Cl)c23)C1]

A title compound (7.6 mg, yield: 37.7%) was prepared in the same manner as in Example 36, except that 5-methyl-isoxazol-4-amine was used instead of 4-(4-methylpiperazin-1-yl)aniline in Example 36.

$^1$H NMR (500 MHz, CD$_3$OD) δ 8.75-8.65 (m, 1H), 6.90-6.50 (m, 2H), 6.25-6.04 (m, 1H), 5.80-5.52 (m, 1H), 4.35-4.20 (m, 1H), 3.90-3.60 (m, 2H), 3.55-3.35 (m, 2H), 2.39 (s, 3H), 2.16-2.05 (m, 1H), 1.90-1.75 (m, 2H), 1.70-1.60 (m, 1H)

Example 100: Preparation of (R)-1-(3-((5-chloro-2-((1-ethyl-1H-pyrazol-4-yl)amino)-7H-pyrrolo[2,3-d]pyrimidin-4-yl)(methyl)amino)piperidin-1-yl)prop-2-en-1-one

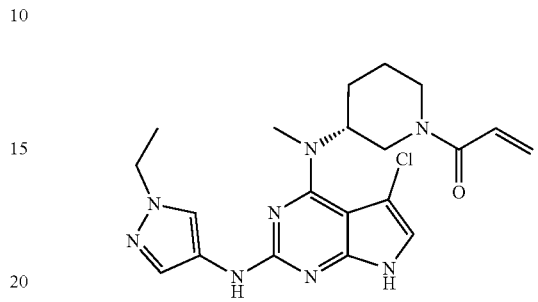

A title compound (9.1 mg, yield: 42.6%) was prepared in the same manner as in Example 36, except using tert-butyl (R)-3-(methylamino)piperidine-1-carboxylate instead of tert-butyl(R)-3-aminopiperidine-1-carboxylate, and 1-ethyl-1H-pyrazol-4-amine instead of 4-(4-methylpiperazin-1-yl)aniline in Example 36.

$^1$H NMR (500 MHz, CD$_3$OD) δ 7.90-7.75 (m, 1H), 7.48 (s, 1H), 6.90-6.60 (m, 1H), 6.40-6.10 (m, 2H), 5.80-5.60 (m, 1H), 4.70-4.50 (m, 2H), 4.20-4.00 (m, 3H), 3.70-3.60 (m, 1H), 3.30-3.20 (m, 3H), 2.20-2.10 (m, 3H), 2.10-1.90 (m, 2H), 1.65-1.50 (m, 2H), 1.45-1.35 (m, 1H)

Example 101: Preparation of (R)-1-(3-((2-((1-ethyl-1H-pyrazol-4-yl)amino)-7H-pyrrolo[2,3-d]pyrimidin-4-yl)(methylamino)piperidin-1-yl)prop-2-en-1-one

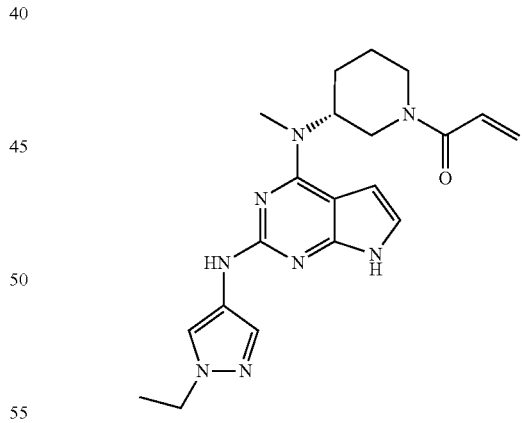

A title compound (8.2 mg, yield: 41.4%) was prepared in the same manner as in Example 1, except using tert-butyl (R)-3-(methylamino)piperidine-1-carboxylate instead of tert-butyl(R)-3-aminopiperidine-1-carboxylate, and 1-ethyl-1H-pyrazol-4-amine instead of 4-(4-methylpiperazin-1-yl)aniline in Example 1.

$^1$H NMR (500 MHz, CDCl$_3$) δ 9.09 (s, 1H), 7.77 (s, 1H), 7.46 (s, 1H), 6.66-6.61 (m, 2H), 6.34-6.31 (m, 3H), 5.67-5.65 (m, 1H), 4.76-4.75 (m, 2H), 4.15-4.07 (m, 3H), 3.28 (s, 3H), 3.07-2.98 (m, 1H), 2.81-2.50 (m, 1H), 2.10-1.87 (m, 5H), 1.69-1.63 (m, 1H)

Example 102: Preparation of (R)-1-(3-((2-(isoxazol-4-ylamino)-7H-pyrrolo[2,3-d]pyrimidin-4-yl)(methyl)amino)piperidin-1-yl)prop-2-en-1-one

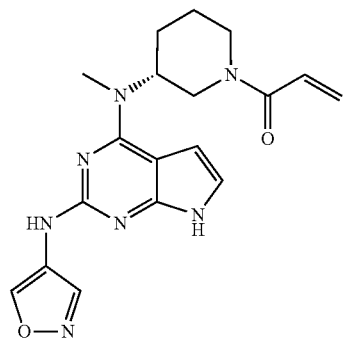 [SMILES: C=CC(=O)N1CCC[C@@H](N(C)c2nc(Nc3cnoc3)nc3[nH]ccc23)C1]

A title compound (8.7 mg, yield: 47.3%) was prepared in the same manner as in Example 1, except using tert-butyl (R)-3-(methylamino)piperidine-1-carboxylate instead of tert-butyl(R)-3-aminopiperidine-1-carboxylate, and isoxazol-4-amine instead of 4-(4-methylpiperazin-1-yl)aniline in Example 1.

$^1$H NMR (500 MHz, CD$_3$OD) δ 8.94 (s, 1H), 8.47 (s, 1H), 6.83-6.74 (m, 2H), 6.52-6.51 (m, 1H), 6.27-6.17 (m, 1H), 5.79-5.66 (m, 1H), 4.60 (s, 1H), 4.14 (s, 1H), 3.67 (s, 3H), 2.03-2.02 (m, 3H), 1.61-1.60 (m, 4H)

Example 103: Preparation of (R)-1-(3-((2-((1-(2,2-difluoroethyl)-1H-pyrazol-4-yl)amino)-7H-pyrrolo[2,3-d]pyrimidin-4-yl)(methylamino)piperidin-1-yl)prop-2-en-1-one

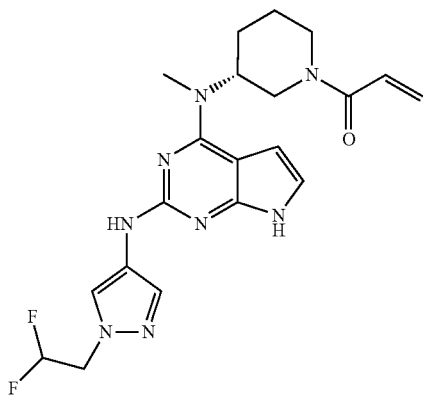 [SMILES: C=CC(=O)N1CCC[C@@H](N(C)c2nc(Nc3cnn(CC(F)F)c3)nc3[nH]ccc23)C1]

A title compound (8.7 mg, yield: 40.6%) was prepared in the same manner as in Example 1, except using tert-butyl (R)-3-(methylamino)piperidine-1-carboxylate instead of tert-butyl(R)-3-aminopiperidine-1-carboxylate, and 1-(2,2-difluoroethyl)-1H-pyrazol-4-amine instead of 4-(4-methylpiperazin-1-yl)aniline in Example 1.

$^1$H NMR (500 MHz, CD$_3$OD) δ 7.97-7.96 (m, 1H), 7.57-7.56 (m, 1H), 6.85-6.79 (m, 2H), 6.49-6.48 (m, 1H), 6.27-6.10 (m, 2H), 5.80-5.62 (m, 1H), 4.73-4.60 (m, 1H), 4.45-4.44 (m, 2H), 4.17-4.14 (m, 1H), 3.30 (s, 3H), 3.11-2.93 (m, 2H), 2.03-2.02 (m, 3H), 1.70-1.60 (m, 2H)

Example 104: Preparation of (R)-1-(3-((2-((1-ethyl-1H-pyrazol-4-yl)amino)-7H-pyrrolo[2,3-d]pyrimidin-4-yl)thio)piperidin-1-yl)prop-2-en-1-one

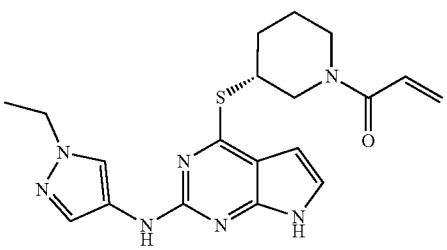 [SMILES: C=CC(=O)N1CCC[C@@H](Sc2nc(Nc3cnn(CC)c3)nc3[nH]ccc23)C1]

A title compound (5.9 mg, yield: 29.9%) was prepared in the same manner as in Example 1, except using tert-butyl (R)-3-mercaptopiperidine-1-carboxylate instead of tert-butyl (R)-3-aminopiperidine-1-carboxylate, and 1-ethyl-1H-pyrazol-4-amine instead of 4-(4-methylpiperazin-1-yl)aniline in Example 1.

$^1$H NMR (500 MHz, CD$_3$OD) δ 7.97 (s, 1H), 7.59-7.58 (m, 1H), 6.92-6.90 (m, 1H), 6.85-6.45 (m, 1H), 6.28-6.02 (m, 2H), 5.80-5.43 (m, 1H), 4.66-4.25 (m, 1H), 4.20-4.00 (m, 3H), 3.90-3.45 (m, 2H), 3.40-3.20 (m, 1H), 2.25-2.15 (m, 1H), 1.90-1.75 (m, 2H), 1.70-1.60 (m, 1H), 1.50-1.40 (m, 3H)

Example 105: Preparation of (R)-1-(3-((6-((1-ethyl-1H-pyrazol-4-yl)amino)-1H-pyrazolo[3,4-d]pyrimidin-4-yl)thio)piperidin-1-yl)prop-2-en-1-one

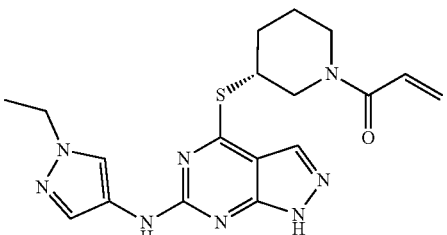

A title compound (8.4 mg, yield: 42.2%) was prepared in the same manner as in Example 30, except using tert-butyl (R)-3-mercaptopiperidine-1-carboxylate instead of tert-butyl (R)-3-aminopiperidine-1-carboxylate, and 1-ethyl-1H-pyrazol-4-amine instead of 4-(4-methylpiperazin-1-yl)aniline in Example 30.

$^1$H NMR (500 MHz, CD$_3$OD) δ 8.20-8.10 (m, 1H), 7.83 (s, 1H), 7.64 (s, 1H), 6.90-6.50 (m, 1H), 6.30-6.10 (m, 1H), 5.80-5.50 (m, 1H), 4.60-6.35 (m, 1H), 4.30-4.00 (m, 3H), 3.90-3.35 (m, 3H), 2.28-2.20 (m, 1H), 1.97-1.80 (m, 2H), 1.77-1.65 (m, 1H), 1.50-1.40 (m, 3H)

Example 106: Preparation of 1-((3R,4R)-3-((6-((1-ethyl-1H-pyrazol-4-yl)amino)-1H-pyrazolo[3,4-d]pyrimidin-4-yl)amino)-4-methylpiperidin-1-yl)prop-2-en-1-one

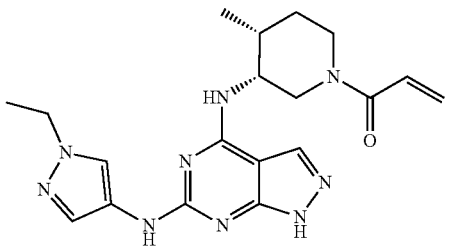 [SMILES: C=CC(=O)N1CC[C@@H](C)[C@@H](Nc2nc(Nc3cnn(CC)c3)nc3[nH]ncc23)C1]

A title compound (8.2 mg, yield: 41.6%) was prepared in the same manner as in Example 30, except using tert-butyl (3R,4R)-3-amino-4-methylpiperidine-1-carboxylate instead of tert-butyl(R)-3-aminopiperidine-1-carboxylate, and 1-ethyl-1H-pyrazol-4-amine instead of 4-(4-methylpiperazin-1-yl)aniline in Example 30.

$^1$H NMR (500 MHz, CD$_3$OD) δ 8.05-7.90 (m, 2H), 7.60-7.55 (m, 1H), 6.88-6.33 (m, 1H), 6.20-5.90 (m, 1H), 5.75-5.30 (m, 1H), 4.70-4.35 (m, 3H), 4.20-4.10 (m, 2H), 4.04-2.80 (m, 1H), 2.25-2.10 (m, 1H), 1.90-1.75 (m, 1H), 1.70-1.40 (m, 5H), 1.10-1.00 (m, 3H)

Example 107: Preparation of 1-((3R,4R)-3-((2-((1-ethyl-1H-pyrazol-4-yl)amino)-7H-pyrrolo[2,3-d]pyrimidin-4-yl)amino)-4-methylpiperidin-1-yl)prop-2-en-1-one

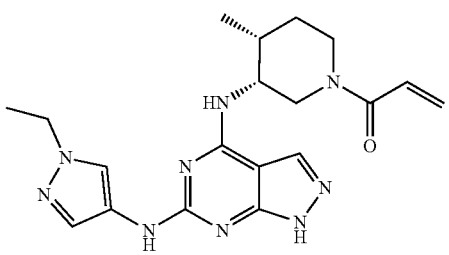 [SMILES: C=CC(=O)N1CC[C@@H](C)[C@@H](Nc2nc(Nc3cnn(CC)c3)nc3[nH]ncc23)C1]

A title compound (5.7 mg, yield: 28.8%) was prepared in the same manner as in Example 1, except using tert-butyl (3R,4R)-3-amino-4-methylpiperidine-1-carboxylate instead of tert-butyl(R)-3-aminopiperidine-1-carboxylate, and 1-ethyl-1H-pyrazol-4-amine instead of 4-(4-methylpiperazin-1-yl)aniline in Example 1.

$^1$H NMR (500 MHz, CD$_3$OD) δ 7.89 (s, 1H), 7.56 (s, 1H), 6.88-6.30 (m, 3H), 6.30-5.30 (m, 2H), 4.60-4.30 (m, 3H), 4.20-4.10 (m, 2H), 3.95-3.35 (m, 1H), 2.98-2.13 (m, 2H), 1.88-1.55 (m, 2H), 1.50-1.40 (m, 3H), 1.10-1.00 (m, 3H)

Example 108: Preparation of (R)-1-(3-((3-chloro-6-((1-ethyl-1H-pyrazol-4-yl)amino)-1H-pyrazolo[3,4-d]pyrimidin-4-yl)thio)piperidin-1-yl)prop-2-en-1-one

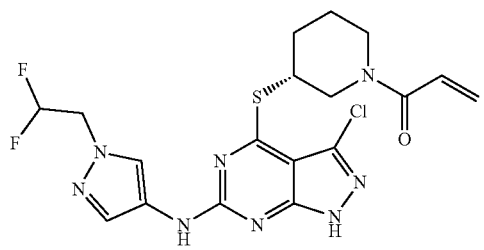 [SMILES: C=CC(=O)N1CCC[C@@H](Sc2nc(Nc3cnn(CC(F)F)c3)nc3[nH]nc(Cl)c23)C1]

A title compound (9.3 mg, yield: 39.7%) was prepared in the same manner as in Example 42, except using tert-butyl (R)-3-mercaptopiperidine-1-carboxylate instead of tert-butyl (R)-3-aminopiperidine-1-carboxylate, and 1-(2,2-difluoroethyl)-1H-pyrazol-4-amine instead of 4-(4-methylpiperazin-1-yl)aniline in Example 42.

$^1$H NMR (500 MHz, CD$_3$OD) δ 8.20-8.05 (m, 1H), 7.75-7.68 (m, 1H), 6.88-6.45 (m, 1H), 6.30-6.00 (m, 2H), 5.80-5.50 (m, 1H), 4.65-4.30 (m, 3H), 4.28-4.00 (m, 1H), 3.92-3.60 (m, 2H), 3.50-3.31 (m, 1H), 2.25-2.18 (m, 1H), 1.95-1.80 (m, 2H), 1.73-1.65 (m, 1H)

Example 109: Preparation of (R)-1-(3-((5-chloro-2-((1-ethyl-1H-pyrazol-4-yl)amino)-7H-pyrrolo[2,3-d]pyrimidin-4-yl)thio)piperidin-1-yl)prop-2-en-1-one

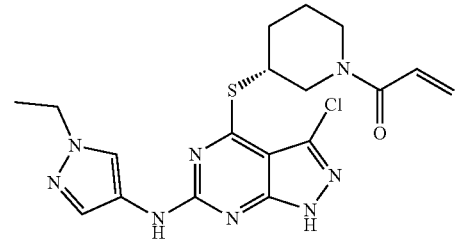 [SMILES: C=CC(=O)N1CCC[C@@H](Sc2nc(Nc3cnn(CC)c3)nc3[nH]nc(Cl)c23)C1]

A title compound (8.2 mg, yield: 37.8%) was prepared in the same manner as in Example 36, except using tert-butyl (R)-3-mercaptopiperidine-1-carboxylate instead of tert-butyl (R)-3-aminopiperidine-1-carboxylate, and 1-ethyl-1H-pyrazol-4-amine instead of 4-(4-methylpiperazin-1-yl)aniline in Example 36.

$^1$H NMR (500 MHz, CD$_3$OD) δ 7.97 (s, 1H), 7.60-7.58 (m, 1H), 6.90-6.88 (m, 1H), 6.87-6.50 (m, 1H), 6.26-6.08 (m, 1H), 5.80-5.50 (m, 1H), 4.70-4.30 (m, 1H), 4.25-4.15 (m, 3H), 3.92-3.80 (m, 1H), 3.70-3.15 (m, 2H), 2.25-2.18 (m, 1H), 1.95-1.75 (m, 2H), 1.73-1.65 (m, 1H), 1.50-1.40 (m, 3H)

Example 110: Preparation of R)-1-(3-((3-chloro-6-((1-cyclopropyl-1H-pyrazol-4-yl)amino)-1H-pyrazolo[3,4-d]pyrimidin-4-yl)thio)piperidin-1-yl)prop-2-en-1-one

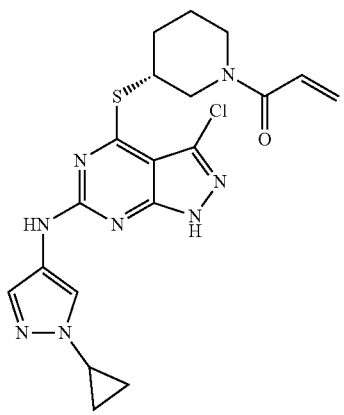 [SMILES: C=CC(=O)N1CCC[C@@H](Sc2nc(Nc3cnn(C4CC4)c3)nc3[nH]nc(Cl)c23)C1]

A title compound (4.4 mg, yield: 19.7%) was prepared in the same manner as in Example 42, except using tert-butyl (R)-3-mercaptopiperidine-1-carboxylate instead of tert-butyl (R)-3-aminopiperidine-1-carboxylate, and 1-cyclopropyl-1H-pyrazol-4-amine instead of 4-(4-methylpiperazin-1-yl)aniline in Example 42.

$^1$H NMR (500 MHz, CD$_3$OD) δ 8.13-8.00 (m, 1H), 7.65-7.55 (m, 1H), 6.88-6.45 (m, 1H), 6.30-6.10 (m, 1H), 5.82-5.50 (m, 1H), 4.68-4.50 (m, 1H), 4.40-4.20 (m, 1H), 4.10-3.97 (m, 1H), 3.92-3.80 (m, 1H), 3.48-3.31 (m, 1H), 2.28-2.15 (m, 1H), 2.08-2.00 (m, 1H), 1.95-1.80 (m, 2H), 1.75-1.60 (m, 1H), 1.13-1.00 (m, 4H)

Example 111: Preparation of (R)-1-(3-((3-chloro-6-((1-ethyl-1H-pyrazol-4-yl)amino)-1H-pyrazolo[3,4-d]pyrimidin-4-yl)thio)piperidin-1-yl)prop-2-en-1-one

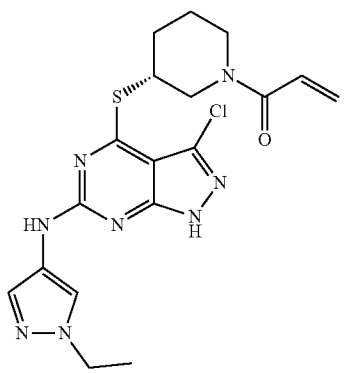 [SMILES: C=CC(=O)N1CCC[C@@H](Sc2nc(Nc3cnn(CC)c3)nc3[nH]nc(Cl)c23)C1]

A title compound (7.5 mg, yield: 34.5%) was prepared in the same manner as in Example 42, except using tert-butyl (R)-3-mercaptopiperidine-1-carboxylate instead of tert-butyl (R)-3-aminopiperidine-1-carboxylate, and 1-ethyl-1H-pyrazol-4-amine instead of 4-(4-methylpiperazin-1-yl)aniline in Example 42.

$^1$H NMR (500 MHz, CD$_3$OD) δ 8.10-7.93 (m, 1H), 7.70-7.60 (m, 1H), 6.88-6.50 (m, 1H), 6.30-6.10 (m, 1H), 5.80-5.50 (m, 1H), 4.65-3.30 (m, 6H), 2.28-2.20 (m, 1H), 2.08-2.00 (m, 1H), 1.95-1.80 (m, 2H), 1.78-1.62 (m, 1H), 1.50-1.40 (m, 3H)

Example 112: Preparation of (R)-1-(3-((6-((1-(tert-butyl)-1H-pyrazol-4-yl)amino)-3-chloro-1H-pyrazolo[3,4-d]pyrimidin-4-yl)thio)piperidin-1-yl)prop-2-en-1-one

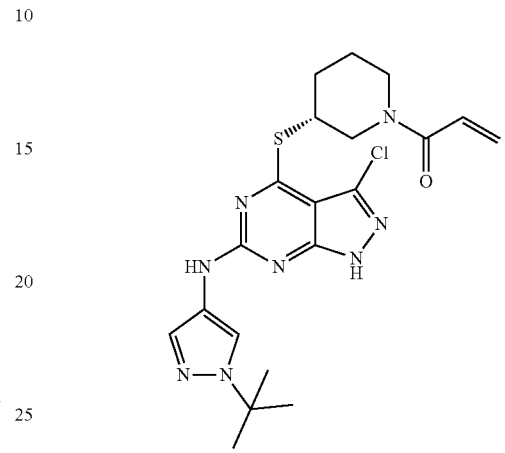

A title compound (10.3 mg, yield: 44.7%) was prepared in the same manner as in Example 42, except using tert-butyl (R)-3-mercaptopiperidine-1-carboxylate instead of tert-butyl (R)-3-aminopiperidine-1-carboxylate, and 1-(tert-butyl)-1H-pyrazol-4-amine instead of 4-(4-methylpiperazin-1-yl)aniline in Example 42.

$^1$H NMR (500 MHz, CD$_3$OD) δ 8.20-8.05 (m, 1H), 7.72-7.65 (m, 1H), 6.88-6.50 (m, 1H), 6.30-6.10 (m, 1H), 5.80-5.50 (m, 1H), 4.70-3.30 (m, 4H), 2.28-2.20 (m, 1H), 2.08-1.98 (m, 1H), 1.97-1.80 (m, 2H), 1.78-1.66 (m, 1H), 1.59 (s, 9H)

Example 113: Preparation of (R)-1-(3-((3-chloro-6-((1-isobutyl-1H-pyrazol-4-yl)amino)-1H-pyrazolo[3,4-d]pyrimidin-4-yl)thio)piperidin-1-yl)prop-2-en-1-one

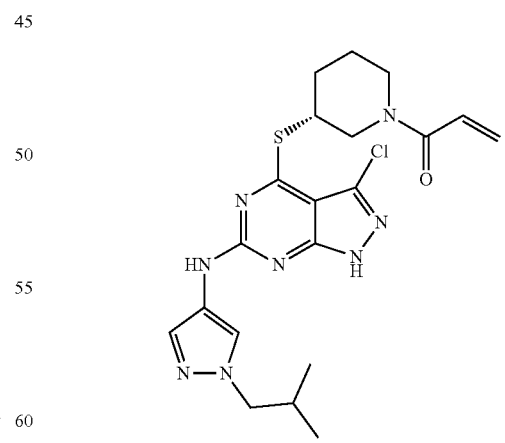

A title compound (4.7 mg, yield: 20.4%) was prepared in the same manner as in Example 42, except using tert-butyl (R)-3-mercaptopiperidine-1-carboxylate instead of tert-butyl (R)-3-aminopiperidine-1-carboxylate, and 1-isobutyl-1H-pyrazol-4-amine instead of 4-(4-methylpiperazin-1-yl)aniline in Example 42.

¹H NMR (500 MHz, CD₃OD) δ 8.10-7.95 (m, 1H), 7.72-7.65 (m, 1H), 6.88-6.50 (m, 1H), 6.30-6.10 (m, 1H), 5.80-5.50 (m, 1H), 4.70-3.35 (m, 6H), 2.28-2.10 (m, 2H), 2.08-1.98 (m, 1H), 1.97-1.80 (m, 2H), 1.78-1.66 (m, 1H), 0.92-0.85 (m, 6H)

Example 114: Preparation of (R)-1-(3-((3-chloro-6-((1-(2,2,2-trifluoroethyl)-1H-pyrazol-4-yl)amino)-1H-pyrazolo[3,4-d]pyrimidin-4-yl)thio)piperidin-1-yl)prop-2-en-1-one

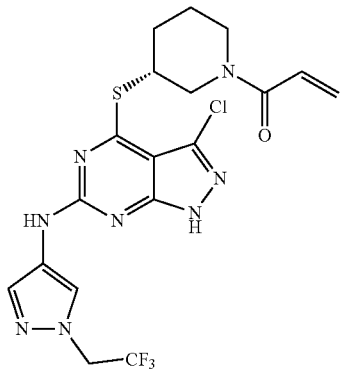 [SMILES: C=CC(=O)N1CCC[C@@H](Sc2nc(Nc3cnn(CC(F)(F)F)c3)nc3[nH]nc(Cl)c23)C1]

A title compound (10.1 mg, yield: 41.5%) was prepared in the same manner as in Example 42, except using tert-butyl (R)-3-mercaptopiperidine-1-carboxylate instead of tert-butyl (R)-3-aminopiperidine-1-carboxylate, and 1-(2,2,2-trifluoroethyl)-1H-pyrazol-4-amine instead of 4-(4-methylpiperazin-1-yl)aniline in Example 42.

¹H NMR (500 MHz, CD₃OD) δ 8.22-8.10 (m, 1H), 7.80-7.70 (m, 1H), 6.88-6.50 (m, 1H), 6.30-6.10 (m, 1H), 5.82-5.50 (m, 1H), 4.90-4.85 (m, 2H), 4.45-3.30 (m, 4H), 2.28-2.15 (m, 1H), 2.08-1.99 (m, 1H), 1.97-1.80 (m, 2H), 1.78-1.65 (m, 1H)

Example 115: Preparation of (R)-1-(3-((3-chloro-6-((1-propyl-1H-pyrazol-4-yl)amino)-1H-pyrazolo[3,4-d]pyrimidin-4-yl)thio)piperidin-1-yl)prop-2-en-1-one

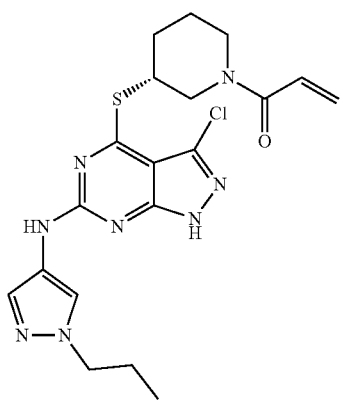 [SMILES: C=CC(=O)N1CCC[C@@H](Sc2nc(Nc3cnn(CCC)c3)nc3[nH]nc(Cl)c23)C1]

A title compound (9.8 mg, yield: 43.8%) was prepared in the same manner as in Example 42, except using tert-butyl (R)-3-mercaptopiperidine-1-carboxylate instead of tert-butyl (R)-3-aminopiperidine-1-carboxylate, and 1-propyl-1H-pyrazol-4-amine instead of 4-(4-methylpiperazin-1-yl)aniline in Example 42.

¹H NMR (500 MHz, CD₃OD) δ 8.10-7.95 (m, 1H), 7.70-7.60 (m, 1H), 6.90-6.50 (m, 1H), 6.30-6.05 (m, 1H), 5.80-5.50 (m, 1H), 4.42-4.20 (m, 2H), 4.10-4.00 (m, 2H), 3.95-3.60 (m, 2H), 3.50-3.30 (m, 1H), 2.28-2.20 (m, 1H), 2.08-1.80 (m, 4H), 1.77-1.50 (m, 2H), 0.96-0.81 (m, 3H)

Example 116: Preparation of (R)-1-(34(3-chloro-6-(isoxazol-4-ylamino)-1H-pyrazolo[3,4-d]pyrimidin-4-yl)thio)piperidin-1-yl)prop-2-en-1-one

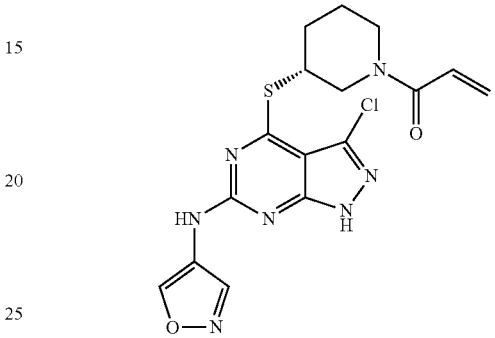

A title compound (9.8 mg, yield: 48.1%) was prepared in the same manner as in Example 42, except using tert-butyl (R)-3-mercaptopiperidine-1-carboxylate instead of tert-butyl (R)-3-aminopiperidine-1-carboxylate, and isoxazol-4-amine instead of 4-(4-methylpiperazin-1-yl)aniline in Example 42.

¹H NMR (500 MHz, CD₃OD) δ 9.20-9.10 (m, 1H), 8.56 (s, 1H), 6.90-6.53 (m, 1H), 6.30-6.10 (m, 1H), 5.80-5.50 (m, 1H), 4.70-3.62 (m, 5H), 2.00-1.80 (m, 1H), 1.79-1.65 (m, 2H), 1.63-1.55 (m, 1H)

Example 117: Preparation of (R)-1-(3-(3-chloro-6-(5-methylisoxazol-4-ylamino)-1H-pyrazolo[3,4-d]pyrimidin-4-ylamino)piperidin-1-yl)prop-2-en-1-one

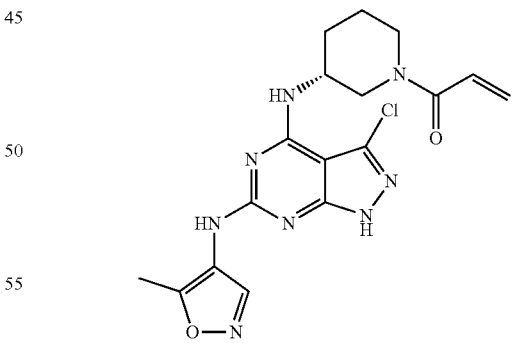

A title compound (4.2 mg, yield: 20.8%) was prepared in the same manner as in Example 42, except that 5-methylisoxazol-4-amine was used instead of 4-(4-methylpiperazin-1-yl)aniline in Example 42.

¹H NMR (500 MHz, CD₃OD) δ 8.70-8.66 (m, 1H), 6.84-6.61 (m, 1H), 6.26-6.11 (m, 1H), 5.79-5.59 (m, 1H), 4.32-4.28 (m, 1H), 3.96-3.84 (m, 2H), 3.63-3.43 (m, 2H), 2.40 (s, 3H), 2.10-2.04 (m, 1H), 1.92-1.83 (m, 2H), 1.65-1.63 (m, 1H)

Example 118: Preparation of (R)-1-(3-((3-chloro-6-((1-ethyl-1H-pyrazol-4-yl)amino)-1H-pyrazolo[3,4-d]pyrimidin-4-yl)(methyl)amino)piperidin-1-yl)prop-2-en-1-one

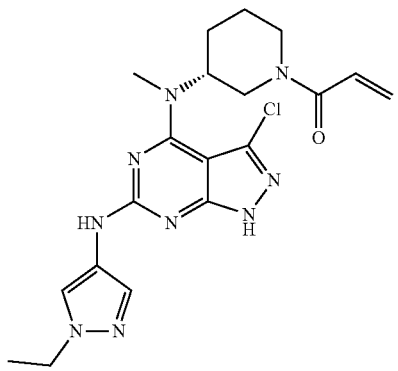 [SMILES: C=CC(=O)N1CCC[C@@H](N(C)c2nc(Nc3cnn(CC)c3)nc3[nH]nc(Cl)c23)C1]

A title compound (9.5 mg, yield: 44.3%) was prepared in the same manner as in Example 42, except that tert-butyl (R)-3-(methylamino)piperidine-1-carboxylate was used instead of tert-butyl(R)-3-aminopiperidine-1-carboxylate, and 1-ethyl-1H-pyrazol-4-amine was used instead of 4-(4-methylpiperazin-1-yl)aniline in Example 42.

$^1$H NMR (500 MHz, CD$_3$OD) δ 7.91 (s, 1H), 7.57-7.55 (m, 1H), 6.83-6.67 (m, 1H), 6.24-6.13 (m, 1H), 5.77-5.64 (m, 1H), 4.74-4.52 (m, 2H), 4.11-4.09 (m, 3H), 3.24 (s, 3H), 3.10-2.62 (m, 2H), 2.00-1.92 (m, 3H), 1.63-1.62 (m, 1H), 1.43 (t, 3H)

Example 119: Preparation of (R)-1-(3-((3-chloro-6-(isoxazol-4-ylamino)-1H-pyrazolo[3,4-d]pyrimidin-4-yl)(methyl)amino)piperidin-1-yl)prop-2-en-1-one

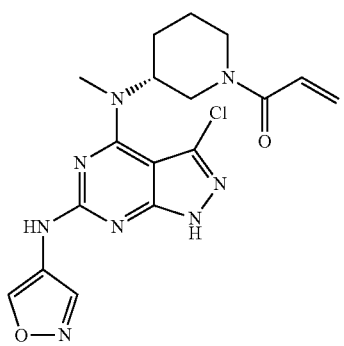 [SMILES: C=CC(=O)N1CCC[C@@H](N(C)c2nc(Nc3cnoc3)nc3[nH]nc(Cl)c23)C1]

A title compound (8.7 mg, yield: 43.3%) was prepared in the same manner as in Example 42, except using tert-butyl (R)-3-(methylamino)piperidine-1-carboxylate instead of tert-butyl(R)-3-aminopiperidine-1-carboxylate, and isoxazol-4-amine instead of 4-(4-methylpiperazin-1-yl)aniline in Example 42.

$^1$H NMR (500 MHz, CD$_3$OD) δ 9.03 (s, 1H), 8.51 (s, 1H), 6.84-6.72 (m, 1H), 6.24-6.16 (m, 1H), 5.78-5.67 (m, 1H), 4.82-4.56 (m, 2H), 4.21-4.13 (m, 1H), 3.31 (s, 3H), 3.11-2.99 (m, 1H), 2.05-1.94 (m, 3H), 1.61-1.60 (m, 2H)

Example 120: Preparation of 1-((3R,4R)-3-((3-chloro-6-((1-(2,2,2-trifluoroethyl)-1H-pyrazol-4-yl)amino)-1H-pyrazolo[3,4-d]pyrimidin-4-yl)amino)-4-methylpiperidin-1-yl)prop-2-en-1-one

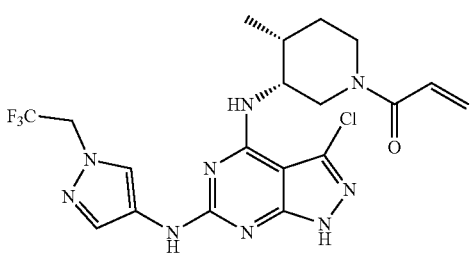 [SMILES: C=CC(=O)N1CC[C@@H](C)[C@@H](Nc2nc(Nc3cnn(CC(F)(F)F)c3)nc3[nH]nc(Cl)c23)C1]

A title compound (8.1 mg, yield: 33.4%) was prepared in the same manner as in Example 42, except using 1-(2,2,2-trifluoroethyl)-1H-pyrazol-4-amine instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 8.11 (s, 1H), 7.67 (s, 1H), 6.86-6.42 (m, 1H), 6.20-6.02 (m, 1H), 5.77-5.42 (m, 1H), 4.66-4.38 (m, 2H), 4.21-4.11 (m, 1H), 3.39-3.35 (m, 1H), 3.12-2.85 (m, 1H), 2.19-2.14 (m, 2H), 2.08-2.00 (m, 1H), 1.76-1.74 (m, 1H), 1.61-1.56 (m, 1H), 1.05-1.04 (d, J=5 Hz, 3H)

Example 121: Preparation of 1-((3R,4R)-3-((3-chloro-6-((1-propyl-1H-pyrazol-4-yl)amino)-1H-pyrazolo[3,4-d]pyrimidin-4-yl)amino)-4-methylpiperidin-1-yl)prop-2-en-1-one

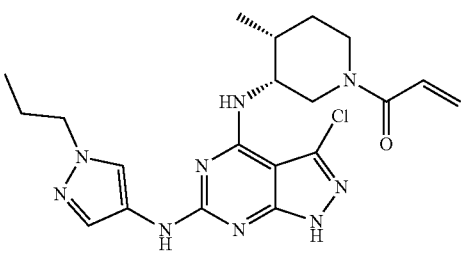 [SMILES: C=CC(=O)N1CC[C@@H](C)[C@@H](Nc2nc(Nc3cnn(CCC)c3)nc3[nH]nc(Cl)c23)C1]

A title compound (7.1 mg, yield: 32.1%) was prepared in the same manner as in Example 42, except using 1-propyl-1H-pyrazol-4-amine instead of 4-(4-methylpiperazin-1-yl)aniline, and tert-butyl(3R,4R)-3-amino-4-methylpiperidine-1-carboxylate instead of tert-butyl (R)-3-aminopiperidine-1-carboxylate in Example 42.

$^1$H NMR (500 MHz, CD$_3$OD) δ 7.95 (s, 1H), 7.57 (s, 1H), 6.86-6.42 (m, 1H), 6.19-6.01 (m, 1H), 5.77-5.42 (m, 1H), 4.68-4.12 (m, 3H), 4.08-4.05 (m, 2H), 3.40-3.36 (m, 1H), 3.12-2.84 (m, 1H), 2.20-2.17 (m, 1H), 1.87-1.83 (m, 2H), 1.76-1.74 (m, 1H), 1.61-1.56 (m, 1H), 1.05-1.04 (d, J=5 Hz, 3H), 0.95-0.89 (m, 3H)

Example 122: Preparation of 1-((3R,4R)-3-((3-chloro-6-((1-(2-(diethylamino)ethyl)-1H-pyrazol-4-yl)amino)-1H-pyrazolo[3,4-d]pyrimidin-4-yl)amino)-4-methylpiperidin-1-yl)prop-2-en-1-one

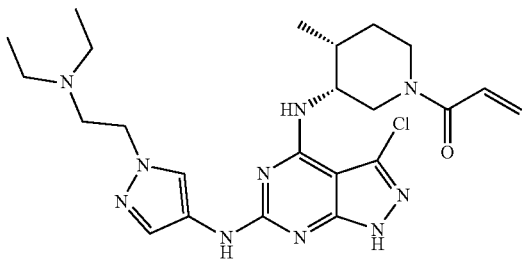 [SMILES: C=CC(=O)N1CC[C@@H](C)[C@@H](Nc2nc(Nc3cnn(CCN(CC)CC)c3)nc3[nH]nc(Cl)c23)C1]

A title compound (6.4 mg, yield: 25.7%) was prepared in the same manner as in Example 42, except using 1-(2-(diethylamino)ethyl)-1H-pyrazol-4-amine instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 8.02 (s, 1H), 7.64 (s, 1H), 6.87-6.43 (m, 1H), 6.20-6.02 (m, 1H), 5.77-5.42 (m, 1H), 4.71-4.20 (m, 5H), 3.39-3.35 (m, 1H), 3.15-3.00 (m, 3H), 2.90-2.85 (m, 1H), 2.78-2.63 (m, 4H), 2.20-2.17 (m, 1H), 1.78-1.75 (m, 1H), 1.61-1.58 (m, 1H), 1.45-1.41 (m, 1H), 1.13-1.10 (m, 4H), 1.05-1.04 (d, J=5 Hz, 3H)

Example 123: Preparation of 1-((3R,4R)-3-((3-chloro-6-((1-(2-morpholinoethyl)-1H-pyrazol-4-yl)amino)-1H-pyrazolo[3,4-d]pyrimidin-4-yl)amino)-4-methylpiperidin-1-yl)prop-2-en-1-one

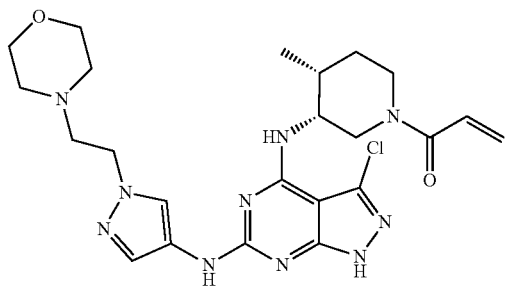 [SMILES: C=CC(=O)N1CC[C@@H](C)[C@@H](Nc2nc(Nc3cnn(CCN4CCOCC4)c3)nc3[nH]nc(Cl)c23)C1]

A title compound (12.4 mg, yield: 48.2%) was prepared in the same manner as in Example 42, except using 1-(2-morpholinoethyl)-1H-pyrazol-4-amine instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 8.00 (s, 1H), 7.63 (s, 1H), 6.87-6.44 (m, 1H), 6.21-6.02 (m, 1H), 5.76-5.42 (m, 1H), 4.70-4.24 (m, 5H), 3.69-3.63 (m, 4H), 3.40-3.38 (m, 1H), 3.12-2.85 (m, 1H), 2.81-2.75 (m, 2H), 2.50-2.45 (m, 4H), 2.19-2.17 (m, 1H), 2.03-2.02 (m, 1H), 1.76-1.74 (m, 1H), 1.44-1.40 (m, 1H), 1.05-1.04 (d, J=5 Hz, 3H)

Example 124: Preparation of 1-((3R,4R)-3-((3-chloro-6-((1-isobutyl-1H-pyrazol-4-yl)amino)-1H-pyrazolo[3,4-d]pyrimidin-4-yl)amino)-4-methylpiperidin-1-yl)prop-2-en-1-one

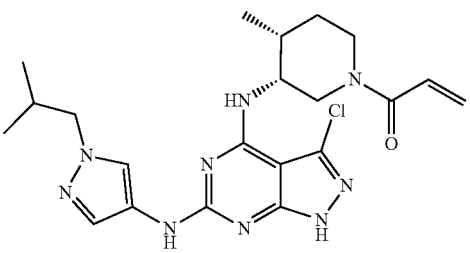 [SMILES: C=CC(=O)N1CC[C@@H](C)[C@@H](Nc2nc(Nc3cnn(CC(C)C)c3)nc3[nH]nc(Cl)c23)C1]

A title compound (8.3 mg, yield: 36.2%) was prepared in the same manner as in Example 42, except using 1-isobutyl-1H-pyrazol-4-amine instead of 4-(4-methylpiperazin-1-yl)aniline, and tert-butyl(3R,4R)-3-amino-4-methylpiperidine-1-carboxylate instead of tert-butyl (R)-3-aminopiperidine-1-carboxylate in Example 42.

$^1$H NMR (500 MHz, CD$_3$OD) δ 7.94 (s, 1H), 7.60 (s, 1H), 6.87-6.43 (m, 1H), 6.20-6.02 (m, 1H), 5.78-5.42 (m, 1H), 4.69-4.11 (m, 3H), 3.90-3.89 (d, J=5 Hz, 2H), 3.40-3.35 (m, 1H), 3.14-2.83 (m, 1H), 2.18-2.11 (m, 2H), 1.75-1.73 (m, 1H), 1.48-1.41 (m, 1H), 1.05-1.04 (d, J=5 Hz, 3H), 0.94-0.93 (d, J=5 Hz, 6H)

Example 125: Preparation of 1-((3R,4R)-3-((3-chloro-6-((1-(3-methoxybenzyl)-1H-pyrazol-4-yl)amino)-1H-pyrazolo[3,4-d]pyrimidin-4-yl)amino)-4-methylpiperidin-1-yl)prop-2-en-1-one

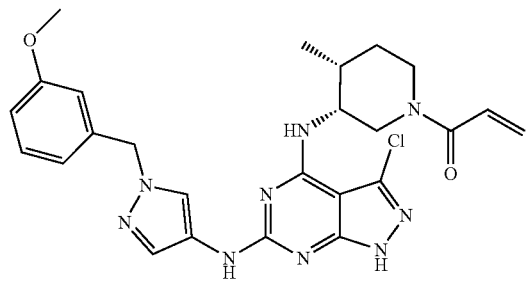 [SMILES: C=CC(=O)N1CC[C@@H](C)[C@@H](Nc2nc(Nc3cnn(Cc4cccc(OC)c4)c3)nc3[nH]nc(Cl)c23)C1]

A title compound (9.8 mg, yield: 37.7%) was prepared in the same manner as in Example 42, except using 1-(3-methoxybenzyl)-1H-pyrazol-4-amine instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 7.99 (s, 1H), 7.60 (s, 1H), 7.28-7.25 (m, 1H), 6.88-6.80 (m, 3H), 6.87-6.43 (m, 1H), 6.19-6.00 (m, 1H), 5.75-5.38 (m, 1H), 5.27 (s, 2H), 4.71-4.11 (m, 3H), 3.76 (s, 3H), 3.32-3.30 (m, 1H), 3.14-2.83 (m, 1H), 2.18-2.06 (m, 1H), 1.75-1.72 (m, 1H), 1.60-1.58 (m, 1H), 1.02-1.01 (d, J=5 Hz, 3H)

Example 126: Preparation of 2-(4-((4-(((3R,4R)-1-acryloyl-4-methylpiperidin-3-yl)amino)-3-chloro-1H-pyrazolo[3,4-d]pyrimidin-6-yl)amino)-1H-pyrazol-1-yl)acetonitrile

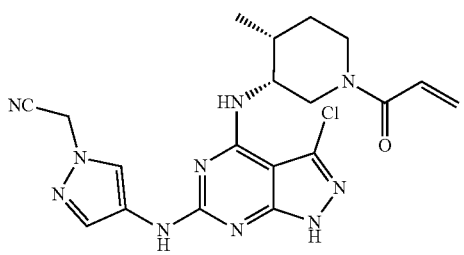 [SMILES: C=CC(=O)N1CC[C@@H](C)[C@@H](Nc2nc(Nc3cnn(CC#N)c3)nc3[nH]nc(Cl)c23)C1]

A title compound (4.1 mg, yield: 18.7%) was prepared in the same manner as in Example 42, except using 2-(4-amino-1H-pyrazol-1-yl) acetonitrile instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 8.12 (s, 1H), 7.69 (s, 1H), 6.87-6.42 (m, 1H), 6.18-6.01 (m, 1H), 5.77-5.41 (m, 1H), 5.28 (s, 2H), 4.76-4.10 (m, 3H), 3.41-3.37 (m, 1H), 3.15-2.84 (m, 1H), 2.20-2.19 (m, 1H), 1.76-1.74 (m, 1H), 1.50-1.41 (m, 1H), 1.05-1.04 (d, J=5 Hz, 3H)

Example 127: Preparation of 1-((3R,4R)-3-((3-chloro-6-((1-(difluoromethyl)-1H-pyrazol-4-yl)amino)-1H-pyrazolo[3,4-d]pyrimidin-4-yl)amino)-4-methylpiperidin-1-yl)prop-2-en-1-one

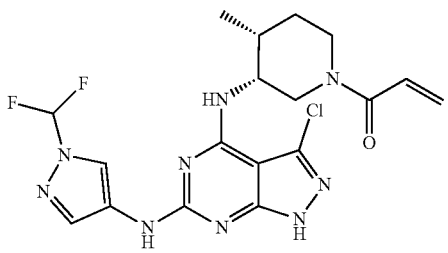 [SMILES: C=CC(=O)N1CC[C@@H](C)[C@@H](Nc2nc(Nc3cnn(C(F)F)c3)nc3[nH]nc(Cl)c23)C1]

A title compound (10.2 mg, yield: 45.1%) was prepared in the same manner as in Example 42, except using 1-difluoromethyl-1H-pyrazol-4-amine instead of 4-(4-methylpiperazin-1-yl)aniline, and tert-butyl(3R,4R)-3-amino-4-methylpiperidine-1-carboxylate instead of tert-butyl(R)-3-aminopiperidine-1-carboxylate in Example 42.

$^1$H NMR (500 MHz, CD$_3$OD) δ 8.40 (s, 1H), 7.79 (s, 1H), 7.40 (t, J=60 Hz, 1H), 6.87-6.41 (m, 1H), 6.19-6.00 (m, 1H), 5.76-5.41 (m, 1H), 4.75-4.11 (m, 3H), 3.41-3.37 (m, 1H), 3.13-2.82 (m, 1H), 2.20-2.19 (m, 1H), 1.76-1.74 (m, 1H), 1.47-1.40 (m, 1H), 1.05-1.04 (d, J=5 Hz, 3H)

Example 128: Preparation of 1-((3R,4R)-3-((3-chloro-6-((1-methyl-1H-pyrazol-4-yl)amino)-1H-pyrazolo[3,4-d]pyrimidin-4-yl)amino)-4-methylpiperidin-1-yl)prop-2-en-1-one

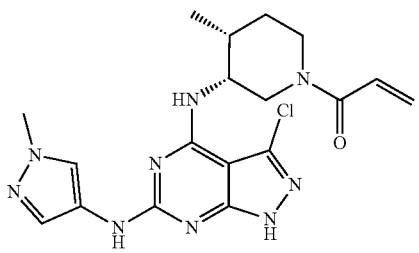 [SMILES: C=CC(=O)N1CC[C@@H](C)[C@@H](Nc2nc(Nc3cnn(C)c3)nc3[nH]nc(Cl)c23)C1]

A title compound (8.0 mg, yield: 38.5%) was prepared in the same manner as in Example 42, except using tert-butyl (3R,4R)-3-amino-4-methylpiperidine-1-carboxylate instead of tert-butyl(R)-3-aminopiperidine-1-carboxylate, and 1-methyl-1H-pyrazol-4-amine instead of 4-(4-methylpiperazin-1-yl)aniline in Example 42.

$^1$H NMR (500 MHz, CD$_3$OD) δ 7.91 (s, 1H), 7.58 (s, 1H), 6.87-6.41 (m, 1H), 6.19-6.00 (m, 1H), 5.77-5.40 (m, 1H), 4.69-4.38 (m, 3H), 3.85 (s, 3H), 3.40-3.37 (m, 1H), 3.12-2.83 (m, 1H), 2.20-2.17 (m, 1H), 2.03-2.02 (m, 1H), 1.75-1.73 (m, 1H), 1.50-1.40 (m, 1H), 1.05-1.04 (d, J=5 Hz, 3H)

Example 129: Preparation of (R)-1-(34(6-((1-cyclopropyl-1H-pyrazol-4-yl)amino)-3-(methylthio)-1H-pyrazolo[3,4-d]pyrimidin-4-yl)amino)piperidin-1-yl)prop-2-en-1-one

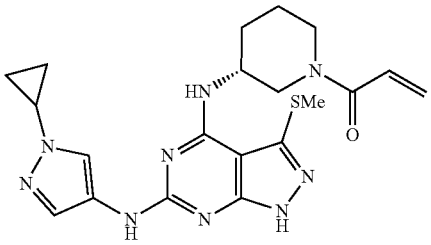 [SMILES: C=CC(=O)N1CCC[C@@H](Nc2nc(Nc3cnn(C4CC4)c3)nc3[nH]nc(SC)c23)C1]

Step 1: Preparation of tert-butyl(R)-3-((6-chloro-3-(methylthio)-1H-pyrazolo[3,4-d]pyrimidin-4-yl)amino) piperidine-1-carboxylate After 4,6-dichloro-3-(methylthio)-1H-pyrazolo[3,4-d]pyrimidine (300.0 mg, 1.3 mmol) was dissolved in ethanol (3 mL), N,N-diisopropylethylamine (333.4 μL, 1.9 mmol) and tert-butyl (R)-3-aminopiperidine-1-carboxylate (383.4 mg, 1.9 mmol) were added thereto. The reaction mixture was stirred at 110° C. for 12 hour. The organic layer was isolated, treated with magnesium sulfate, filtered, and then concentrated under reduced pressure. The residue was isolated by column chromatography to obtain a title compound (403.2 mg, yield: 79.4%).

¹H NMR (500 MHz, CD₃OD) δ 4.77-4.59 (m, 1H), 4.30-4.25 (m, 1H), 3.86-3.65 (m, 2H), 3.54-3.51 (m, 1H), 2.59 (s, 3H), 2.05-1.92 (m, 2H), 1.75-1.66 (m, 2H), 1.43-1.22 (m, 9H)

Step 2: Preparation of (R)-6-chloro-3-(methylthio)-N-(piperidin-3-yl)-1H-pyrazolo[3,4-d]pyrimidin-4-amine hydrochloride To tert-butyl(R)-3-((6-chloro-3-(methylthio)-1H-pyrazolo[3,4-d]pyrimidin-4-yl)amino)piperidine-1-carboxylate (403.2 mg, 1.0 mmol) was added 6 N hydrochloric acid solution (2.0 mL, excessive amount) dissolved in methanol. After stirring at room temperature for 30 minutes, the reaction mixture was concentrated and the subsequent reaction was carried out without isolation.

¹H NMR (500 MHz, CD₃OD) δ 4.60-4.57 (m, 1H), 3.64-3.61 (m, 1H), 3.44-3.34 (m, 1H), 3.16-2.97 (m, 1H), 2.62 (s, 3H), 2.20-2.07 (m, 2H), 1.98-1.80 (m, 2H)

Step 3: Preparation of (R)-1-(3-((6-chloro-3-(methylthio)-1H-pyrazolo[3,4-d]pyrimidin-4-yl)amino)piperidin-1-yl)prop-2-en-1-one After (R)-6-chloro-3-(methylthio)-N-(piperidin-3-yl)-1H-pyrazolo[3,4-d]pyrimidin-4-amine hydrochloride (339.6 mg, 1.0 mmol) was dissolved in a 3:1 mixed solution of tetrahydrofuran:distilled water (4 ml), sodium bicarbonate (255.3 mg, 1.1 mmol) was added thereto at −20° C. and the mixture was stirred for 30 minutes. Acryloyl chloride (86.4 µL, 1.1 mmol) was slowly added dropwise to the reaction mixture and then stirred at −20° C. for 1 hour. The organic layer was isolated, treated with magnesium sulfate, filtered, and then concentrated under reduced pressure. The residue was isolated by column chromatography to obtain a title compound (207.0 mg, yield 58.1%).

¹H NMR (500 MHz, CD₃OD) δ 6.83-6.72 (m, 1H), 6.22-6.12 (m, 1H), 5.78-5.62 (m, 1H), 4.79-4.26 (m, 1H), 4.10-4.02 (m, 1H), 3.80-3.60 (m, 3H), 2.57 (d, 3H), 2.11-1.93 (m, 2H), 1.88-1.72 (m, 2H)

Step 4: Preparation of (R)-1-(3-((6-(l-cyclopropyl-1H-pyrazol-4-yl)amino)-3-(methylthio)-1H-pyrazolo[3,4-d]pyrimidin-4-yl)amino)piperidin-1-yl)prop-2-en-1-one (R)-1-(3-((6-chloro-3-(methylthio)-1H-pyrazolo[3,4-d]pyrimidin-4-yl)amino)piperidin-1-yl)prop-2-en-1-one (30.0 mg, 0.09 mmol) and 1-cyclopropyl-1H-pyrazol-4-amine (9.6 mg, 0.08 mmol) were dissolved in 2-butanol (2.0 mL). Trifluoroacetic acid (5.2 µL, 0.07 mmol) was added to the reaction mixture, followed by reacting at 120° C. for 3 hours, and then the solvent was concentrated. This reaction mixture was neutralized by adding 7 N ammonia solution dissolved in methanol. The residue was isolated by column chromatography to obtain a title compound (16.9 mg, yield: 58.9%).

¹H NMR (500 MHz, CD₃OD) δ 8.00 (s, 1H), 7.54 (s, 1H), 6.86-6.52 (m, 1H), 6.25-6.05 (m, 1H), 5.78-5.50 (m, 1H), 4.36-4.30 (m, 1H), 4.20-4.11 (m, 1H), 3.90-3.74 (m, 2H), 3.65-3.58 (m, 2H), 2.52 (s, 3H), 2.08-2.05 (m, 1H), 1.93-1.85 (m, 2H), 1.70-1.65 (m, 1H), 1.07-1.00 (m, 4H)

Example 130: Preparation of (R)-1-(3-((6-(isoxazol-4-ylamino)-3-(methylthio)-1H-pyrazolo[3,4-d]pyrimidin-4-yl)amino)piperidin-1-yl)prop-2-en-1-one

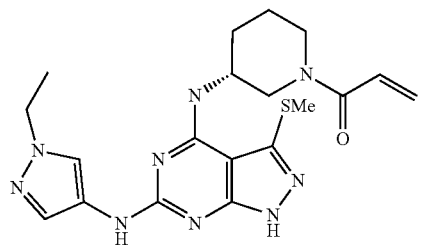 [SMILES: C=CC(=O)N1CCC[C@@H](Nc2nc(Nc3cnn(CC)c3)nc3[nH]nc(SC)c23)C1]

A title compound (9.8 mg, yield: 48.9%) was prepared in the same manner as in Example 129, except that isoxazol-4-amine was used instead of 1-cyclopropyl-1H-pyrazol-4-amine in Example 129.

¹H NMR (500 MHz, CD₃OD) δ 9.10-9.00 (m, 1H), 8.52-8.45 (m, 1H), 6.90-6.50 (m, 1H), 6.30-6.02 (m, 1H), 5.80-5.50 (m, 1H), 4.40-4.25 (m, 1H), 4.20-3.40 (m, 4H), 2.51 (s, 3H), 2.10-1.98 (m, 1H), 1.97-1.60 (m, 3H)

Example 131: Preparation of (R)-1-(3-((6-((1-ethyl-1H-pyrazol-4-yl)amino)-3-(methylthio)-1H-pyrazolo[3,4-d]pyrimidin-4-yl)(methyl)amino)piperidin-1-yl)prop-2-en-1-one

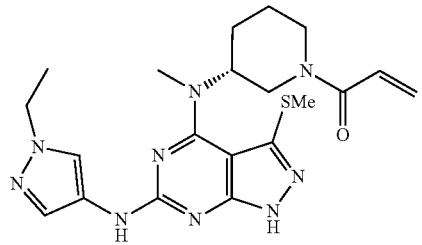 [SMILES: C=CC(=O)N1CCC[C@@H](N(C)c2nc(Nc3cnn(CC)c3)nc3[nH]nc(SC)c23)C1]

A title compound (6.4 mg, yield: 28.9%) was prepared in the same manner as in Example 129, except using tert-butyl (R)-3-(methylamino)piperidine-1-carboxylate instead of tert-butyl(R)-3-aminopiperidine-1-carboxylate, and 1-ethyl-1H-pyrazol-4-amine instead of 1-cyclopropyl-1H-pyrazol-4-amine in Example 129.

¹H NMR (500 MHz, CD₃OD) δ 7.98-7.90 (m, 1H), 7.60-7.50 (m, 1H), 6.85-6.57 (m, 1H), 6.22-6.05 (m, 1H), 5.77-5.55 (m, 1H), 4.70-4.40 (m, 2H), 4.20-4.05 (m, 3H), 3.40-2.60 (m, 5H), 2.54 (s, 3H), 2.10-1.85 (m, 3H), 1.70-1.50 (m, 1H), 1.45-1.35 (m, 3H)

Example 132: Preparation of 1-((3R,4R)-3-((6-((1-ethyl-1H-pyrazol-4-yl)amino)-3-(methylthio)-1H-pyrazolo[3,4-d]pyrimidin-4-yl)amino)-4-methylpiperidin-1-yl)prop-2-en-1-one

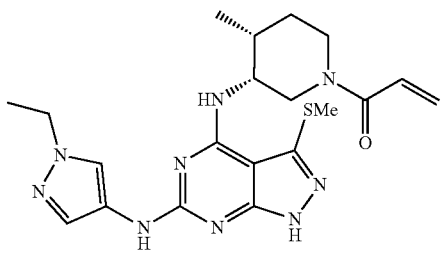 [SMILES: C=CC(=O)N1CC[C@@H](C)[C@@H](Nc2nc(Nc3cnn(CC)c3)nc3[nH]nc(SC)c23)C1]

A title compound (10.1 mg, yield: 45.8%) was prepared in the same manner as in Example 129, except using tert-butyl (3R,4R)-3-amino-4-methylpiperidine-1-carboxylate instead of tert-butyl(R)-3-aminopiperidine-1-carboxylate, and 1-ethyl-1H-pyrazol-4-amine instead of 1-cyclopropyl-1H-pyrazol-4-amine in Example 129.

$^1$H NMR (500 MHz, CD$_3$OD) δ 8.15-7.90 (m, 1H), 7.62-7.55 (m, 1H), 6.90-6.38 (m, 1H), 6.20-5.90 (m, 1H), 5.80-5.30 (m, 1H), 4.80-4.35 (m, 3H), 4.20-4.07 (m, 2H), 3.40-3.20 (m, 1H), 3.10-2.70 (m, 1H), 2.54-2.40 (m, 3H), 2.20-2.10 (m, 1H), 1.80-1.70 (m, 1H), 1.50-1.38 (m, 4H), 1.10-0.98 (m, 3H)

Example 133: Preparation of 1-((3R,4R)-3-((6-((1-(2,2-difluoroethyl)-1H-pyrazol-4-yl)amino)-3-(methylthio)-1H-pyrazolo[3,4-d]pyrimidin-4-yl)amino)-4-methylpiperidin-1-yl)prop-2-en-1-one

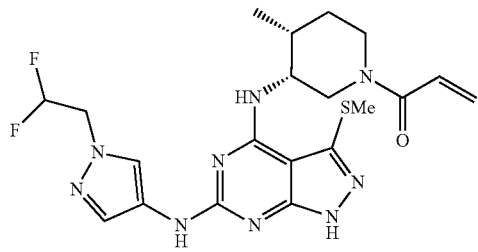 [SMILES: C=CC(=O)N1CC[C@@H](C)[C@@H](Nc2nc(Nc3cnn(CC(F)F)c3)nc3[nH]nc(SC)c23)C1]

A title compound (5.2 mg, yield: 21.6%) was prepared in the same manner as in Example 129, except using tert-butyl (3R,4R)-3-amino-4-methylpiperidine-1-carboxylate instead of tert-butyl(R)-3-aminopiperidine-1-carboxylate, and 1-(2,2-difluoroethyl)-1H-pyrazol-4-amine instead of 1-cyclopropyl-1H-pyrazol-4-amine in Example 129.

$^1$H NMR (500 MHz, CD$_3$OD) δ 8.10-8.00 (m, 1H), 7.70-7.62 (m, 1H), 6.90-6.35 (m, 1H), 6.30-5.90 (m, 2H), 5.80-5.30 (m, 1H), 4.75-4.35 (m, 5H), 4.20-3.30 (m, 1H), 3.10-2.80 (m, 1H), 2.50-2.40 (m, 3H), 2.20-2.10 (m, 1H), 1.80-1.40 (m, 2H), 1.10-1.00 (m, 3H)

Example 134: Preparation of 2-(4-((4-(((3R,4R)-1-acryloyl-4-methylpiperidin-3-yl)amino)-3-(methylthio)-1H-pyrazolo[3,4-d]pyrimidin-6-yl)amino)-1H-pyrazol-1-yl)acetonitrile

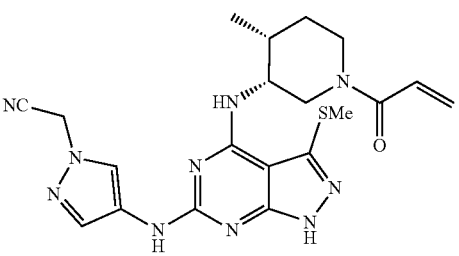 [SMILES: C=CC(=O)N1CC[C@@H](C)[C@@H](Nc2nc(Nc3cnn(CC#N)c3)nc3[nH]nc(SC)c23)C1]

A title compound (10.3 mg, yield: 45.5%) was prepared in the same manner as in Example 129, except using tert-butyl (3R,4R)-3-amino-4-methylpiperidine-1-carboxylate instead of tert-butyl(R)-3-aminopiperidine-1-carboxylate, and 2-(4-amino-1H-pyrazol-1-yl)acetonitrile instead of 1-cyclopropyl-1H-pyrazol-4-amine in Example 129.

$^1$H NMR (500 MHz, CD$_3$OD) δ 8.20-8.10 (m, 1H), 7.72-7.62 (m, 1H), 6.90-6.35 (m, 1H), 6.20-5.90 (m, 1H), 5.80-5.35 (m, 1H), 5.28 (s, 2H), 4.80-4.35 (m, 3H), 4.20-3.30 (m, 1H), 3.13-2.75 (m, 1H), 2.50-2.40 (m, 3H), 2.25-2.18 (m, 1H), 1.80-1.40 (m, 2H), 1.20-1.10 (m, 3H)

Example 135: Preparation of 1-((3R,4R)-3-((6-((1-cyclopropyl-1H-pyrazol-4-yl)amino)-3-(methylthio)-1H-pyrazolo[3,4-d]pyrimidin-4-yl)amino)-4-methylpiperidin-1-yl)prop-2-en-1-one

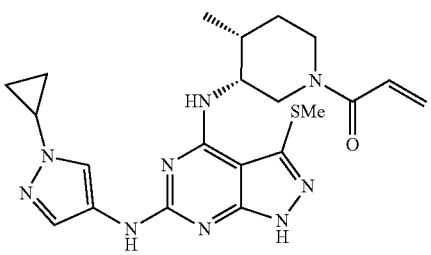 [SMILES: C=CC(=O)N1CC[C@@H](C)[C@@H](Nc2nc(Nc3cnn(C4CC4)c3)nc3[nH]nc(SC)c23)C1]

A title compound (5.2 mg, yield: 21.6%) was prepared in the same manner as in Example 129, except that tert-butyl (3R,4R)-3-amino-4-methylpiperidine-1-carboxylate was used instead of tert-butyl(R)-3-aminopiperidine-1-carboxylate in Example 129.

$^1$H NMR (500 MHz, CD$_3$OD) δ 8.10-7.90 (m, 1H), 7.60-7.50 (m, 1H), 6.90-6.35 (m, 1H), 6.20-5.95 (m, 1H), 5.80-5.35 (m, 1H), 4.80-4.10 (m, 3H), 3.60-3.50 (m, 1H), 3.40-2.75 (m, 2H), 2.50-2.40 (m, 3H), 2.25-2.18 (m, 1H), 1.80-1.40 (m, 2H), 1.10-1.00 (m, 7H)

Example 136: Preparation of 3-((3S,4R)-3-((3-chloro-6-(1-ethyl-1H-pyrazol-4-yl)amino)-1H-pyrazolo[3,4-d]pyrimidin-4-yl)amino)-4-4-fluoropiperidin-1-yl)-3-oxopropenenitrile

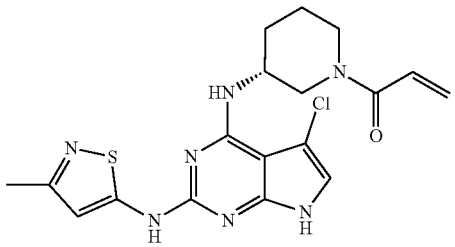 [SMILES: C=CC(=O)N1CCC[C@@H](Nc2nc(Nc3cc(C)ns3)nc3[nH]cc(Cl)c23)C1]

Step 1: Preparation of 2,4,5-trichloro-1H-pyrrolo[2,3-d]pyrimidine 2,4-dichloro-7H-pyrrolo[2,3-d]pyrimidine (5.0 g, 26.6 mmol) and N-chlorosuccinimide (5.3 g, 39.9 mmol) were dissolved in N,N-dimethylformamide (50.0 mL) and then stirred at room temperature for 24 hours. The organic layer was isolated, treated with magnesium sulfate, filtered, and then concentrated under reduced pressure. The residue was isolated by column chromatography to obtain a title compound (5.5 g, yield: 93.4%).

$^1$H NMR (500 MHz, CD$_3$OD) δ 7.54 (s, 1H)

Step 2: Preparation of tert-butyl(R)-3-((2,5-dichloro-7H-pyrrolo[2,3-d]pyrimidin-4-yl)amino)-piperidine-1-carboxylate After 2,4,5-trichloro-7H-pyrrolo[2,3-d]pyrimidine (2.2 g, 9.9 mmol) was dissolved in N,N-dimethylformamide, sodium hydride (262.0 mg, 10.9 mmol) was added dropwise thereto at 0° C. After stirring for 30 minutes, (2-(chloromethoxy)ethyl)trimethylsilane (1.7 mL, 9.89 mmol) was added dropwise and the mixture was stirred at room temperature for 3 hours and 30 minutes. Then, the organic layer was isolated, treated with sodium sulfate, filtered, and then concentrated under reduced pressure. The residue was isolated by column chromatography to obtain a title compound (2.0 g, yield: 58.3%).

$^1$H NMR (500 MHz, CD$_3$OD) δ 7.74 (s, 1H), 5.60-5.59 (m, 2H), 3.59-3.58 (m, 2H), 0.91-0.89 (m, 2H), 0.01 (m, 9H)

Step 3: Preparation of (R)-tert-butyl 3-((2,5-dichloro-7-((2-(trimethylsilyl)ethoxy)methyl)-7H-pyrrolo[2,3-d]pyrimidin-4-yl)amino)piperidine-1-carboxylate Tert-butyl(R)-3-((2,5-dichloro-7H-pyrrolo[2,3-d]pyrimidin-4-yl)amino)-piperidine-1-carboxylate (2.0 g, 5.7 mmol), (R)-tert-butyl 3-aminopiperidine-1-carboxylate (1.4 g, 3.97 mmol) and N,N-diisopropylethylamine (1.5 mL, 5.96 mmol) were dissolved in ethanol (30.0 mL), and then stirred at 105° C. for 7 hours. Subsequently, the residue was isolated by column chromatography to obtain a title compound (2.2 g, yield: 74.4%).

$^1$H NMR (500 MHz, CD$_3$OD) δ 7.24 (s, 1H), 5.48-5.43 (m, 2H), 4.30-4.10 (m, 1H), 3.80-3.50 (m, 5H), 2.08-1.90 (m, 1H), 1.90-1.82 (m, 1H), 1.79-1.70 (m, 1H), 1.69-1.60 (m, 1H), 1.57-1.01 (m, 10H), 0.90-0.81 (m, 2H), 0.01 (m, 9H)

Step 4: Preparation of tert-butyl(R)-3-((5-chloro-24 (3-methylisothiazol-5-yl)amino)-7-((2-(trimethylsilyl)ethoxy)methyl)-7H-pyrrolo[2,3-d]pyrimidin-4-yl)amino)piperidine-1-carboxylate (R)-tert-butyl 3-((2,5-dichloro-7-((2-(trimethylsilyl)ethoxy)methyl)-7H-pyrrolo[2,3-d]pyrimidin-4-yl)amino)piperidine-1-carboxylate (200.0 mg, 0.39 mmol), 3-methylisothiazol-5-amine (39.8 mg, 0.35 mmol), tris(dibenzylideneacetone)dipalladium(18.0 mg, 0.002 mmol), 2-dicyclohexylphosphino-2',4',6'-triisopropylbiphenyl (18.5 mg, 0.39 eq), and potassium carbonate (118.0 mg, 0.86 eq) were dissolved in t-butanol, and the mixture was stirred at room temperature for 45 minutes, followed by stirring at 105° C. for 24 hours. Then, the reaction solution was filtered through celite while dissolving it in methanol and then isolated by column chromatography to obtain the title compound (120.0 mg, yield: 52.0%).

$^1$H NMR (500 MHz, CD$_3$OD) δ 7.00 (s, 1H), 6.56 (s, 1H), 6.52-6.48 (m, 2H), 4.55-4.20 (m, 1H), 4.08-3.85 (m, 1H), 3.70-3.50 (m, 4H), 2.33 (s, 3H), 2.10-2.00 (m, 2H), 1.98-1.55 (m, 3H), 1.50-1.10 (m, 9H), 0.91-0.83 (m, 2H), 0.01 (m, 9H)

Step 5: Preparation of (R)-5-chloro-N2-(3-methylisothiazol-5-yl)-N4-(piperidin-3-yl)-7H-pyrrolo[2,3-d]pyrimidine-2,4-diamine After tert-Butyl (R)-3-((5-chloro-2-((3-methylisothiazol-5-yl)amino)-7-((2-(trimethylsilyl)ethoxy)-methyl)-7H-pyrrolo[2,3-d]pyrimidin-4-yl)amino)piperidine-1-carboxylate (567.0 mg, 1.76 mmol) was dissolved in dichloromethane, trifluoro acetic acid (1.5 mL) was added dropwise thereto and the mixture was stirred at 60° C. for 12 hours. After disappearance of the starting material was identified by TLC, the reaction mixture was neutralized with sodium bicarbonate and extracted with ethyl acetate and H$_2$O. The organic layer was dried with sodium sulfate and then concentrated under reduced pressure to obtain a title compound (100.0 mg, yield: 29.0%).

$^1$H NMR (500 MHz, CD$_3$OD) δ 7.05-6.92 (m, 1H), 6.60-6.50 (m, 1H), 4.40-4.20 (m, 1H), 3.33-3.25 (m, 1H), 2.98-2.90 (m, 1H), 2.70-2.55 (m, 1H), 2.40-2.30 (m, 3H), 2.10-2.00 (m, 1H), 1.90-1.72 (m, 2H), 1.71-1.54 (m, 2H)

Step 6: Preparation of (R)-1-(3-((5-chloro-2-((3-methylisothiazol-5-yl)amino)-7H-pyrrolo[2,3-d]pyrimidin-4-yl)amino)piperidin-1-yl)prop-2-en-1-one After (R)-5-chloro-N2-(3-methylisothiazol-5-yl)-N4-(piperidin-3-yl)-7H-pyrrolo[2,3-d]pyrimidine-2,4-diamine (40.0 mg, 0.11 mmol) was dissolved in a 20:3 mixed solution of tetrahydrofuran:H$_2$O, sodium bicarbonate (27.7 mg, 0.33 eq) was added thereto at 0° C. and then stirred for 15 minutes. Acryloyl chloride (8.9 μL, 0.11 eq) was added to the reaction mixture and then stirred at 0° C. for 15 minutes. The organic layer was isolated, treated with magnesium sulfate, filtered, and then concentrated under reduced pressure. The residue was isolated by column chromatography to obtain a title compound (4.2 mg, yield 9.2%).

$^1$H NMR (500 MHz, CD$_3$OD) δ 6.88-6.50 (m, 3H), 6.35-6.02 (m, 1H), 5.80-5.45 (m, 1H), 4.60-4.50 (m, 1H), 3.90-3.75 (m, 2H), 3.65-3.50 (m, 1H), 2.3 (s, 3H), 2.20-2.10 (m, 1H), 1.99-1.60 (m, 4H)

Example 137: Preparation of (R)-1-(3-((5-chloro-2-(pyridin-3-ylamino)-7H-pyrrolo[2,3-d]pyrimidin-4-yl)amino)piperidin-1-yl)prop-2-en-1-one

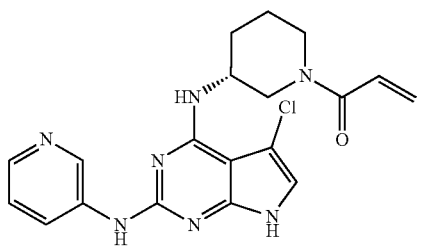 [SMILES: C=CC(=O)N1CCC[C@@H](Nc2nc(Nc3cccnc3)nc3[nH]cc(Cl)c23)C1]

A title compound (33.1 mg, yield: 23.5%) was prepared in the same manner as in Example 136, except that pyridin-3-amine was used instead of 3-methylisothiazol-5-amine in Example 136.

$^1$H NMR (500 MHz, CD$_3$OD) δ 8.95-8.88 (m, 1H), 8.35-8.23 (m, 1H), 8.10-8.00 (m, 1H), 7.38-7.27 (m, 1H), 7.02-6.50 (m, 2H), 6.30-6.00 (m, 1H), 5.80-5.40 (m, 1H), 4.70-4.55 (m, 1H), 4.40-4.27 (m, 1H), 3.90-3.40 (m, 3H), 2.15-1.55 (m, 4H)

Example 138: Preparation of 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropanenitrile

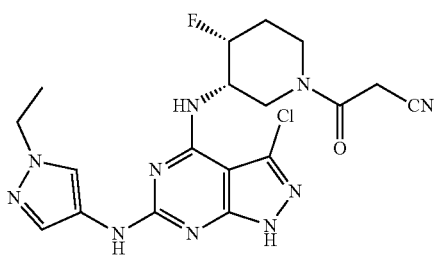 [SMILES: CCn1cc(Nc2nc(N[C@H]3CN(C(=O)CC#N)CC[C@H]3F)c3c(Cl)n[nH]c3n2)cn1]

Step 1: Preparation of 3,4,6-trichloro-1H-pyrazolo[3,4-d]pyrimidine 4,6-dichloro-1H-pyrazolo[3,4-d]pyrimidine (5.0 g, 26.5 mmol) and N-chlorosuccinimide (5.3 g, 39.7 mmol) were dissolved in N,N-dimethylformamide (50.0 mL), and then stirred at room temperature for 24 hours. The organic layer was isolated, treated with magnesium sulfate, filtered, and then concentrated under reduced pressure. The residue was isolated by column chromatography to obtain a title compound (3.3 g, yield: 56.0%).

$^1$H NMR (500 MHz, DMSO-d$_6$) δ 13.07 (s, 1H), 7.94 (s, 1H)

Step 2: Preparation of tert-butyl(3S,4R)-3-((3,6-dichloro-1H-pyrazolo[3,4-d]pyrimidin-4-yl)amino)-4-fluoropiperidine-1-carboxylate After 3,4,6-trichloro-1H-pyrazolo[3,4-d]pyrimidine (350.0 mg, 1.5 mmol) was dissolved in ethanol (50 mL), N,N-diisopropylethylamine (391.8 μL, 2.3 mmol) and tert-butyl (3S,4R)-3-amino-4-fluoropiperidine-1-carboxylate (490.9 mg, 2.3 mmol) were added thereto. The reaction mixture was stirred at 110° C. for 12 hours. The organic layer was isolated, treated with magnesium sulfate, filtered and then concentrated under reduced pressure. The residue was isolated by column chromatography to obtain a title compound (350.0 mg, yield: 57.7%).

$^1$H NMR (500 MHz, CD$_3$OD) δ 5.10-5.00 (m, 1H), 4.58-4.50 (m, 1H), 3.85-3.80 (m, 1H), 3.26-3.16 (m, 3H), 2.10-1.89 (m, 2H), 1.46 (s, 9H)

Step 3: Preparation of (3S,4R)-3-(3-chloro-6-((1-ethyl-1H-pyrazol-4-yl)amino)-1H-pyrazolo[3,4-d]pyrimidin-4-yl)amino)-4-fluoropiperidine-1-carboxylate Tert-butyl(3S,4R)-3-((3,6-dichloro-1H-pyrazolo[3,4-d]pyrimidin-4-yl)amino)-4-fluoropiperidine-1-carboxylate (150.0 mg, 0.4 mmol) and 1-ethyl-1H-pyrazol-4-amine (31.6 mg, 0.3 mmol) were dissolved in 2-butanol (3.0 mL). Trifluoroacetic acid (26.2 μL, 0.3 mmol) was added to the reaction mixture, followed by reacting at 120° C. for 5 hours, and then the solvent was concentrated. This reaction mixture was neutralized by adding 7 N ammonia solution dissolved in methanol. The residue was isolated by column chromatography to obtain a title compound (49.8 mg, yield: 36.8%).

$^1$H NMR (500 MHz, CD$_3$OD) δ 7.97 (s, 1H) 7.56 (s, 1H), 5.10-5.00 (m, 1H), 4.55-4.35 (m, 1H), 4.16-4.09 (m, 2H), 3.90-3.50 (m, 2H), 3.16-2.95 (m, 1H), 2.20-1.85 (m, 3H), 1.46-1.22 (m, 12H)

Step 4: Preparation of 3-chloro-N6-(1-ethyl-1H-pyrazol-4-yl)-N4-((3S,4R)-4-fluoropiperidin-3-yl)-1H-pyrazolo[3,4-d]pyrimidin-4,6-diamine hydrochloride To (3S,4R)-3-(3-chloro-6-((1-ethyl-1H-pyrazol-4-yl)amino)-1H-pyrazolo[3,4-d]pyrimidin-4-yl)amino)-4-fluoropiperidine-1-carboxylate (45.0 mg, 0.09 mmol) was added 6 N hydrochloric acid solution (2.0 mL, excess) dissolved in methanol. After stirring at room temperature for 30 minutes, the reaction mixture was concentrated and the subsequent reaction was carried out without isolation.

$^1$H NMR (500 MHz, CD$_3$OD) δ 7.97 (s, 1H) 7.56 (s, 1H), 5.10-5.00 (m, 1H), 4.55-4.35 (m, 1H), 4.16-4.09 (m, 2H), 3.90-3.50 (m, 2H), 3.16-2.95 (m, 1H), 2.20-1.85 (m, 3H), 1.46-1.39 (m, 3H)

Step 5: Preparation of 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropenenitrile After 2-cyanocetic acid (20.9 mg, 0.2 mmol) was dissolved in N,N-dimethylformamide (2.0 mL), 1-[bis(dimethylamino)methylene]-1H-1,2,3-triazolo[4,5-b]pyridinium 3-oxide hexafluorophosphate (93.5 mg, 0.3 mmol), N,N-diisopropylethylamine (51.6 μL, 0.6 mmol) and 3-chloro-N6-(1-ethyl-1H-pyrazolo[3,4-d]pyrimidin-4,6-diamine hydrochloride (85.3 mg, 0.2 mmol) were added thereto. The reaction mixture was stirred at room temperature for 24 hours. The organic layer was isolated, treated with magnesium sulfate, filtered and then concentrated in reduced pressure. The residue was isolated by column chromatography to obtain a title compound (60.0 mg, yield: 65.5%).

$^1$H NMR (500 MHz, CD$_3$OD) δ 7.95 (s, 1H), 7.61 (s, 1H), 5.07-5.05 (m, 1H), 4.49-4.37 (m, 1H), 4.17-4.13 (m, 2H), 3.59-3.40 (m, 2H), 3.16-2.94 (m, 1H), 2.80 (s, 2H), 2.25-2.15 (m, 1H), 2.10-1.90 (m, 2H), 1.46-1.43 (m, 3H)

Example 139: Preparation of (R)-3-(3-(((3-chloro-6-((1-cyclopropyl-1H-pyrazol-4-yl)amino)-1H-pyrazolo[3,4-d]pyrimidin-4-yl)amino)piperidin-1-yl)-3-oxopropanenitrile

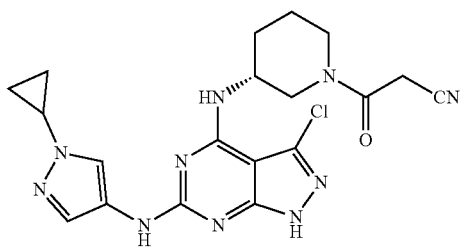 [SMILES: N#CCC(=O)N1CCC[C@@H](Nc2nc(Nc3cnn(C4CC4)c3)nc3[nH]nc(Cl)c23)C1]

A title compound (7.9 mg, yield: 35.7%) was prepared in the same manner as in Example 138, except using tert-butyl (R)-3-aminopiperidine-1-carboxylate instead of tert-butyl (3S,4R)-3-amino-4-fluoropiperidine-1-carboxylate, and 1-cyclopropyl-1H-pyrazol-4-amine instead of 1-ethyl-1H-pyrazol-4-amine in Example 138.

$^1$H NMR (500 MHz, CD$_3$OD) δ 8.00 (s, 1H), 7.58-7.54 (m, 1H), 4.59 (s, 1H), 4.50-4.00 (m, 3H), 3.64-3.59 (m, 2H), 3.19-3.14 (m, 2H), 2.20-2.01 (m, 2H), 1.91-1.80 (m, 3H), 1.72-7.60 (m, 3H)

Example 140: Preparation of (R,E)-1-(3-((5-chloro-2-((4-(4-methylpiperazin-1-yl)phenyl)amino)-7H-pyrrolo[2,3-d]pyrimidin-4-yl)amino)piperidin-1-yl)but-2-en-1-one

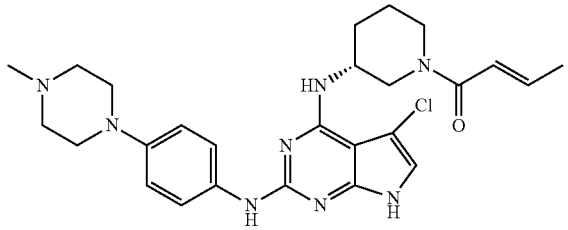 [SMILES: C/C=C/C(=O)N1CCC[C@@H](Nc2nc(Nc3ccc(N4CCN(C)CC4)cc3)nc3[nH]cc(Cl)c23)C1]

A title compound (11.6 mg, yield: 45.7%) was prepared in the same manner as in Example 138, except using 2,4-dichloro-7H-pyrrolo[2,3-d]pyrimidine instead of 4,6-dichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, 4-(4-methylpiperazin-1-yl)aniline instead of 1-ethyl-1H-pyrazol-4-amine, and (E)-but-2-enoic acid instead of 2-cyanoacetic acid in Example 138.

$^1$H NMR (500 MHz, CD$_3$OD) δ 7.65-7.50 (m, 2H), 6.90-6.80 (m, 2H), 6.78-6.70 (m, 1H), 6.65-6.45 (m, 1H), 6.20-6.10 (m, 1H), 4.40-4.20 (m, 1H), 3.85-3.40 (m, 3H), 3.20-3.05 (m, 4H), 2.70-2.55 (m, 4H), 2.35 (s, 3H), 2.10-1.50 (m, 8H)

Example 141: Preparation of (R)-1-(3-((5-chloro-2-((4-(4-methylpiperazin-1-yl)phenyl)amino)-7H-pyrrolo[2,3-d]pyrimidin-4-yl)amino)piperidin-1-yl)-3-cyclopropylprop-2-yn-1-one

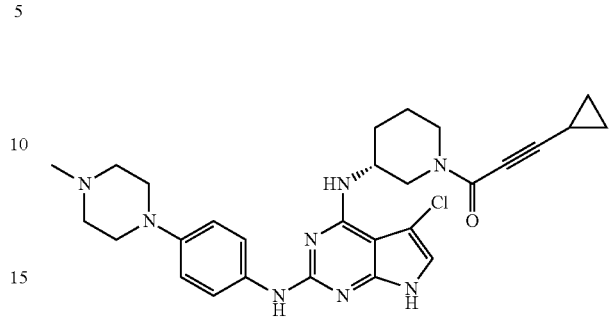

A title compound (7.8 mg, yield: 29.3%) was prepared in the same manner as in Example 138, except using 2,4-dichloro-7H-pyrrolo[2,3-d]pyrimidine instead of 4,6-dichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, 4-(4-methylpiperazin-1-yl)aniline instead of 1-ethyl-1H-pyrazol-4-amine, and 3-cyclopropylpropiolic acid instead of 2-cyanoacetic acid in Example 138.

$^1$H NMR (500 MHz, CD$_3$OD) δ 7.60-7.50 (m, 2H), 7.00-6.90 (m, 2H), 6.80-6.70 (m, 1H), 4.40-4.20 (m, 2H), 4.10-3.80 (m, 2H), 3.60-3.35 (m, 1H), 3.20-3.10 (m, 4H), 2.70-2.60 (m, 4H), 2.36 (s, 3H), 2.10-1.50 (m, 4H), 1.15-0.40 (m, 5H)

Example 142: Preparation of (R)-1-(3-((5-chloro-2-((4-(4-methylpiperazin-1-yl)phenyl)amino)-7H-pyrrolo[2,3-d]pyrimidin-4-yl)amino)piperidin-1-yl)pent-2-yn-1-one

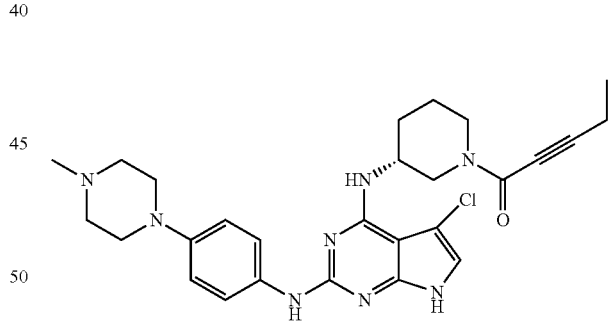

A title compound (7.5 mg, yield: 28.9%) was prepared in the same manner as in Example 138, except using 2,4-dichloro-7H-pyrrolo[2,3-d]pyrimidine instead of 4,6-dichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, 4-(4-methylpiperazin-1-yl)aniline instead of 1-ethyl-1H-pyrazol-4-amine, and pent-2-ynoic acid instead of 2-cyanoacetic acid in Example 138.

$^1$H NMR (500 MHz, CD$_3$OD) δ 7.60-7.50 (m, 2H), 6.97-6.90 (m, 2H), 6.80-6.70 (m, 1H), 4.40-3.80 (m, 4H), 3.60-3.40 (m, 1H), 3.20-3.10 (m, 4H), 2.70-2.60 (m, 4H), 2.30 (s, 3H), 2.12-1.45 (m, 6H), 1.25-0.80 (m, 3H)

Example 143: Preparation of (R)-1-(3-((5-chloro-2-((4-(4-methylpiperazin-1-yl)phenyl)amino)-7H-pyrrolo[2,3-d]pyrimidin-4-yl)amino)piperidin-1-yl)but-2-yn-1-one

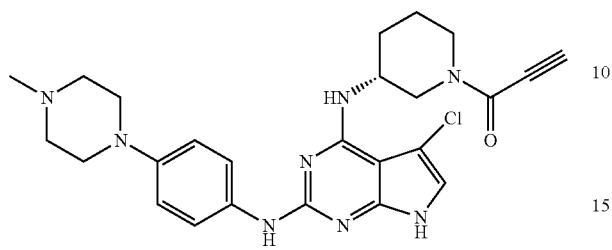

A title compound (6.2 mg, yield: 24.3%) was prepared in the same manner as in Example 138, except using 2,4-dichloro-7H-pyrrolo[2,3-d]pyrimidine instead of 4,6-dichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, 4-(4-methylpiperazin-1-yl)aniline instead of 1-ethyl-1H-pyrazol-4-amine, and but-2-ynoic acid instead of 2-cyanoacetic acid in Example 138.

$^1$H NMR (500 MHz, CD$_3$OD) δ 7.60-7.50 (m, 2H), 7.00-6.90 (m, 2H), 6.78-6.70 (m, 1H), 4.40-3.70 (m, 4H), 3.60-3.40 (m, 1H), 3.20-3.10 (m, 4H), 2.70-2.60 (m, 4H), 2.37 (s, 3H), 2.15-1.55 (m, 7H)

Example 144: Preparation of (R)-1-(3-((6-((1-(2,2,2-trifluoroethyl)-1H-pyrazol-4-yl)amino)-1H-pyrazolo[3,4-d]pyrimidin-4-yl)amino)piperidin-1-yl)prop-2-en-1-one

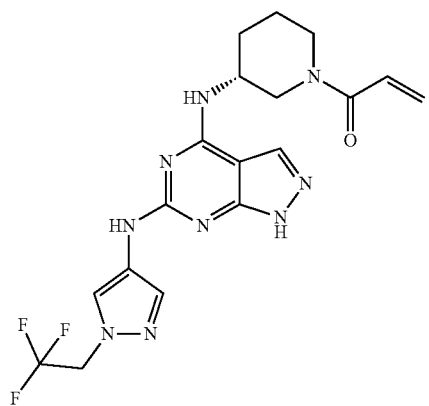 [SMILES: C=CC(=O)N1CCC[C@@H](Nc2nc(Nc3cnn(CC(F)(F)F)c3)nc3[nH]ncc23)C1]

A title compound (5.3 mg, yield: 24.5%) was prepared in the same manner as in Example 30, except that 1-(2,2,2-trifluoroethyl)-1H-pyrazol-4-amine was used instead of 4-(4-methylpiperazin-1-yl)aniline in Example 30.

$^1$H NMR (500 MHz, CD$_3$OD) δ 8.20-8.01 (m, 1H), 7.92 (s, 1H), 7.69-7.60 (m, 1H), 6.86-6.80 (m, 1H), 6.28-6.07 (m, 1H), 5.80-5.51 (m, 1H), 4.27-4.02 (m, 4H), 3.50-3.16 (m, 1H), 2.67-2.15 (m, 2H), 1.97-1.92 (m, 1H), 1.79-1.72 (m, 1H), 1.61-1.60 (m, 1H), 1.31-1.27 (m, 1H)

Example 145: Preparation of (R)-1-(3-((6-((1-(2-(diethylamino)ethyl)-1H-pyrazol-4-yl)amino)-1H-pyrazolo[3,4-d]pyrimidin-4-yl)amino)piperidin-1-yl)prop-2-en-1-one

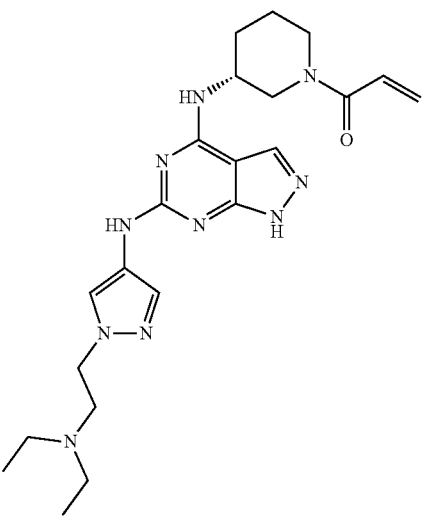 [SMILES: C=CC(=O)N1CCC[C@@H](Nc2nc(Nc3cnn(CCN(CC)CC)c3)nc3[nH]ncc23)C1]

A title compound (4.9 mg, yield: 21.7%) was prepared in the same manner as in Example 30, except that 1-(2-(diethylamino)ethyl)-1H-pyrazol-4-amine was used instead of 4-(4-methylpiperazin-1-yl)aniline in Example 30.

$^1$H NMR (500 MHz, CD$_3$OD) δ 8.03-7.99 (m, 2H), 7.61-7.60 (m, 1H), 6.85-6.58 (m, 1H), 6.26-6.07 (m, 1H), 5.79-5.54 (m, 1H), 4.25-4.20 (m, 3H), 4.08-4.05 (m, 2H), 3.27-3.17 (m, 1H), 3.06-2.99 (m, 2H), 2.72-2.66 (m, 4H), 2.20-2.15 (m, 2H), 2.03-1.95 (m, 1H), 1.80-1.66 (m, 2H), 1.10 (t, 6H)

Example 146: Preparation of (R)-1-(3-((6-(isoxazol-4-ylamino)-1H-pyrazolo[3,4-d]pyrimidin-4-yl)amino)piperidin-1-yl)prop-2-en-1-one

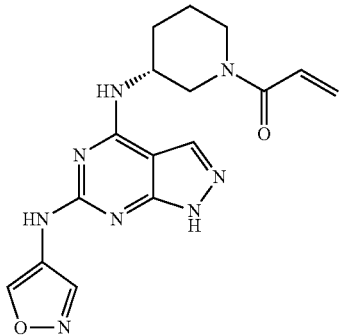 [SMILES: C=CC(=O)N1CCC[C@@H](Nc2nc(Nc3cnoc3)nc3[nH]ncc23)C1]

A title compound (7.1 mg, yield: 39.9%) was prepared in the same manner as in Example 30, except that isoxazol-4-amine was used instead of 4-(4-methylpiperazin-1-yl)aniline.

$^1$H NMR (500 MHz, CD$_3$OD) δ 9.07 (s, 1H), 8.51-8.50 (m, 1H), 7.94-7.92 (m, 1H), 6.85-6.55 (m, 1H), 6.27-6.09 (m, 1H), 5.79-5.56 (m, 1H), 4.27-4.04 (m, 3H), 3.48-3.20 (m, 2H), 2.20-2.16 (m, 2H), 1.80-1.61 (m, 2H)

Example 147: Preparation of (R)-1-(3-((3-chloro-6-((1-ethyl-1H-pyrazol-4-yl)amino)-1H-pyrazolo[3,4-d]pyrimidin-4-yl)oxy)piperidin-1-yl)prop-2-en-1-one

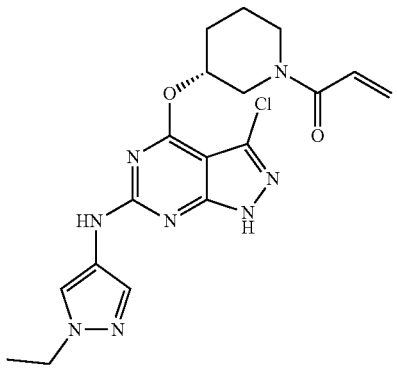 [SMILES: C=CC(=O)N1CCC[C@@H](Oc2nc(Nc3cnn(CC)c3)nc3[nH]nc(Cl)c23)C1]

Step 1: Preparation of 3,4,6-trichloro-1H-pyrazolo[3,4-d]pyrimidine 4,6-dichloro-1H-pyrazolo[3,4-d]pyrimidine (2.5 g, 13.3 mmol) and N-chlorosuccinimide (2.7 g, 19.9 mmol) were dissolved in N,N-dimethylformamide (30.0 mL), and then stirred at room temperature for 24 hours. The organic layer was isolated, treated with magnesium sulfate, filtered, and then concentrated under reduced pressure. The residue was isolated by column chromatography to obtain a title compound (1.6 g, yield: 56.0%).

Step 2: Preparation of 3,4,6-trichloro-14(2-(trimethylsilyl)ethoxy)methyl)-1H-pyrazolo[3,4-d]pyrimidine 3,4,6-trichloro-1H-pyrazolo[3,4-d]pyrimidine (1.3 g, 5.8 mmol) was dissolved in N,N-dimethylformamide (10.0 mL), to which sodium hydride (207.1 mg, 8.6 eq) was added and then stirred for 30 minutes. To this reaction mixture was added (2-(chloromethoxy)ethyl)trimethylsilane (840.0 μL, 5.8 mmol), followed by reacting at room temperature for 3 hours, to which water was added and extracted with ethyl acetate. The isolated organic layer was dried over anhydrous magnesium sulfate and then concentrated under reduced pressure. The obtained residue was isolated by column chromatography to obtain a title compound (1.6 g, yield: 81.0%).

$^1$H NMR (500 MHz, CDCl$_3$) δ 5.69 (s, 2H), 3.66 (t, 2H), 0.92 (t, 2H), −0.05 (s, 9H)

Step 3: Preparation of tert-butyl(R)-3-((3,6-dichloro-1-((2-(trimethylsilyl)ethoxy)methyl)-1H-pyrazolo[3,4-d]pyrimidin-4-yl)oxy)piperidine-1-carboxylate Tert-butyl(R)-3-hydroxypiperidine-1-carboxylate (800.0 mg, 2.26 mmol) was dissolved in tetrahydrofuran (10.0 mL) and then cooled to 0° C. in an ice bath. Sodium hydride (303.2 mg, 4.52 mmol) was added to the reaction mixture and then stirred for 30 minutes. Subsequently, 3,4,6-trichloro-1-((2-(trimethylsilyl)ethoxy)methyl)-1H-pyrazolo[3,4-d]pyrimidine (1.3 g, 2.0 eq) was added and then stirred for 2 hours, to which water was added and extracted with ethyl acetate. The isolated organic layer was dried over anhydrous magnesium sulfate and then concentrated under reduced pressure. The obtained residue was isolated by column chromatography to obtain a title compound (1.3 g, yield: 67.7%).

$^1$H NMR (500 MHz, CDCl$_3$) δ 5.64 (s, 2H), 5.47-5.35 (m, 1H), 4.02-4.00 (m, 1H), 3.77-3.74 (m, 2H), 3.64 (t, 2H), 3.51-3.40 (m, 1H), 3.21 (s, 1H), 2.02-1.98 (m, 2H), 1.61 (s, 1H), 1.44-1.21 (m, 10H), 0.92 (t, 2H), −0.05 (s, 9H)

Step 4: Preparation of tert-butyl(R)-3-((3-chloro-6-((1-ethyl-1H-pyrazol-4-yl)amino)-1-((2-(trimethylsilyl)ethoxy)methyl)-1H-pyrazolo[3,4-d]pyrimidin-4-yl)oxy)piperidine-1-carboxylate After tert-butyl(R)-3-((3,6-dichloro-1-((2-(trimethylsilyl)ethoxy)methyl)-1H-pyrazolo[3,4-d]pyrimidin-4-yl)oxy)piperidine-1-carboxylate (250.0 mg, 0.48 mmol) was dissolved in tert-butanol (3.0 mL), 1-ethyl-1H-pyrazol-4-amine (64. mg, 0.53 mmol), tris(dibenzylideneacetone)dipalladium (44.9 mg, 0.024 mmol), 2-dicyclohexylphosphino-2',4',6'-triisopropylbiphenyl(23.8 mg, 0.048 mmol), and potassium carbonate (135.4 mg, 0.96 mmol) were added thereto and then reacted at 110° C. for 12 hours, to which water was added and extracted with ethyl acetate. The isolated organic layer was dried over anhydrous magnesium sulfate and then concentrated under reduced pressure. The obtained residue was isolated by column chromatography to obtain a title compound (182.0 mg, yield: 62.5%).

$^1$H NMR (500 MHz, CDCl$_3$) δ 7.54 (s, 1H), 7.30-7.06 (m, 1H), 5.54 (s, 1H), 5.21 (s, 1H), 4.17-4.12 (m, 2H), 3.98-3.68 (m 2H), 3.64 (t, 2H), 3.46-3.45 (m, 1H), 3.21-3.20 (m, 1H), 2.12-1.96 (m, 3H), 1.60-1.22 (m, 13H), 0.92 (t, 2H), −0.05 (s, 9H)

Step 5: Preparation of tert-butyl(R)-3-((3-chloro-6-((1-ethyl-1H-pyrazol-4-yl)amino)-1H-pyrazolo[3,4-d]pyrimidin-4-yl)oxy)piperidine-1-carboxylate After tert-butyl(R)-3-((3-chloro-6-((1-ethyl-1H-pyrazol-4-yl)amino)-1-((2-(trimethylsilyl)ethoxy)methyl)-1H-pyrazolo[3,4-d]pyrimidin-4-yl)oxy)piperidine-1-carboxylate (182.0 mg, 0.30 mmol) was dissolved in tetrahydrofuran (2.0 mL), tetrabutylammonium fluoride (2.0 mL, excessive amount) was added thereto and then stirred for 20 hours. Water was then added and extracted with ethyl acetate. The isolated organic layer was dried over anhydrous magnesium sulfate and then concentrated under reduced pressure. The obtained residue was isolated by column chromatography to obtain a title compound (126.0 mg, yield: 87.5%).

$^1$H NMR (500 MHz, CDCl$_3$) δ 7.56 (s, 1H), 7.29-7.05 (m, 1H), 5.19 (s, 1H), 3.95-3.65 (m 2H), 3.64 (t, 2H), 3.46-3.45 (m, 1H), 3.23-3.20 (m, 1H), 2.10-1.94 (m, 3H), 1.59-1.20 (m, 13H)

Step 6: Preparation of (R)-3-chloro-N-(1-ethyl-1H-pyrazol-4-yl)-4-(piperidin-3-yloxy)-1H-pyrazolo[3,4-d]pyrimidin-6-amine hydrochloride Tert-butyl(R)-3-((3-chloro-6-((1-ethyl-1H-pyrazol-4-yl)amino)-1H-pyrazolo[3,4-d]pyrimidin-4-yl)oxy)piperidine- 1-carboxylate (126.0 mg, 0.27 mmol) was dissolved in 1,4 dioxane (0.5 mL), followed by the addition of 4 N HCl in dioxane (3.0 mL, excessive amount). The mixture was then stirred at room temperature for 2 hours. The reaction product was concentrated to obtain a title compound (98.1 mg, yield: 100%).

$^1$H NMR (500 MHz, CDCl$_3$) δ 7.58 (s, 1H), 7.25-7.06 (m, 1H), 5.24 (s, 1H), 3.94-3.64 (m, 5H), 3.50-3.45 (m, 1H), 3.25-3.20 (m, 1H), 2.12-1.96 (m, 3H), 1.60-1.22 (m, 4H)

Step 7: Preparation of (R)-1-(3-((3-chloro-6-((1-ethyl-1H-pyrazol-4-yl)amino)-1H-pyrazolo[3,4-d]pyrimidin-4-yl)oxy)piperidin-1-yl)prop-2-en-1-one After (R)-3-chloro-N-(1-ethyl-1H-pyrazol-4-yl)-4-(piperidin-3-yloxy)-1H-pyrazolo[3,4-d]pyrimidin-6-amine hydrochloride (30.0 mg, 0.07 mmol) was dissolved in THF:H$_2$O=3:1 (1.0/0.3 mL), sodium bicarbonate (20.7 mg, 0.22 mmol) was added thereto at −20° C. and then stirred for 30 minutes. Acryloyl chloride (8.0 μL, 0.8 mmol) was added to the reaction mixture, followed by stirring at −20° C. for 1 hour, to which water was added and extracted with ethyl acetate. The isolated organic layer was dried over anhydrous magnesium sulfate and then concentrated under reduced pressure. The obtained residue was isolated by column chromatography to obtain a title compound (4.9 mg, yield: 15.3%).

$^1$H NMR (500 MHz, CD$_3$OD) δ 8.05 (s, 1H), 7.62 (s, 1H), 6.85-6.55 (m, 1H), 6.17-6.04 (m, 1H), 6.01-5.72 (m, 1H), 5.61-5.44 (m, 2H), 4.30-4.28 (m, 1H), 4.17-4.13 (m, 2H), 3.75-3.68 (m, 2H), 2.09-2.01 (m, 3H), 1.67-1.65 (m, 1H), 1.47-1.44 (m, 3H)

Example 148: Preparation of (R)-4-((1-acryloylpiperidin-3-yl)oxy)-2-((1-cyclopropyl-1H-pyrazol-4-yl)amino)-7H-pyrrolo[2,3-d]pyrimidine-5-carbonitrile

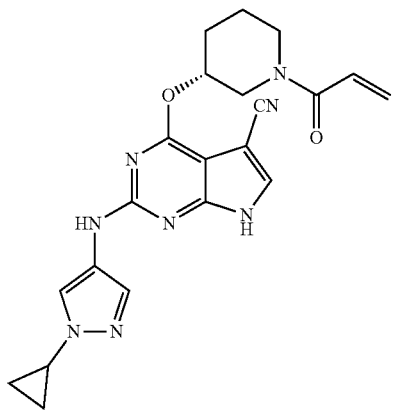 [SMILES: C=CC(=O)N1CCC[C@@H](Oc2nc(Nc3cnn(C4CC4)c3)nc3[nH]cc(C#N)c23)C1]

A title compound (7.8 mg, yield: 37.5%) was prepared in the same manner as in Example 147, except using 1-cyclopropyl-1H-pyrazol-4-amine instead of 1-ethyl-1H-pyrazol-4-amine, and 2,4-dichloro-7H-pyrrolo[2,3-d]pyrimidine-5-carbonitrile instead of 3,4,6-trichloro-1H-pyrazolo[3,4-d]pyrimidine in Example 147.

$^1$H NMR (500 MHz, CD$_3$OD) δ 8.02-8.01 (m, 1H), 7.58-7.55 (m, 1H), 6.80-6.40 (m, 1H), 6.13-5.92 (m, 1H), 5.72-5.36 (m, 2H), 4.70-4.10 (m, 2H), 3.73-3.57 (m, 3H), 2.13-2.07 (m, 3H), 1.66-1.65 (m, 1H), 1.09-1.01 (m, 4H)

Example 149: Preparation of (R)-4-((1-acryloylpiperidin-3-yl)oxy)-2-((1-(2,2-difluoroethyl)-1H-pyrazol-4-yl)amino)-7H-pyrrolo[2,3-d]pyrimidine-5-carbonitrile

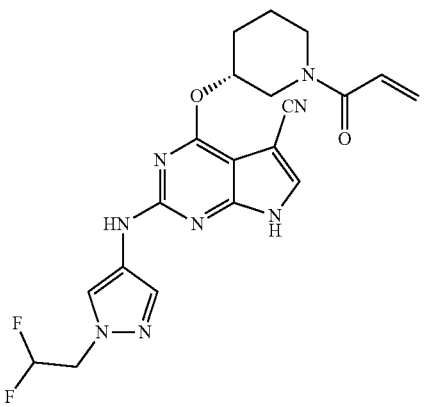 [SMILES: C=CC(=O)N1CCC[C@@H](Oc2nc(Nc3cnn(CC(F)F)c3)nc3[nH]cc(C#N)c23)C1]

A title compound (9.0 mg, yield: 40.5%) was prepared in the same manner as in Example 147, except using 1-(2,2-difluoroethyl)-1H-pyrazol-4-amine instead of 1-ethyl-1H-pyrazol-4-amine in Example 147, and 2,4-dichloro-7H-pyrrolo[2,3-d]pyrimidine-5-carbonitrile instead of 3,4,6-trichloro-1H-pyrazolo[3,4-d]pyrimidine in Step 2.

$^1$H NMR (500 MHz, CD$_3$OD) δ 8.06 (s, 1H), 7.67-7.58 (m, 2H), 6.80-6.39 (m, 1H), 6.14-6.11 (m, 1H), 5.94-5.40 (m, 1H), 5.37-5.35 (m, 1H), 4.53-4.47 (m, 2H), 4.23-4.17 (m, 1H), 3.78-3.55 (m, 2H), 3.30-3.23 (m, 2H), 2.11-2.00 (m, 3H), 1.65-1.64 (m, 1H)

Example 150: Preparation of (R)-4-((1-acryloylpiperidin-3-yl)oxy)-2-((1-ethyl-1H-pyrazol-4-yl)amino)-7H-pyrrolo[2,3-d]pyrimidine-5-carbonitrile

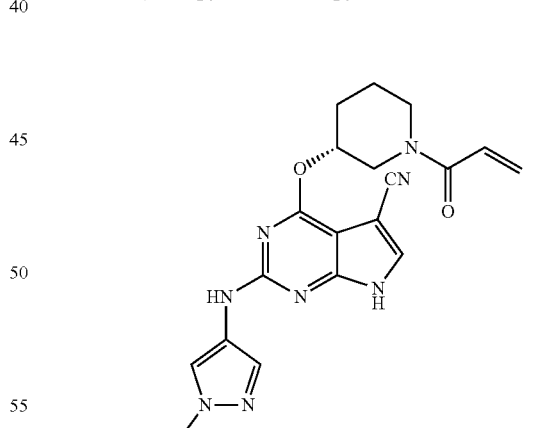

A title compound (4.3 mg, yield: 21.1%) was prepared in the same manner as in Example 147, except using 2,4-dichloro-7H-pyrrolo[2,3-d]pyrimidine-5-carbonitrile instead of 3,4,6-trichloro-1H-pyrazolo[3,4-d]pyrimidine in Example 147.

$^1$H NMR (500 MHz, CD$_3$OD) δ 7.98 (s, 1H), 7.60-7.57 (m, 2H), 6.81-6.41 (m, 1H), 6.13-5.92 (m, 1H), 5.72-5.39 (m, 2H), 4.25-4.09 (m, 4H), 3.85-3.55 (m, 3H), 2.20-2.00 (m, 3H), 1.66-1.65 (m, 1H), 1.46-1.44 (m, 3H)

Example 151: Preparation of (R)-1-(3-((2-((1-ethyl-1H-pyrazol-4-yl)amino)-7H-pyrrolo[2,3-d]pyrimidin-4-yl)oxy)piperidin-1-yl)prop-2-en-1-one

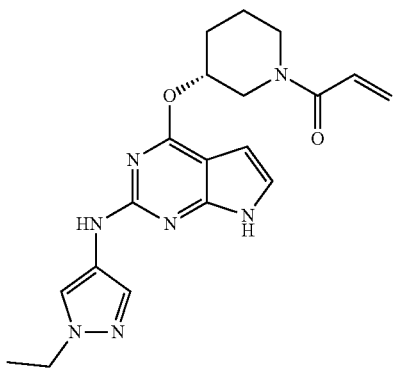 [SMILES: C=CC(=O)N1CCC[C@@H](Oc2nc(Nc3cnn(CC)c3)nc3[nH]ccc23)C1]

A title compound (5.9 mg, yield: 30.9%) was prepared in the same manner as in Example 147, except using 2,4-dichloro-7H-pyrrolo[2,3-d]pyrimidine instead of 3,4,6-trichloro-1H-pyrazolo[3,4-d]pyrimidine in Example 147.

$^1$H NMR (500 MHz, CD$_3$OD) δ 7.98-7.96 (m, 1H), 7.57-7.55 (m, 1H), 6.84-6.50 (m, 2H), 6.25-6.05 (m, 2H), 5.70-5.47 (m, 2H), 4.16-4.12 (m, 4H), 3.77-3.59 (m, 2H), 2.03-1.92 (m, 3H), 1.66-1.64 (m, 1H), 1.47-1.44 (m, 3H)

Example 152: Preparation of (R)-1-(34(24(4-morpholinophenyl)amino)-7H-pyrrolo[2,3-d]pyrimidin-4-yl)oxy)piperidin-1-yl)prop-2-en-1-one

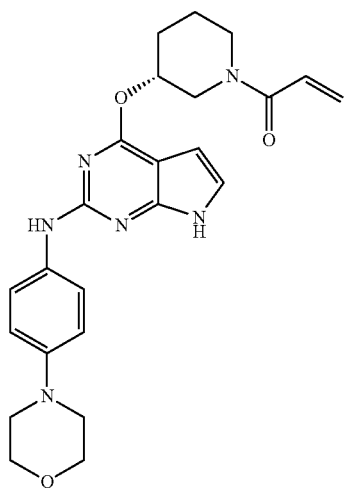 [SMILES: C=CC(=O)N1CCC[C@@H](Oc2nc(Nc3ccc(N4CCOCC4)cc3)nc3[nH]ccc23)C1]

A title compound (7.2 mg, yield: 32.3%) was prepared in the same manner as in Example 147, except using 4-morpholinoaniline instead of 1-ethyl-1H-pyrazol-4-amine, and 2,4-dichloro-7H-pyrrolo[2,3-d]pyrimidine instead of 3,4,6-trichloro-1H-pyrazolo[3,4-d]pyrimidine in Example 147.

$^1$H NMR (500 MHz, CD$_3$OD) δ 7.57-7.55 (m, 2H), 6.93-6.91 (m, 2H), 6.84-6.83 (m, 1H), 6.26-6.03 (m, 2H), 6.00-5.75 (m, 1H), 5.61-5.44 (m, 1H), 5.35-5.34 (m, 1H), 4.08-4.05 (m, 2H), 3.83-3.81 (m, 4H), 3.75-3.72 (m, 2H), 3.05-3.04 (m, 4H), 2.07-1.94 (m, 3H), 1.70-1.60 (m, 1H)

Example 153: Preparation of (R)-1-(3-((3-chloro-6-((1-cyclopropyl-1H-pyrazol-4-yl)amino)-1H-pyrazolo[3,4-d]pyrimidin-4-yl)oxy)piperidin-1-yl)prop-2-en-1-one

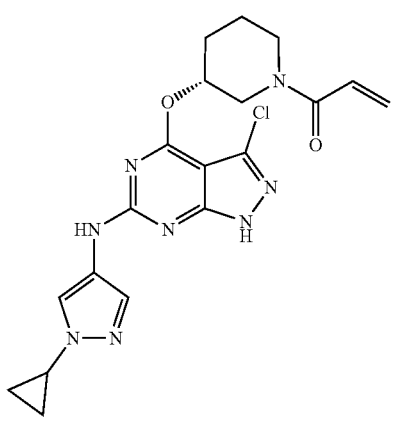 [SMILES: C=CC(=O)N1CCC[C@@H](Oc2nc(Nc3cnn(C4CC4)c3)nc3[nH]nc(Cl)c23)C1]

A title compound (7.5 mg, yield: 35.2%) was prepared in the same manner as in Example 147, except that 1-cyclopropyl-1H-pyrazol-4-amine was used instead of 1-ethyl-1H-pyrazol-4-amine in Example 147.

$^1$H NMR (500 MHz, CD$_3$OD) δ 8.01 (s, 1H), 7.58-7.57 (m, 1H), 7.80-7.50 (m, 1H), 6.17-6.01 (m, 2H), 5.74-5.58 (m, 1H), 4.32-4.29 (m, 2H), 3.69-3.58 (m, 3H), 2.07-1.99 (m, 3H), 1.66-1.64 (m, 1H), 1.09-1.00 (m, 4H)

Example 154: Preparation of (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile

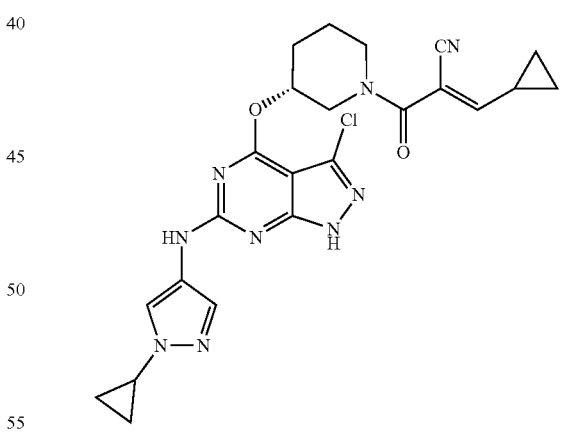

Step 1: Preparation of (R)-3-chloro-N-(1-cyclopropyl-1H-pyrazol-4-yl)-4-(piperidin-3-yloxy)-1H-pyrazolo[3,4-d]pyrimidin-6-amine hydrochloride A title compound (102.5 mg, yield: 45.8%) was prepared in the same manner as in Example 147, except that 1-cyclopropyl-1H-pyrazol-4-amine was used instead of 1-ethyl-1H-pyrazol-4-amine in Example 147.

$^1$H NMR (500 MHz, CD$_3$OD) δ 8.25 (s, 1H), 7.88 (s, 1H), 5.61 (s, 1H), 3.73-3.71 (m, 2H), 3.68-3.58 (m, 1H), 3.52-

3.49 (m, 2H), 3.24-3.18 (m, 1H), 2.26-2.19 (m, 1H), 1.96-1.93 (m, 1H), 1.19-1.13 (m, 4H)

Step 2: Preparation of (R)-1-(3-((3-chloro-6-((1-cyclopropyl-1H-pyrazol-4-yl)amino)-1H-pyrazolo[3,4-d]pyrimidin-4-yl)oxy)piperidin-1-yl)prop-2-en-1-one After (R)-3-chloro-N-(1-cyclopropyl-1H-pyrazol-4-yl)-4-(piperidin-3-yloxy)-1H-pyrazolo[3,4-d]pyrimidin-6-amine hydrochloride (85.3 mg, 0.24 mmol), and 2-cyanocetic acid (20.0 mg, 0.24 mmol) were dissolved in N,N-dimethylformamide (2.0 mL), 1-[bis(dimethylamino)methylene]-1H-1,2,3-triazolo[4,5-b]pyridinium 3-oxide hexafluorophosphate (112.2 mg, 0.36 mmol) was added thereto. The reaction mixture was stirred at room temperature for 24 hours, and then the organic layer was isolated, treated with magnesium sulfate, filtered and then concentrated under reduced pressure. The residue was isolated by column chromatography to obtain a title compound (72.0 mg, yield 65.5%).

$^1$H NMR (500 MHz, CD$_3$OD) δ 8.21 (s, 1H), 7.84 (s, 1H), 5.60 (s, 1H), 3.73-3.71 (m, 2H), 3.68-3.58 (m, 1H), 3.51-3.48 (m, 2H), 3.31 (s, 2H), 3.23-3.15 (m, 1H), 2.24-2.18 (m, 1H), 1.94-1.90 (m, 1H), 1.15-1.10 (m 4H)

Step 3: Preparation of (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile After (R)-1-(3-((3-chloro-6-((1-cyclopropyl-1H-pyrazol-4-yl)amino)-1H-pyrazolo[3,4-d]pyrimidin-4-yl)oxy)piperidin-1-yl)prop-2-en-1-one (50.0 mg, 0.12 mmol) was dissolved in methanol, piperidine (23.0 µL, 0.23 mmol) and cyclopropanecarbaldehyde (13.2 µL, 0.18 mmol) were added thereto. After stirring at room temperature for 5 hours, the organic layer was isolated, treated with magnesium sulfate, filtered, and then concentrated under reduced pressure. The residue was isolated by column chromatography to obtain a title compound (9.6 mg, yield 33.2%).

$^1$H NMR (500 MHz, CD$_3$OD) δ 8.07 (s, 1H), 7.60 (s, 1H), 6.27-6.24 (m, 1H), 5.48 (s, 1H), 4.57 (s, 2H), 3.61-3.51 (m, 2H), 2.12-2.01 (m, 3H), 1.76-1.70 (m, 3H), 1.13-1.03 (m, 6H), 0.99-0.89 (m, 3H)

Example 155: Preparation of (R,E)-2-(3-((3-chloro-6-((1-ethyl-1H-pyrazol-4-yl)amino)-1H-pyrazolo[3,4-d]pyrimidin-4-yl)oxy)piperidine-1-carbonyl)-3-cyclopropylacrylonitrile

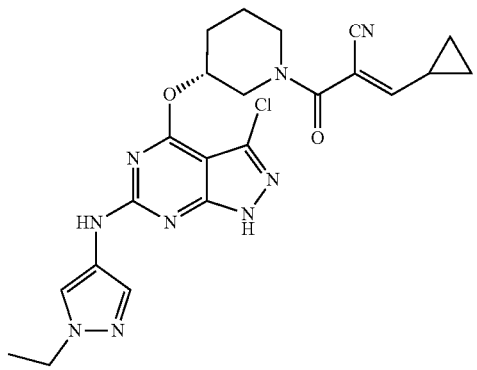 [SMILES: CCn1cc(Nc2nc(O[C@@H]3CCCN(C(=O)/C(C#N)=C/C4CC4)C3)c3c(Cl)n[nH]c3n2)cn1]

A title compound (11.2 mg, yield: 46.3%) was prepared in the same manner as in Example 154, except that 1-ethyl-1H-pyrazol-4-amine was used instead of 1-cyclopropyl-1H-pyrazol-4-amine in Example 154.

$^1$H NMR (500 MHz, CD$_3$OD) δ 8.03 (s, 1H), 7.62 (s, 1H), 6.27-6.25 (m, 1H), 5.49 (s, 1H), 4.63-4.41 (m, 2H), 3.65-3.45 (m, 2H), 2.13-2.03 (m, 4H), 1.69-1.59 (m, 3H), 1.32 (s, 3H), 1.13-0.89 (m, 4H)

Example 156: Preparation of (R,E)-4-((1-(2-cyano-4-methyl pent-2-enoyl)piperidin-3-yl)oxy)-2-((1-ethyl-1H-pyrazol-4-yl)amino)-7H-pyrrolo[2,3-d]pyrimidine-5-carbonitrile

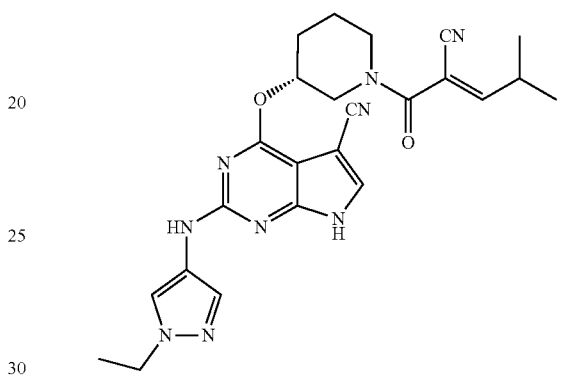

A title compound (4.5 mg, yield: 15.3%) was prepared in the same manner as in Example 154, except using (R)-4-((1-(2-cyanoacetyl)piperidin-3-yl)oxy)-2-((1-ethyl-1H-pyrazol-4-yl)amino)-7H-pyrrolo[2,3-d]pyrimidine-5-carbonitrile instead of (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile, and isobutyraldehyde instead of cyclopropanecarbaldehyde in Example 154.

$^1$H NMR (500 MHz, CD$_3$OD) δ 7.97 (s, 1H), 7.62-7.61 (m, 2H), 6.92-6.52 (m, 1H), 5.51 (s, 1H), 4.50-3.90 (m, 4H), 3.63-3.54 (m, 1H), 3.02-2.81 (m 1H), 2.55-2.03 (m, 4H), 1.72-1.71 (m, 1H), 1.45 (t, 3H), 1.16-1.15 (m, 3H), 0.89-0.88 (m, 3H)

Example 157: Preparation of (R,E)-4-((1-(2-cyano-3-cyclopropylacryloyl)piperidin-3-yl)oxy)-2-((1-ethyl-1H-pyrazol-4-yl)amino)-7H-pyrrolo[2,3-d]pyrimidine-5-carbonitrile

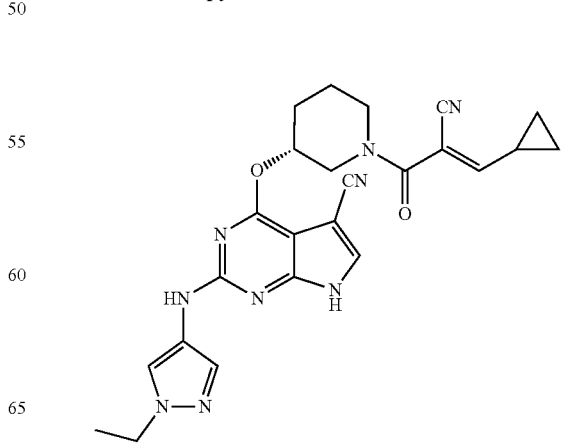

A title compound (5.3 mg, yield: 16.8%) was prepared in the same manner as in Example 154, except that (R)-4-((1-(2-cyanoacetyl)piperidin-3-yl)oxy)-2-((1-ethyl-1H-pyrazol-4-yl)amino)-7H-pyrrolo[2,3-d]pyrimidine-5-carbonitrile was used instead of ((R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile in Example 154.

$^1$H NMR (500 MHz, CD$_3$OD) δ 7.98 (s, 1H), 7.60-7.59 (m, 2H), 6.69-6.22 (m, 1H), 5.49-5.45 (m, 1H), 4.56-4.44 (m, 1H), 4.37-4.00 (m, 3H), 3.51-3.00 (m, 2H), 2.15-2.13 (m, 3H), 1.33-1.32 (m, 1H), 1.50-1.54 (m, 3H), 1.01-0.89 (m, 5H)

Example 158: Preparation of (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-4-methylpent-2-enenitrile

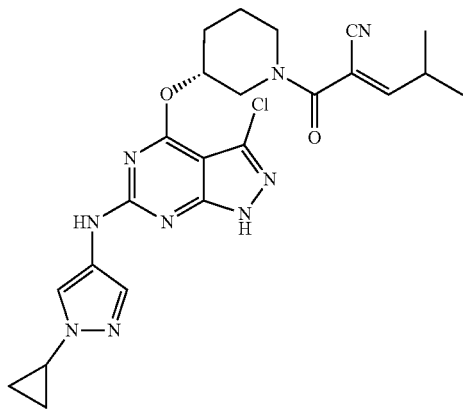 [SMILES: CC(C)/C=C(\C#N)C(=O)N1CCC[C@@H](Oc2nc(Nc3cnn(C4CC4)c3)nc3[nH]nc(Cl)c23)C1]

A title compound (11.8 mg, yield: 47.4%) was prepared in the same manner as in Example 154, except that isobutyraldehyde was used instead of cyclopropanecarbaldehyde in Example 154.

$^1$H NMR (500 MHz, CD$_3$OD) δ 8.07 (s, 1H), 7.58-7.57 (m, 1H), 6.80-6.60 (m, 1H), 5.54 (s, 1H), 4.38-3.90 (m, 2H), 3.61-3.45 (m, 3H), 3.02-2.60 (m, 1H), 2.13-2.03 (m, 3H), 1.73-1.72 (m, 1H), 1.15-1.13 (m, 4H), 1.07-1.04 (m, 6H)

Example 159: Preparation of (1-((3R,4R)-3-((3-chloro-6-((1-ethyl-1H-pyrazol-4-yl)amino)-1H-pyrazolo[3,4-d]pyrimidin-4-yl)(methyl)amino)-4-methylpiperidin-1-yl)prop-2-en-1-one

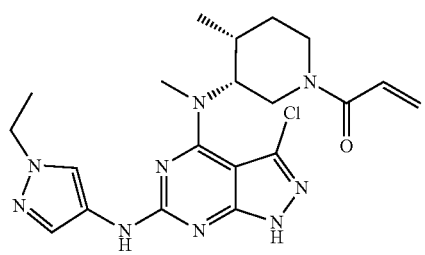 [SMILES: C=CC(=O)N1CC[C@@H](C)[C@@H](N(C)c2nc(Nc3cnn(CC)c3)nc3[nH]nc(Cl)c23)C1]

Step 1: Preparation of 3,4,6-trichloro-1H-pyrazolo[3,4-d]pyrimidine 4,6-dichloro-1H-pyrazolo[3,4-d]pyrimidine (1.0 g, 5.3 mmol), and N-chlorosuccinimide (1.0 g, 7.9 mmol) were dissolved in N,N-dimethylformamide (15.0 mL), and then stirred at room temperature for 8 hours. Purified water was added until crystals were formed, and then stirred for 10 minutes. Thereafter, purified water was added until a large amount of crystals was shown, followed by filtering while washing with purified water. The filtered solid was dissolved in excessive amount of ethyl acetate and dichloromethane, treated with sodium sulfate, washed with ethyl acetate and filtered. The organic layer was concentrated under reduced pressure to obtain a title compound (1.1 g, yield: 93.4%).

Step 2: Preparation of N-((3R,4R)-1-benzyl-4-methylpiperidin-3-yl)-3,6-dichloro-N-methyl-1H-pyrazolo[3,4-d]pyrimidin-4-amine After (3R,4R)-1-benzyl-N,4-dimethylpiperidin-3-amine dihydrochloride (195.5 mg, 0.6 mmol) was dissolved in ethanol (5.0 ml), N,N-diisopropyletheylamine (350.8 μL, 2.0 mmol) was added dropwise thereto, and the mixture was stirred at room temperature for 10 minutes. 3,4,6-trichloro-1H-pyrazolo[3,4-d]pyrimidine (50.0 mg, 0.4 mmol) was added, the temperature was raised to 100° C. and stirring was further carried out for 2 hours. Thereafter, the solution was filtered under reduced pressure, and the obtained residue was isolated by column chromatography to obtain a title compound (45.1 mg, yield: 24.9%).

$^1$H NMR (500 MHz, CD$_3$OD) δ 7.32-7.21 (m, 5H), 5.11-5.07 (m, 1H), 3.69 (s, 3H), 3.52-3.48 (m, 2H), 2.98-2.70 (m, 2H), 2.62-2.59 (m, 1H), 2.25-2.14 (m, 2H), 1.73-1.72 (m, 2H), 0.95-0.94 (d, J=5 Hz, 3H)

Step 3: Preparation of N4-((3R,4R)-1-benzyl-4-methylpiperidin-3-yl)-3-chloro-N6-(1-ethyl-1H-pyrazol-4-yl)-N4-methyl-1H-pyrazolo[3,4-d]pyrimidine-4,6-diamine N-((3R,4R)-1-benzyl-4-methylpiperidin-3-yl)-3,6-dichloro-N-methyl-1H-pyrazolo[3,4-d]pyrimidin-4-amine (54.5 mg, 0.1 mmol) and 1-ethyl-1H-pyrazol-4-amine (11.5 mg, 0.1 mmol) were dissolved in 2-butanol (2.0 mL). Trifluoroacetic acid (9.5 μL, 0.1 mmol) was added to the reaction mixture, followed by reacting at 190° C. for 15 hours, and then the reactant was concentrated. The reaction mixture was neutralized by adding 7 N ammonia solution dissolved in methanol, and the residue was isolated by column chromatography to obtain a title compound (10.4 mg, yield: 16.1%).

$^1$H NMR (500 MHz, CD$_3$OD) δ 7.91 (s, 1H), 7.57 (s, 1H), 7.35-7.21 (m, 5H), 5.04-5.01 (m, 1H), 4.16-4.11 (m, 2H), 3.63 (s, 3H), 3.54-3.50 (m, 2H), 3.01-2.77 (m, 2H), 2.68-2.59 (m, 1H), 2.28-2.12 (m, 2H), 1.76-1.74 (m, 2H), 1.47-1.42 (m, 3H), 0.95-0.94 (d, J=5 Hz, 3H)

Step 4: Preparation of 3-chloro-N6-(1-ethyl-1H-pyrazol-4-yl)-N4-methyl-N4-((3R,4R)-4-methylpiperidin-3-yl)-1H-pyrazolo[3,4-d]pyrimidine-4,6-diamine N4-((3R,4R)-1-benzyl-4-methylpiperidin-3-yl)-3-chloro-N6-(1-ethyl-1H-pyrazol-4-yl)-N4-methyl-1H-pyrazolo[3,4-d]pyrimidine-4,6-diamine (10.4 mg, 0.02 mmol) was dissolved in methanol (1.0 mL), to which Pd/C (3.0 mg) was added and H2 gas was added. The reaction mixture was stirred at room temperature for 3 hours and filtered through celite. The filtrate was concentrated to obtain a title compound (9.0 mg, yield 100%).

¹H NMR (500 MHz, CD₃OD) δ 7.91 (s, 1H), 7.57 (s, 1H), 5.04-5.01 (m, 1H), 4.49-4.41 (m, 2H), 3.54 (s, 3H), 3.12-2.72 (m, 2H), 2.68-2.59 (m, 1H), 2.20-2.01 (m, 2H), 1.60-1.58 (m, 2H), 1.48-1.43 (m, 3H), 0.90-0.89 (d, J=5 Hz, 3H)

Step 5: Preparation of 14(3R,4R)-3-((3-chloro-6-((1-ethyl-1H-pyrazol-4-yl)amino)-1H-pyrazolo[3,4-d]pyrimidin-4-yl)(methyl)amino)-4-methylpiperidin-1-yl)prop-2-en-1-one 3-chloro-N6-(1-ethyl-1H-pyrazol-4-yl)-N4-methyl-N4-((3R,4R)-4-methylpiperidin-3-yl)-1H-pyrazolo[3,4-d]pyrimidine-4,6-diamine (9.0 mg, 0.02 mmol) was dissolved in a 3:1 mixed solution of tetrahydrofuran:H2O (1.0 mL), sodium bicarbonate (5.8 mg, 0.07 mmol) was added thereto at 0° C. and then stirred for 10 minutes. Acryloyl chloride (1.9 µL, 0.02 mmol) was slowly added dropwise to the reaction mixture, and then stirred at 0° C. for 10 minutes. The organic layer was isolated, treated with magnesium sulfate, filtered, and then concentrated under reduced pressure. The residue was isolated by column chromatography to obtain a title compound (4.7 mg, yield: 45.9%).
¹H NMR (500 MHz, CD₃OD) δ 7.91 (s, 1H), 7.57 (s, 1H), 6.88-6.78 (m, 1H), 6.24-6.20 (m, 1H), 5.78-5.71 (m, 1H), 4.99-4.92 (m, 1H), 4.24-4.21 (m, 1H), 4.16-4.11 (m, 2H), 3.92-3.87 (m, 1H), 3.60-3.56 (m, 1H), 3.37 (s, 3H), 2.44-2.42 (m, 1H), 2.20-2.19 (m, 1H), 1.81-1.78 (m, 2H), 1.46-1.44 (m, 3H), 1.07-1.06 (d, J=5 Hz, 3H)

Example 160: Preparation of (E)-2-((3S,4R)-3-((3-chloro-6-((1-ethyl-1H-pyrazol-4-yl)amino)-1H-pyrazolo[3,4-d]pyrimidin-4-yl)amino)-4-fluoropiperidine-1-carbonyl)-4-methylpent-2-enenitrile

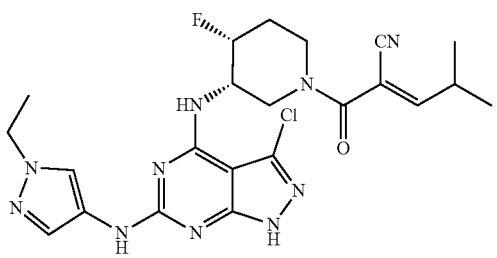 [SMILES: CCn1cc(Nc2nc(N[C@H]3CN(C(=O)/C(C#N)=C/C(C)C)CC[C@H]3F)c3c(Cl)n[nH]c3n2)cn1]

Step 1: Preparation of 3,4,6-trichloro-1H-pyrazolo[3,4-d]pyrimidine 4,6-dichloro-1H-pyrazolo[3,4-d]pyrimidine (10.0 g, 53.0 mmol) and N-chlorosuccinimide (10.6 g, 79.4 mmol) were dissolved in N,N-dimethylformamide (100.0 mL) and then stirred at room temperature for 24 hours. The organic layer was isolated, treated with magnesium sulfate, filtered, and then concentrated under reduced pressure. The residue was isolated by column chromatography to obtain a title compound (6.6 g, yield: 56.0%).
¹H NMR (500 MHz, DMSO-d₆) δ 13.07 (s, 1H), 7.94 (s, 1H)

Step 2: Preparation of tert-butyl(3S,4R)-3-((3,6-dichloro-1H-pyrazolo[3,4-d]pyrimidin-4-yl)amino)-4-fluoropiperidine-1-carboxylate After 3,4,6-trichloro-1H-pyrazolo[3,4-d]pyrimidine (700.0 mg, 3.0 mmol) was dissolved in ethanol (100 mL), N,N-diisopropylethylamine (783.6 µL, 4.6 mmol) and tert-butyl (3S,4R)-3-amino-4-fluoropiperidine-1-carboxylate (981.8 mg, 4.6 mmol) were added thereto. The reaction mixture was stirred at 110° C. for 12 hours, and then the organic layer was isolated, treated with magnesium sulfate, filtered, and then concentrated under reduced pressure. The residue was isolated by column chromatography to obtain a title compound (700.0 mg, yield: 57.7%).
¹H NMR (500 MHz, CD₃OD) δ 5.10-5.00 (m, 1H), 4.58-4.50 (m, 1H), 3.85-3.80 (m, 1H), 3.26-3.16 (m, 3H), 2.10-1.89 (m, 2H), 1.46 (s, 9H)

Step 3: Preparation of (3S,4R)-3-(3-chloro-6-((1-ethyl-1H-pyrazol-4-yl)amino)-1H-pyrazolo[3,4-d]pyrimidin-4-yl)amino)-4-fluoropiperidine-1-carboxylate (3S,4R)-3-((3,6-dichloro-1H-pyrazolo[3,4-d]pyrimidin-4-yl)amino)-4-fluoropiperidine-1-carboxylate (300.0 mg, 0.8 mmol) and 1-ethyl-1H-pyrazol-4-amine (63.2 mg, 0.6 mmol) were dissolved in 2-butanol (6.0 mL). Trifluoroacetic acid (52.4 µL, 0.6 mmol) was added to the reaction mixture, followed by reacting at 120° C. for 5 hours, and then the solvent was concentrated. The reaction mixture was neutralized by adding 7 N ammonia solution dissolved in methanol, and the residue was isolated by column chromatography to obtain a title compound (99.6 mg, yield: 36.8%).
¹H NMR (500 MHz, CD₃OD) δ 7.97 (s, 1H) 7.56 (s, 1H), 5.10-5.00 (m, 1H), 4.55-4.35 (m, 1H), 4.16-4.09 (m, 2H), 3.90-3.50 (m, 2H), 3.16-2.95 (m, 1H), 2.20-1.85 (m, 3H), 1.46-1.22 (m, 12H)

Step 4: Preparation of 3-chloro-N6-(1-ethyl-1H-pyrazol-4-yl)-N4-((3S,4R)-4-fluoropiperidin-3-yl)-1H-pyrazolo[3,4-d]pyrimidine-4,6-diamine hydrochloride To (3S,4R)-3-(3-chloro-6-((1-ethyl-1H-pyrazol-4-yl)amino)-1H-pyrazolo[3,4-d]pyrimidin-4-yl)amino)-4-fluoropiperidine-1-carboxylate (90.0 mg, 0.18 mmol) was added 6 N hydrochloric acid solution (4.0 mL, excessive amount) dissolved in methanol. After stirring at room temperature for 30 minutes, the reaction mixture was concentrated and the subsequent reaction was carried out without isolation.
¹H NMR (500 MHz, CD₃OD) δ 7.97 (s, 1H) 7.56 (s, 1H), 5.10-5.00 (m, 1H), 4.55-4.35 (m, 1H), 4.16-4.09 (m, 2H), 3.90-3.50 (m, 2H), 3.16-2.95 (m, 1H), 2.20-1.85 (m, 3H), 1.46-1.39 (m, 3H)

Step 5: Preparation of 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropenenitrile After 2-cyanoacetic acid (41.8 mg, 0.4 mmol) was dissolved in N,N-dimethylformamide (4.0 mL), 1-[bis(dimethylamino)methylene]-1H-1,2,3-triazolo[4,5-b]pyridinium 3-oxide hexafluorophosphate (187.0 mg, 0.6 mmol), N,N-diisopropylethylamine (103.2 µL, 1.2 mmol) and 3-chloro-N6-(1-ethyl-1H-pyrazol-4-yl)-N4-((3S,4R)-4-fluoropiperidin-3-yl)-1H-pyrazolo[3,4-d]pyrimidine-4,6-diamine hydrochloride (170.6 mg, 0.4 mmol) were added thereto.

The reaction mixture was stirred at room temperature for 24 hours, and then the organic layer was isolated, treated with magnesium sulfate, filtered and then concentrated under reduced pressure. The residue was isolated by column chromatography to obtain a title compound (120.0 mg, yield: 65.5%).

$^1$H NMR (500 MHz, CD$_3$OD) δ 7.95 (s, 1H), 7.61 (s, 1H), 5.07-5.05 (m, 1H), 4.49-4.37 (m, 1H), 4.17-4.13 (m, 2H), 3.59-3.40 (m, 2H), 3.16-2.94 (m, 1H), 2.80 (s, 2H), 2.25-2.15 (m, 1H), 2.10-1.90 (m, 2H), 1.46-1.43 (m, 3H)

Step 6: Preparation of (E)-2-((3S,4R)-3-((3-chloro-6-((1-ethyl-1H-pyrazol-4-yl)amino)-1H-pyrazolo[3,4-d]pyrimidin-4-yl)amino)-4-fluoropiperidine-1-carbonyl)-4-methylpent-2-enenitrile After 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropenenitrile (25.0 mg, 0.06 mmol) was dissolved in methanol, piperidine (11.1 μL, 0.08 mmol) and isobutylaldehyde (67.7 mg, 0.08 mmol) were added thereto. After stirring at room temperature for 5 hours, the organic layer was isolated, treated with magnesium sulfate, filtered, and then concentrated under reduced pressure. The residue was isolated by column chromatography to obtain a title compound (4.8 mg, yield: 17.1%).

$^1$H NMR (500 MHz, CD$_3$OD) δ 7.98 (s, 1H), 7.56 (s, 1H), 6.71 (d, 1H), 5.18-5.09 (m, 1H), 4.82-4.60 (m, 1H), 4.35-4.25 (m, 1H) 4.16-4.12 (m, 2H), 4.08-3.80 (m, 1H), 3.70-3.50 (m, 1H), 3.22-320 (m, 1H), 2.85-2.65 (m, 1H), 2.30-2.00 (m, 1H), 1.89-1.74 (m, 1H), 1.58-1.54 (m, 3H), 1.19-1.13 (m, 6H).

Example 161: Preparation of (E)-2-((3S,4R)-3-((3-chloro-6-((1-ethyl-1H-pyrazol-4-yl)amino)-1H-pyrazolo[3,4-d]pyrimidin-4-yl)amino)-4-fluoropiperidine-1-carbonyl)-3-cyclopropylacrylonitrile

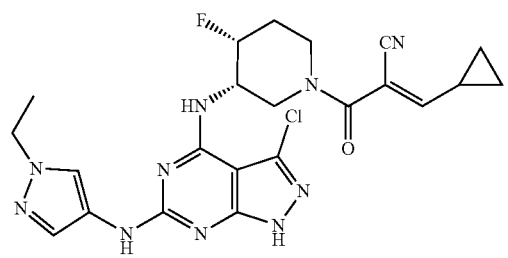 [SMILES: CCn1cc(Nc2nc(N[C@H]3CN(C(=O)/C(C#N)=C/C4CC4)CC[C@H]3F)c3c(Cl)n[nH]c3n2)cn1]

A title compound (3.6 mg, yield: 12.9%) was prepared in the same manner as in Example 160, except that cyclopropanecarbaldehyde was used instead of isobutylaldehyde in Example 160.

$^1$H NMR (500 MHz, CD$_3$OD) δ8.01 (s, 1H), 7.60 (s, 1H), 6.70-6.55 (m, 1H), 4.65-4.58 (m, 1H), 4.16-4.11 (m, 2H), 3.94-3.90 (m, 1H), 3.51-3.44 (m, 1H), 2.22-2.00 (m, 2H), 1.89-1.58 (m, 2H), 1.46-1.43 (m, 3H). 1.28-1.18 (m, 1H), 0.98-0.90 (m, 4H)

Example 162: Preparation of (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-4-methylpent-2-enenitrile

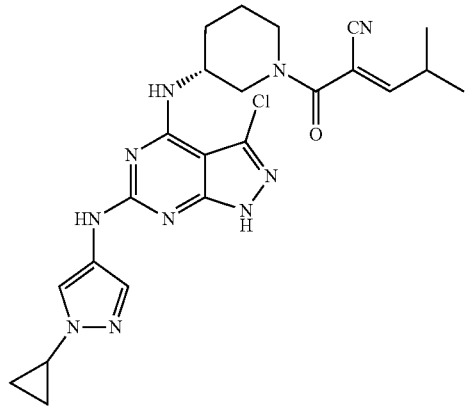 [SMILES: CC(C)/C=C(\C#N)C(=O)N1CCC[C@@H](Nc2nc(Nc3cnn(C4CC4)c3)nc3[nH]nc(Cl)c23)C1]

A title compound (7.0 mg, yield: 28.2%) was prepared in the same manner as in Example 160, except using 1-cyclopropyl-1H-pyrazol-4-amine instead of 1-ethyl-1H-pyrazol-4-amine, and tert-butyl(R)-3-aminopiperidine-1-carboxylate instead of tert-butyl(3S,4R)-3-amino-4-fluoropiperidine-1-carboxylate in Example 160.

$^1$H NMR (500 MHz, CD$_3$OD) δ 7.96 (s, 1H), 7.54 (s, 1H), 6.96-6.65 (m, 1H), 3.64-3.60 (m, 2H), 3.59-3.48 (m, 1H), 2.20 (s, 1H), 1.92 (s, 1H), 1.91-1.88 (m, 2H), 1.71-1.69 (m, 2H), 1.606-1.59 (m, 2H), 1.65-1.05 (m, 6H), 0.92-0.89 (m, 4H)

Example 163: Preparation of (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-4,4-dimethylpent-2-enenitrile

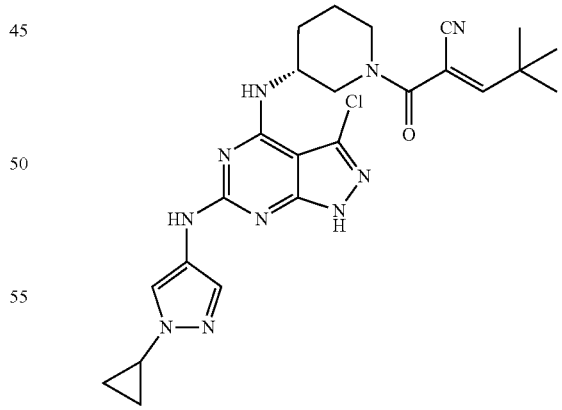

A title compound (9.7 mg, yield: 38.1%) was prepared in the same manner as in Example 160, except using tert-butyl (R)-3-aminopiperidine-1-carboxylate instead of tert-butyl (3S,4R)-3-amino-4-fluoropiperidine-1-carboxylate, pivalaldehyde instead of isobutyraldehyde, and 1-cyclopropyl-1H-pyrazol-4-amine instead of 1-ethyl-1H-pyrazol-4-amine in Example 160.

¹H NMR (500 MHz, CD₃OD) δ 7.98 (s, 1H), 7.56 (s, 1H), 6.92-6.62 (m, 1H), 4.38 (s, 1H), 3.61-3.55 (m, 2H), 2.15 (s, 1H), 2.19-1.99 (m, 2H), 1.98-1.94 (m, 1H), 1.89-1.82 (m, 2H), 1.76-1.68 (m, 1H), 1.39-1.31 (m, 9H), 1.09-0.99 (m, 4H)

Example 164: Preparation of (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-3-cyclopropylacrylonitrile

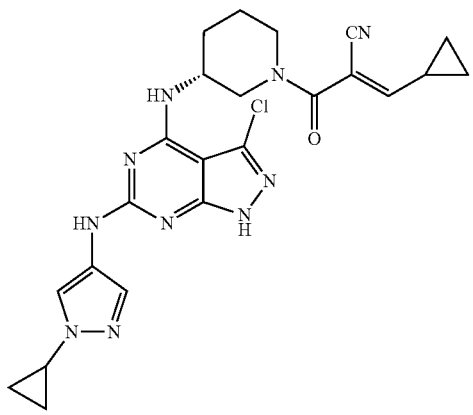

A title compound (11.6 mg, yield: 47.2%) was prepared in the same manner as in Example 160, except using tert-butyl (R)-3-aminopiperidine-1-carboxylate instead of tert-butyl (3S,4R)-3-amino-4-fluoropiperidine-1-carboxylate, cyclopropanecarbaldehyde instead of isobutyraldehyde, and 1-cyclopropyl-1H-pyrazol-4-amine instead of 1-ethyl-1H-pyrazol-4-amine in Example 160.

¹H NMR (500 MHz, CD₃OD) δ 7.99 (s, 1H), 7.55 (s, 1H), 6.65-6.34 (m, 1H), 4.57 (s, 1H), 4.35 (s, 1H), 2.07 (s, 1H), 2.06-1.99 (m, 1H), 1.92-1.88 (m, 2H), 1.85-1.83 (m, 1H), 1.76 (s, 1H), 1.52-1.48 (m, 2H), 1.20-1.15 (m, 2H), 1.08-1.03 (m, 4H), 0.99-0.87 (m, 4H)

Example 165: Preparation of (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-3-cyclopentylacrylonitrile

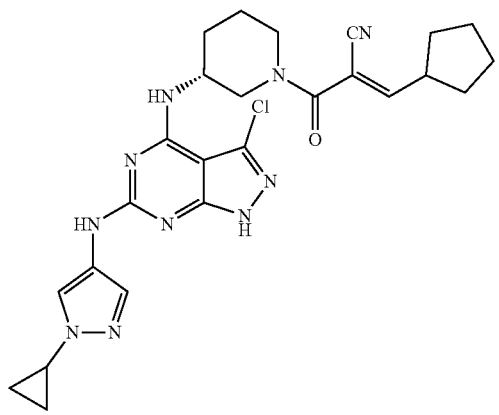 [SMILES: N#C/C(=C\C1CCCC1)C(=O)N1CCC[C@@H](Nc2nc(Nc3cnn(C4CC4)c3)nc3[nH]nc(Cl)c23)C1]

A title compound (8.7 mg, yield: 33.5%) was prepared in the same manner as in Example 160, except using tert-butyl (R)-3-aminopiperidine-1-carboxylate instead of tert-butyl (3S,4R)-3-amino-4-fluoropiperidine-1-carboxylate, cyclopentanecarbaldehyde instead of isobutyraldehyde, and 1-cyclopropyl-1H-pyrazol-4-amine instead of 1-ethyl-1H-pyrazol-4-amine in Example 160.

¹H NMR (500 MHz, CD₃OD) δ 8.00 (s, 1H), 7.55 (s, 1H), 7.00-6.65 (m, 1H), 4.39 (s, 1H), 3.62-3.57 (m, 5H), 2.19-1.88 (m, 5H), 1.74-1.28 (m, 8H), 0.91-0.88 (m, 5H)

Example 166: Preparation of (R,E)-2-(3-((3-chloro-6-((1-ethyl-1H-pyrazol-4-yl)amino)-1H-pyrazolo[3,4-d]pyrimidin-4-yl)amino)piperidine-1-carbonyl)-3-cyclopropylacrylonitrile

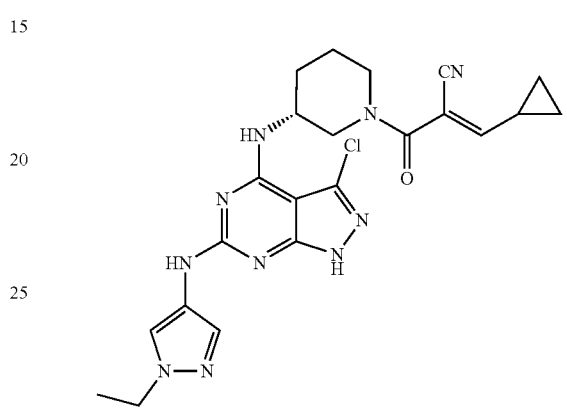

A title compound (8.9 mg, yield: 36.9%) was prepared in the same manner as in Example 160, except using tert-butyl (R)-3-aminopiperidine-1-carboxylate instead of tert-butyl (3S,4R)-3-amino-4-fluoropiperidine-1-carboxylate, and cyclopropanecarbaldehyde instead of isobutyraldehyde in Example 160.

¹H NMR (500 MHz, CD₃OD) δ 7.97 (s, 1H), 7.58 (s, 1H), 6.60-6.30 (m, 1H), 4.36-4.35 (m, 1H), 4.14-4.13 (m, 2H), 3.79-3.47 (m, 3H), 2.13-2.02 (m, 2H), 1.95-1.89 (m, 2H), 1.73-1.72 (m, 2H), 1.48-1.40 (m, 3H), 1.20-0.80 (m, 4H)

Example 167: Preparation of (R,E)-2-(3-((3-chloro-6-((1-ethyl-1H-pyrazol-4-yl)amino)-1H-pyrazolo[3,4-d]pyrimidin-4-yl)(methyl)amino)piperidine-1-carbonyl)-3-cyclopropylacrylonitrile

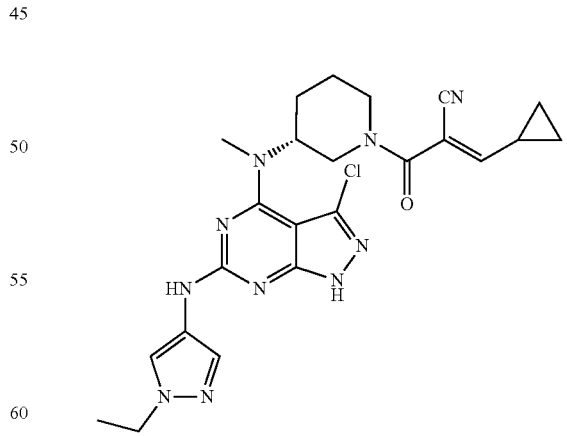

A title compound (6.1 mg, yield: 24.8%) was prepared in the same manner as in Example 160, except using tert-butyl (R)-3-(methylamino)piperidine-1-carboxylate instead of tert-butyl(3S,4R)-3-amino-4-fluoropiperidine-1-carboxylate, and cyclopropanecarbaldehyde instead of isobutyraldehyde in Example 160.

¹H NMR (500 MHz, CD₃OD) δ 7.94 (s, 1H), 7.58 (s, 1H), 6.50 (s, 1H), 4.61-4.55 (m, 2H), 4.14-3.98 (m, 3H), 3.30-3.26 (m, 3H), 2.19-2.03 (m, 5H), 1.71-1.60 (m, 2H), 1.45 (t, 3H), 0.89-0.88 (m, 4H)

Example 168: Preparation of (R,E)-2-(3-((3-chloro-6-((1-ethyl-1H-pyrazol-4-yl)amino)-1H-pyrazolo[3,4-d]pyrimidin-4-yl)(methyl)amino)piperidine-1-carbonyl)-4-methylpent-2-enenitrile

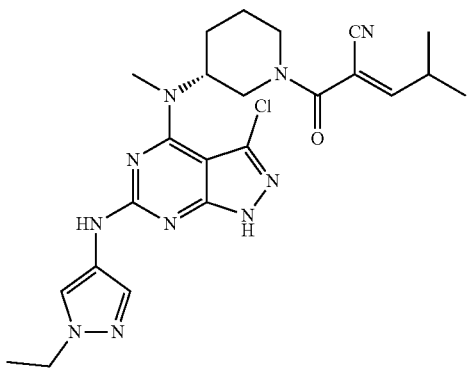 [SMILES: CCn1cc(Nc2nc(N(C)[C@@H]3CCCN(C(=O)/C(C#N)=C/C(C)C)C3)c3c(Cl)n[nH]c3n2)cn1]

A title compound (4.9 mg, yield: 19.7%) was prepared in the same manner as in Example 160, except that tert-butyl (R)-3-(methylamino)piperidine-1-carboxylate was used instead of tert-butyl(3S,4R)-3-amino-4-fluoropiperidine-1-carboxylate in Example 160.
¹H NMR (500 MHz, CD₃OD) δ 7.95 (s, 1H), 7.63-7.59 (m, 1H), 6.90-6.60 (m, 1H), 4.58-4.56 (m, 2H), 4.15-4.12 (m, 2H), 3.34 (s, 3H), 3.23-3.20 (m, 1H), 2.05-2.01 (m, 3H), 1.97-1.94 (m, 1H), 1.85-1.60 (m, 2H), 1.45 (t, 3H), 1.14-1.00 (m, 6H)

Example 169: Preparation of (E)-2-((3R,4R)-3-((3-chloro-6-((1-ethyl-1H-pyrazol-4-yl)amino)-1H-pyrazolo[3,4-d]pyrimidin-4-yl)amino)-4-methylpiperidine-1-carbonyl)-3-cyclopropylacrylonitrile

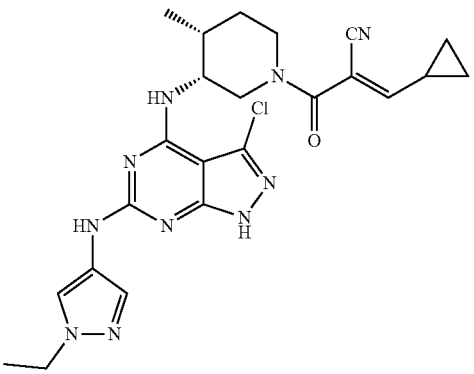 [SMILES: CCn1cc(Nc2nc(N[C@H]3CN(C(=O)/C(C#N)=C/C4CC4)CC[C@H]3C)c3c(Cl)n[nH]c3n2)cn1]

A title compound (11.1 mg, yield: 44.9%) was prepared in the same manner as in Example 160, except using tert-butyl (3R,4R)-3-amino-4-methylpiperidine-1-carboxylate instead of tert-butyl(3S,4R)-3-amino-4-fluoropiperidine-1-carboxylate, and cyclopropanecarbaldehyde instead of isobutyraldehyde in Example 160.
¹H NMR (500 MHz, CD₃OD) δ 7.96 (s, 1H), 7.60 (s, 1H), 6.30-6.24 (m, 1H), 4.64-4.63 (m, 1H), 4.32-4.31 (m, 1H), 4.15-4.13 (m, 2H), 3.33-3.32 (m, 1H), 2.98-2.96 (m, 1H), 2.22-2.02 (m, 3H), 1.90-1.57 (m, 4H), 1.45 (t, 3H), 1.08-1.00 (m, 6H)

Example 170: Preparation of (E)-2-((3R,4R)-3-((3-chloro-6-((1-ethyl-1H-pyrazol-4-yl)amino)-1H-pyrazolo[3,4-d]pyrimidin-4-yl)amino)-4-methylpiperidine-1-carbonyl)-4-methylpent-2-enenitrile

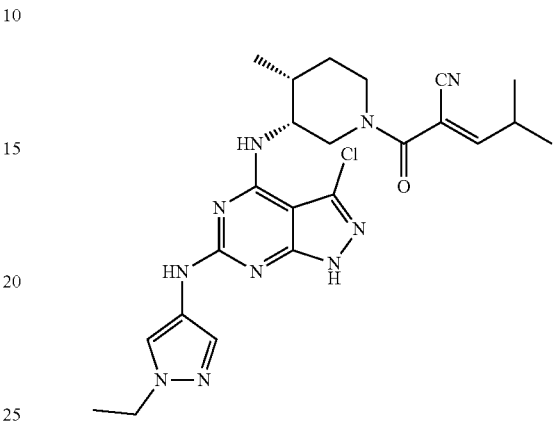

A title compound (10.7 mg, yield: 43.1%) was prepared in the same manner as in Example 160, except that tert-butyl (3R,4R)-3-amino-4-methylpiperidine-1-carboxylate was used instead of tert-butyl(3S,4R)-3-amino-4-fluoropiperidine-1-carboxylate in Example 160.
¹H NMR (500 MHz, CD₃OD) δ 7.97 (s, 1H), 7.60-7.58 (m, 1H), 6.70-6.40 (m, 1H), 4.44-4.40 (m, 2H), 4.15-4.13 (m, 2H), 3.46-3.37 (m, 1H), 3.09-3.08 (m, 1H), 2.56-2.55 (m, 1H), 2.23-2.20 (m, 1H), 2.19-2.17 (m, 1H), 1.89-1.80 (m, 1H), 1.70-1.51 (m, 2H), 1.45-1.40 (m, 3H), 1.08-1.01 (m, 5H), 0.91-0.88 (m, 3H)

Example 171: Preparation of (R,E)-3-cyclopropyl-2-(3-((2-((1-ethyl-1H-pyrazol-4-yl)amino)-7H-pyrrolo[2,3-d]pyrimidin-4-yl)amino)piperidine-1-carbonyl)acrylonitrile

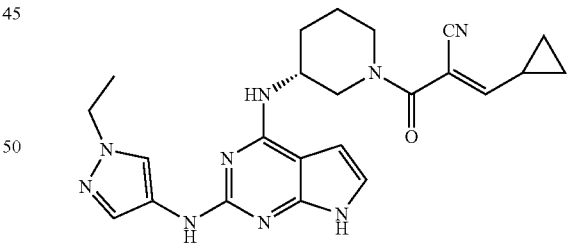

A title compound (8.9 mg, yield: 40.1%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, and cyclopropanecarbaldehyde instead of isobutyraldehyde in Example 160.
¹H NMR (500 MHz, CD₃OD) δ 7.91 (s, 1H), 7.54 (s, 1H), 6.74 (d, J=3.5 Hz, 1H), 6.57-6.14 (m, 2H), 4.27-4.24 (m, 1H), 4.14-4.11 (m, 2H), 4.05-3.59 (m, 3H), 2.15-2.10 (m, 1H), 2.03-1.98 (m, 2H), 1.82-1.59 (m, 4H), 1.45-1.42 (m, 3H), 1.51-1.32 (m, 1H), 0.66-0.24 (m, 2H)

Example 172: Preparation of (R,E)-2-(3-((2-((1-ethyl-1H-pyrazol-4-yl)amino)-7H-pyrrolo[2,3-d]pyrimidin-4-yl)amino)piperidine-1-carbonyl)-4-methylpent-2-enenitrile

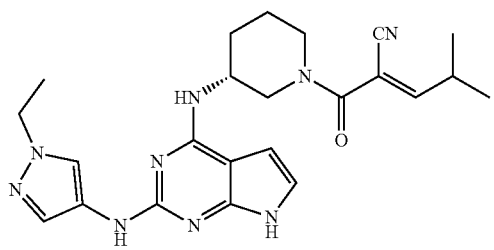 [SMILES: CCn1cc(Nc2nc(N[C@@H]3CCCN(C(=O)/C(C#N)=C/C(C)C)C3)c3cc[nH]c3n2)cn1]

A title compound (4.3 mg, yield: 19.1%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, and tert-butyl(R)-3-aminopiperidine-1-carboxylate instead of tell-butyl(3S,4R)-3-amino-4-fluoropiperidine-1-carboxylate in Example 160.

¹H NMR (500 MHz, CD₃OD) δ 7.90 (s, 1H), 7.53 (s, 1H), 6.86-6.53 (m, 2H), 6.41 (d, J=3.5 Hz, 1H), 4.69-4.64 (m, 1H), 4.32-4.23 (m, 1H), 4.15-4.11 (m, 2H), 3.96-3.52 (m, 3H), 2.14-2.11 (m, 1H), 2.04-1.95 (m, 2H), 1.86-1.58 (m, 3H), 1.46-1.42 (m, 3H), 1.18-1.13 (m, 2H), 1.11-1.00 (m, 2H), 0.74-0.72 (m, 1H)

Example 173: Preparation of (R,E)-3-cyclopropyl-2-(3-((2-((1-ethyl-1H-pyrazol-4-yl)amino)-7H-pyrrolo[2,3-d]pyrimidin-4-yl)thio)piperidine-1-carbonyl)acrylonitrile

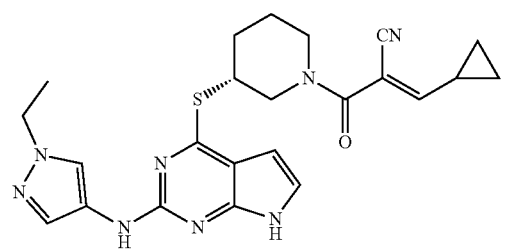 [SMILES: CCn1cc(Nc2nc(S[C@@H]3CCCN(C(=O)/C(C#N)=C/C4CC4)C3)c3cc[nH]c3n2)cn1]

A title compound (10.8 mg, yield: 46.9%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, tert-butyl(R)-3-mercaptopiperidine-1-carboxylate instead of tell-butyl(3S,4R)-3-amino-4-fluoropiperidine-1-carboxylate, and cyclopropanecarbaldehyde instead of isobutyraldehyde in Example 160.

¹H NMR (500 MHz, CD₃OD) δ 7.97 (s, 1H), 7.61 (s, 1H), 6.92 (d, J=3.5 Hz, 1H), 6.54-6.02 (m, 2H), 4.31-4.29 (m, 1H), 4.15-4.12 (m, 2H), 4.05-3.47 (m, 3H), 2.25-2.18 (m, 1H), 2.03-1.57 (m, 5H), 1.46-1.43 (m, 3H), 1.16-1.01 (m, 2H), 0.84-0.12 (m, 2H)

Example 174: Preparation of (R,E)-2-(3-((2-((1-ethyl-1H-pyrazol-4-yl)amino)-7H-pyrrolo[2,3-d]pyrimidin-4-yl)thio)piperidine-1-carbonyl)-4-methylpent-2-enenitrile

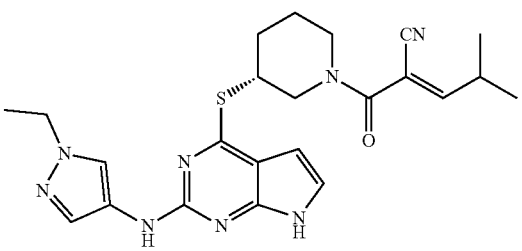 [SMILES: CCn1cc(Nc2nc(S[C@@H]3CCCN(C(=O)/C(C#N)=C/C(C)C)C3)c3cc[nH]c3n2)cn1]

A title compound (10.8 mg, yield: 46.3%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, and tert-butyl(R)-3-aminopiperidine-1-carboxylate instead of tell-butyl(3S,4R)-3-amino-4-fluoropiperidine-1-carboxylate in Example 160.

¹H NMR (500 MHz, CD₃OD) δ 7.97 (s, 1H), 6.12 (s, 1H), 7.00-6.90 (m, 1H), 6.60-6.10 (m, 2H), 4.40-4.20 (m, 1H), 4.18-4.10 (m, 2H), 3.90-3.70 (m, 2H), 3.50-3.32 (m, 1H), 2.30-2.15 (m, 1H), 2.10-1.80 (m, 3H), 1.79-1.50 (m, 2H), 1.50-1.40 (m, 3H), 1.20-0.90 (m, 2H), 0.85-0.10 (m, 2H)

Example 175: Preparation of (R,E)-3-cyclopropyl-2-(3-(((6-((1-ethyl-1H-pyrazol-4-yl)amino)-1H-pyrazolo[3,4-d]pyrimidin-4-yl)amino)piperidine-1-carbonyl)acrylonitrile

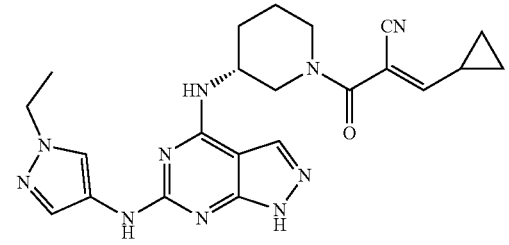 [SMILES: CCn1cc(Nc2nc(N[C@@H]3CCCN(C(=O)/C(C#N)=C/C4CC4)C3)c3cn[nH]c3n2)cn1]

A title compound (7.3 mg, yield: 32.7%) was prepared in the same manner as in Example 160, except using 4,6-dichloro-1H-pyrazolo[3,4-d]pyrimidine instead of 3,4,6-trichloro-1H-pyrazolo[3,4-d]pyrimidine, tert-butyl(R)-3-aminopiperidine-1-carboxylate instead of tert-butyl (3S,4R)-3-amino-4-fluoropiperidine-1-carboxylate, and cyclopropanecarbaldehyde instead of isobutyraldehyde in Example 160.

¹H NMR (500 MHz, CD₃OD) δ 7.97 (s, 1H), 7.92 (s, 1H), 7.57 (s, 1H), 6.57-6.10 (m, 1H), 4.27-4.24 (m, 1H), 4.15-4.12 (m, 2H), 4.02-3.44 (m, 3H), 2.15-2.11 (m, 1H), 2.04-1.97 (m, 2H), 1.84-1.57 (m, 4H), 1.46-1.43 (m, 3H), 1.18-1.14 (m, 1H), 0.74-0.28 (m, 2H)

Example 176: Preparation of (R,E)-3-cyclopropyl-2-(3-((6-((1-ethyl-1H-pyrazol-4-yl)amino)-1H-pyrazolo[3,4-d]pyrimidin-4-yl)thio)piperidine-1-carbonyl)acrylonitrile

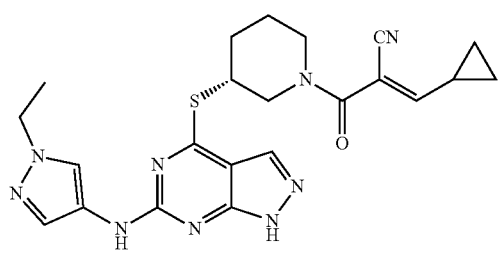 [SMILES: CCn1cc(Nc2nc(S[C@@H]3CCCN(C(=O)/C(C#N)=C/C4CC4)C3)c3cn[nH]c3n2)cn1]

A title compound (11.1 mg, yield: 47.8%) was prepared in the same manner as in Example 160, except using 4,6-dichloro-1H-pyrazolo[3,4-d]pyrimidine instead of 3,4,6-trichloro-1H-pyrazolo[3,4-d]pyrimidine, tert-butyl(R)-3-mercaptopiperidine-1-carboxylate instead of tert-butyl(3S, 4R)-3-amino-4-fluoropiperidine-1-carboxylate, and cyclopropanecarbaldehyde instead of isobutyraldehyde in Example 160.

$^1$H NMR (500 MHz, CD$_3$OD) δ 8.10-7.60 (m, 3H), 6.40-6.00 (m, 1H), 4.40-4.25 (m, 2H), 4.20-4.10 (m, 2H), 4.05-3.30 (m, 3H), 2.30-2.20 (m, 1H), 2.05-1.50 (m, 4H), 1.49-1.40 (m, 3H), 0.80-0.10 (m, 4H)

Example 177: Preparation of (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-3-cyclopropylacrylonitrile

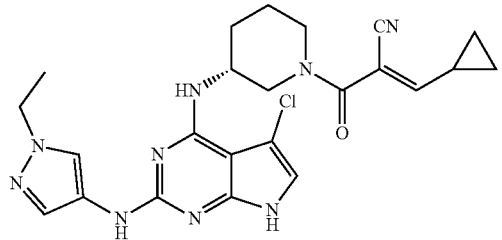 [SMILES: CCn1cc(Nc2nc(N[C@@H]3CCCN(C(=O)/C(C#N)=C/C4CC4)C3)c3c(Cl)c[nH]c3n2)cn1]

A title compound (8.5 mg, yield: 35.4%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, tert-butyl(R)-3-aminopiperidine-1-carboxylate instead of tert-butyl (3S, 4R)-3-amino-4-fluoropiperidine-1-carboxylate, and cyclopropanecarbaldehyde instead of isobutyraldehyde, $^1$H NMR (500 MHz, CD$_3$OD) δ 7.95-7.88 (m, 1H), 7.60-7.50 (m, 1H), 6.80-6.70 (m, 1H), 6.50-6.00 (m, 1H), 4.40-4.30 (m, 1H), 4.35-4.00 (m, 3H), 4.00-3.40 (m, 2H), 2.15-1.50 (m, 6H), 1.50-1.40 (m, 3H), 1.20-0.95 (m, 2H), 0.80-0.10 (m, 2H)

Example 178: Preparation of (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-4-methylpent-2-enenitrile

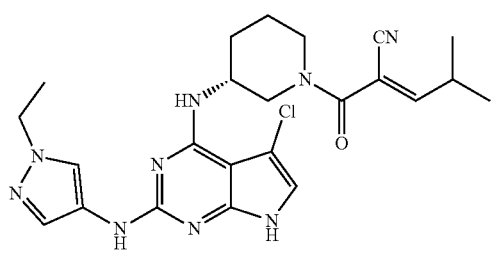 [SMILES: CCn1cc(Nc2nc(N[C@@H]3CCCN(C(=O)/C(C#N)=C/C(C)C)C3)c3c(Cl)c[nH]c3n2)cn1]

A title compound (4.5 mg, yield: 18.8%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, and tert-butyl(R)-3-aminopiperidine-1-carboxylate instead of tell-butyl(3S, 4R)-3-amino-4-fluoropiperidine-1-carboxylate in Example 160.

$^1$H NMR (500 MHz, CD$_3$OD) δ 7.95-7.88 (m, 1H), 7.60-7.50 (m, 1H), 6.90-6.50 (m, 2H), 4.40-4.30 (m, 1H), 4.25-4.00 (m, 2H), 3.98-3.40 (m, 3H), 2.70-2.50 (m, 1H), 2.15-1.50 (m, 5H), 1.48-1.40 (m, 3H), 1.20-0.55 (m, 6H)

Example 179: Preparation of (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-3-cyclopropylacrylonitrile

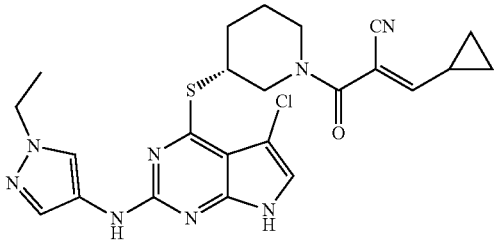 [SMILES: CCn1cc(Nc2nc(S[C@@H]3CCCN(C(=O)/C(C#N)=C/C4CC4)C3)c3c(Cl)c[nH]c3n2)cn1]

A title compound (6.4 mg, yield: 25.7%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, tert-butyl(R)-3-mercaptopiperidine-1-carboxylate instead of tell-butyl(3S, 4R)-3-amino-4-fluoropiperidine-1-carboxylate, and cyclopropanecarbaldehyde instead of isobutyraldehyde.

$^1$H NMR (500 MHz, CD$_3$OD) δ 7.97 (s, 1H), 7.61 (s, 1H), 6.93-6.88 (m, 1H), 6.45-5.98 (m, 1H), 4.40-4.30 (m, 1H), 4.20-4.10 (m, 2H), 4.04-3.60 (m, 3H), 2.30-2.17 (m, 1H), 2.05-1.50 (m, 5H), 1.49-1.40 (m, 3H), 1.20-0.93 (m, 2H), 0.75-0.20 (m, 2H)

Example 180: Preparation of (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-4-methylpent-2-enenitrile

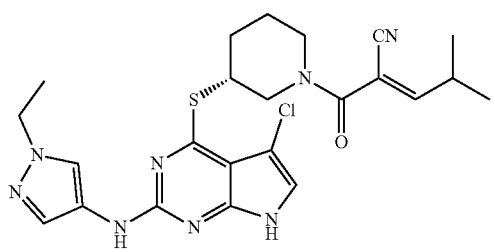 [SMILES: CCn1cc(Nc2nc(S[C@@H]3CCCN(C(=O)/C(C#N)=C/C(C)C)C3)c3c(Cl)c[nH]c3n2)cn1]

A title compound (10.4 mg, yield: 41.7%) was prepared in the same manner as in Example 160, except using 2,4-dichloro-7H-pyrrolo[2,3-d]pyrimidine instead of 3,4,6-trichloro-1H-pyrazolo[3,4-d]pyrimidine, and tert-butyl(R)-3-mercaptopiperidine-1-carboxylate instead of tert-butyl (3S,4R)-3-amino-4-fluoropiperidine-1-carboxylate in Example 160.

$^1$H NMR (500 MHz, CD$_3$OD) δ 7.97 (s, 1H), 7.61 (s, 1H), 6.93-6.89 (m, 1H), 6.70-6.48 (m, 1H), 4.50-4.38 (m, 1H), 4.20-4.10 (m, 2H), 4.04-3.85 (m, 2H), 3.50-3.35 (m, 1H), 2.30-2.20 (m, 1H), 2.08-1.70 (m, 5H), 1.62-1.50 (m, 1H), 1.49-1.40 (m, 3H), 1.25-0.98 (m, 3H), 0.75-0.55 (m, 2H)

Example 181: Preparation of (R,E)-2-(3-((3-chloro-6-((1-ethyl-1H-pyrazol-4-yl)amino)-1H-pyrazolo[3,4-d]pyrimidin-4-yl)thio)piperidine-1-carbonyl)-3-cyclopropylacrylonitrile

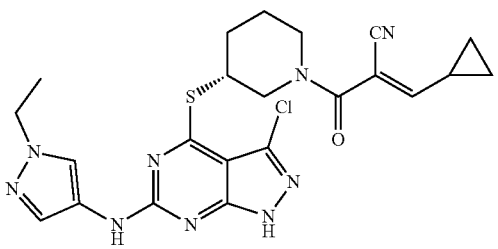 [SMILES: CCn1cc(Nc2nc(S[C@@H]3CCCN(C(=O)/C(C#N)=C/C4CC4)C3)c3c(Cl)n[nH]c3n2)cn1]

A title compound (7.6 mg, yield: 30.6%) was prepared in the same manner as in Example 160, except using tert-butyl (R)-3-mercaptopiperidine-1-carboxylate instead of tell-butyl(3S,4R)-3-amino-4-fluoropiperidine-1-carboxylate, and cyclopropanecarbaldehyde instead of isobutyraldehyde in Example 160.

$^1$H NMR (500 MHz, CD$_3$OD) δ 8.05 (s, 1H), 7.65 (s, 1H), 6.55-6.20 (m, 1H), 4.45-4.25 (m, 2H), 4.20-4.10 (m, 2H), 4.04-3.65 (m, 2H), 2.30-2.20 (m, 1H), 2.08-1.55 (m, 8H), 1.20-0.90 (m, 2H), 0.80-0.20 (m, 2H)

Example 182: Preparation of (R,E)-3-cyclopropyl-2-(3-((2-((1-ethyl-1H-pyrazol-4-yl)amino)-5-fluoro-7H-pyrrolo[2,3-d]pyrimidin-4-yl)amino)piperidine-1-carbonyl)acrylonitrile

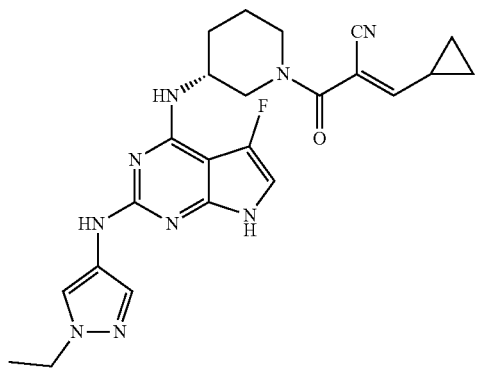 [SMILES: CCn1cc(Nc2nc(N[C@@H]3CCCN(C(=O)/C(C#N)=C/C4CC4)C3)c3c(F)c[nH]c3n2)cn1]

Step 1: Preparation of (R)-3-(3-((2-((1-ethyl-1H-pyrazol-4-yl)amino)-5-fluoro-7H-pyrrolo[2,3-d]pyrimidin-4-yl)amino)piperidin-1-yl)-3-oxopropanenitrile After 2-cyanoacetic acid (83.6 mg, 0.8 mmol) was dissolved in N,N-dimethylformamide (8.0 mL), 1-[bis(dimethylamino)methylene]-1H-1,2,3-triazolo[4,5-b]pyridinium 3-oxide hexafluorophosphate (374.0 mg, 1.2 mmol), N,N-diisopropylethylamine (206.4 μL, 2.4 mmol) and (R)—N2-(1-ethyl-1H-pyrazol-4-yl)-5-fluoro-N4-(piperidin-3-yl)-7H-pyrrolo[2,3-d]pyrimidin-2,4-diamine hydrochloride (Step 5 of Example 82) (341.2 mg, 0.8 mmol) were added thereto. The reaction mixture was stirred at room temperature for 24 hours, and then the organic layer was isolated, treated with magnesium sulfate, filtered and then concentrated under reduced pressure. The residue was isolated by column chromatography to obtain a title compound (240.0 mg, yield: 64.9%).

$^1$H NMR (500 MHz, CD$_3$OD) δ 7.97-7.45 (m, 3H), 4.30-4.20 (m, 1H), 4.18-4.10 (m, 2H), 3.90-3.79 (m, 2H), 3.70-3.60 (m, 3H), 2.18-1.75 (m, 4H), 1.73-1.50 (m, 2H), 1.45-1.38 (m, 2H)

Step 2: Preparation of (R,E)-3-cyclopropyl-2-(3-((2-((1-ethyl-1H-pyrazol-4-yl)amino)-5-fluoro-7H-pyrrolo[2,3-d]pyrimidin-4-yl)amino)piperidine-1-carbonyl)acrylonitrile After (R)-3-(3-((2-((1-ethyl-1H-pyrazol-4-yl)amino)-5-fluoro-7H-pyrrolo[2,3-d]pyrimidin-4-yl)amino)piperidin-1-yl)-3-oxopropanenitrile (50.0 mg, 0.12 mmol) was dissolved in methanol, piperidine (22.2 μL, 0.16 mmol) and cyclopropanecarbaldehyde (135.4 mg, 0.16 mmol) were added thereto. The reaction mixture was stirred at room temperature for 5 hours, and then the organic layer was isolated, treated with magnesium sulfate, filtered and then concentrated under reduced pressure. The residue was isolated by column chromatography to obtain a title compound (9.6 mg, yield: 17.1%).

¹H NMR (500 MHz, CD₃OD) δ 7.97-7.45 (m, 3H), 6.55-6.25 (m, 1H), 4.30-4.20 (m, 1H), 4.18-4.10 (m, 2H), 3.90-3.79 (m, 2H), 3.70-3.60 (m, 1H), 2.18-1.75 (m, 4H), 1.73-1.50 (m, 2H), 1.45-1.38 (m, 3H), 1.20-1.00 (m, 4H)

Example 183: Preparation of 2-chloro-1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)ethan-1-one

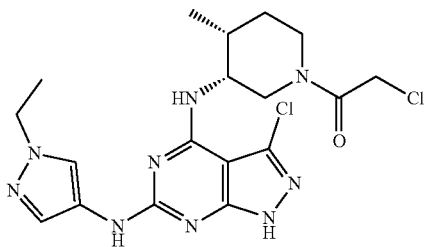 [SMILES: CCn1cc(Nc2nc(N[C@H]3CN(C(=O)CCl)CC[C@H]3C)c3c(Cl)n[nH]c3n2)cn1]

A title compound (4.7 mg, yield: 15.5%) was prepared in the same manner as in Example 138, except using tert-butyl (3R,4R)-3-amino-4-methylpiperidine-1-carboxylate instead of (3S,4R)-3-amino-4-fluoropiperidine-1-carboxylate, and 2-chloroacetic acid instead of 2-cyanocetic acid in Example 138.

¹H NMR (500 MHz, CD₃OD) δ 8.00 (s, 1H), 7.59 (s, 1H), 4.79-4.39 (m, 3H), 4.23-4.12 (m, 3H), 4.03-3.98 (m, 2H), 3.16-2.92 (m, 1H), 2.25-2.15 (m, 1H), 1.89-1.77 (m, 1H), 1.62-1.60 (m, 1H), 1.46-1.44 (m, 3H), 1.07-1.04 (m, 3H)

Example 184: Preparation of (R)-1-(3-((6-((1-(2,2-difluoroethyl)-1H-pyrazol-4-yl)amino)-3-methyl-1H-pyrazolo[3,4-d]pyrimidin-4-yl)amino)piperidin-1-yl)prop-2-en-1-one

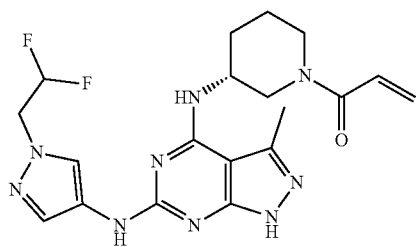 [SMILES: C=CC(=O)N1CCC[C@@H](Nc2nc(Nc3cnn(CC(F)F)c3)nc3[nH]nc(C)c23)C1]

Step 1: Preparation of tert-butyl(R)-3-((6-chloro-3-methyl-1H-pyrazolo[3,4-d]pyrimidin-4-yl)amino)piperidine-1-carboxylate After 4,6-dichloro-3-methyl-1H-pyrazolo[3,4-d]pyrimidine (300.0 mg, 1.5 mmol) was dissolved in ethanol (10 mL), N,N-diisopropylethylamine (695.0 µL, 2.2 mmol) and tert-butyl(R)-3-aminopiperidine-1-carboxylate (355.0 mg, 1.8 mmol) were added thereto. The reaction mixture was stirred at 110° C. for 12 hours, and then the organic layer was isolated, treated with magnesium sulfate, filtered and then concentrated under reduced pressure. The residue was isolated by column chromatography to obtain a title compound (414.5 mg, yield: 76.3%).

¹H NMR (500 MHz, CD₃OD) δ 4.59-4.50 (m, 1H), 4.30-4.24 (m, 1H), 3.93-3.89 (m, 1H), 3.72-3.67 (m, 1H), 3.19-3.17 (m, 1H), 2.59 (s, 3H), 2.10-2.00 (m, 1H), 1.88-1.77 (m, 2H), 1.63-1.30 (m, 10H)

Step 2: Preparation of (R)-6-chloro-3-methyl-N-(piperidin-3-yl)-1H-pyrazolo[3,4-d]pyrimidine-4-amine hydrochloride To tert-butyl(R)-3-((6-chloro-3-methyl-1H-pyrazolo[3,4-d]pyrimidin-4-yl)amino)piperidine-1-carboxylate (414.5 Mg, 1.1 mmol) was added 6 N hydrochloric acid solution (2.0 mL, excessive amount) dissolved in methanol. After stirring at room temperature for 30 minutes, the reaction mixture was concentrated and the subsequent reaction was carried out without isolation.

¹H NMR (500 MHz, CD₃OD) δ 4.71-4.65 (m, 2H), 3.61-3.59 (m, 1H), 3.40-3.34 (m, 1H), 3.07-2.97 (m, 2H), 2.69-2.66 (m, 2H), 2.17-2.09 (m, 2H), 1.98-1.87 (m, 2H)

Step 3: Preparation of (R)-1-(3-((6-chloro-3-methyl-7H-pyrazolo[3,4-d]pyrimidin-4-yl)amino)piperidin-1-yl)prop-2-en-1-one After (R)-6-chloro-3-methyl-N-(piperidin-3-yl)-1H-pyrazolo[3,4-d]pyrimidine-4-amine hydrochloride was dissolved in a 3:1 mixed solution of tetrahydrofuran:distilled water (4 mL), sodium bicarbonate (349.9 mg, 4.2 mmol) was added thereto at −20° C., and then stirred for 30 minutes. Acryloyl chloride (131.4 µL, 1.5 mmol) was slowly added dropwise to the reaction mixture, and then stirred at −20° C. for 1 hour. The organic layer was isolated, treated with magnesium sulfate, filtered, and then concentrated under reduced pressure. The residue was isolated by column chromatography to obtain a title compound (265.4 mg, yield: 56.4%).

¹H NMR (500 MHz, CD₃OD) δ 6.91-6.79 (m, 1H), 6.25-6.17 (m, 1H), 5.79-5.70 (m, 1H), 4.37-4.30 (m, 2H), 4.18-4.15 (m, 1H), 3.54-3.48 (m, 1H), 3.20-2.96 (m, 1H), 2.58 (s, 3H), 2.15-2.13 (m, 1H), 2.10-1.82 (m, 2H), 1.70-1.65 (m, 1H)

Step 4: Preparation of (R)-1-(3-((6-((1-(2,2-difluoroethyl)-1H-pyrazol-4-yl)amino)-3-methyl-1H-pyrazolo[3,4-d]pyrimidin-4-yl)amino)piperidin-1-yl)prop-2-en-1-one (R)-1-(3-((6-chloro-3-methyl-7H-pyrazolo[3,4-d]pyrimidin-4-yl)amino)piperidin-1-yl)prop-2-en-1-one (30.0 mg, 0.09 mmol) and 1-(2,2-difluoroethyl)-1H-pyrazol-4-amine (10.6 mg, 0.07 mmol) were dissolved in 2-butanol (2.0 mL). Trifluoroacetic acid (6.6 µL, 0.09 mmol) was added to the reaction mixture, followed by reacting at 120° C. for 3 hours, and then the solvent was concentrated. The reaction mixture was neutralized by adding 7 N ammonia solution dissolved in methanol, and the residue was isolated by column chromatography to obtain a title compound (16.7 mg, yield: 55.3%).

¹H NMR (500 MHz, CD₃OD) δ 8.05 (d, 1H), 7.61 (d, 1H), 6.87-6.53 (m, 1H), 6.28-6.11 (m, 2H), 6.08-5.54 (m, 1H), 4.58-4.32 (m, 4H), 4.05-3.95 (m, 2H), 3.50-3.12 (m, 1H), 2.5 (s, 3H), 2.15-2.11 (m, 1H), 1.95-1.86 (m, 2H), 1.65-1.63 (m, 1H)

Example 185: Preparation of (R)-1-(3-((6-((1-ethyl-1H-pyrazol-4-yl)amino)-3-methyl-1H-pyrazolo[3,4-d]pyrimidin-4-yl)amino)piperidin-1-yl)prop-2-en-1-one

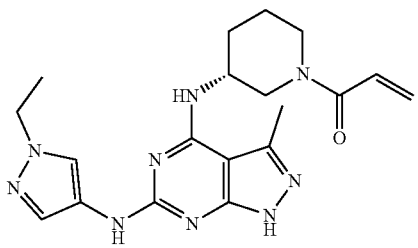 [SMILES: C=CC(=O)N1CCC[C@@H](Nc2nc(Nc3cnn(CC)c3)nc3[nH]nc(C)c23)C1]

A title compound (21.9 mg, yield: 79.3%) was prepared in the same manner as in Example 184, except that 1-ethyl-1H-pyrazol-4-amine was used instead of 1-(2,2-difluoroethyl)-1H-pyrazol-4-amine in Example 184.
$^1$H NMR (500 MHz, CD$_3$OD) δ 7.95 (d, 1H), 7.54 (d, 1H), 6.87-6.55 (m, 1H), 6.28-6.08 (m, 1H), 5.81-5.54 (m, 1H), 4.51-3.92 (m, 5H), 3.50-3.18 (m, 2H), 2.49 (s, 3H), 2.20-2.10 (m, 1H), 1.96-1.89 (m, 2H), 1.64-1.62 (m, 1H)

Example 186: Preparation of (R)-1-(3-((6-((1-isobutyl-1H-pyrazol-4-yl)amino)-3-methyl-1H-pyrazolo[3,4-d]pyrimidin-4-yl)amino)piperidin-1-yl)prop-2-en-1-one

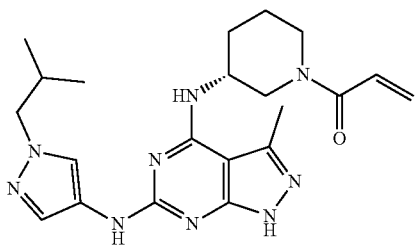 [SMILES: C=CC(=O)N1CCC[C@@H](Nc2nc(Nc3cnn(CC(C)C)c3)nc3[nH]nc(C)c23)C1]

A title compound (19.4 mg, yield: 65.5%) was prepared in the same manner as in Example 184, except that 1-isobutyl-1H-pyrazol-4-amine was used instead of 1-(2,2-difluoroethyl)-1H-pyrazol-4-amine in Example 184.
$^1$H NMR (500 MHz, CD$_3$OD) δ 7.93 (d, 1H), 7.55 (d, 1H), 6.87-6.55 (m, 1H), 6.29-6.09 (m, 1H), 5.81-5.56 (m, 1H), 4.52-3.93 (m, 3H), 3.87-3.85 (m, 2H), 3.50-3.15 (m, 2H), 2.49 (s, 3H), 2.16-2.08 (m, 2H), 1.93-1.87 (m, 2H). 1.63-1.61 (m, 1H), 0.90 (s, 6H)

Example 187: Preparation of (R)-1-(3-((6-((1-(tert-butyl)-1H-pyrazol-4-yl)amino)-3-methyl-1H-pyrazolo[3,4-d]pyrimidin-4-yl)amino)piperidin-1-yl)prop-2-en-1-one

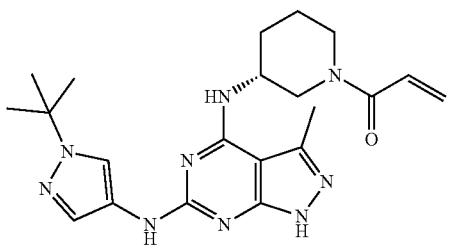 [SMILES: C=CC(=O)N1CCC[C@@H](Nc2nc(Nc3cnn(C(C)(C)C)c3)nc3[nH]nc(C)c23)C1]

A title compound (17.8 mg, yield: 60.1%) was prepared in the same manner as in Example 184, except that 1-(tert-butyl)-1H-pyrazol-4-amine was used instead of 1-(2,2-difluoroethyl)-1H-pyrazol-4-amine in Example 184.
$^1$H NMR (500 MHz, CD$_3$OD) δ 8.04 (s, 1H), 7.59 (s, 1H), 6.85-6.58 (m, 1H), 6.27-6.06 (m, 1H), 5.80-5.54 (m, 1H), 4.36-4.30 (m, 1H), 4.06-4.04 (m, 1H), 3.90-3.87 (m, 1H), 3.45-3.22 (m, 2H), 2.49 (s, 3H), 2.12-2.09 (m, 1H), 2.00-1.85 (m, 2H), 1.63-1.50 (m, 10H)

Example 188: Preparation of (R)-1-(3-((6-((1-cyclopropyl-1H-pyrazol-4-yl)amino)-3-methyl-1H-pyrazolo[3,4-d]pyrimidin-4-yl)amino)piperidin-1-yl)prop-2-en-1-one

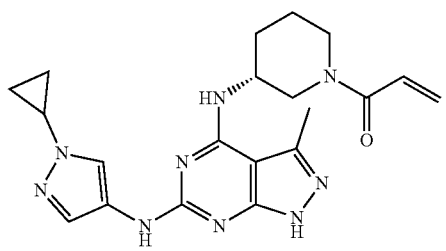 [SMILES: C=CC(=O)N1CCC[C@@H](Nc2nc(Nc3cnn(C4CC4)c3)nc3[nH]nc(C)c23)C1]

A title compound (21.9 mg, yield: 79.3%) was prepared in the same manner as in Example 184, except that 1-cyclopropyl-1H-pyrazol-4-amine was used instead of 1-(2,2-difluoroethyl)-1H-pyrazol-4-amine in Example 184.
$^1$H NMR (500 MHz, CD$_3$OD) δ 7.99 (s, 1H), 7.51 (s, 1H), 6.87-6.55 (m, 1H), 6.27-6.08 (m, 1H), 5.80-5.54 (m, 1H), 4.48-3.91 (m, 3H), 3.57-3.56 (m, 1H), 3.50-3.22 (m, 3H), 2.50 (s, 3H), 2.20-2.11 (m, 1H), 1.97-1.87 (m, 2H), 1.65-1.63 (m, 1H), 1.04-1.00 (m, 4H)

Example 189: Preparation of (R)-1-(3-((6-((1-ethyl-1H-pyrazol-4-yl)amino)-3-(methylthio)-1H-pyrazolo[3,4-d]pyrimidin-4-yl)amino)piperidin-1-yl)prop-2-en-1-one

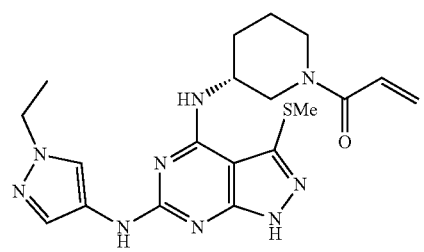 [SMILES: C=CC(=O)N1CCC[C@@H](Nc2nc(Nc3cnn(CC)c3)nc3[nH]nc(SC)c23)C1]

A title compound (20.4 mg, yield: 79.6%) was prepared in the same manner as in Example 129, except that 1-ethyl-1H-pyrazol-4-amine was used instead of 1-cyclopropyl-1H-pyrazol-4-amine in Example 129.
$^1$H NMR (500 MHz, CD$_3$OD) δ 7.97 (s, 1H), 7.56 (d, 1H), 6.90-6.50 (m, 1H), 6.26-6.08 (m, 1H), 5.80-5.55 (m, 1H), 4.38-4.30 (m, 1H), 4.15-4.07 (m, 2H), 3.95-3.79 (m, 2H)

3.59-3.50 (m, 1H), 2.51 (s, 3H), 2.15-2.08 (m, 1H), 1.94-1.85 (m, 2H), 1.75-1.69 (m, 1H), 1.44-1.40 (m, 3H)

Example 190: Preparation of (R)-1-(3-((6-((1-(2,2-difluoroethyl)-1H-pyrazol-4-yl)amino)-3-(methylthio)-1H-pyrazolo[3,4-d]pyrimidin-4-yl)amino)piperidin-1-yl)prop-2-en-1-one

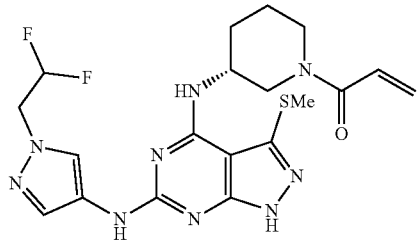 [SMILES: C=CC(=O)N1CCC[C@@H](Nc2nc(Nc3cnn(CC(F)F)c3)nc3[nH]nc(SC)c23)C1]

A title compound (16.1 mg, yield: 57.9%) was prepared in the same manner as in Example 129, except that 1-(2,2-difluoroethyl-1H-pyrazol-4-amine was used instead of 1-cyclopropyl-1H-pyrazol-4-amine in Example 129.

$^1$H NMR (500 MHz, CD$_3$OD) δ 8.06 (d, 1H), 7.63 (d, 1H), 6.85-6.50 (m, 1H), 6.26-6.04 (m, 2H), 5.79-5.52 (m, 1H), 4.52-4.47 (m, 2H), 4.38-4.33 (m, 2H), 3.96-3.90 (m, 1H), 3.79-3.77 (m, 1H), 3.55-3.48 (m, 1H), 2.52 (s, 3H), 2.09-2.07 (m, 1H), 1.93-1.81 (m, 2H), 1.75-1.70 (m, 1H)

Example 191: Preparation of (R)-1-(3-((6-((1-methyl-1H-pyrazol-4-yl)amino)-3-(methylthio)-1H-pyrazolo[3,4-d]pyrimidin-4-yl)amino)piperidin-1-yl)prop-2-en-1-one

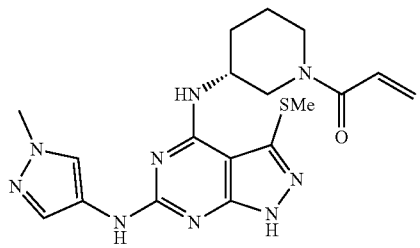 [SMILES: C=CC(=O)N1CCC[C@@H](Nc2nc(Nc3cnn(C)c3)nc3[nH]nc(SC)c23)C1]

A title compound (10.6 mg, yield: 42.7%) was prepared in the same manner as in Example 129, except that 1-methyl-1H-pyrazol-4-amine was used instead of 1-cyclopropyl-1H-pyrazol-4-amine in Example 129.

$^1$H NMR (500 MHz, CD$_3$OD) δ 8.54 (s, 1H), 7.92 (s, 1H), 6.86-6.52 (m, 1H), 6.25-6.04 (m, 1H), 5.79-5.49 (m, 1H), 4.36-4.19 (m, 1H), 3.84-3.75 (m, 4H), 3.60-3.54 (m, 2H), 2.51 (s, 3H), 2.15-2.05 (m, 1H), 1.95-1.84 (m, 2H), 1.75-1.70 (m, 1H)

Example 192: Preparation of (R)-1-(3-((6-((1-(tert-butyl)-1H-pyrazol-4-yl)amino)-3-(methylthio)-1H-pyrazolo[3,4-d]pyrimidin-4-yl)amino)piperidin-1-yl)prop-2-en-1-one

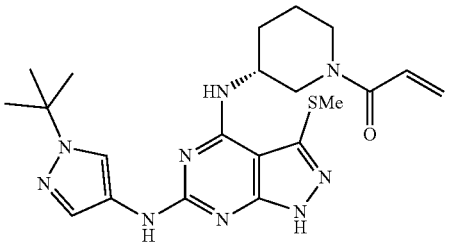 [SMILES: C=CC(=O)N1CCC[C@@H](Nc2nc(Nc3cnn(C(C)(C)C)c3)nc3[nH]nc(SC)c23)C1]

A title compound (16.8 mg, yield: 61.5%) was prepared in the same manner as in Example 129, except that 1-(tert-butyl)-1H-pyrazol-4-amine was used instead of 1-cyclopropyl-1H-pyrazol-4-amine in Example 129.

$^1$H NMR (500 MHz, CD$_3$OD) δ 8.06 (s, 1H), 7.61 (s, 1H), 6.85-6.55 (m, 1H), 6.24-6.04 (m, 1H), 5.79-5.50 (m, 1H), 4.37-4.35 (m, 1H), 3.88-3.48 (m, 4H), 2.51 (s, 3H), 2.09-2.00 (m, 1H), 1.93-1.84 (m, 2H), 1.70-1.65 (m, 1H), 1.57 (s, 9H)

Example 193: Preparation of 1-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)prop-2-en-1-one

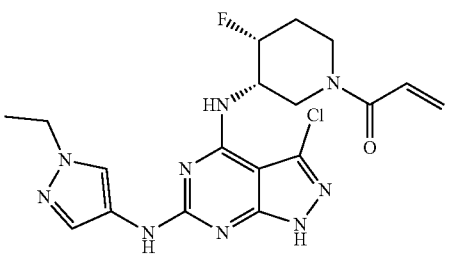 [SMILES: C=CC(=O)N1CC[C@@H](F)[C@@H](Nc2nc(Nc3cnn(CC)c3)nc3[nH]nc(Cl)c23)C1]

A title compound (8.2 mg, yield: 37.8%) was prepared in the same manner as in Example 46, except that tert-butyl (3S,4R)-3-amino-4-fluoropiperidine-1-carboxylate was used instead of tert-butyl(R)-3-aminopiperidine-1-carboxylate in Example 46.

$^1$H NMR (500 MHz, CD$_3$OD) δ 7.99 (s, 1H), 7.57 (s, 1H), 6.85-6.70 (m, 1H), 6.31-6.27 (m, 1H), 5.83-5.65 (m, 1H), 5.15-5.05 (m, 1H), 4.58-4.25 (m, 1H), 4.13-4.03 (m, 3H), 3.60-3.43 (m, 1H), 3.34-3.05 (m, 2H), 2.22-2.15 (m, 1H), 2.01-1.90 (m, 2H), 1.43-1.42 (m, 3H)

Experimental Example 1: Measurement of JAK 3 and BTK Enzyme Inhibitory Activity

JAK3 and BTK kinase inhibitory activities were measured for the compounds prepared in the above Examples through in vitro analysis on the ADP Glow (Glo) platform.

Specifically, the inhibitory activities of JAK3 and BTK kinase were measured using a JAK3 kinase assay kit (Promega, V9441) and a BTK kinase assay kit (Promega, V9071) which were purchased from Promega. Recombinant purified human JAK3 and BTK were diluted with 1×kinase reaction buffer (JAK3: 40 mM Tris-Cl, pH 7.5, 20 mM $MgCl_2$, 0.1 mg/mL BSA and 50 uM DTT/BTK: 40 mM Tris-Cl, pH 7.5, 20 mM $MgCl_2$, 0.1 mg/mL BSA, 2 mM $MnCl_2$ and 50 uM DTT) and added to a 96 well plate (JAK3: final concentration of 4 ng per reaction/BTK: final concentration of 8 ng per reaction). The compounds were treated so as to be finally a 1% DMSO aqueous solution, and a substrate cocktail containing ATP (JAK3: final concentration of 5 uM/BTK: final concentration of 10 uM) and 0.2 μg/μL of Poly(Glu4, Tyr1) peptide (JAK3 and BTK final concentration) in the total 254 reactants was added to a 96-well plate to initiate enzymatic reaction. After incubation (30° C.) for 1 hour, equivalent volume (254 per reaction) of ADP Glo was added and incubated (30° C.) for 40 minutes at room temperature. Then, a kinase detection reagent (504 per reaction) was added and incubated (30° C.) for 30 minutes at room temperature. The kinase activity was measured by chemiluminescence according to the instructions of ADP Glo kinase assay kit, and the inhibitory activity of the compounds according to the present invention was calculated. For the analysis of the results of each compound, Microsoft Excel was used, and $IC_{50}$ values were calculated by SigmaPlot software. The results are shown in Tables 1 to 5 below.

TABLE 1

| Ex. No. | JAK3 $IC_{50}$ (nM) | BTK $IC_{50}$ (nM) |
|---|---|---|
| 1 | 3.73 | 10.7 |
| 2 | 8.9 | 27 |
| 3 | 28.2% inhibition @100 nM | 30.0% inhibition @100 nM |
| 4 | 6.9 | 26.7 |
| 5 | 24.6 | 76.7 |
| 6 | 4.6 | 9.6 |
| 7 | 5 | 14 |
| 8 | 1.3 | 14.3 |
| 9 | 3.9 | 20.5 |
| 10 | 32.8% inhibition@100 nM | 23.7% inhibition@100 nM |
| 11 | 36.0% inhibition@100 nM | 26.5% inhibition@100 nM |
| 12 | 1.3 | 10.6 |
| 13 | 0.4% inhibition@1 uM | 1% inhibition@1 uM |
| 14 | 1.1 | 19.2 |
| 15 | 0.3 | 7.2 |
| 16 | 0.4 | 10.1 |
| 17 | 0.6 | 11.8 |
| 18 | 0.3 | 8.8 |
| 19 | 0.5 | 8.7 |
| 20 | 0.7 | 9.5 |
| 21 | 0.4 | 4.5 |
| 22 | 17.3% inhibition@100 nM | 8.9% inhibition@100 nM |
| 23 | 0.9 | 13.9 |
| 24 | 0.4 | 15.3 |
| 25 | 11.2 | 39.3% inhibition@100 nM |
| 26 | 39.2 | 10.3% inhibition@100 nM |
| 27 | 32.8% inhibition@1 uM | 48.0% inhibition@100 nM |
| 28 | 185.5 | 3.3% inhibition@100 nM |

TABLE 1-continued

| Ex. No. | JAK3 $IC_{50}$ (nM) | BTK $IC_{50}$ (nM) |
|---|---|---|
| 29 | 66.2 | 47.1% inhibition@100 nM |
| 30 | 52.6% inhibition@100 nM | 6 |
| 31 | 3.4 | 2.2 |
| 32 | 10.7 | 2.8 |
| 33 | 4.9 | 1.6 |
| 34 | 3.4 | 2.1 |
| 35 | 5.2 | 2.1 |
| 36 | 1.1 | 16.5 |
| 37 | 0.1 | 2.5 |
| 38 | 0.1 | 4.3 |
| 39 | 0.1 | 1.9 |
| 40 | 0.2 | 1.8 |

TABLE 2

| Ex. No. | JAK3 $IC_{50}$ (nM) | BTK $IC_{50}$ (nM) |
|---|---|---|
| 41 | 0.5 | 1.8 |
| 42 | 5.1 | 3.2 |
| 43 | 9.9 | 6.7 |
| 44 | 0.3 | 2.5 |
| 45 | 0.7 | 2.9 |
| 46 | 0.6 | 2 |
| 47 | 1.1 | 5.2 |
| 48 | 0.4 | 0.9 |
| 49 | 0.7 | 0.9 |
| 50 | 0.8 | 1.8 |
| 51 | 0.8 | 1.8 |
| 52 | 0.2 | 0.8 |
| 53 | 1 | 0.9 |
| 54 | 0.7 | 1.8 |
| 55 | 1.3 | 1.2 |
| 56 | 0.3 | 1.8 |
| 57 | 0.4 | 1.8 |
| 58 | 0.5 | 1.8 |
| 59 | 1.4 | 1.8 |
| 60 | 0.2 | 1.7 |
| 61 | 1.1 | 1.7 |
| 62 | 0.2 | 1.7 |
| 63 | 0.3 | 1.7 |
| 64 | 0.7 | 1.7 |
| 65 | 5.5 | 1.7 |
| 66 | 3.7 | 1.7 |
| 67 | 5.7 | 1.7 |
| 68 | 0.7 | 12.1 |
| 69 | 0.3 | 8.6 |
| 70 | 0.2 | 2.3 |
| 71 | 2.8 | 1.3 |
| 72 | 2.2 | 1.1 |
| 73 | 4.4 | 1.1 |
| 74 | 5.4 | 1.7 |
| 75 | 0.2 | 4.1 |
| 76 | 0.3 | 1.0 |
| 77 | 6.0 | 1.1 |
| 78 | 0.7 | 11.5 |
| 79 | 0.4 | 9.2 |
| 80 | 8.4 | 33.3 |

TABLE 3

| Ex. No. | JAK3 $IC_{50}$ (nM) | BTK $IC_{50}$ (nM) |
|---|---|---|
| 81 | 3.8 | 25.5 |
| 82 | 0.3 | 0.9 |
| 83 | 1.2 | 3.4 |
| 84 | 3.8 | 6.6 |
| 85 | 1.5 | 2.2 |
| 86 | 0.4 | 1.0 |
| 87 | 16.4 | 42.2 |
| 88 | 0.2 | 1.1 |
| 89 | 0.138 | 0.864 |

TABLE 3-continued

| Ex. No. | JAK3 IC$_{50}$ (nM) | BTK IC$_{50}$ (nM) |
|---|---|---|
| 90 | 0.5 | 1.0 |
| 91 | 1.1 | 1.1 |
| 92 | 4.5 | 2.1 |
| 93 | 2.0 | 1.3 |
| 94 | 4.5 | 1.7 |
| 95 | 0.5 | 5.9 |
| 96 | 0.7 | 24.0 |
| 97 | >80 | 707.7 |
| 98 | 2.4 | 14.1 |
| 101 | 1.8 | 7.4 |
| 102 | 13.2 | 146.1 |
| 103 | 1.3 | 21.0 |
| 104 | 0.3 | 2.7 |
| 105 | 3.6 | 1.9 |
| 106 | 54.8 | 1.8 |
| 107 | 3.7 | 7.8 |
| 108 | 0.6 | 1.3 |
| 109 | 0.3 | 2.0 |
| 110 | 1.7 | 1.4 |
| 111 | 1.1 | 1.3 |
| 112 | 1.6 | 1.8 |
| 113 | 2.8 | 2.3 |
| 114 | 0.9 | 2.3 |
| 115 | 1.7 | 2.0 |
| 116 | 19.5 | 25.3 |
| 117 | >400 | 81.2 |
| 118 | 3.2 | 1.3 |
| 119 | 32.5 | 11.1 |
| 120 | 7.8 | 7.5 |
| 121 | 18.0 | 4.9 |
| 122 | 8.1 | 6.0 |

TABLE 4

| Ex. No. | JAK3 IC$_{50}$ (nM) | BTK IC$_{50}$ (nM) |
|---|---|---|
| 123 | 7.9 | 5.8 |
| 124 | 8.4 | 3.5 |
| 125 | 20.4 | 8.2 |
| 126 | 2.9 | 1.2 |
| 127 | 43.1 | 1.5 |
| 128 | 14.6 | 5.8 |
| 129 | 42.3 | 2.3 |
| 130 | 9.0 | 1.1 |
| 131 | 24.5 | 1.6 |
| 132 | 25.5 | 2.1 |
| 133 | 16 | 1.6 |
| 134 | 17.7 | 1.8 |
| 135 | 42.3 | 2.3 |
| 136 | 0.1 | 1.1 |
| 137 | 2.6 | 19.6 |
| 138 | >80 | 92.7 |
| 139 | >80 | 142.8 |
| 140 | >80 | 985.9 |
| 141 | 38.5 | 306.5 |
| 142 | 22.4 | 210.1 |
| 143 | 19.3 | 165.1 |
| 144 | 1.4 | 1.5 |
| 145 | 1.7 | 1.4 |
| 146 | 7.4 | 1.4 |
| 147 | 1.4 | 2.1 |
| 148 | 0.3 | 1.6 |
| 149 | 0.2 | 1.6 |
| 150 | 0.3 | 1.6 |
| 151 | 0.4 | 3.0 |
| 152 | 2.0 | 4.5 |
| 153 | 1.6 | 2.2 |
| 154 | 54.2 | 2.5 |
| 155 | 53.7 | 2.2 |
| 156 | 0.5 | 1.1 |
| 157 | 0.6 | 1.4 |
| 158 | 2.9 | 1.2 |
| 159 | 27.1 | 4.5 |
| 160 | 1.5 | 3.4 |

TABLE 4-continued

| Ex. No. | JAK3 IC$_{50}$ (nM) | BTK IC$_{50}$ (nM) |
|---|---|---|
| 161 | 5.0 | 1.3 |
| 162 | 3.0 | 4.8 |

TABLE 5

| Ex. No. | JAK3 IC$_{50}$ (nM) | BTK IC$_{50}$ (nM) |
|---|---|---|
| 163 | 2.7 | 1.2 |
| 164 | 8.8 | 2.2 |
| 165 | 2.2 | 1.9 |
| 166 | 5.6 | 1.2 |
| 167 | 43.1 | 1.5 |
| 168 | 18.0 | 4.3 |
| 169 | 240.9 | 2.2 |
| 170 | 11.4 | 2.9 |
| 171 | 0.9 | 2.2 |
| 172 | 0.9 | 1.6 |
| 173 | 1.0 | 6.0 |
| 174 | 0.7 | 2.0 |
| 175 | 14.9 | 1.4 |
| 176 | 42.1 | 3.0 |
| 177 | 0.4 | 1.2 |
| 178 | 0.5 | 0.9 |
| 179 | 1.1 | 8.3 |
| 180 | 1.5 | 3.1 |
| 181 | 30.2 | 2.2 |
| 182 | 2.3 | 2.1 |
| 183 | 0.8 | 1.6 |
| 184 | 4.4 | 1.4 |
| 185 | 15.1 | 2.1 |
| 186 | 18.0 | 1.6 |
| 187 | 14.6 | 1.8 |
| 188 | 23.5 | 2.9 |
| 189 | 3.4 | 0.721 |
| 190 | 2.0 | 0.760 |
| 191 | 4.2 | 0.760 |
| 192 | 3.0 | 0.726 |
| 193 | 0.5 | 0.9 |

What is claimed is:

1. A compound represented by the following Chemical Formula 1, or a pharmaceutically acceptable salt thereof:

[Chemical Formula 1]

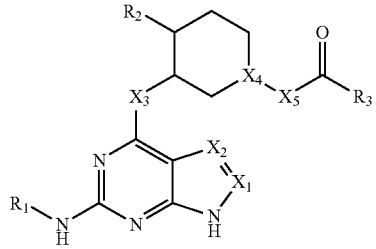

in Chemical Formula 1, $R_1$ is benzothiazolyl, isothiazolyl, isoxazolyl, phenyl, or pyrazolyl;
  wherein $R_1$ is unsubstituted, or substituted with a substituent selected from the group consisting of piperazinyl unsubstituted or substituted with $C_{1-4}$ alkyl; benzyl unsubstituted or substituted with $C_{1-4}$ alkoxy; one or two $C_{1-4}$ alkyl unsubstituted or substituted with morpholino, —N($C_{1-4}$ alkyl)$_2$, $C_{1-4}$ alkoxy, cyano, or —CONH($C_{1-4}$ alkyl); $C_{1-4}$ haloalkyl; $C_{3-6}$ cycloalkyl; morpholino; —CO-(molpolino); morpholino and halogen; —N(C$_{1-4}$ alkyl)$_2$; —NHCO(C$_{2-4}$ alkenyl); —NHCO(pyrrolidinyl); C$_{1-4}$ alkoxy unsubstituted or substituted with —N(C$_{1-4}$ alkyl)$_2$; C$_{6-10}$ aryloxy; pyrazolyl unsubstituted or substituted with one or two C$_{1-4}$ alkyl; pyrrolidinyl; tetrahydropyranyl; and halogen, R$_2$ is hydrogen, C$_{1-4}$ alkyl, or halogen;

R$_3$ is C$_{1-4}$ alkyl unsubstituted or substituted with cyano, or halogen; C$_{2-6}$ alkenyl unsubstituted or substituted with one or two substituents independently selected from the group consisting of cyano, C$_{3-6}$ cycloalkyl, and —N(C$_{1-4}$ alkyl)$_2$; or C$_{2-4}$ alkynyl unsubstituted or substituted with C$_{3-6}$ cycloalkyl, X$_1$ is CR$_4$ or N,
wherein R$_4$ is hydrogen, C$_{1-4}$ alkyl, or halogen, X$_2$ is CR$_5$,
wherein R$_5$ is hydrogen, C$_{1-4}$ alkyl, C$_{1-4}$ alkoxy, C$_{1-4}$ haloalkyl, halogen, cyano, or C$_{1-4}$ alkylthio, X$_3$ is NR$_6$, O, or S,
wherein R$_6$ is hydrogen or C$_{1-4}$ alkyl, X$_4$ is CH, or N, and X$_5$ is a bond, or NH.

2. The compound or a pharmaceutically acceptable salt thereof according to claim 1, wherein R$_1$ is
unsubstituted benzothiazolyl;
isothiazolyl substituted by C$_{1-4}$ alkyl;
isoxazolyl unsubstituted or substituted by C$_{1-4}$ alkyl;
pyrazolyl substituted by benzyl substituted by C$_{1-4}$ alkoxy, one or two C$_{1-4}$ alkyl unsubstituted or substituted by morpholino, —N(C$_{1-4}$ alkyl)$_2$, C$_{1-4}$ alkoxy, cyano, or —CONH(C$_{1-4}$ alkyl), C$_{1-4}$ haloalkyl, C$_{3-6}$ cycloalkyl, or tetrahydropyranyl; or
phenyl substituted by piperazinyl substituted by C$_{1-4}$ alkyl, morpholino, —CO-(morpholino), morpholino and halogen, —N(C$_{1-4}$ alkyl)$_2$, —NHCO(C$_{2-4}$ alkenyl), —NHCO(pyrrolidinyl), C$_{1-4}$ alkoxy substituted by —N(C$_{1-4}$ alkyl)$_2$, phenoxy, pyrazolyl unsubstituted or substituted by one or two C$_{1-4}$ alkyl, or pyrrolidinyl.

3. The compound or a pharmaceutically acceptable salt thereof according to claim 1, wherein R$_2$ is hydrogen, methyl, or fluoro.

4. The compound or a pharmaceutically acceptable salt thereof according to claim 1, wherein R$_3$ is —CH$_2$Cl, —CH$_2$CN, —CH=CH$_2$, —CH=CHCH$_3$, —C(CN)=CHCH(CH$_3$)$_2$, —C(CN)=CH(cyclopentyl), —C(CN)=CH(cyclopropyl), —C(CN)=CHC(CH$_3$)$_3$, —C(CN)=CHCH(CH$_3$)$_2$, —C≡CCH$_3$, —C≡CCH$_2$CH$_3$, or —C≡C-(cyclopropyl).

5. The compound or a pharmaceutically acceptable salt thereof according to claim 1, wherein X$_1$ is CH, or N.

6. The compound or a pharmaceutically acceptable salt thereof according to claim 1, wherein X$_2$ is CR$_5$, and R$_5$ is hydrogen, methyl, fluoro, chloro, cyano, or methylthio.

7. The compound or a pharmaceutically acceptable salt thereof according to claim 1, wherein X$_3$ is NH, N(CH$_3$), S, or O.

8. The compound or a pharmaceutically acceptable salt thereof according to claim 1,
wherein X$_4$ is N, and X$_5$ is a bond, or
X$_4$ is CH, and X$_5$ is NH.

9. The compound or a pharmaceutically acceptable salt thereof according to claim 1, wherein the compound represented by Chemical Formula 1 is represented by the following Chemical Formula 1-1:

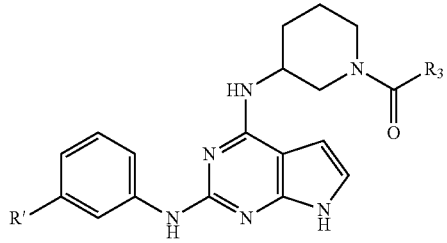

[Chemical Formula 1-1]

in Chemical Formula 1-1,
R' is —NHCO(C$_{2-4}$ alkenyl); —NHCO(pyrrolidinyl); or pyrazolyl unsubstituted or substituted with two C$_{1-4}$ alkyl,
R$_3$ is C$_{1-4}$ alkyl unsubstituted or substituted with cyano; or C$_{2-4}$ alkenyl unsubstituted or substituted with cyano or —N(C$_{1-4}$ alkyl).

10. The compound or a pharmaceutically acceptable salt thereof according to claim 1, wherein the compound represented by Chemical Formula 1 is represented by the following Chemical Formula 1-2:

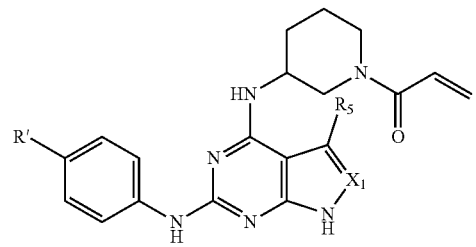

[Chemical Formula 1-2]

in Chemical Formula 1-2,
X$_1$ is CH, or N,
R' is piperazinyl unsubstituted or substituted with C$_{1-4}$ alkyl; morpholino; —CO-(molpolino); —N(C$_{1-4}$ alkyl)$_2$; C$_{1-4}$ alkoxy unsubstituted or substituted with —N(C$_{1-4}$ alkyl)$_2$; phenoxy; pyrazolyl unsubstituted or substituted with one or two C$_{1-4}$ alkyl; or pyrrolidinyl, and
R$_5$ is hydrogen or halogen.

11. The compound or a pharmaceutically acceptable salt thereof according to claim 1, wherein the compound represented by Chemical Formula 1 is represented by the following Chemical Formula 1-3:

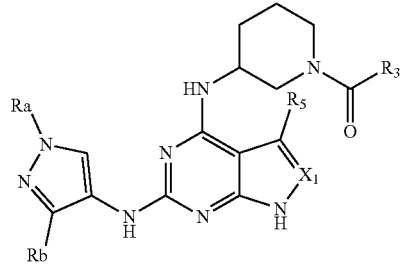

[Chemical Formula 1-3]

in Chemical Formula 1-3,
X$_1$ is CH, or N,
Ra is benzyl unsubstituted or substituted with C$_{1-4}$ alkoxy; C$_{1-4}$ alkyl unsubstituted or substituted with morpholino, —N(C$_{1-4}$ alkyl)$_2$, C$_{1-4}$ alkoxy, cyano, or —CONH(C$_{1-4}$ alkyl); C$_{1-4}$ haloalkyl; C$_{3-6}$ cycloalkyl; or tetrahydropyranyl, Rb is hydrogen or C$_{1-4}$ alkyl, R$_3$ is C$_{2-4}$ alkenyl unsubstituted or substituted with cyano or —N(C$_{1-4}$ alkyl)$_2$; or C$_{2-4}$ alkynyl, and R$_5$ is hydrogen or halogen.

12. A compound or a pharmaceutically acceptable salt thereof wherein the compound is selected from the group consisting of:

1) (R)-1-(3-(2-(4-(4-methylpiperazin-1-yl)phenylamino)-7H-pyrrolo[2,3-d]pyrimidin-4-ylamino)piperidin-1-yl)prop-2-en-1-one,
2) (R)—N-(3-(4-(1-acryloylpiperidin-3-ylamino)-7H-pyrrolo[2,3-d]pyrimidin-2-ylamino)phenyl)pyrrolidine-1-carboxamide,
3) (S)—N-(3-(4-(1-acryloylpiperidin-3-ylamino)-7H-pyrrolo[2,3-d]pyrimidin-2-ylamino)phenyl)pyrrolidine-1-carboxamide,
4) (R)-1-(3-(2-(4-morpholinophenylamino)-7H-pyrrolo[2,3-d]pyrimidin-4-ylamino)piperidin-1-yl)prop-2-en-1-one,
5) (R)-1-(3-(2-(4-(pyrrolidin-1-yl)phenylamino)-7H-pyrrolo[2,3-d]pyrimidin-4-ylamino)piperidin-1-yl)prop-2-en-1-one,
6) (R)-1-(3-(2-(4-(3,5-dimethyl-1H-pyrazol-1-yl)phenylamino)-7H-pyrrolo[2,3-d]pyrimidin-4-ylamino)piperidin-1-yl)prop-2-en-1-one,
7) (R)-1-(3-(2-(4-(2-(diethylamino)ethoxy)phenylamino)-7H-pyrrolo[2,3-d]pyrimidin-4-ylamino)piperidin-1-yl)prop-2-en-1-one,
8) (R)-1-(3-(2-(4-(morpholine-4-carbonyl)phenylamino)-7H-pyrrolo[2,3-d]pyrimidin-4-ylamino)piperidin-1-yl)prop-2-en-1-one,
9) (R)-1-(3-(2-(4-(dimethylamino)phenylamino)-7H-pyrrolo[2,3-d]pyrimidin-4-ylamino)piperidin-1-yl)prop-2-en-1-one,
10) (R)-1-(3-(2-(3-(3,5-dimethyl-1H-pyrazol-1-yl)phenylamino)-7H-pyrrolo[2,3-d]pyrimidin-4-ylamino)piperidin-1-yl)prop-2-en-1-one,
11) (S)-1-(3-(2-(4-(4-methylpiperazin-1-yl)phenylamino)-7H-pyrrolo[2,3-d]pyrimidin-4-ylamino)piperidin-1-yl)prop-2-en-1-one,
12) (R)-1-(3-(2-(benzo[d]thiazol-6-ylamino)-7H-pyrrolo[2,3-d]pyrimidin-4-ylamino)piperidin-1-yl)prop-2-en-1-one,
13) (R)-1-(3-(2-(4-phenoxyphenylamino)-7H-pyrrolo[2,3-d]pyrimidin-4-ylamino)piperidin-1-yl)prop-2-en-1-one,
14) (R)-1-(3-(2-(1-methyl-1H-pyrazol-4-ylamino)-7H-pyrrolo[2,3-d]pyrimidin-4-ylamino)piperidin-1-yl)prop-2-en-1-one,
15) (R)-1-(3-(2-(1-(2,2-difluoroethyl)-1H-pyrazol-4-ylamino)-7H-pyrrolo[2,3-d]pyrimidin-4-ylamino)piperidin-1-yl)prop-2-en-1-one,
16) (R)-1-(3-(2-(1-(difluoromethyl)-1H-pyrazol-4-ylamino)-7H-pyrrolo[2,3-d]pyrimidin-4-ylamino)piperidin-1-yl)prop-2-en-1-one,
17) (R)-1-(3-(2-(1-(2-methoxyethyl)-1H-pyrazol-4-ylamino)-7H-pyrrolo[2,3-d]pyrimidin-4-ylamino)piperidin-1-yl)prop-2-en-1-one,
18) (R)-1-(3-(2-(1-(2-morpholinoethyl)-1H-pyrazol-4-ylamino)-7H-pyrrolo[2,3-d]pyrimidin-4-ylamino)piperidin-1-yl)prop-2-en-1-one,
19) (R)-1-(3-(2-(1-(2-(diethylamino)ethyl)-1H-pyrazol-4-ylamino)-7H-pyrrolo[2,3-d]pyrimidin-4-ylamino)piperidin-1-yl)prop-2-en-1-one,
20) (R)-1-(3-(2-(1-(3-methoxybenzyl)-1H-pyrazol-4-ylamino)-7H-pyrrolo[2,3-d]pyrimidin-4-ylamino)piperidin-1-yl)prop-2-en-1-one,
21) (R)-1-(3-(2-(1-ethyl-1H-pyrazol-4-ylamino)-7H-pyrrolo[2,3-d]pyrimidin-4-ylamino)piperidin-1-yl)prop-2-en-1-one,
22) (R)-1-(3-(2-(1,3-dimethyl-1H-pyrazol-4-ylamino)-7H-pyrrolo[2,3-d]pyrimidin-4-ylamino)piperidin-1-yl)prop-2-en-1-one,
23) (R)-1-(3-(2-(isoxazol-4-ylamino)-7H-pyrrolo[2,3-d]pyrimidin-4-ylamino)piperidin-1-yl)prop-2-en-1-one,
24) (R)-2-(4-(4-(1-acryloylpiperidin-3-ylamino)-7H-pyrrolo[2,3-d]pyrimidin-2-ylamino)-1H-pyrazol-1-yl)-N-methylacetamide,
25) (R)-1-(3-(2-(1-(2,2-difluoroethyl)-1H-pyrazol-4-ylamino)-7H-pyrrolo[2,3-d]pyrimidin-4-ylamino)piperidin-1-yl)but-2-yn-1-one,
26) (R)—N-(3-(4-(1-(2-cyanoacetyl)piperidin-3-ylamino)-7H-pyrrolo[2,3-d]pyrimidin-2-ylamino)phenyl)acrylamide,
27) 1-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)prop-2-en-1-one,
28) 3-((3R,4R)-4-methyl-3-(methyl(2-(4-(4-methylpiperazin-1-yl)phenylamino)-7H-pyrrolo[2,3-d]pyrimidin-4-yl)amino)piperidin-1-yl)-3-oxopropanenitrile,
29) N-(3-(2-(4-(4-methylpiperazin-1-yl)phenylamino)-7H-pyrrolo[2,3-d]pyrimidin-4-ylamino)cyclohexyl)acrylamide,
30) (R)-1-(3-(6-(4-(4-methylpiperazin-1-yl)phenylamino)-1H-pyrazolo[3,4-d]pyrimidin-4-ylamino)piperidin-1-yl)prop-2-en-1-one,
31) (R)-1-(3-(6-(1-(2,2-difluoroethyl)-1H-pyrazol-4-ylamino)-1H-pyrazolo[3,4-d]pyrimidin-4-ylamino)piperidin-1-yl)prop-2-en-1-one,
32) (R)-1-(3-(6-(1-methyl-H-pyrazol-4-ylamino)-1H-pyrazolo[3,4-d]pyrimidin-4-ylamino)piperidin-1-yl)prop-2-en-1-one,
33) (R)-1-(3-(6-(1-ethyl-1H-pyrazol-4-ylamino)-1H-pyrazolo[3,4-d]pyrimidin-4-ylamino)piperidin-1-yl)prop-2-en-1-one,
34) (R)-1-(3-(6-(1-(difluoromethyl)-1H-pyrazol-4-ylamino)-1H-pyrazolo[3,4-d]pyrimidin-4-ylamino)piperidin-1-yl)prop-2-en-1-one,
35) (R)-2-(4-(4-(1-acryloylpiperidin-3-ylamino)-1H-pyrazolo[3,4-d]pyrimidin-6-ylamino)-1H-pyrazol-1-yl)-N-methylacetamide,
36) (R)-1-(3-(5-chloro-2-(4-(4-methylpiperazin-1-yl)phenylamino)-7H-pyrrolo[2,3-d]pyrimidin-4-ylamino)piperidin-1-yl)prop-2-en-1-one,
37) (R)-1-(3-(5-chloro-2-(1-ethyl-1H-pyrazol-4-ylamino)-7H-pyrrolo[2,3-d]pyrimidin-4-ylamino)piperidin-1-yl)prop-2-en-1-one,
38) (R)-1-(3-(5-chloro-2-(1-(difluoromethyl)-1H-pyrazol-4-ylamino)-7H-pyrrolo[2,3-d]pyrimidin-4-ylamino)piperidin-1-yl)prop-2-en-1-one,
39) (R)-1-(3-(5-chloro-2-(1-(2,2-difluoroethyl)-1H-pyrazol-4-ylamino)-7H-pyrrolo[2,3-d]pyrimidin-4-ylamino)piperidin-1-yl)prop-2-en-1-one,
40) (R)-1-(3-(5-chloro-2-(1-(2-morpholinoethyl)-1H-pyrazol-4-ylamino)-7H-pyrrolo[2,3-d]pyrimidin-4-ylamino)piperidin-1-yl)prop-2-en-1-one,
41) (R)-1-(3-(5-chloro-2-(1-(3-methoxybenzyl)-1H-pyrazol-4-ylamino)-7H-pyrrolo[2,3-d]pyrimidin-4-ylamino)piperidin-1-yl)prop-2-en-1-one,
42) (R)-1-(3-(3-chloro-6-(4-(4-methylpiperazin-1-yl)phenylamino)-1H-pyrazolo[3,4-d]pyrimidin-4-ylamino)piperidin-1-yl)prop-2-en-1-one,
43) (R)-1-(3-(3-chloro-6-(4-(3,5-dimethyl-1H-pyrazol-1-yl)phenylamino)-1H-pyrazolo[3,4-d]pyrimidin-4-ylamino)piperidin-1-yl)prop-2-en-1-one, 44) (R)-1-(3-(3-chloro-6-(1-(2,2-difluoroethyl)-1H-pyrazol-4-ylamino)-1H-pyrazolo[3,4-d]pyrimidin-4-ylamino)piperidin-1-yl)prop-2-en-1-one,
45) (R)-1-(3-(3-chloro-6-(1-methyl-1H-pyrazol-4-ylamino)-1H-pyrazolo[3,4-d]pyrimidin-4-ylamino)piperidin-1-yl)prop-2-en-1-one,
46) (R)-1-(3-(3-chloro-6-(1-ethyl-1H-pyrazol-4-ylamino)-1H-pyrazolo[3,4-d]pyrimidin-4-ylamino)piperidin-1-yl)prop-2-en-1-one,
47) (R)-2-(4-(4-(1-acryloylpiperidin-3-ylamino)-3-chloro-1H-pyrazolo[3,4-d]pyrimidin-6-ylamino)-1H-pyrazol-1-yl)-N-methylacetamide,
48) (R)-1-(3-(3-chloro-6-(1-(tetrahydro-2H-pyran-4-yl)-1H-pyrazol-4-ylamino)-1H-pyrazolo[3,4-d]pyrimidin-4-ylamino)piperidin-1-yl)prop-2-en-1-one,
49) (R)-1-(3-(3-chloro-6-(1-cyclopropyl-1H-pyrazol-4-ylamino)-1H-pyrazolo[3,4-d]pyrimidin-4-ylamino)piperidin-1-yl)prop-2-en-1-one,
50) (R)-1-(3-(3-chloro-6-(1-isopropyl-1H-pyrazol-4-ylamino)-1H-pyrazolo[3,4-d]pyrimidin-4-ylamino)piperidin-1-yl)prop-2-en-1-one,
51) (R)-1-(3-(3-chloro-6-(1-propyl-1H-pyrazol-4-ylamino)-1H-pyrazolo[3,4-d]pyrimidin-4-ylamino)piperidin-1-yl)prop-2-en-1-one,
52) (R)-2-(4-(4-(1-acryloylpiperidin-3-ylamino)-3-chloro-1H-pyrazolo[3,4-d]pyrimidin-6-ylamino)-1H-pyrazol-1-yl)acetonitrile,
53) (R)-1-(3-(6-(1-tert-butyl-1H-pyrazol-4-ylamino)-3-chloro-1H-pyrazolo[3,4-d]pyrimidin-4-ylamino)piperidin-1-yl)prop-2-en-1-one,
54) (R)-1-(3-(3-chloro-6-(1-(2-morpholinoethyl)-1H-pyrazol-4-ylamino)-1H-pyrazolo[3,4-d]pyrimidin-4-ylamino)piperidin-1-yl)prop-2-en-1-one,
55) (R)-1-(3-(3-chloro-6-(1-isobutyl-1H-pyrazol-4-ylamino)-1H-pyrazolo[3,4-d]pyrimidin-4-ylamino)piperidin-1-yl)prop-2-en-1-one,
56) (R)-1-(3-(3-chloro-6-(1-(2,2,2-trifluoroethyl)-1H-pyrazol-4-ylamino)-1H-pyrazolo[3,4-d]pyrimidin-4-ylamino)piperidin-1-yl)prop-2-en-1-one,
57) (R)-1-(3-(3-chloro-6-(1-(2-(diethylamino)ethyl)-1H-pyrazol-4-ylamino)-1H-pyrazolo[3,4-d]pyrimidin-4-ylamino)piperidin-1-yl)prop-2-en-1-one,
58) (R)-1-(3-(3-chloro-6-(1-(3-methoxybenzyl)-1H-pyrazol-4-ylamino)-1H-pyrazolo[3,4-d]pyrimidin-4-ylamino)piperidin-1-yl)prop-2-en-1-one,
59) (R)-1-(3-(3-chloro-6-(isoxazol-4-ylamino)-1H-pyrazolo[3,4-d]pyrimidin-4-ylamino)piperidin-1-yl)prop-2-en-1-one,
60) (R)-2-(4-((4-((1-acryloylpiperidin-3-yl)amino)-5-chloro-7H-pyrrolo[2,3-d]pyrimidin-2-yl)amino)-1H-pyrazol-1-yl)-N-methylacetamide,
61) (R)-1-(3-((5-chloro-2-((4-morpholinophenyl)amino)-7H-pyrrolo[2,3-d]pyrimidin-4-yl)amino)piperidin-1-yl)prop-2-en-1-one,
62) (R)-1-(3-((5-chloro-2-((1-cyclopropyl-1H-pyrazol-4-yl)amino)-7H-pyrrolo[2,3-d]pyrimidin-4-yl)amino)piperidin-1-yl)prop-2-en-1-one,
63) (R)-1-(3-((5-chloro-2-((1-isobutyl-1H-pyrazol-4-yl)amino)-7H-pyrrolo[2,3-d]pyrimidin-4-yl)amino)piperidin-1-yl)prop-2-en-1-one,
64) (R)-1-(3-((3-chloro-6-((1-(difluoromethyl)-1H-pyrazol-4-yl)amino)-1H-pyrazolo[3,4-d]pyrimidin-4-yl)amino)piperidin-1-yl)prop-2-en-1-one,
65) (R)-1-(3-((6-((1-isobutyl-1H-pyrazol-4-yl)amino)-1H-pyrazolo[3,4-d]pyrimidin-4-yl)amino)piperidin-1-yl)prop-2-en-1-one,
66) (R)-1-(3-((6-((1-(tert-butyl)-1H-pyrazol-4-yl)amino)-1H-pyrazolo[3,4-d]pyrimidin-4-yl)amino)piperidin-1-yl)prop-2-en-1-one,
67) (R)-1-(3-((6-((1-cyclopropyl-1H-pyrazol-4-yl)amino)-1H-pyrazolo[3,4-d]pyrimidin-4-yl)amino)piperidin-1-yl)prop-2-en-1-one,
68) (R)-1-(3-((5-chloro-2-((4-(morpholine-4-carbonyl)phenyl)amino)-7H-pyrrolo[2,3-d]pyrimidin-4-yl)amino)piperidin-1-yl)prop-2-en-1-one,
69) (R)-1-(3-((5-chloro-2-((1-methyl-1H-pyrazol-4-yl)amino)-7H-pyrrolo[2,3-d]pyrimidin-4-yl)amino)piperidin-1-yl)prop-2-en-1-one,
70) (R)-1-(3-((2-((1-(tert-butyl)-1H-pyrazol-4-yl)amino)-5-chloro-7H-pyrrolo[2,3-d]pyrimidin-4-yl)amino)piperidin-1-yl)prop-2-en-1-one,
71) (R)-1-(3-((6-((1-(tetrahydro-2H-pyran-4-yl)-1H-pyrazol-4-yl)amino)-1H-pyrazolo[3,4-d]pyrimidin-4-yl)amino)piperidin-1-yl)prop-2-en-1-one,
72) (R)-1-(3-((6-((1-(2-morpholinoethyl)-1H-pyrazol-4-yl)amino)-1H-pyrazolo[3,4-d]pyrimidin-4-yl)amino)piperidin-1-yl)prop-2-en-1-one,
73) (R)-1-(3-((6-((1-propyl-1H-pyrazol-4-yl)amino)-1H-pyrazolo[3,4-d]pyrimidin-4-yl)amino)piperidin-1-yl)prop-2-en-1-one,
74) (R)-1-(3-((6-((1-(2-methoxyethyl)-1H-pyrazol-4-yl)amino)-1H-pyrazolo[3,4-d]pyrimidin-4-yl)amino)piperidin-1-yl)prop-2-en-1-one,
75) (R)-1-(3-((2-((3-methylisothiazol-5-yl)amino)-7H-pyrrolo[2,3-d]pyrimidin-4-yl)amino)piperidin-1-yl)prop-2-en-1-one,
76) 1-((3S,4R)-3-((2-((1-ethyl-1H-pyrazol-4-yl)amino)-7H-pyrrolo[2,3-d]pyrimidin-4-yl)amino)-4-fluoropiperidin-1-yl)prop-2-en-1-one,
77) 1-((3S,4R)-3-((6-((1-ethyl-1H-pyrazol-4-yl)amino)-1H-pyrazolo[3,4-d]pyrimidin-4-yl)amino)-4-fluoropiperidin-1-yl)prop-2-en-1-one,
78) (R)-1-(3-((2-((1-cyclopropyl-1H-pyrazol-4-yl)amino)-5-methyl-7H-pyrrolo[2,3-d]pyrimidin-4-yl)amino)piperidin-1-yl)prop-2-en-1-one,
79) (R)-1-(3-((2-((1-ethyl-1H-pyrazol-4-yl)amino)-5-methyl-7H-pyrrolo[2,3-d]pyrimidin-4-yl)amino)piperidin-1-yl)prop-2-en-1-one,
80) (R)-1-(3-((2-((4-(3,5-dimethyl-1H-pyrazol-1-yl)phenyl)amino)-5-methyl-7H-pyrrolo[2,3-d]pyrimidin-4-yl)amino)piperidin-1-yl)prop-2-en-1-one,
81) (R)-1-(3-((2-(benzo[d]thiazol-6-ylamino)-5-methyl-7H-pyrrolo[2,3-d]pyrimidin-4-yl)amino)piperidin-1-yl)prop-2-en-1-one,
82) (R)-1-(3-((2-((1-ethyl-1H-pyrazol-4-yl)amino)-5-fluoro-7H-pyrrolo[2,3-d]pyrimidin-4-yl)amino)piperidin-1-yl)prop-2-en-1-one,
83) (R)-1-(3-((5-fluoro-2-((3-methylisothiazol-5-yl)amino)-7H-pyrrolo[2,3-d]pyrimidin-4-yl)amino)piperidin-1-yl)prop-2-en-1-one,
84) 1-((3R,4R)-3-((2-((1-ethyl-1H-pyrazol-4-yl)amino)-5-fluoro-7H-pyrrolo[2,3-d]pyrimidin-4-yl)amino)-4-methylpiperidin-1-yl)prop-2-en-1-one,
85) (R)-1-(3-((2-((1-ethyl-1H-pyrazol-4-yl)amino)-5-fluoro-7H-pyrrolo[2,3-d]pyrimidin-4-yl)thio)piperidin-1-yl)prop-2-en-1-one,
86) 1-((3S,4R)-3-((2-((1-ethyl-1H-pyrazol-4-yl)amino)-5-fluoro-7H-pyrrolo[2,3-d]pyrimidin-4-yl)amino)-4-fluoropiperidin-1-yl)prop-2-en-1-one,
87) (R)-1-(3-((2-((1-ethyl-1H-pyrazol-4-yl)amino)-5-fluoro-7H-pyrrolo[2,3-d]pyrimidin-4-yl)(methyl)amino)piperidin-1-yl)prop-2-en-1-one,
88) (R)-4-((1-acryloylpiperidin-3-yl)amino)-2-((1-ethyl-1H-pyrazol-4-yl)amino)-7H-pyrrolo[2,3-d]pyrimidine-5-carbonitrile,
89) (R)-4-((1-acryloylpiperidin-3-yl)amino)-2-((1-cyclopropyl-1H-pyrazol-4-yl)amino)-7H-pyrrolo[2,3-d]pyrimidine-5-carbonitrile, 90) (R)-1-(3-((3-chloro-6-((1-(2,2-difluoroethyl)-1H-pyrazol-4-yl)amino)-1H-pyrazolo[3,4-d]pyrimidin-4-yl)amino)piperidin-1-yl)prop-2-en-1-one,
91) (R)-1-(3-((3-chloro-6-((1-ethyl-1H-pyrazol-4-yl)amino)-1H-pyrazolo[3,4-d]pyrimidin-4-yl)amino)piperidin-1-yl)prop-2-en-1-one,
92) 1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)prop-2-en-1-one,
93) 1-((3R,4R)-3-((3-chloro-6-((1-(2,2-difluoroethyl)-1H-pyrazol-4-yl)amino)-1H-pyrazolo[3,4-d]pyrimidin-4-yl)amino)-4-methylpiperidin-1-yl)prop-2-en-1-one,
94) 1-((3R,4R)-3-((3-chloro-6-((1-cyclopropyl-1H-pyrazol-4-yl)amino)-1H-pyrazolo[3,4-d]pyrimidin-4-yl)amino)-4-methylpiperidin-1-yl)prop-2-en-1-one,
95) (R)-1-(3-((5-chloro-2-((1-(2-(diethylamino)ethyl)-1H-pyrazol-4-yl)amino)-7H-pyrrolo[2,3-d]pyrimidin-4-yl)amino)piperidin-1-yl)prop-2-en-1-one,
96) (R)-1-(3-((5-chloro-2-(isoxazol-4-ylamino)-7H-pyrrolo[2,3-d]pyrimidin-4-yl)amino)piperidin-1-yl)prop-2-en-1-one,
97) (R)-1-(3-((5-chloro-2-((2-fluoro-4-morpholinophenyl)amino)-7H-pyrrolo[2,3-d]pyrimidin-4-yl)amino)piperidin-1-yl)prop-2-en-1-one,
98) (R)-1-(3-((5-chloro-2-((3-fluoro-4-morpholinophenyl)amino)-7H-pyrrolo[2,3-d]pyrimidin-4-yl)amino)piperidin-1-yl)prop-2-en-1-one,
99) (R)-1-(3-((5-chloro-2-((5-methylisoxazol-4-yl)amino)-7H-pyrrolo[2,3-d]pyrimidin-4-yl)amino)piperidin-1-yl)prop-2-en-1-one,
100) (R)-1-(3-((5-chloro-2-((1-ethyl-1H-pyrazol-4-yl)amino)-7H-pyrrolo[2,3-d]pyrimidin-4-yl)(methyl)amino)piperidin-1-yl)prop-2-en-1-one,
101) (R)-1-(3-((2-((1-ethyl-1H-pyrazol-4-yl)amino)-7H-pyrrolo[2,3-d]pyrimidin-4-yl)(methyl)amino)piperidin-1-yl)prop-2-en-1-one,
102) (R)-1-(3-((2-(isoxazol-4-ylamino)-7H-pyrrolo[2,3-d]pyrimidin-4-yl)(methyl)amino)piperidin-1-yl)prop-2-en-1-one,
103) (R)-1-(3-((2-((1-(2,2-difluoroethyl)-1H-pyrazol-4-yl)amino)-7H-pyrrolo[2,3-d]pyrimidin-4-yl)(methyl)amino)piperidin-1-yl)prop-2-en-1-one,
104) (R)-1-(3-((2-((1-ethyl-1H-pyrazol-4-yl)amino)-7H-pyrrolo[2,3-d]pyrimidin-4-yl)thio)piperidin-1-yl)prop-2-en-1-one,
105) (R)-1-(3-((6-((1-ethyl-1H-pyrazol-4-yl)amino)-1H-pyrazolo[3,4-d]pyrimidin-4-yl)thio)piperidin-1-yl)prop-2-en-1-one,
106) 1-((3R,4R)-3-((6-((1-ethyl-1H-pyrazol-4-yl)amino)-1H-pyrazolo[3,4-d]pyrimidin-4-yl)amino)-4-methylpiperidin-1-yl)prop-2-en-1-one,
107) 1-((3R,4R)-3-((2-((1-ethyl-1H-pyrazol-4-yl)amino)-7H-pyrrolo[2,3-d]pyrimidin-4-yl)amino)-4-methylpiperidin-1-yl)prop-2-en-1-one,
108) (R)-1-(3-((3-chloro-6-((1-(2,2-difluoroethyl)-1H-pyrazol-4-yl)amino)-1H-pyrazolo[3,4-d]pyrimidin-4-yl)thio)piperidin-1-yl)prop-2-en-1-one,
109) (R)-1-(3-((5-chloro-2-((1-ethyl-1H-pyrazol-4-yl)amino)-7H-pyrrolo[2,3-d]pyrimidin-4-yl)thio)piperidin-1-yl)prop-2-en-1-one,
110) (R)-1-(3-((3-chloro-6-((1-cyclopropyl-1H-pyrazol-4-yl)amino)-1H-pyrazolo[3,4-d]pyrimidin-4-yl)thio)piperidin-1-yl)prop-2-en-1-one,
111) (R)-1-(3-((3-chloro-6-((1-ethyl-1H-pyrazol-4-yl)amino)-1H-pyrazolo[3,4-d]pyrimidin-4-yl)thio)piperidin-1-yl)prop-2-en-1-one,
112) (R)-1-(3-((6-((1-(tert-butyl)-1H-pyrazol-4-yl)amino)-3-chloro-1H-pyrazolo[3,4-d]pyrimidin-4-yl)thio)piperidin-1-yl)prop-2-en-1-one,
113) (R)-1-(3-((3-chloro-6-((1-isobutyl-1H-pyrazol-4-yl)amino)-1H-pyrazolo[3,4-d]pyrimidin-4-yl)thio)piperidin-1-yl)prop-2-en-1-one,
114) (R)-1-(3-((3-chloro-6-((1-(2,2,2-trifluoroethyl)-1H-pyrazol-4-yl)amino)-1H-pyrazolo[3,4-d]pyrimidin-4-yl)thio)piperidin-1-yl)prop-2-en-1-one,
115) (R)-1-(3-((3-chloro-6-((1-propyl-1H-pyrazol-4-yl)amino)-1H-pyrazolo[3,4-d]pyrimidin-4-yl)thio)piperidin-1-yl)prop-2-en-1-one,
116) (R)-1-(3-((3-chloro-6-(isoxazol-4-ylamino)-1H-pyrazolo[3,4-d]pyrimidin-4-yl)thio)piperidin-1-yl)prop-2-en-1-one,
117) (R)-1-(3-(3-chloro-6-(5-methylisoxazol-4-ylamino)-1H-pyrazolo[3,4-d]pyrimidin-4-ylamino)piperidin-1-yl)prop-2-en-1-one,
118) (R)-1-(3-((3-chloro-6-((1-ethyl-1H-pyrazol-4-yl)amino)-1H-pyrazolo[3,4-d]pyrimidin-4-yl)(methyl)amino)piperidin-1-yl)prop-2-en-1-one,
119) (R)-1-(3-((3-chloro-6-(isoxazol-4-ylamino)-1H-pyrazolo[3,4-d]pyrimidin-4-yl)(methyl)amino)piperidin-1-yl)prop-2-en-1-one,
120) 1-((3R,4R)-3-((3-chloro-6-((1-(2,2,2-trifluoroethyl)-1H-pyrazol-4-yl)amino)-1H-pyrazolo[3,4-d]pyrimidin-4-yl)amino)-4-methylpiperidin-1-yl)prop-2-en-1-one,
121) 1-((3R,4R)-3-((3-chloro-6-((1-propyl-1H-pyrazol-4-yl)amino)-1H-pyrazolo[3,4-d]pyrimidin-4-yl)amino)-4-methylpiperidin-1-yl)prop-2-en-1-one,
122) 1-((3R,4R)-3-((3-chloro-6-((1-(2-(diethylamino)ethyl)-1H-pyrazol-4-yl)amino)-1H-pyrazolo[3,4-d]pyrimidin-4-yl)amino)-4-methylpiperidin-1-yl)prop-2-en-1-one,
123) 1-((3R,4R)-3-((3-chloro-6-((1-(2-morpholinoethyl)-1H-pyrazol-4-yl)amino)-1H-pyrazolo[3,4-d]pyrimidin-4-yl)amino)-4-methylpiperidin-1-yl)prop-2-en-1-one,
124) 1-((3R,4R)-3-((3-chloro-6-((1-isobutyl-1H-pyrazol-4-yl)amino)-1H-pyrazolo[3,4-d]pyrimidin-4-yl)amino)-4-methylpiperidin-1-yl)prop-2-en-1-one,
125) 1-((3R,4R)-3-((3-chloro-6-((1-(3-methoxybenzyl)-1H-pyrazol-4-yl)amino)-1H-pyrazolo[3,4-d]pyrimidin-4-yl)amino)-4-methylpiperidin-1-yl)prop-2-en-1-one,
126) 2-(4-(((3R,4R)-1-acryloyl-4-methylpiperidin-3-yl)amino)-3-chloro-1H-pyrazolo[3,4-d]pyrimidin-6-yl)amino)-1H-pyrazol-1-yl)acetonitrile,
127) 1-((3R,4R)-3-((3-chloro-6-((1-(difluoromethyl)-1H-pyrazol-4-yl)amino)-1H-pyrazolo[3,4-d]pyrimidin-4-yl)amino)-4-methylpiperidin-1-yl)prop-2-en-1-one,
128) 1-((3R,4R)-3-((3-chloro-6-((1-methyl-1H-pyrazol-4-yl)amino)-1H-pyrazolo[3,4-d]pyrimidin-4-yl)amino)-4-methylpiperidin-1-yl)prop-2-en-1-one,
129) (R)-1-(3-((6-((1-cyclopropyl-1H-pyrazol-4-yl)amino)-3-(methylthio)-1H-pyrazolo[3,4-d]pyrimidin-4-yl)amino)piperidin-1-yl)prop-2-en-1-one,
130) (R)-1-(3-((6-(isoxazol-4-ylamino)-3-(methylthio)-1H-pyrazolo[3,4-d]pyrimidin-4-yl)amino)piperidin-1-yl)prop-2-en-1-one,
131) (R)-1-(3-((6-((1-ethyl-1H-pyrazol-4-yl)amino)-3-(methylthio)-1H-pyrazolo[3,4-d]pyrimidin-4-yl)(methyl)amino)piperidin-1-yl)prop-2-en-1-one,
132) 1-((3R,4R)-3-((6-((1-ethyl-1H-pyrazol-4-yl)amino)-3-(methylthio)-1H-pyrazolo[3,4-d]pyrimidin-4-yl)amino)-4-methylpiperidin-1-yl)prop-2-en-1-one,
133) 1-((3R,4R)-3-((6-((1-(2,2-difluoroethyl)-1H-pyrazol-4-yl)amino)-3-(methylthio)-1H-pyrazolo[3,4-d]pyrimidin-4-yl)amino)-4-methylpiperidin-1-yl)prop-2-en-1-one, 134) 2-(4-(((3R,4R)-1-acryloyl-4-methylpiperidin-3-yl)amino)-3-(methylthio)-1H-pyrazolo[3,4-d]pyrimidin-6-yl)amino)-1H-pyrazol-1-yl)acetonitrile,
135) 1-((3R,4R)-3-((6-((1-cyclopropyl-1H-pyrazol-4-yl)amino)-3-(methylthio)-1H-pyrazolo[3,4-d]pyrimidin-4-yl)amino)-4-methylpiperidin-1-yl)prop-2-en-1-one,
136) (R)-1-(3-((5-chloro-2-((3-methylisothiazol-5-yl)amino)-7H-pyrrolo[2,3-d]pyrimidin-4-yl)amino)piperidin-1-yl)prop-2-en-1-one,
137) (R)-1-(3-((5-chloro-2-(pyridin-3-ylamino)-7H-pyrrolo[2,3-d]pyrimidin-4-yl)amino)piperidin-1-yl)prop-2-en-1-one,
138) 3-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)-3-oxopropanenitrile,
139) (R)-3-(3-((3-chloro-6-((1-cyclopropyl-1H-pyrazol-4-yl)amino)-1H-pyrazolo[3,4-d]pyrimidin-4-yl)amino)piperidin-1-yl)-3-oxopropanenitrile,
140) (R,E)-1-(3-((5-chloro-2-((4-(4-methylpiperazin-1-yl)phenyl)amino)-7H-pyrrolo[2,3-d]pyrimidin-4-yl)amino)piperidin-1-yl)but-2-en-1-one,
141) 1-((R)-3-((5-chloro-2-((4-(4-methylpiperazin-1-yl)phenyl)amino)-7H-pyrrolo[2,3-d]pyrimidin-4-yl)amino)piperidin-1-yl)-3-cyclopropylprop-2-yn-1-ol,
142) 1-((R)-3-((5-chloro-2-((4-(4-methylpiperazin-1-yl)phenyl)amino)-7H-pyrrolo[2,3-d]pyrimidin-4-yl)amino)piperidin-1-yl)pent-2-yn-1-ol,
143) 1-((R)-3-((5-chloro-2-((4-(4-methylpiperazin-1-yl)phenyl)amino)-7H-pyrrolo[2,3-d]pyrimidin-4-yl)amino)piperidin-1-yl)but-2-yn-1-ol,
144) (R)-1-(3-((6-((1-(2,2,2-trifluoroethyl)-1H-pyrazol-4-yl)amino)-1H-pyrazolo[3,4-d]pyrimidin-4-yl)amino)piperidin-1-yl)prop-2-en-1-one,
145) (R)-1-(3-((6-((1-(2-(diethylamino)ethyl)-1H-pyrazol-4-yl)amino)-1H-pyrazolo[3,4-d]pyrimidin-4-yl)amino)piperidin-1-yl)prop-2-en-1-one,
146) (R)-1-(3-((6-(isoxazol-4-ylamino)-1H-pyrazolo[3,4-d]pyrimidin-4-yl)amino)piperidin-1-yl)prop-2-en-1-one,
147) (R)-1-(3-((3-chloro-6-((1-ethyl-1H-pyrazol-4-yl)amino)-1H-pyrazolo[3,4-d]pyrimidin-4-yl)oxy)piperidin-1-yl)prop-2-en-1-one,
148) (R)-4-((1-acryloylpiperidin-3-yl)oxy)-2-((1-cyclopropyl-1H-pyrazol-4-yl)amino)-7H-pyrrolo[2,3-d]pyrimidine-5-carbonitrile,
149) (R)-4-((1-acryloylpiperidin-3-yl)oxy)-2-((1-(2,2-difluoroethyl)-1H-pyrazol-4-yl)amino)-7H-pyrrolo[2,3-d]pyrimidine-5-carbonitrile,
150) (R)-4-((1-acryloylpiperidin-3-yl)oxy)-2-((1-ethyl-1H-pyrazol-4-yl)amino)-7H-pyrrolo[2,3-d]pyrimidine-5-carbonitrile,
151) (R)-1-(3-((2-((1-ethyl-1H-pyrazol-4-yl)amino)-7H-pyrrolo[2,3-d]pyrimidin-4-yl)oxy)piperidin-1-yl)prop-2-en-1-one,
152) (R)-1-(3-((2-((4-morpholinophenyl)amino)-7H-pyrrolo[2,3-d]pyrimidin-4-yl)oxy)piperidin-1-yl)prop-2-en-1-one,
153) (R)-1-(3-((3-chloro-6-((1-cyclopropyl-1H-pyrazol-4-yl)amino)-1H-pyrazolo[3,4-d]pyrimidin-4-yl)oxy)piperidin-1-yl)prop-2-en-1-one,
154) (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-3-cyclopropylacrylonitrile,
155) (R,E)-2-(3-((3-chloro-6-((1-ethyl-1H-pyrazol-4-yl)amino)-1H-pyrazolo[3,4-d]pyrimidin-4-yl)oxy)piperidine-1-carbonyl)-3-cyclopropylacrylonitrile,
156) (R,E)-4-((1-(2-cyano-4-methylpent-2-enoyl)piperidin-3-yl)oxy)-2-((1-ethyl-1H-pyrazol-4-yl)amino)-7H-pyrrolo[2,3-d]pyrimidine-5-carbonitrile,
157) (R,E)-4-((1-(2-cyano-3-cyclopropylacryloyl)piperidin-3-yl)oxy)-2-((1-ethyl-1H-pyrazol-4-yl)amino)-7H-pyrrolo[2,3-d]pyrimidine-5-carbonitrile,
158) (R,E)-2-(3-((3-chloro-6-((1-cyclopropyl-1H-pyrazol-4-yl)amino)-1H-pyrazolo[3,4-d]pyrimidin-4-yl)oxy)piperidine-1-carbonyl)-4-methylpent-2-enenitrile,
159) 1-((3R,4R)-3-((3-chloro-6-((1-ethyl-1H-pyrazol-4-yl)amino)-1H-pyrazolo[3,4-d]pyrimidin-4-yl)(methyl)amino)-4-methylpiperidin-1-yl)prop-2-en-1-one,
160) (E)-2-((3S,4R)-3-((3-chloro-6-((1-ethyl-1H-pyrazol-4-yl)amino)-1H-pyrazolo[3,4-d]pyrimidin-4-yl)amino)-4-fluoropiperidine-1-carbonyl)-4-methylpent-2-enenitrile,
161) (E)-2-((3S,4R)-3-((3-chloro-6-((1-ethyl-1H-pyrazol-4-yl)amino)-1H-pyrazolo[3,4-d]pyrimidin-4-yl)amino)-4-fluoropiperidine-1-carbonyl)-3-cyclopropylacrylonitrile,
162) (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-4-methylpent-2-enenitrile,
163) (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-4,4-dimethylpent-2-enenitrile,
164) (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-3-cyclopropylacrylonitrile,
165) (R,E)-2-(3-((3-chloro-6-((1-cyclopropyl-1H-pyrazol-4-yl)amino)-1H-pyrazolo[3,4-d]pyrimidin-4-yl)amino)piperidine-1-carbonyl)-3-cyclopentylacrylonitrile,
166) (R,E)-2-(3-((3-chloro-6-((1-ethyl-1H-pyrazol-4-yl)amino)-1H-pyrazolo[3,4-d]pyrimidin-4-yl)amino)piperidine-1-carbonyl)-3-cyclopropylacrylonitrile,
167) (R,E)-2-(3-((3-chloro-6-((1-ethyl-1H-pyrazol-4-yl)amino)-1H-pyrazolo[3,4-d]pyrimidin-4-yl)(methyl)amino)piperidine-1-carbonyl)-3-cyclopropylacrylonitrile,
168) (R,E)-2-(3-((3-chloro-6-((1-ethyl-1H-pyrazol-4-yl)amino)-1H-pyrazolo[3,4-d]pyrimidin-4-yl)(methyl)amino)piperidine-1-carbonyl)-4-methylpent-2-enenitrile,
169) (E)-2-((3R,4R)-3-((3-chloro-6-((1-ethyl-1H-pyrazol-4-yl)amino)-1H-pyrazolo[3,4-d]pyrimidin-4-yl)amino)-4-methylpiperidine-1-carbonyl)-3-cyclopropylacrylonitrile,
170) (E)-2-((3R,4R)-3-((3-chloro-6-((1-ethyl-1H-pyrazol-4-yl)amino)-1H-pyrazolo[3,4-d]pyrimidin-4-yl)amino)-4-methylpiperidine-1-carbonyl)-4-methylpent-2-enenitrile,
171) (R,E)-3-cyclopropyl-2-(3-((2-((1-ethyl-1H-pyrazol-4-yl)amino)-7H-pyrrolo[2,3-d]pyrimidin-4-yl)amino)piperidine-1-carbonyl)acrylonitrile,
172) (R,E)-2-(3-((2-((1-ethyl-1H-pyrazol-4-yl)amino)-7H-pyrrolo[2,3-d]pyrimidin-4-yl)amino)piperidine-1-carbonyl)-4-methylpent-2-enenitrile,
173) (R,E)-3-cyclopropyl-2-(3-((2-((1-ethyl-1H-pyrazol-4-yl)amino)-7H-pyrrolo[2,3-d]pyrimidin-4-yl)thio)piperidine-1-carbonyl)acrylonitrile,
174) (R,E)-2-(3-((2-((1-ethyl-1H-pyrazol-4-yl)amino)-7H-pyrrolo[2,3-d]pyrimidin-4-yl)thio)piperidine-1-carbonyl)-4-methylpent-2-enenitrile,
175) (R,E)-3-cyclopropyl-2-(3-((6-((1-ethyl-1H-pyrazol-4-yl)amino)-1H-pyrazolo[3,4-d]pyrimidin-4-yl)amino)piperidine-1-carbonyl)acrylonitrile,
176) (R,E)-3-cyclopropyl-2-(3-((6-((1-ethyl-1H-pyrazol-4-yl)amino)-1H-pyrazolo[3,4-d]pyrimidin-4-yl)thio)piperidine-1-carbonyl)acrylonitrile, 177) (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-3-cyclopropylacrylonitrile,
178) (R,E)-2-(3-((5-chloro-2-((1-ethyl-1H-pyrazol-4-yl)amino)-7H-pyrrolo[2,3-d]pyrimidin-4-yl)amino)piperidine-1-carbonyl)-4-methylpent-2-enenitrile,
179) (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-3-cyclopropylacrylonitrile,
180) (R,E)-2-(3-((5-chloro-2-((1-ethyl-1H-pyrazol-4-yl)amino)-7H-pyrrolo[2,3-d]pyrimidin-4-yl)thio)piperidine-1-carbonyl)-4-methylpent-2-enenitrile,
181) (R,E)-2-(3-((3-chloro-6-((1-ethyl-1H-pyrazol-4-yl)amino)-1H-pyrazolo[3,4-d]pyrimidin-4-yl)thio)piperidine-1-carbonyl)-3-cyclopropylacrylonitrile,
182) (R,E)-3-cyclopropyl-2-(3-((2-((1-ethyl-1H-pyrazol-4-yl)amino)-5-fluoro-7H-pyrrolo[2,3-d]pyrimidin-4-yl)amino)piperidine-1-carbonyl)acrylonitrile,
183) 2-chloro-1-((3R,4R)-3-((3-chloro-6-((1-ethyl-1H-pyrazol-4-yl)amino)-1H-pyrazolo[3,4-d]pyrimidin-4-yl)amino)-4-methylpiperidin-1-yl)ethan-1-one,
184) (R)-1-(3-((6-((1-(2,2-difluoroethyl)-1H-pyrazol-4-yl)amino)-3-methyl-1H-pyrazolo[3,4-d]pyrimidin-4-yl)amino)piperidin-1-yl)prop-2-en-1-one,
185) (R)-1-(3-((6-((1-ethyl-1H-pyrazol-4-yl)amino)-3-methyl-1H-pyrazolo[3,4-d]pyrimidin-4-yl)amino)piperidin-1-yl)prop-2-en-1-one,
186) (R)-1-(3-((6-((1-isobutyl-1H-pyrazol-4-yl)amino)-3-methyl-1H-pyrazolo[3,4-d]pyrimidin-4-yl)amino)piperidin-1-yl)prop-2-en-1-one,
187) (R)-1-(3-((6-((1-(tert-butyl)-1H-pyrazol-4-yl)amino)-3-methyl-1H-pyrazolo[3,4-d]pyrimidin-4-yl)amino)piperidin-1-yl)prop-2-en-1-one,
188) (R)-1-(3-((6-((1-cyclopropyl-1H-pyrazol-4-yl)amino)-3-methyl-1H-pyrazolo[3,4-d]pyrimidin-4-yl)amino)piperidin-1-yl)prop-2-en-1-one,
189) (R)-1-(3-((6-((1-ethyl-1H-pyrazol-4-yl)amino)-3-(methylthio)-1H-pyrazolo[3,4-d]pyrimidin-4-yl)amino)piperidin-1-yl)prop-2-en-1-one,
190) (R)-1-(3-((6-((1-(2,2-difluoroethyl)-1H-pyrazol-4-yl)amino)-3-(methylthio)-1H-pyrazolo[3,4-d]pyrimidin-4-yl)amino)piperidin-1-yl)prop-2-en-1-one,
191) (R)-1-(3-((6-((1-methyl-1H-pyrazol-4-yl)amino)-3-(methylthio)-1H-pyrazolo[3,4-d]pyrimidin-4-yl)amino)piperidin-1-yl)prop-2-en-1-one,
192) (R)-1-(3-((6-((1-(tert-butyl)-1H-pyrazol-4-yl)amino)-3-(methylthio)-1H-pyrazolo[3,4-d]pyrimidin-4-yl)amino)piperidin-1-yl)prop-2-en-1-one, and
193) 1-((3S,4R)-3-((3-chloro-6-((1-ethyl-1H-pyrazol-4-yl)amino)-1H-pyrazolo[3,4-d]pyrimidin-4-yl)amino)-4-fluoropiperidin-1-yl)prop-2-en-1-one.

13. A pharmaceutical composition for the treatment of inflammatory disease, autoimmune disease, proliferative disease, hyperproliferative disease, immunity mediated disease, cancer or tumor, comprising the compound according to claim 1 or a pharmaceutically acceptable salt thereof.

* * * * *